US011446274B2

(12) United States Patent
Bacha et al.

(10) Patent No.: US 11,446,274 B2
(45) Date of Patent: Sep. 20, 2022

(54) USE OF DIANHYDROGALACTITOL OR DERIVATIVES OR ANALOGS THEREOF FOR TREATMENT OF PEDIATRIC CENTRAL NERVOUS SYSTEM MALIGNANCIES

(71) Applicant: DelMar Pharmaceuticals, Inc., Vancouver (CA)

(72) Inventors: Jeffrey A. Bacha, Vancouver (CA); Dennis M. Brown, Menlo Park, CA (US); Anne Steinø, Vancouver (CA)

(73) Assignee: DEL MAR PHARMACEUTICALS (BC) LTD., Vancouver (CA)

( * ) Notice: Subject to any disclaimer, the term of this patent is extended or adjusted under 35 U.S.C. 154(b) by 0 days.

(21) Appl. No.: 15/771,631

(22) PCT Filed: Oct. 26, 2016

(86) PCT No.: PCT/US2016/058861

§ 371 (c)(1),
(2) Date: Apr. 27, 2018

(87) PCT Pub. No.: WO2017/075052

PCT Pub. Date: May 4, 2017

(65) Prior Publication Data

US 2019/0175541 A1 Jun. 13, 2019

Related U.S. Application Data

(60) Provisional application No. 62/247,350, filed on Oct. 28, 2015.

(51) Int. Cl.

| | |
|---|---|
| ***A61K 31/336*** | (2006.01) |
| ***A61K 45/06*** | (2006.01) |
| ***A61K 33/243*** | (2019.01) |
| ***A61K 31/282*** | (2006.01) |
| ***A61K 31/4745*** | (2006.01) |
| ***A61K 31/495*** | (2006.01) |
| ***A61K 31/502*** | (2006.01) |
| ***A61K 31/7048*** | (2006.01) |
| ***A61P 35/00*** | (2006.01) |
| ***A61N 5/10*** | (2006.01) |

(52) U.S. Cl.

CPC .......... *A61K 31/336* (2013.01); *A61K 31/282* (2013.01); *A61K 31/4745* (2013.01); *A61K 31/495* (2013.01); *A61K 31/502* (2013.01); *A61K 31/7048* (2013.01); *A61K 33/243* (2019.01); *A61K 45/06* (2013.01); *A61N 5/10* (2013.01); *A61P 35/00* (2018.01); *A61N 2005/1098* (2013.01)

(58) Field of Classification Search

CPC combination set(s) only.
See application file for complete search history.

(56) References Cited

U.S. PATENT DOCUMENTS

| | | | |
|---|---|---|---|
| 2002/0128228 | A1 | 9/2002 | Hwu |
| 2014/0377336 | A1 | 12/2014 | Brown et al. |

FOREIGN PATENT DOCUMENTS

| | | | |
|---|---|---|---|
| WO | 2014/004376 | A3 | 1/2014 |
| WO | 2015/154064 | A2 | 10/2015 |

OTHER PUBLICATIONS

Stehman (Phase II Trial of Galactitol 1,2:5,6-Dianhydro (NSC 132313) in the Treatment of Advanced Gynecologic Malignancies: A Gynecologic Oncology Group Study, Gynecologic Oncology 15, 381-390 (1983)).*

Bixel (Olaparib in the management of ovarian cancer, Pharmacogenomics and Personalized Medicine, Aug. 2015:8 127-135).*

Chamberlain, M.C., et al., "Chronic Oral VP-16 for Recurrent Medulloblastoma," Pediatric Neurology 17(3)1230-234, Oct. 1997.

Geoerger, B., et al., "Phase II Trial of Temsirolimus in Children With High-Grade Glioma, Neuroblastoma and Rhabdomyosarcoma," European Journal of Cancer 48(2)1253-262, Jan. 2012.

Huang, S.Y., and J-Y. Yang, "Targeting the Hedgehog Pathway in Pediatric Medulloblastoma," Cancers 7(4)12110-2123, Oct. 2015.

Sutherland, B.W., et al., "Akt Phosphorylates the Y-Box Binding Protein 1 at Ser102 Located in the Cold Shock Domain and Affects the Anchorage-Independent Growth of Breast Cancer Cells," Oncogene 24(26)14281-4292, Apr. 2005.

Vasudevan, K.M., et al., "Suppression of PTEN Expression by NF-kB Prevents Apoptosis," Molecular and Cellular Biology 24(3):1007-1021, Feb. 2004.

(Continued)

*Primary Examiner* — Kathrien A Cruz

(74) *Attorney, Agent, or Firm* — Christensen O'Connor Johnson Kindness PLLC

(57) ABSTRACT

The use of dianhydrogalactitol provides a novel therapeutic modality for the treatment of malignancies of the central nervous system in pediatric patients, including glioblastoma multiforme (GBM) high grade glioma, and medulloblastoma. Dianhydrogalactitol acts as an alkylating agent on DNA that creates $N^7$ methylation and that can induce double-stranded breaks in DNA. Dianhydrogalactitol is effective in suppressing the growth of cancer stem cells and is active against tumors that are refractory to temozolomide, cisplatin, and tyrosine kinase inhibitors; the drug acts independently of the MGMT repair mechanism. Dianhydrogalactitol can be used together with other anti-neoplastic agents (e.g. cisplatin) and can possess additive or super-additive effects.

4 Claims, 45 Drawing Sheets

(56) References Cited

OTHER PUBLICATIONS

International Search Report and Written Opinion dated Mar. 31, 2017, in corresponding International Application No. PCT/US2016/58861, filed Oct. 26, 2016, 22 pages.
International Preliminary Report on Patentability dated Mar. 13, 2018, in corresponding International Application No. PCT/US2016/58861, filed Oct. 26, 2016, 14 pages.

* cited by examiner

* GBM STEM CELL LINE FROM PATIENTS

| CELL LINE | MGMT | TMZ SENSITIVE | VAL083 SENSITIVE |
|---|---|---|---|
| SF188 | METHYLATED | NO | YES |
| U251 | METHYLATED | YES | YES |
| T98G | UNMETHYLATED | NO | YES |
| U87 | METHYLATED | YES | |
| BT74* | UNMETHYLATED | NO | YES |
| aBT001* | ? | NO | YES |
| MEDULLOBLASTOMA | | | |
| DAOY | | NO | YES |

FIG. 1

- THREE CELL LINES USED:

| | TMZ RESISTANCE | MGMT STATUS |
|---|---|---|
| SF188 | ++ | - |
| U251 | + | - |
| T98G | +++ | + |

SF188 COLONY ASSAY FOR 7 DAYS
>95% SUPPRESSION

DAOY (MEDULLOBLASTOMA) COLONY ASSAY FOR 7 DAYS
100% SUPPRESSION
CONTROL
VAL 5uM
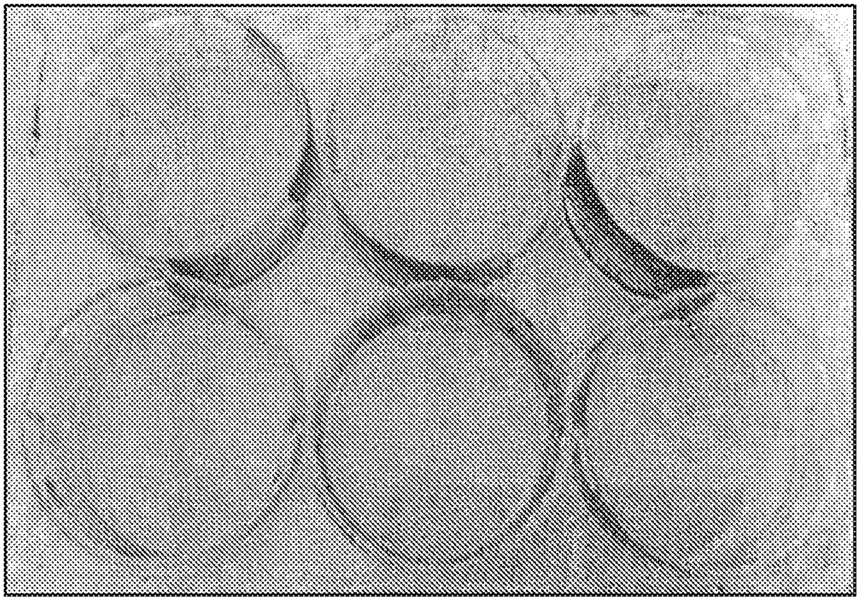
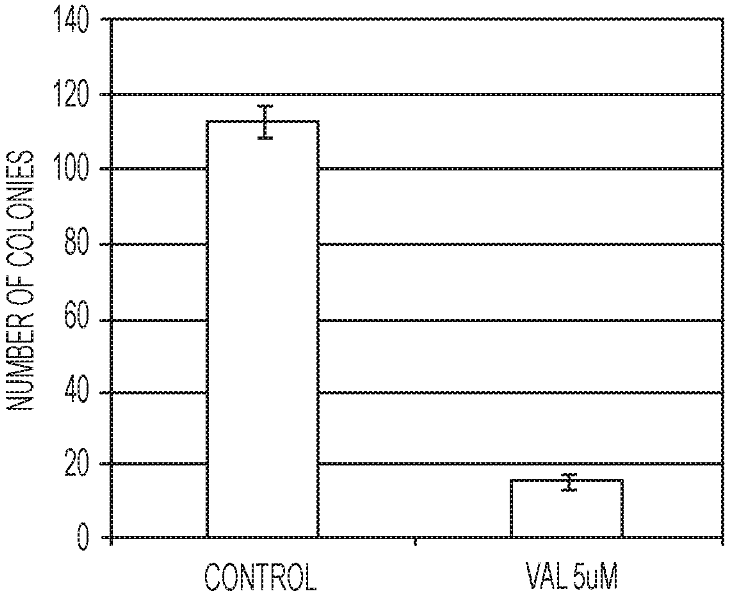
FIG. 8

SF188 COLONY ASSAY FOR 7 DAYS
>80% SUPPRESSION
CONTROL
VAL 5uM
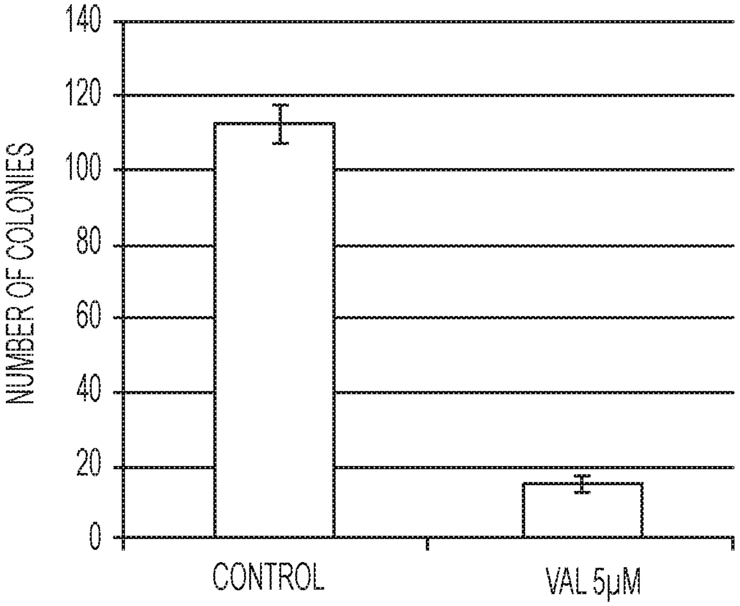
FIG. 8
CONTINUED

REGULAR DOSE-RESPONSE CURVES

SIGMOIDAL DOSE-RESPONSE FIT (NEEDED TO CREATE IC50 VALUES)

IC50 VALUES

| VAL-083 AND TMZ *IN VITRO* EFFECT ON GBM CELLS | | | | | | |
|---|---|---|---|---|---|---|
| CELL LINE | VAL-083 | | | TMZ* | | |
| | IC50 (μM) | SE (μM) | 95% CONFIDENCE INTERVAL (μM) | IC50 (μM) | SE (μM) | 95% CONFIDENCE INTERVAL (μM) |
| U251 | 1.8 | 1.1 | 1.4-2.4 | 22.7 | 1.5 | 9.4-54.8 |
| T98G | 1.8 | 1.2 | 1.2-2.6 | n / a** | n / a | n / a |
| SF188 | 4.5 | 1.1 | 3.9-5.1 | 710 | 3.3 | 61.3-8233 |

*THE IC50 VALUES FOR TMZ ARE CREATED BASED ON INADEQUATE DOSE-RESPONSE CURVES, AS THE TESTED CELL LINES WERE MODERATELY OR FULLY RESISTANT TO TMZ.

**THE IC50 VALUES FOR TMZ IN T98G COULD NOT BE DEDUCED, AS THE CELL LINE IS COMPLETELY RESISTANT TO TMZ AND THE RESPONSE THUS NEVER REACHES 50%.

FIG. 16

INHIBITION OF YB-1 IN ADULT GLIOBLASTOMA INCREASES SENSITIVITY TO TEMOZOLOMIDE.

YB-1 HAS DNA REPAIR ACTIVITY

YB-1 REMAINS NUCLEAR IN THE PRESENCE OF TMZ

CONTROL 200X

TMZ 10μM 200X

IN CONCLUSION THERE DOES NOT APPEAR TO BE AN ADDED BENEFIT OF TREATING WITH VAL083 PRIOR TO TREATMENT WITH BI6727 IN GLIOBLASTOMA. HOWEVER, IN THE U251 CELLS PRE-TREATED WITH 5uM VAL083 THERE DOES APPEAR TO BE AN INCREASE IN GROWTH INHIBITION AT 5nM BI6727 TREATMENT ONLY.

IN CONCLUSION, THE MEDULLOBLASTOMA CELL LINES DO RESPOND TO VAL083 TREATMENT, HOWEVER THEY REQUIRE VERY HIGH CONCENTRATIONS OF VAL083 (100uM) IN ORDER TO GET CONSISTENT GROWTH INHIBITION ACROSS THE FOUR CELL LINES.

DOSE-RESPONSE CURVES IN OVARIAN TUMOR CELL PANEL TREATED WITH INCREASING CONCENTRATIONS OF VAL-083.

A2780: p53 WILD-TYPE, MMR PROFICIENT; 2780CP-16: p53 MUTANT, MMR DEFICIENT; OVCAR-10: p53 MUTANT, MMR PROFICIENT; HEY: p53 MUTANT, MMR PROFICIENT; OVCA-433: p53 MUTANT, MMR PROFICIENT.

$IC_{50}$ OF VAL-083 IN A HUMAN OVARIAN TUMOR PANEL (N=3)

| CELL LINE | IC50 (uM) | AVERAGE | SD |
|---|---|---|---|
| A2780 | 0.47 | 0.54 | 0.08 |
| | 0.63 | | |
| | 0.53 | | |
| 2780CP-16 | 2.35 | 2.2 | 0.5 |
| | 1.62 | | |
| | 2.5 | | |
| OVCAR-10 | 3.25 | 3.6 | 0.3 |
| | 3.84 | | |
| | 3.69 | | |
| HEY | 2.58 | 2.1 | 0.5 |
| | 1.88 | | |
| | 1.71 | | |
| OVCA-433 | 2.34 | 2.3 | 0.1 |
| | 2.18 | | |
| | 2.44 | | |

A2780: p53 WILD-TYPE, MMR PROFICIENT; 2780CP-16: p53 MUTANT, MMR DEFICIENT; OVCAR-10: p53 MUTANT, MMR PROFICIENT; HEY: p53 MUTANT, MMR PROFICIENT; OVCA-433: p53 MUTANT, MMR PROFICIENT.

FIG. 37

HUMAN H460 NSCLC CELL LINE (p53 WT, EGFR WT)
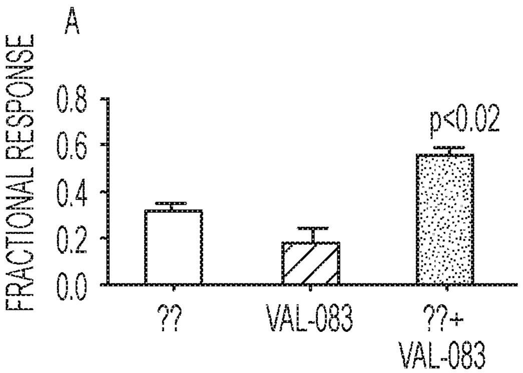
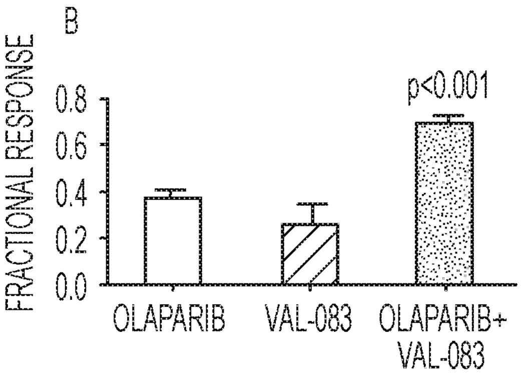
| ?? LEVEL (Fa) | ?? | | C1 |
|---|---|---|---|
| | VAL-083 | ?? | |
| ED75 | 0.42 | 0.38 | 0.02 |
| ED80 | 0.02 | 0.05 | 0.81 |
| ED85 | 0.50 | 1.45 | 0.90 |
| ?? LEVEL (Fa) | ?? | | C1 |
|---|---|---|---|
| | VAL-083 | ?? | |
| ED85 | 0.20 | 0.21 | 0.04 |
| ED90 | 0.04 | 0.37 | 0.80 |
| ED95 | 0.75 | 0.64 | 0.87 |
FIG. 41

HUMAN A549 NSCLC CELL LINE (p53 WT, EGFR WT)

| ?? LEVEL (Fa) | ?? | | C1 |
|---|---|---|---|
| | VAL-083 | ?? | |
| ED75 | 1.10 | 0.07 | 0.87 |
| ED80 | 1.00 | 1.14 | 0.52 |
| ED85 | 4.48 | 1.05 | 0.70 |

| ?? LEVEL (Fa) | ?? | | C1 |
|---|---|---|---|
| | VAL-083 | ?? | |
| ED75 | 1.55 | 0.55 | 0.01 |
| ED90 | 7.20 | 0.60 | 0.78 |
| ED95 | 2.92 | 0.68 | 0.71 |

| ?? LEVEL (Fa) | ?? | | C1 |
|---|---|---|---|
| | VAL-083 | ?? | |
| ED75 | 0.97 | 0.40 | 0.38 |
| ED80 | 2.01 | 1.00 | ?? |
| ED85 | 3.30 | 1.65 | 0.03 |

| ?? LEVEL (Fa) | ?? | | C1 |
|---|---|---|---|
| | VAL-083 | ?? | |
| ED85 | 0.70 | 0.44 | 0.65 |
| ED90 | 1.40 | 3.84 | 0.55 |
| ED95 | 2.38 | 1.21 | 0.46 |

USE OF DIANHYDROGALACTITOL OR DERIVATIVES OR ANALOGS THEREOF FOR TREATMENT OF PEDIATRIC CENTRAL NERVOUS SYSTEM MALIGNANCIES

CROSS-REFERENCES TO RELATED APPLICATIONS

This application is the National Stage of International Application No. PCT/US2016/058861, filed Oct. 26, 2016, which claims the benefit of U.S. Provisional Application No. 62/247,350, filed Oct. 28, 2015, the disclosures of which are hereby incorporated in their entirety by this reference.

FIELD OF THE INVENTION

This invention is directed to compositions and methods employing dianhydrogalactitol, diacetyldianhydrogalactitol, or derivatives or analogs thereof for the treatment of pediatric central nervous system malignancies, including medulloblastoma and high grade glioma, including glioblastoma multiforme.

BACKGROUND OF THE INVENTION

The search for and identification of cures for many life-threatening diseases that plague humans still remains an empirical and sometimes serendipitous process. While many advances have been made from basic scientific research to improvements in practical patient management, there still remains tremendous frustration in the rational and successful discovery of useful therapies particularly for life-threatening diseases such as cancer, inflammatory conditions, infection, and other conditions. Since the "War on Cancer" began in the early 1970's by the United States National Cancer Institute (NCI) of the National Institutes of Health (NIH), a wide variety of strategies and programs have been created and implemented to prevent, diagnose, treat and cure cancer. One of the oldest and arguably most successful programs has been the synthesis and screening of small chemical entities (<1500 MW) for biological activity against cancer. This program was organized to improve and streamline the progression of events from chemical synthesis and biological screening to preclinical studies for the logical progression into human clinical trials with the hope of finding cures for the many types of life-threatening malignant tumors. The synthesis and screening of hundreds of thousands of chemical compounds from academic and industrial sources, in addition to the screening of natural products and extracts from prokaryotes, invertebrate animals, plant collections, and other sources from all over the world has been and continues to be a major approach for the identification of novel lead structures as potential new and useful medicines. This is in addition to other programs including biotherapeutics designed to stimulate the human immune system with vaccines, therapeutic antibodies, cytokines, lymphokines, inhibitors of tumor blood vessel development (angiogenesis) or gene and antisense therapies to alter the genetic make-up of cancer cells, and other biological response modifiers.

The work supported by the NCI, other governmental agencies both domestic and foreign in academic or industrial research and development laboratories has resulted in an extraordinary body of biological, chemical and clinical information. In addition, large chemical libraries have been created, as well as highly characterized in vitro and in vivo biological screening systems that have been successfully used. However, from the tens of billions of dollars spent over the past thirty years supporting these programs both preclinically and clinically, only a small number of compounds have been identified or discovered that have resulted in the successful development of useful therapeutic products. Nevertheless, the biological systems both in vitro and in vivo and the "decision trees" used to warrant further animal studies leading to clinical studies have been validated. These programs, biological models, clinical trial protocols, and other information developed by this work remain critical for the discovery and development of any new therapeutic agent.

Unfortunately, many of the compounds that have successfully met the preclinical testing and federal regulatory requirements for clinical evaluation were either unsuccessful or disappointing in human clinical trials. Many compounds were found to have untoward or idiosyncratic side-effects that were discovered during human clinical Phase I dose-escalation studies used to determine the maximum tolerated dose (MTD) and side-effect profile. In some cases, these toxicities or the magnitude of their toxicity were not identified or predicted in preclinical toxicology studies. In other cases, chemical agents where in vitro and in vivo studies suggested a potentially unique activity against a particular tumor type, molecular target or biological pathway were not successful in human Phase II clinical trials where specific examination of particular cancer indications/types were evaluated in government sanctioned (e.g., U.S. FDA), IRB approved clinical trials. In addition, there are those cases where potential new agents were evaluated in randomized Phase III clinical trials where a significant clinical benefit could not be demonstrated; such cases have also been the cause of great frustration and disappointment. Finally, a number of compounds have reached commercialization but their ultimate clinical utility has been limited by poor efficacy as monotherapy (<25% response rates) and untoward dose-limiting side-effects (Grade III and IV) (e.g., myelosuppression, neurotoxicity, cardiotoxicity, gastrointestinal toxicities, or other significant side effects).

In many cases, after the great time and expense of developing and moving an investigational compound into human clinical trials and where clinical failure has occurred, the tendency has been to return to the laboratory to create a better analog, look for agents with different structures but potentially related mechanisms of action, or try other modifications of the drug. In some cases, efforts have been made to try additional Phase I or II clinical trials in an attempt to make some improvement with the side-effect profile or therapeutic effect in selected patients or cancer indications. In many of those cases, the results did not realize a significant enough improvement to warrant further clinical development toward product registration. Even for commercialized products, their ultimate use is still limited by suboptimal performance.

With so few therapeutics approved for cancer patients and the realization that cancer is a collection of diseases with a multitude of etiologies and that a patient's response and survival from therapeutic intervention is complex with many factors playing a role in the success or failure of treatment including disease indication, stage of invasion and metastatic spread, patient gender, age, health conditions, previous therapies or other illnesses, genetic markers that can either promote or retard therapeutic efficacy, and other factors, the opportunity for cures in the near term remains elusive. In addition, with advances in diagnosis such as mammography for breast cancer and PSA tests for prostate cancer, more patients are being diagnosed at a younger age. For difficult to treat cancers, a patient's treatment options are often exhausted quickly resulting in a desperate need for additional treatment regimens. Even for the most limited of patient populations, any additional treatment opportunities would be of considerable value. This invention focuses on inventive compositions and methods for improving therapeutic benefit of suboptimally administered chemical compounds including substituted hexitols such as dianhydrogalactitol.

Glioblastoma multiforme (GBM) is the most common and aggressive malignant primary brain tumor occurring in humans. GBM involves glial cells; it accounts for 52% of all functional tissue brain tumor cases and 20% of all intracranial tumors. Its estimated frequency of occurrence is 2-3 cases per 100,000 people in Europe and North America.

GBM has an extremely poor prognosis, despite various treatment methods including open craniotomy with surgical resection of as much of the tumor as possible, followed by sequential or concurrent chemoradiotherapy, antiangiogenic therapy with bevacizumab, gamma knife radiosurgery, and symptomatic management with corticosteroids. The median survival time for GBM is only 14 months.

Common symptoms of GBM include seizures, nausea, vomiting, headache, and hemiparesis. However, the most prevalent symptoms of GBM are progressive memory, personality, or neurological deficit due to involvement of the temporal or frontal lobe of the brain. The kind of symptoms produced by GBM depends highly on the location of the tumor and less on its exact pathology. The tumor can start producing symptoms quickly, but occasionally is asymptomatic until it reaches an extremely large size.

The etiology of GBM is largely unknown. For unknown reasons, GBM occurs more frequently in males. Most glioblastoma tumors appear to be sporadic, without any significant genetic predisposition. No links have been found between GBM, and several known carcinogenic risk factors, including diet, smoking, and exposure to electromagnetic fields. There have been some suggestions of a viral etiology, possibly SV40 or cytomegalovirus. There may also be some association between exposure to ionizing radiation and GBM. Additionally, it has been proposed that there is a link between polyvinyl chloride exposure and GBM; lead exposure in the workplace has also been suggested as a possible cause. There is an association of brain tumor incidence and malaria, suggesting that the *anopheles* mosquito, the carrier of malaria, might transmit a virus or other causative agent of GBM.

GBM is also relatively more common in people over 50 years of age, in Caucasians or Asians, and in patients that have already developed a low-grade astrocytoma which can develop into a higher grade tumor. Additionally, having one of the following genetic disorders is associated with an increased incidence of GBM: neurofibromatosis, tuberous sclerosis, Von Hippel-Lindau disease, Li-Fraumeni syndrome, or Turcot syndrome.

GBM tumors are typically characterized by the presence of small areas of necrotizing tissue that are surrounded by anaplastic cells. These characteristics, together with the presence of hyperplastic blood vessels, differentiate these malignancies from Grade 3 astrocytomas, which do not have these features.

There are four subtypes of glioblastoma. An extremely large fraction (97%) of tumors in the so-called "classical" subtype carry extra copies of the epidermal growth factor receptor (EGFR) gene and most of these tumors have higher than normal expression of EGFR, whereas the gene TP53, a tumor suppressor gene that has a number of anticancer activities, and which is often mutated in glioblastoma, is rarely mutated in this subtype. In contrast, the proneural subtype often has high rates of alteration in TP53 and in PDGFRA, the gene encoding the α-type platelet-derived growth factor receptor, as well as in IDH1, the gene encoding isocitrate dehydrogenase-1. The mesenchymal subtype is characterized by high rates of mutations or alterations in NF1, the gene encoding Neurofibromin type 1 and fewer alterations in the EGFR gene and less expression of EGFR than the other subtypes.

GBM usually forms in the cerebral white matter, grows quickly, and can become very large before producing symptoms. Less than 10% of GBMs form more slowly following degeneration of low-grade astrocytoma or anaplastic astrocytoma; such tumors are called secondary GBMs and are relatively more common in younger patients. The tumor may extend into the meninges or the ventricular wall leading to abnormally high protein content in the cerebrospinal fluid (CSF) (>100 mg/dL), as well as an occasional pleocytosis of 10 to 100 cells, mostly lymphocytes. Malignant cells present in the CSF can rarely spread to the spinal cord or cause meningeal gliomatosis; however, metastasis of GBM beyond the central nervous system is extremely unusual. About 50% of GBM tumors occupy more than one lobe of a hemisphere or are bilateral. Tumors of this type usually arise from the cerebrum and may rarely exhibit the classic infiltration across the corpus callosum, producing a bilateral ("butterfly") glioma. The tumor can take on a variety of appearances, depending on the amount of hemorrhage or necrosis present or the age of the tumor. A CT scan of a GBM tumor will usually show an inhomogeneous mass with a hypodense center and a variable ring of enhancement surrounded by edema. The mass effect from the tumor and the surrounding edema may compress the ventricles and cause hydrocephalus.

Cancer cells with stem-cell-like properties have been found in glioblastomas. This may be one cause of their resistance to conventional treatments and their high recurrence rate.

GBM often presents typical features on MRI, but these features are not specific for GBM and may be caused by other conditions. Specifically, when viewed with MRI, GBMs often appear as ring-enhancing lesions. However, other lesions such as abscesses, metastases of malignancies arising outside the central nervous system, tumefactive multiple sclerosis, or other conditions may have a similar appearance. The definitive diagnosis of a suspected GBM on CT or MRI requires a stereotactic biopsy or a craniotomy with tumor resection and pathologic confirmation. Because the grade of the tumor is based on the most malignant portion of the tumor, biopsy or subtotal tumor resection can result in undergrading of the tumor. Imaging of tumor blood flow using perfusion MRI and measuring tumor metabolite concentration with MR spectroscopy may add value to standard MRI, but pathology remains the gold standard for GBM diagnosis.

The treatment of GBM is extremely difficult due to several factors: (1) the tumor cells are very resistant to conventional therapies; (2) the brain is susceptible to damage using conventional therapy; (3) the brain has a very limited capacity for self-repair; and (4) many therapeutic drugs cannot cross the blood-brain barrier to act on the tumor. Symptomatic therapy, including the use of corticosteroids and anticonvulsant agents, focuses on relieving symptoms and improving the patient's neurologic function. However, such symptomatic therapy does nothing to slow the progression of the tumor, and, in the case of administration of phenytoin concurrently with radiation therapy, can result in substantial side effects including erythema multiforme and Steven-Johnson syndrome.

Palliative therapy usually is conducted to improve quality of life and to achieve a longer survival time. Palliative therapy can include surgery, radiation therapy, and chemotherapy. A maximally feasible resection with maximally tumor-free margins is generally performed along with external beam radiation and chemotherapy. Gross total resection of tumor is associated with better prognoses.

Surgery is the first stage of treatment of glioblastoma. An average GBM tumor contains $10^{11}$ cells, which is on average reduced to $10^9$ cells after surgery (a reduction of 99%). Surgery is used to take a section for a pathological diagnosis, to remove some of the symptoms of a large mass pressing against the brain, to remove disease before secondary resistance to radiotherapy and chemotherapy, and to prolong survival. The greater the extent of tumor removal, the better is the outcome. Removal of 98% or more of the tumor has been associated with a significantly longer and healthier survival time than if less than 98% of the tumor is removed. The chances of near-complete initial removal of the tumor can be greatly increased if the surgery is guided by a fluorescent dye known as 5-aminolevulinic acid. GBM cells are widely infiltrative through the brain at diagnosis, and so despite a "total resection" of all obvious tumor, most people with GBM later develop recurrent tumors either near the original site or at more distant "satellite lesions" within the brain. Other modalities, including radiation, are used after surgery in an effort to suppress and slow recurrent disease.

After surgery, radiotherapy is the mainstay of treatment for people with glioblastoma. A pivotal clinical trial carried out in the early 1970s showed that among 303 GBM patients randomized to radiation or nonradiation therapy, those who received radiation had a median survival more than double those who did not. Subsequent clinical research has attempted to build on the backbone of surgery followed by radiation. On average, radiotherapy after surgery can reduce the tumor size to $10^7$ cells. Whole brain radiotherapy does not improve the results when compared to the more precise and targeted three-dimensional conformal radiotherapy. A total radiation dose of 60-65 Gy has been found to be optimal for treatment.

The use of chemotherapy in GBM in addition to radiation has thus far only resulted in marginal improvements in survival as compared with radiation alone. In the treatment of other malignancies, the addition of chemotherapy to radiation has resulted in substantial improvements in survival, but this has not yet proven to be the case for GBM. One drug that does show results in connection with radiation is temozolomide (TMZ). TMZ plus radiation is now standard for most cases of GBM. TMZ seems to work by sensitizing the tumor cells to radiation.

However, TMZ is often ineffective due to drug resistance as the result of the catalytic activity of the enzyme $O^6$-methylguanine-DNA methyltransferase (MGMT), which results in repair of the lesion at $O^6$ of the guanine of DNA molecules. In addition to MGMT, a deficient or inhibited DNA mismatch repair (MMR) system also leads to TMZ resistance. Chemoresistance to TMZ as a result of the activity of MGMT is frequently associated with poor outcomes in TMZ-treated patients, and patients in whom TMZ or bevacizumab is ineffective are left with few if any treatment options.

Additionally, cancer stem cells (CSC) are a subpopulation of the tumor that resist therapy and give rise to relapse.

Another therapeutic approach involves the use of the monoclonal antibody bevacizumab, which is a humanized monoclonal antibody that inhibits vascular endothelial growth factor A (VEGF-A) and thus acts as an angiogenesis inhibitor. Although bevacizumab may retard the progression of the disease, the first-line use of bevacizumab does not improve overall survival in patients with newly diagnosed GBM (M. R. Gilbert et al., "A Randomized Trial of Bevacizumab for Newly Diagnosed Glioblastoma," *New Engl. J. Med.* 370: 699-708 (2014)). Additionally, unlike some other malignancies in which the use of bevacizumab results in a potentiation of chemotherapy, in GBM, the addition of chemotherapy to bevacizumab did not improve on results from bevacizumab alone. Bevacizumab reduces brain edema and consequent symptoms, and it may be that the benefit from this drug is due to its action against edema rather than any action against the tumor itself. Some patients with brain edema do not actually have any active tumor remaining, but rather develop the edema as a late effect of prior radiation treatment. This type of edema is difficult to distinguish from that due to tumor, and both may coexist. Both respond to bevacizumab. However, patients in which both temozolomide and bevacizumab have been ineffective have few if any treatment options.

Another approach that has been proposed is gene transfer. Although gene transfer therapy has the potential to kill cancer cells while leaving healthy cells unharmed, this approach has been beset with many difficulties in other diseases, including the possibility for induction of other types of malignancies and interference with the functioning of the immune system.

Still other treatment modalities have been proposed for GBM, including the use of protein therapeutics, including the soluble CD95-Fc fusion protein APG101, immunotherapy with tumor vaccines, alternating electrical fields, and metabolic therapy. The value of these treatment modalities remains to be determined.

In GBM, the median survival time from the time of diagnosis without any treatment is 3 months, but with treatment survival of 1-2 years is common. Increasing age (>60 years of age) carries a worse prognostic risk. Death is usually due to cerebral edema or increased intracranial pressure.

A good initial Karnofsky Performance Status (KPS) and methylation of the promoter of the $O^6$-methylguanine-DNA methyltransferase (MGMT) gene are associated with longer survival. A DNA test can be carried out on glioblastomas to determine whether the promoter of the MGMT gene is methylated. Even in patients less than 50 years of age with a KPS (Karnofsky Performance Status) of equal to or greater than 90%, the 5-year survival rate is only 14%.

Medulloblastoma (MB) is the most common malignant pediatric brain tumor, accounting for 15-30% of all childhood intracranial neoplasms. High grade gliomas (HGG) are much rarer in children than in adults, comprising only 5%-10% of childhood brain tumors. Although multidisciplinary treatment has improved the 5-year survival rates in children significantly, the prognosis for recurrent MB and HGG remains poor with median overall survival <1 year. Temozolomide (TMZ) is frequently employed in the treatment of pediatric HGG; however, clinical evidence is lacking and poor outcomes due to high-expression of the repair protein $O^6$-methylguanine-DNA methyltransferase (MGMT), which is correlated with TMZ resistance, have been reported. The status of p53 is also significant for the prognosis and treatment options in MB, particularly in the Sonic Hedgehog (SHH) and Group 3 subgroups. Mutations in p53 in these groups, and especially in recurrent SHH, are correlated with treatment resistance and poor prognosis. The standard of care for MB includes radiation and a combination of chemotherapeutic agents (cisplatin, vincristine, cyclophosphamide, and lomustine) which has severe side-effects in 100% of patients, and survivors suffer significant long-term side-effects on the developing brain.

Therefore, there is a need for improved therapies for glioblastoma multiforme and medulloblastoma that provide improved survival with reduced side effects and impairment of function in surviving patients, especially in pediatric patients. See K. Hu et al., "VAL-083, a N7 Alkylating Agent, Provides a New Potential Treatment for Glioblastoma Multiforme Because It Bypasses Temozolomide Resistance," AACR (2012). However, this does not reference the specific treatment of pediatric glioblastoma or pediatric medulloblastoma, and there are additional considerations, including tolerability of medications and the immaturity of the immune system response, that must be addressed in pediatric patients.

There is a particular need for therapeutic modalities that can cross the blood-brain barrier (BBB), that can suppress the growth and division of cancer stem cells (CSC), and that can avoid inactivation by $O^6$-methylguanine-DNA methyltransferase (MGMT). There is also a particular need for therapeutic modalities that yield increased response rates and improved quality of life for patients with these malignancies. There is also a particular need for therapeutic modalities that are effective in patients in which either or both of temozolomide and bevacizumab have proven ineffective. There is also a particular need for improved treatments of malignancies such as high grade glioma, including glioblastoma multiforme, and medulloblastoma in pediatric patients.

SUMMARY OF THE INVENTION

The use of a substituted hexitol derivative such as dianhydrogalactitol, diacetyldianhydrogalactitol, or a derivative or analog of dianhydrogalactitol or diacetyldianhydrogalactitol to treat malignancies of the central nervous system such as glioblastoma multiforme or medulloblastoma in pediatric patients provides an improved therapy for these malignancies that yields increased survival and is substantially free of side effects. In general, the substituted hexitols usable in methods and compositions according to the present invention include galactitols, substituted galacitols, dulcitols, and substituted dulcitols. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. A particularly preferred substituted hexitol derivative is dianhydrogalactitol (DAG). The substituted hexitol derivative can be employed together with other therapeutic modalities for these malignancies. Dianhydrogalactitol is particularly suited for the treatment of these malignancies because it crosses the blood-brain barrier, because it can suppress the growth of cancer stem cells (CSC), and because it is resistant to drug inactivation by $O^6$-methylguanine-DNA methyltransferase (MGMT). The substituted hexitol derivative yields increased response rates and improved quality of life for pediatric patients with these patients.

Dianhydrogalactitol is a novel alkylating agent that targets the N7 of guanine leading to an interstrand crosslink between two guanines on opposite DNA strands.

In particular, dianhydrogalactitol has been shown to have substantial efficacy in inhibiting the growth of glioblastoma multiforme (GBM) cells. In the case of GBM, DAG has proven to be more effective in suppressing the growth of GBM cells than temozolomide (TMZ), the current chemotherapy of choice for GBM. As detailed below, DAG can effectively cross the blood-brain barrier and can effectively suppress the growth of cancer stem cells (CSCs). DAG acts independently of the MGMT repair mechanism. DAG activity also appears independent of the MMR repair system. DAG has also shown efficacy in treating medulloblastoma cell lines, as detailed further below. DAG is less dependent on p53 status than other alkylating agents used in the treatment of medulloblastoma.

Therefore, compositions and methods according to the present invention that include dianhydrogalactitol or a derivative or analog thereof have demonstrated efficacy in treating pediatric central nervous system malignancies, including glioblastoma and medulloblastoma. As detailed below, dianhydrogalactitol can be used in treating these malignancies as a single agent or in combination with other agents, such as, but not limited to, temozolomide, either with simultaneous administration or sequential administration. Dianhydrogalactitol acts independently of MGMT, also acts independently of MMR mismatch repair, and can overcome cisplatin resistance associated with deficiency of normal p53 activity.

Particular therapeutic combinations according to the present invention include dianhydrogalactitol and temozolomide; dianhydrogalactitol and an inhibitor of Polo-like kinase; dianhydrogalactitol and an agent that reduces the activity or expression of YB-1; dianhydrogalactitol and an inhibitor of Akt; dianhydrogalactitol and an inhibitor of RSK; dianhydrogalactitol and the PARP inhibitor olaparib; dianhydrogalactitol and cisplatin or oxaliplatin; and dianhydrogalactitol and the topoisomerase II inhibitor etoposide. For dianhydrogalactitol and temozolomide, synergy exists when the two agents are administered sequentially, typically by the administration of temozolomide for three days followed by the administration of dianhydrogalactitol for three days, but not when the agents are administered simultaneously. For other alternatives, the agents can be administered simultaneously or sequentially. Other therapeutic combinations are described below.

As further detailed below, treatment of glioblastoma multiforme (GBM) in pediatric patients includes and is particularly directed to treatment of high grade glioma (HGG) in such patients. This applies with respect to methods and compositions according to the present invention that are intended for the treatment of GBM in pediatric patients; such methods and compositions are particularly useful for the treatment of HGG in such patients. One aspect of the activity of the methods and compositions of the present invention is the suppression of proliferation of cancer stem cells (CSCs).

Accordingly, one aspect of the present invention is a method to improve the efficacy and/or reduce the side effects of the administration of a substituted hexitol derivative for treatment of central nervous system malignancies in pediatric patients comprising the steps of:

(1) identifying at least one factor or parameter associated with the efficacy and/or occurrence of side effects of the administration of the substituted hexitol derivative for treatment of central nervous system malignancies in pediatric patients; and (2) modifying the factor or parameter to improve the efficacy and/or reduce the side effects of the administration of the substituted hexitol derivative for treatment of central nervous system malignancies in pediatric patients.

Typically, the central nervous system malignancy is selected from the group consisting of medulloblastoma and high grade glioma.

Typically, the factor or parameter is selected from the group consisting of:

(1) dose modification;
(2) route of administration;
(3) schedule of administration;
(4) selection of disease stage;
(5) patient selection;
(6) patient/disease phenotype;
(7) patient/disease genotype;
(8) pre/post-treatment preparation
(9) toxicity management;
(10) pharmacokinetic/pharmacodynamic monitoring;
(11) drug combinations;
(12) chemosensitization;
(13) chemopotentiation;
(14) post-treatment patient management;
(15) alternative medicine/therapeutic support;
(16) bulk drug product improvements;
(17) diluent systems;
(18) solvent systems;
(19) excipients;
(20) dosage forms;
(21) dosage kits and packaging;
(22) drug delivery systems;
(23) drug conjugate forms;
(24) compound analogs;
(25) prodrugs;
(26) multiple drug systems;
(27) biotherapeutic enhancement;
(28) biotherapeutic resistance modulation;
(29) radiation therapy enhancement;
(30) novel mechanisms of action;
(31) selective target cell population therapeutics;
(32) use with ionizing radiation;
(33) use with an agent enhancing its activity;
(34) use with an agent that counteracts myelosuppression; and
(35) use with an agent that increases the ability of the substituted hexitol to pass through the blood-brain barrier.

As detailed above, typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

In one alternative of this method, at least two anti-neoplastic therapeutic agents are administered. The at least two anti-neoplastic agents can be administered simultaneously or substantially simultaneously, such as in a single pharmaceutical composition. In another alternative, the at least two anto-neoplastic agents can be administered sequentially. Some possible alternatives for the at least two anti-neoplastic therapeutic agents include: dianhydrogalactitol and temozolomide; dianhydrogalactitol and an inhibitor of Polo-like kinase; dianhydrogalactitol and an agent that reduces the activity or expression of YB-1; dianhydrogalactitol and an inhibitor of Akt; dianhydrogalactitol and an inhibitor of RSK; dianhydrogalactitol and an inhibitor of PARP; and dianhydrogalactitol and an agent that counters loss of PTEN function.

Another aspect of the present invention is a composition to improve the efficacy and/or reduce the side effects of suboptimally administered drug therapy employing a substituted hexitol derivative for treatment of central nervous system malignancies in pediatric patients comprising an alternative selected from the group consisting of:

(i) a therapeutically effective quantity of a modified substituted hexitol derivative or a derivative, analog, or prodrug of a substituted hexitol derivative or a modified substituted hexitol derivative, wherein the modified substituted hexitol derivative or the derivative, analog or prodrug of the substituted hexitol derivative or modified substituted hexitol derivative possesses increased therapeutic efficacy or reduced side effects for treatment of central nervous system malignancies in pediatric patients as compared with an unmodified substituted hexitol derivative;

(ii) a composition comprising:

(a) a therapeutically effective quantity of a substituted hexitol derivative, a modified substituted hexitol derivative, or a derivative, analog, or prodrug of a substituted hexitol derivative or a modified substituted hexitol derivative; and (b) at least one additional therapeutic agent, therapeutic agent subject to chemosensitization, therapeutic agent subject to chemopotentiation, diluent, excipient, solvent system, drug delivery system, agent to counteract myelosuppression, or agent that increases the ability of the substituted hexitol to pass through the blood-brain barrier, wherein the composition possesses increased therapeutic efficacy or reduced side effects for treatment of central nervous system malignancies in pediatric patients as compared with an unmodified substituted hexitol derivative;

(iii) a therapeutically effective quantity of a substituted hexitol derivative, a modified substituted hexitol derivative or a derivative, analog, or prodrug of a substituted hexitol derivative or a modified substituted hexitol derivative that is incorporated into a dosage form, wherein the substituted hexitol derivative, the modified substituted hexitol derivative or the derivative, analog, or prodrug of a substituted hexitol derivative or a modified substituted hexitol derivative incorporated into the dosage form possesses increased therapeutic efficacy or reduced side effects for treatment of central nervous system malignancies in pediatric patients as compared with an unmodified substituted hexitol derivative;

(iv) a therapeutically effective quantity of a substituted hexitol derivative, a modified substituted hexitol derivative or a derivative, analog, or prodrug of a substituted hexitol derivative or a modified substituted hexitol derivative that is incorporated into a dosage kit and packaging, wherein the substituted hexitol derivative, the modified substituted hexitol derivative or the derivative, analog, or prodrug of a substituted hexitol derivative or a modified substituted hexitol derivative incorporated into the dosage kit and packaging possesses increased therapeutic efficacy or reduced side effects for treatment of central nervous system malignancies in pediatric patients as compared with an unmodified substituted hexitol derivative; and (v) a therapeutically effective quantity of a substituted hexitol derivative, a modified substituted hexitol derivative or a derivative, analog, or prodrug of a substituted hexitol derivative or a modified substituted hexitol derivative that is subjected to a bulk drug product improvement, wherein substituted hexitol derivative, a modified substituted hexitol derivative or a derivative, analog, or prodrug of a substituted hexitol derivative or a modified substituted hexitol derivative subjected to the bulk drug product improvement possesses increased therapeutic efficacy or reduced side effects for treatment of central nervous system malignancies in pediatric patients as compared with an unmodified substituted hexitol derivative.

Typically, the central nervous system malignancy is selected from the group consisting of medulloblastoma and high grade glioma.

As detailed above, typically the unmodified substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the unmodified substituted hexitol derivative is dianhydrogalactitol.

Another aspect of the present invention is a method of treating a central nervous system malignancy in a pediatric patient comprising the step of administering a therapeutically effective quantity of a substituted hexitol derivative to a patient suffering from the malignancy. As detailed above, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

Typically, when the substituted hexitol derivative is dianhydrogalactitol, the therapeutically effective quantity of dianhydrogalactitol is a dosage from about 1 $mg/m^2$ to about 40 $mg/m^2$. Preferably, the therapeutically effective quantity of dianhydrogalactitol is a dosage from about 5 $mg/m^2$ to about 25 $mg/m^2$. Other dosages are described below.

Typically, the substituted hexitol derivative, such as dianhydrogalactitol, is administered by a route selected from the group consisting of intravenous and oral. Other potential routes of administration are described below.

The method can further comprise the step of administering a therapeutically effective dose of ionizing radiation. The method can further comprise the step of administering a therapeutically effective quantity of temozolomide, bevacizumab, or a corticosteroid.

The method can further comprise the administration of a therapeutically effective quantity of a tyrosine kinase inhibitor as described below.

The method can further comprise the administration of a therapeutically effective quantity of an epidermal growth factor receptor (EGFR) inhibitor as described below. The EGFR inhibitor can affect either wild-type binding sites or mutated binding sites, including Variant III, as described below.

BRIEF DESCRIPTION OF THE DRAWINGS

The following invention will become better understood with reference to the specification, appended claims, and accompanying drawings, where:

FIG. 1 is a table showing a summary of glioblastoma multiforme (GBM) models and their response to dianhydrogalactitol (VAL-083).

In FIG. 2, the protein actin is used as a control. Western blots are shown.

FIG. 8 shows that dianhydrogalactitol at 5 μM provided 100 percent suppression of colony formation for DAOY medulloblastoma cells and >80% suppression of colony formation for SF188 glioblastoma cells.

FIG. 16 is a table showing IC50 values calculated from the sigmoidal dose response curves of FIG. 15.

FIG. 37 is a table showing the $IC_{50}$ of dianhydrogalactitol in a human ovarian tumor panel in connection with the demonstration of MMR independence and p53 independence of dianhydrogalactitol anti-neoplastic activity in Example 3. A2780 has wild-type p53 and is MMR-proficient. 2780CP-16 has mutated p53 and is MMR-deficient (lacking MLH1 protein). OVCAR10 has mutated p53 and is MMR-proficient. HEY has mutated p53 and is MMR-proficient. OVCA-433 has mutated p53 and is MMR-proficient.

FIG. 41 is a graph showing the synergism of dianhydrogalactitol with cisplatin and oxaliplatin in the NSCLC cell line H460 (wild-type p53 and wild-type EGFR) in Example 5.

DETAILED DESCRIPTION OF THE INVENTION

Figure 2:
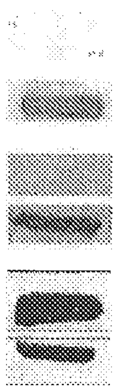
FIG. 2 shows the temozolomide (TMZ) resistance and MGMT status for three cell lines, SF188, U251, and T98G. SF188 is a pediatric high grade glioma cell line.

The compound dianhydrogalactitol (DAG) has been shown to have substantial efficacy in inhibiting the growth of glioblastoma multiforme (GBM) cells. In the case of GBM, DAG has proven to be more effective in suppressing the growth of GBM cells than temozolomide (TMZ), the current chemotherapy of choice for GBM. As detailed below, DAG can effectively cross the blood-brain barrier and can effectively suppress the growth of cancer stem cells (CSCs). DAG acts independently of the MGMT repair mechanism. DAG activity also appears independent of the MMR repair system. DAG has also shown efficacy in treating medulloblastoma cell lines, as detailed further below. DAG is less dependent on p53 status than other alkylating agents commonly used in the treatment of medulloblastoma.

Therefore, compositions and methods according to the present invention that include dianhydrogalactitol or a derivative or analog thereof have demonstrated efficacy in treating pediatric central nervous system malignancies, including glioblastoma and medulloblastoma. As detailed below, dianhydrogalactitol can be used in treating these malignancies as a single agent or in combination with other agents, such as, but not limited to, temozolomide, either with simultaneous administration or sequential administration. Dianhydrogalactitol acts independently of MGMT, also acts independently of MMR mismatch repair, and can overcome cisplatin resistance associated with deficiency of normal p53 activity.

Compositions suitable for administration of dianhydrogalactitol and derivatives or analogs thereof for the treatment of pediatric malignancies of the central nervous system are also described below. The compositions can, for example, include additional therapeutic agents, prodrugs, conjugates, drug delivery systems, agents for countering myelosuppression, or agents that increase the ability of the substituted hexitol to pass through the blood-brain barrier.

The structure of dianhydrogalactitol (DAG) is shown in Formula (I), below.

(I)

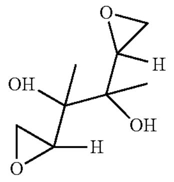

As detailed below, other substituted hexitols can be used in methods and compositions according to the present invention. In general, the substituted hexitols usable in methods and compositions according to the present invention include galactitols, substituted galacitols, dulcitols, and substituted dulcitols, including dianhydrogalactitol, diacetyldianhydrogalactitol, dibromodulcitol, and derivatives and analogs thereof. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

These galactitols, substituted galacitols, dulcitols, and substituted dulcitols are either alkylating agents or prodrugs of alkylating agents, as discussed further below.

Also within the scope of the invention are derivatives of dianhydrogalactitol that, for example, have one or both hydrogens of the two hydroxyl groups of dianhydrogalactitol replaced with lower alkyl, have one or more of the hydrogens attached to the two epoxide rings replaced with lower alkyl, or have the methyl groups present in dianhydrogalactitol and that are attached to the same carbons that bear the hydroxyl groups replaced with $C_2$-$C_6$ lower alkyl or substituted with, for example, halo groups by replacing a hydrogen of the methyl group with, for example a halo group. As used herein, the term "halo group," without further limitation, refers to one of fluoro, chloro, bromo, or iodo. As used herein, the term "lower alkyl," without further limitation, refers to $C_1$-$C_6$ groups and includes methyl. The term "lower alkyl" can be further limited, such as "$C_2$-$C_6$ lower alkyl," which excludes methyl. The term "lower alkyl", unless further limited, refers to both straight-chain and branched alkyl groups. These groups can, optionally, be further substituted, as described below.

The structure of diacetyldianhydrogalactitol is shown in Formula (II), below.

(II)

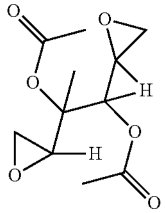

Also within the scope of the invention are derivatives of diacetyldianhydrogalactitol that, for example, have one or both of the methyl groups that are part of the acetyl moieties replaced with $C_2$-$C_6$ lower alkyl, have one or both of the hydrogens attached to the epoxide ring replaced with lower alkyl, or have the methyl groups attached to the same carbons that bear the acetyl groups replaced with lower alkyl or substituted with, for example, halo groups by replacing a hydrogen with, for example, a halo group.

The structure of dibromodulcitol is shown in Formula (III), below. Dibromodulcitol can be produced by the reaction of dulcitol with hydrobromic acid at elevated temperatures, followed by crystallization of the dibromodulcitol. Some of the properties of dibromodulcitol are described in N. E. Mischler et al., "Dibromoducitol," *Cancer Treat. Rev.* 6: 191-204 (1979). In particular, dibromodulcitol, as an α, ω-dibrominated hexitol, dibromodulcitol shares many of the biochemical and biological properties of similar drugs such as dibromomannitol and mannitol myleran. Activation of dibromodulcitol to the diepoxide dianhydrogalactitol occurs in vivo, and dianhydrogalactitol may represent a major active form of the drug; this means that dibromogalactitol has many of the properties of a prodrug. Absorption of dibromodulcitol by the oral route is rapid and fairly complete. Dibromodulcitol has known activity in melanoma, breast lymphoma (both Hodgkins and non-Hodgkins), colorectal cancer, acute lymphoblastic leukemia and has been shown to lower the incidence of central nervous system leukemia, non-small cell lung cancer, cervical carcinoma, bladder carcinoma, and metastatic hemangiopericytoma.

(III)

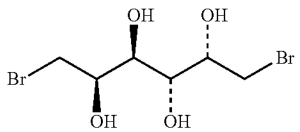

Also within the scope of the invention are derivatives of dibromodulcitol that, for example, have one or more hydrogens of the hydroxyl groups replaced with lower alkyl, or have one or both of the bromo groups replaced with another halo group such as chloro, fluoro, or iodo.

In general, for optional substituents at saturated carbon atoms such as those that are part of the structures of dianhydrogalactitol, derivatives of dianhydrogalactitol, diacetyldianhydrogalactitol, derivatives of diacetyldianhydrogalactitol, dibromodulcitol, and derivatives of dibromodulcitol, the following substituents can be employed: $C_6$-$C_{10}$ aryl, heteroaryl containing 1-4 heteroatoms selected from N, O, and S, $C_1$-$C_{10}$ alkyl, $C_1$-$C_{10}$ alkoxy, cycloalkyl, F, amino ($NR^1R^2$), nitro, —SR, —S(O)R, —$S(O_2)R$, —$S(O_2)NR^1R^2$, and —$CONR^1R^2$, which can in turn be optionally substituted. Further descriptions of potential optional substituents are provided below.

Optional substituents as described above that are within the scope of the present invention do not substantially affect the activity of the derivative or the stability of the derivative, particularly the stability of the derivative in aqueous solution.

Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. Examples of alkyl groups include, but are not limited to, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, and 1-octyl. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl and naphthyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicylic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S.

The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxyheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. The term "heterocycloalkyl" denotes a monocyclic or bicyclic carbocyclic moiety containing from 3 to 10 ring members, interrupted with one or more heteroatoms, which may be identical or different, selected from oxygen, nitrogen or sulfur atoms; for example, morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyran, oxodihydropyridazinyl, or oxetanyl moieties, all of these moieties can be optionally substituted.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C═O), the group takes up two available valences on the carbon atom to which the optional substituent is attached, so the total number of substituents that may be included is reduced according to the number of available valiences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, ═O, —$OZ^b$, —$SZ^b$, ═$S^-$, —$NZ^cZ^c$, ═$NZ^b$, ═N—$OZ^b$, trihalomethyl, —$CF_3$, —CN, —OCN, —SCN, —NO, —$NO_2$, ═$N_2$, —$N_3$, —$S(O)_2Z^b$, —$S(O)_2NZ^b$, —$S(O_2)O^-$, —$S(O_2)OZ^b$, —$OS(O_2)OZ^b$, —$OS(O_2)O$—, —$OS(O_2)OZ^b$, —P(O)(O−$)_2$, —P(O)($OZ^b$)($O^-$), —P(O)($OZ^b$)($OZ^b$), —C(O)$Z^b$, —C(S)$Z^b$, —C($NZ^b$)$Z^b$, —C(O)O—, —C(O)$OZ^b$, —C(S)$OZ^b$, —C(O)$NZ^cZ^c$, —C($NZ^b$)$NZ^cZ^c$, —OC(O)$Z^b$, —OC(S)$Z^b$, —OC(O)$O^-$, —OC(O)$OZ^b$, —OC(S)$OZ^b$, —$NZ^b$C(O)$Z^b$, —$NZ^b$C(S)$Z^b$, —$NZ^b$C(O)O—, —$NZ^b$C(O)$OZ^b$, —$NZ^b$C(S)$OZ^b$, —$NZ^b$C(O)$NZ^cZ^c$, —$NZ^b$C($NZ^b$)$Z^b$, —$NZ^b$C($NZ^b$)$NZ^cZ^c$, wherein $Z^a$ is selected from the group consisting of alkyl, cycloalkyl, heteroalkyl, cycloheteroalkyl, aryl, arylalkyl, heteroaryl and heteroarylalkyl; each $Z^b$ is independently hydrogen or $Z^a$; and each $Z^c$ is independently $Z^b$ or, alternatively, the two $Z^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —$NZ^cZ^c$ is meant to include —$NH_2$, —NH-alkyl, —N-pyrrolidinyl, and —N-morpholinyl, but is not limited to those specific alternatives and includes other alternatives known in the art. Similarly, as another specific example, a substituted alkyl is meant to include—alkylene-O-alkyl, -alkylene-heteroaryl, -alkylene-cycloheteroaryl, -alkylene-C(O)$OZ^b$, -alkylene-C(O)$NZ^bZ^b$, and —$CH_2$—$CH_2$—C(O)—$CH_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —$Z^a$, halo, —$O^-$, —$OZ^b$, —$SZ^b$, —$S^-$, —$NZ^cZ^c$, trihalomethyl, —$CF_3$, —CN, —OCN, —SCN, —NO, —$NO_2$, —$N_3$, —$S(O)_2Z^b$, —$S(O_2)O$—, —$S(O_2)OZ^b$, —$OS(O_2)OZ^b$, —$OS(O_2)O$—, —P(O)($O^-$$)_2$, —P(O)($OZ^b$)($O^-$), —P(O)($OZ^b$)($OZ^b$), —C(O)$Z^b$, —C(S)$Z^b$, —C($NZ^b$)$Z^b$, —C(O)$O^-$, —C(O)$OZ^b$, —C(S)$OZ^b$, —C(O)$NZ^cZ^c$, —C($NZ^b$)$NZ^cZ^c$, —OC(O)$Z^b$, —OC(S)$Z^b$, —OC(O)$O^-$, —OC(O)$OZ^b$, —OC(S)$OZ^b$, —$NZ^b$C(O)$OZ^b$, —$NZ^b$C(S)$OZ^b$, —$NZ^b$C(O)$NZ^cZ^c$, —$NZ^b$C($NZ^b$)$Z^b$, and —$NZ^b$C($NZ^b$)$NZ^cZ^c$, wherein $Z^a$, $Z^b$, and $Z^c$ are as defined above.

Similarly, substituent groups useful for substituting nitrogen atoms in heteroalkyl and cycloheteroalkyl groups include, but are not limited to, —$Z^a$, halo, —O—, —$OZ^b$, —$SZ^b$, —$S^-$, —$NZ^cZ^c$, trihalomethyl, —$CF_3$, —CN, —OCN, —SCN, —NO, —$NO_2$, —$S(O)_2Z^b$, —$S(O_2)O$—, —$S(O_2)OZ^b$, —$OS(O_2)OZ^b$, —$OS(O_2)O$—, —P(O)($O^-$$)_2$, —P(O)($OZ^b$)($O^-$), —P(O)($OZ^b$)($OZ^b$), —C(O)$Z^b$, —C(S)$Z^b$, —C($NZ^b$)$Z^b$, —C(O)$OZ^b$, —C(S)$OZ^b$, —C(O)$NZ^cZ^c$, —C($NZ^b$)$NZ^cZ^c$, —OC(O)$Z^b$, —OC(S)$Z^b$, —OC(O)$OZ^b$, —OC(S)$OZ^b$, —$NZ^b$C(O)$Z^b$, —$NZ^b$C(S)$Z^b$, —$NZ^b$C(O)$OZ^b$, —$NZ^b$C(S)$OZ^b$, —$NZ^b$C(O)$NZ^cZ^c$, —$NZ^b$C($NZ^b$)$Z^b$, and —$NZ^b$C($NZ^b$)$NZ^cZ^c$, wherein $Z^a$, $Z^b$, and $Z^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolyzable esters of the present compounds are the compounds whose carboxyls are present in the form of hydrolyzable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to $-(CH_2)_n-$ where n is 1-8 and preferably n is 1-4, though where specified, an alkylene can also be substituted by other groups, and can be of other lengths, and the open valences need not be at opposite ends of a chain.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to $-NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising at least one heteroatom. The carbocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

As used herein, the term "alkanoyl" refers to an alkyl group covalently linked to a carbonyl (C═O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Alk_2$ and -$Alk_1$-N($Alk_2$)($Alk_3$), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —$S(O)_2$—Ar wherein Ar refers to an aryl group as described above. The term "aryloxyalkylsulfonyl" refers to a group of the structure —$S(O)_2$-Alk-O—Ar, where Alk is an alkyl group as described above and Ar is an aryl group as described above. The term "arylalkylsulfonyl" refers to a group of the structure —$S(O)_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is $CH_3CH_2OC(O)$—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

For the aspects described below relating to improvement in the therapeutic employment of a substituted hexitol derivative, typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol, unless otherwise specified. Preferably, the substituted hexitol derivative is dianhydrogalactitol, unless otherwise specified. In some cases, derivatives of dianhydrogalactitol such as compound analogs or prodrugs are preferred, as stated below.

As used herein, the terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The results of treatment can be determined by methods known in the art, such as determination of reduction of pain as measured by reduction of requirement for administration of opiates or other pain medication, determination of reduction of tumor burden, determination of restoration of function as determined by an improvement in the Karnofsky Performance Score, or other methods known in the art. The use of terms such as "treat" or "treatment" is not to be understood as implying a cure for any disease or condition.

As used herein, the term "synergistic" as used herein refers to a therapeutic combination which is more effective than the additive effects of the two or more single agents. A determination of a synergistic interaction between: (i) dianhydrogalactitol, diacetyldianhydrogalactitol, or a derivative or analog thereof; and (ii) one or more additional chemotherapeutic agents may be assessed using assays as known in the art and can be analyzed using the Chou and Talalay combination method and Dose-Effect Analysis with CalcuSyn software in order to obtain a Combination Index (Chou and Talalay, 1984, Adv. Enzyme Regul. 22:27-55). Combination Index values less than 0.8 indicates synergy, values greater than 1.2 indicate antagonism and values between 0.8 to 1.2 indicate additive effects. The combination therapy may provide "synergy" and prove "synergistic," i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes or using other routes of administration. In general, during alternation therapy, an effective dosage of each active ingredient is administered sequentially, i.e., serially, whereas in combination therapy, effective dosages of two or more active ingredients are administered together. Combination effects can also be evaluated using both the BLISS independence model and the highest single agent (HSA) model (Lehar et al. 2007, Molecular Systems Biology 3:80). BLISS scores quantify degree of potentiation from single agents and a BLISS score>0 suggests greater than simple additivity. In some alternatives, combination effects can be evaluated using both the BLISS independence model and the highest single agent (HSA) model (Lehar et al. 2007, Molecular Systems Biology 3:80). BLISS scores quantify degree of potentiation from single agents and a BLISS score>0 suggests greater than simple additivity. An HSA score>0 suggests a combination effect greater than the maximum of the single agent responses at corresponding concentrations. An HSA score>0 suggests a combination effect greater than the maximum of the single agent responses at corresponding concentrations.

Particular therapeutic combinations according to the present invention include dianhydrogalactitol and temozolomide; dianhydrogalactitol and an inhibitor of Polo-like kinase; dianhydrogalactitol and an agent that reduces the activity or expression of YB-1; dianhydrogalactitol and an inhibitor of Akt; dianhydrogalactitol and an inhibitor of RSK; dianhydrogalactitol and the PARP inhibitor olaparib; dianhydrogalactitol and cisplatin or oxaliplatin; and dianhydrogalactitol and the topoisomerase II inhibitor etoposide. For dianhydrogalactitol and temozolomide, synergy exists when the two agents are administered sequentially, typically by the administration of temozolomide for three days followed by the administration of dianhydrogalactitol for three days, but not when the agents are administered simultaneously. For other alternatives, the agents can be administered simultaneously or sequentially. Other therapeutic combinations are described below.

As further detailed below, treatment of glioblastoma multiforme (GBM) in pediatric patients includes and is particularly directed to treatment of high grade glioma (HGG) in such patients. One aspect of the activity of the methods and compositions of the present invention is the suppression of proliferation of cancer stem cells (CSCs).

Accordingly, one aspect of the present invention is a method to improve the efficacy and/or reduce the side effects of the administration of a substituted hexitol derivative such as dianhydrogalactitol for treatment of malignancies of the central nervous system such as glioblastoma multiforme or medulloblastoma in pediatric patients comprising the steps of:

(1) identifying at least one factor or parameter associated with the efficacy and/or occurrence of side effects of the administration of the substituted hexitol derivative such as dianhydrogalactitol for treatment of malignancies of the central nervous system such as glioblastoma multiforme or medulloblastoma in pediatric patients; and (2) modifying the factor or parameter to improve the efficacy and/or reduce the side effects of the administration of the substituted hexitol derivative such as dianhydrogalactitol for treatment of malignancies of the central nervous system such as glioblastoma multiforme or medulloblastoma in pediatric patients.

Typically, the factor or parameter is selected from the group consisting of:

(1) dose modification;
(2) route of administration;
(3) schedule of administration;
(4) selection of disease stage;
(5) patient selection;
(6) patient/disease phenotype;
(7) patient/disease genotype;
(8) pre/post-treatment preparation
(9) toxicity management;
(10) pharmacokinetic/pharmacodynamic monitoring;
(11) drug combinations;
(12) chemosensitization;
(13) chemopotentiation;
(14) post-treatment patient management;
(15) alternative medicine/therapeutic support;
(16) bulk drug product improvements;
(17) diluent systems;
(18) solvent systems;
(19) excipients;
(20) dosage forms;
(21) dosage kits and packaging;
(22) drug delivery systems;
(23) drug conjugate forms;
(24) compound analogs;
(25) prodrugs;
(26) multiple drug systems;
(27) biotherapeutic enhancement;
(28) biotherapeutic resistance modulation;
(29) radiation therapy enhancement;
(30) novel mechanisms of action;
(31) selective target cell population therapeutics;
(32) use with ionizing radiation;
(33) use with an agent enhancing its activity;
(34) use with an agent that counteracts myelosuppression; and
(35) use with an agent that increases the ability of the substituted hexitol to pass through the blood-brain barrier.

As detailed above, in general, the substituted hexitol derivative usable in methods and compositions according to the present invention include galactitols, substituted galactitols, dulcitols, and substituted dulcitols, including dianhydrogalactitol, diacetyldianhydrogalactitol, dibromodulcitol, and derivatives and analogs thereof. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

When the improvement made by is dose modification, the dose modification can be, but is not limited to, at least one dose modification selected from the group consisting of:

(a) continuous i.v. infusion for hours to days;
(b) biweekly administration;
(c) doses greater than 5 mg/$m^2$/day;
(d) progressive escalation of dosing from 1 mg/$m^2$/day based on patient tolerance;
(e) use of caffeine to modulate metabolism;
(f) use of isoniazid to modulate metabolism;
(g) selected and intermittent boosting of dosage administration;
(h) administration of single and multiple doses escalating from 5 mg/$m^2$/day via bolus;
(i) oral dosages of below 30 mg/$m^2$;
(j) oral dosages of above 130 mg/$m^2$;
(k) oral dosages up to 40 mg/$m^2$ for 3 days and then a nadir/recovery period of 18-21 days;
(l) dosing at a lower level for an extended period (e.g., 21 days);
(m) dosing at a higher level;
(n) dosing with a nadir/recovery period longer than 21 days;
(o) dosing at a level to achieve a concentration of the substituted hexitol derivative such as dianhydrogalactitol in the cerebrospinal fluid (CSF) of equal to or greater than 5 μM;
(p) dosing at a level to achieve a cytotoxic concentration in the CSF;
(q) the use of a substituted hexitol derivative such as dianhydrogalactitol as a single cytotoxic agent;
(r) administration on a 33-day cycle with a cumulative dose of about 9 mg/$m^2$;
(s) administration on a 33-day cycle with a cumulative dose of about 10 mg/$m^2$;
(t) administration on a 33-day cycle with a cumulative dose of about 20 mg/$m^2$;
(u) administration on a 33-day cycle with a cumulative dose of about 40 mg/$m^2$;
(v) administration on a 33-day cycle with a cumulative dose of about 80 mg/$m^2$;
(w) administration on a 33-day cycle with a cumulative dose of about 160 mg/$m^2$;
(x) administration on a 33-day cycle with a cumulative dose of about 240 mg/$m^2$;
(y) administration so that the plasma half-life is about 1-2 hours;
(z) administration so that the $C_{max}$ is <200 ng/ml; and
(aa) administration so that the substituted hexitol derivative has a half-life of >20 hours in the cerebrospinal fluid.

When the improvement is made by route of administration, the route of administration can be, but is not limited to, at least one route of administration selected from the group consisting of:

(a) topical administration;
(b) oral administration;
(c) slow release oral delivery;
(d) intrathecal administration;
(e) intraarterial administration;
(f) continuous infusion;
(g) intermittent infusion;
(h) intravenous administration, such as intravenous administration for 30 minutes;
(i) administration through a longer infusion;
(j) administration through IV push; and
(k) administration to maximize the concentration of the substituted hexitol derivative such as dianhydrogalactitol in the CSF.

When the improvement is made by schedule of administration, the schedule of administration can be, but is not limited to, at least one schedule of administration selected from the group consisting of:

(a) daily administration;
(b) weekly administration;
(c) weekly administration for three weeks;
(d) biweekly administration;
(e) biweekly administration for three weeks with a 1-2 week rest period;
(f) intermittent boost dose administration;
(g) daily administration for one week for multiple weeks; and
(h) administration on days 1, 2, and 3 of a 33-day cycle.

When the improvement is made by selection of disease stage, the selection of disease stage can be, but is not limited to, at least one selection of disease stage selected from the group consisting of:

(a) use in an appropriate disease stage for pediatric GBM, including high grade glioma (HGG), or pediatric medulloblastoma;
(b) use with an angiogenesis inhibitor to prevent or limit metastatic spread;
(c) use for newly diagnosed disease;
(d) use for recurrent disease; and
(e) use for resistant or refractory disease.

When the improvement is made by patient selection, the patient selection can be, but is not limited to, a patient selection carried out by a criterion selected from the group consisting of:

(a) selecting patients with a disease condition characterized by a high level of a metabolic enzyme selected from the group consisting of histone deacetylase and ornithine decarboxylase;
(b) selecting patients with a low or high susceptibility to a condition selected from the group consisting of thrombocytopenia and neutropenia;
(c) selecting patients intolerant of GI toxicities;
(d) selecting patients characterized by over- or under-expression of a gene selected from the group consisting of c-Jun, a GPCR, a signal transduction protein, VEGF, a prostate-specific gene, and a protein kinase.
(e) selecting patients characterized by carrying extra copies of the EGFR gene for pediatric GBM;
(f) selecting patients characterized by mutations in at least one gene selected from the group consisting of TP53, PDGFRA, IDH1, and NF1 for pediatric GBM;
(g) selecting patients characterized by methylation or lack of methylation of the promoter of the MGMT gene;
(h) selecting patients characterized by the existence of an IDH1 mutation;
(i) selecting patients characterized by the presence of IDH1 wild-type gene;

(j) selecting patients characterized by the presence of 1 p/19 q co-deletion;
(k) selecting patients characterized by the absence of an 1 p/19 q co-deletion;
(l) selecting patients characterized by an unmethylated promoter region of MGMT ($O^6$-methylguanine methyltransferase);
(m) selecting patients characterized by a methylated promoter region of MGMT;
(n) selecting patients characterized by a high expression of MGMT;
(o) selecting patients characterized by a low expression of MGMT; and
(p) selecting patients characterized by a mutation in EGFR, including, but not limited to EGFR Variant III.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994). GPCR receptors include, but are not limited to, acetylcholine receptors, P3-adrenergic receptors, $P_3$-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

EGFR mutations can be associated with sensitivity to therapeutic agents such as gefitinib, as described in J. G. Paez et al., "EGFR Mutations in Lung Cancer: Correlation with Clinical Response to Gefitinib," *Science* 304: 1497-1500 (2004). One specific mutation in EGFR that is associated with resistance to tyrosine kinase inhibitors is known as EGFR Variant III, which is described in C. A. Learn et al., "Resistance to Tyrosine Kinase Inhibition by Mutant Epidermal Growth Factor Variant III Contributes to the Neoplastic Phenotype of Glioblastoma Multiforme," *Clin. Cancer Res.* 10: 3216-3224 (2004). EGFR Variant III is characterized by a consistent and tumor-specific in-frame deletion of 801 bp from the extracellular domain that splits a codon and produces a novel glycine at the fusion junction. This mutation encodes a protein with a constituently active thymidine kinase that enhances the tumorigenicity of the cells carrying this mutation. This mutated protein sequence is clonally expressed on a significant proportion of glioblastomas but is absent from normal tissues.

When the improvement is made by analysis of patient or disease phenotype, the analysis of patient or disease phenotype can be, but is not limited to, a method of analysis of patient or disease phenotype carried out by a method selected from the group consisting of:
(a) use of a diagnostic tool, a diagnostic technique, a diagnostic kit, or a diagnostic assay to confirm a patient's particular phenotype;
(b) use of a method for measurement of a marker selected from the group consisting of histone deacetylase, ornithine decarboxylase, VEGF, a protein that is a gene product of jun, and a protein kinase;
(c) surrogate compound dosing; and
(d) low dose pre-testing for enzymatic status.

When the improvement is made by analysis of patient or disease genotype, the analysis of patient or disease genotype can be, but is not limited to, a method of analysis of patient or disease genotype carried out by a method selected from the group consisting of:
(a) use of a diagnostic tool, a diagnostic technique, a diagnostic kit, or a diagnostic assay to confirm a patient's particular genotype;
(b) use of a gene chip;
(c) use of gene expression analysis;
(d) use of single nucleotide polymorphism (SNP) analysis;
(e) measurement of the level of a metabolite or a metabolic enzyme;
(f) determination of mutation of PDGFRA gene;
(g) determination of mutation of IDH1 gene;
(h) determination of mutation of NF1 gene;
(i) determination of copy number of the EGFR gene;
(j) determination of status of methylation of promoter of MGMT gene;
(k) determination of the existence of an IDH1 mutation;
(l) determination of the existence of IDH1 wild-type;
(m) determination of the existence of a 1 p/19 q co-deletion;
(n) determination of the absence of a 1 p/19 q co-deletion;
(o) determination of the existence of an unmethylated promoter region of the MGMT gene;
(p) determination of the existence of a methylated promoter region of the MGMT gene;
(q) determination of the existence of high expression of MGMT; and (r) determination of the existence of low expression of MGMT.

The use of gene chips is described in A. J. Lee & S. Ramaswamy, "DNA Microarrays in Biological Discovery and Patient Care" *in Essentials of Genomic and Personalized Medicine* (G. S. Ginsburg & H. F. Willard, eds., Academic Press, Amsterdam, 2010), ch. 7, pp. 73-88.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation"

*in Essentials of Genomic and Personalized Medicine* (G. S. Ginsburg & H. F. Willard, eds., Academic Press, Amsterdam, 2010), ch. 3, pp. 27-37.

Still other genomic techniques such as copy number variation analysis and analysis of DNA methylation can be employed. Copy number variation analysis is described in C. Lee et al., "Copy Number Variation and Human Health" *in Essentials of Genomic and Personalized Medicine* (G. S. Ginsburg & H. F. Willard, eds., Academic Press, Amsterdam, 2010), ch. 5, pp. 46-59. This is particularly significant for GBM as an increase in copy number of EGFR is associated with particular subtypes of GBM, and may be useful in other malignancies treatable by compositions and methods according to the present invention. DNA methylation analysis is described in S. Cottrell et al., "DNA Methylation Analysis: Providing New Insight into Human Disease" *in Essentials of Genomic and Personalized Medicine* (G. S. Ginsburg & H. F. Willard, eds., Academic Press, Amsterdam, 2010), ch. 6, pp. 60-72. This is particularly significant for GBM in that the prognosis for GBM varies with the degree of methylation of the promoter of the MGMT gene, and may be useful in other malignancies treatable by compositions and methods according to the present invention.

When the improvement is made by pre/post-treatment preparation, the pre/post-treatment preparation can be, but is not limited to, a method of pre/post treatment preparation selected from the group consisting of:

(a) the use of colchicine or an analog thereof;
(b) the use of a diuretic;
(c) the use of a uricosuric;
(d) the use of uricase;
(e) the non-oral use of nicotinamide;
(f) the use of a sustained-release form of nicotinamide;
(g) the use of an inhibitor of poly-ADP ribose polymerase;
(h) the use of caffeine;
(i) the use of leucovorin rescue;
(j) infection control; and
(k) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity. Other diuretics are well known in the art, and include, but are not limited to, hydrochlorothiazide, carbonic anhydrase inhibitors, furosemide, ethacrynic acid, amiloride, and spironolactone.

Poly-ADP ribose polymerase inhibitors are described in G. J. Southan & C. Szabó, "Poly(ADP-Ribose) Inhibitors," *Curr. Med. Chem.* 10: 321-240 (2003), and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

When the improvement is made by toxicity management, the toxicity management can be, but is not limited to, a method of toxicity management selected from the group consisting of:

(a) the use of colchicine or an analog thereof;
(b) the use of a diuretic;
(c) the use of a uricosuric;
(d) the use of uricase;
(e) the non-oral use of nicotinamide;
(f) the use of a sustained-release form of nicotinamide;
(g) the use of an inhibitor of poly-ADP ribose polymerase;
(h) the use of caffeine;
(i) the use of leucovorin rescue;
(j) the use of sustained-release allopurinol;
(k) the non-oral use of allopurinol;
(l) the use of bone marrow transplants;
(m) the use of a blood cell stimulant;
(n) the use of blood or platelet infusions;
(o) the administration of an agent selected from the group consisting of filgrastim, G-CSF, and GM-CSF;
(p) the application of a pain management technique;
(q) the administration of an anti-inflammatory agent;
(r) the administration of fluids;
(s) the administration of a corticosteroid;
(t) the administration of an insulin control medication;
(u) the administration of an antipyretic;
(v) the administration of an anti-nausea treatment;
(w) the administration of an anti-diarrheal treatment;
(x) the administration of N-acetylcysteine; and
(y) the administration of an antihistamine.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" *in Goodman & Gilman's The Pharmacoloqical Basis of Therapeutics* (L. L. Brunton, ed., $11^{th}$ ed., McGraw-Hill, New York, 2006), ch. 59, pp. 1587-1612.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

Poly-ADP ribose polymerase (PARP) inhibitors include, but are not limited to: (1) derivatives of tetracycline as described in U.S. Pat. No. 8,338,477 to Duncan et al.; (2) 3,4-dihydro-5-methyl-1(2H)-isoquinoline, 3-aminobenzamide, 6-aminonicotinamide, and 8-hydroxy-2-methyl-4(3H)-quinazolinone, as described in U.S. Pat. No. 8,324,282 by Gerson et al.; (3) 6-(5H)-phenanthridinone and 1,5-isoquinolinediol, as described in U.S. Pat. No. 8,324,262 by Yuan et al.; (4) (R)-3-[2-(2-hydroxymethylpyrrolidin-1-yl)ethyl]-5-methyl-2H-isoquinolin-1-one, as described in U.S. Pat. No. 8,309,573 to Fujio et al.; (5) 6-alkenyl-substituted 2-quinolinones, 6-phenylalkyl-substituted quinolinones, 6-alkenyl-substituted 2-quinoxalinones, 6-phenylalkyl-substituted 2-quinoxalinones, substituted 6-cyclohexylalkyl substituted 2-quinolinones, 6-cyclohexylalkyl substituted 2-quinoxalinones, substituted pyridones, quinazolinone derivatives, phthalazine derivatives, quinazolinedione derivatives, and substituted 2-alkyl quinazolinone derivatives, as described in U.S. Pat. No. 8,299,256 to Vialard et al.; (6) 5-bromoisoquinoline, as described in U.S. Pat. No. 8,299,088 to Mateucci et al.; (7) 5-bis-(2-chloroethyl)amino]-1-methyl-2-benzimidazolebutyric acid, 4-iodo-3-nitrobenzamide, 8-fluoro-5-(4-((methylamino)methyl)phenyl)-3,4-dihydro-2H-azepino[5,4,3-cd]indol-1(6H)-one phosphoric acid, and N-[3-(3,4-dihydro-4-oxo-1-phthalazinyl)phenyl]-4-morpholinebutanamide methanesulfonate, as described in U.S. Pat. No. 8,227,807 to Gallagher et al.; (8) pyridazinone derivatives, as described in U.S. Pat. No. 8,268,827 to Branca et al.; (9) 4-[3-(4-cyclopropanecarbonyl-piperazine-1-carbonyl)-4-fluorobenzyl]-2H-phthalazin-1-one, as described in U.S. Pat. No. 8,247,416 to Menear et al.; (10) tetraaza phenalen-3-one compounds, as described in U.S. Pat. No. 8,236,802 to Xu et al.; (11) 2-substituted-1H-benzimidazole-4-carboxamides, as described in U.S. Pat. No. 8,217,070 to Zhu et al.; (12) substituted 2-alkyl quinazolinones, as described in U.S. Pat. No. 8,188,103 to Van der Aa et al.; (13) 1H-benzimidazole-4-carboxamides, as described in U.S. Pat. No. 8,183,250 to Penning et al.; (14) indenoisoquinolinone analogs, as described in U.S. Pat. No. 8,119,654 to Jagtap et al.; (15) benzoxazole carboxamides, described in U.S. Pat. No. 8,088,760 to Chu et al; (16) diazabenzo[de]anthracen-3-one compounds, described in U.S. Pat. No. 8,058,075 to Xu et al.; (17) dihydropyridophthalazinones, described in U.S. Pat. No. 8,012,976 to Wang et al., (18) substituted azaindoles, described in U.S. Pat. No. 8,008,491 to Jiang et al.; (19) fused tricyclic compounds, described in U.S. Pat. No. 7,956,064 to Chua et al.; (20) substituted 6a,7,8,9-tetrahydropyrido[3,2-e]pyrrolo[1,2-a]pyrazin-6(5H)-ones, described in U.S. Pat. No. 7,928,105 to Gangloff et al.; and (21) thieno[2,3-c]isoquinolines, described in U.S. Pat. No. 7,825,129. Other PARP inhibitors are known in the art.

When the improvement is made by pharmacokinetic/pharmacodynamic monitoring, the pharmacokinetic/pharmacodynamic monitoring can be, but is not limited to a method selected from the group consisting of:

(a) multiple determinations of blood plasma levels; and (b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

When the improvement is made by drug combination, the drug combination can be, but is not limited to, a drug combination selected from the group consisting of:

(a) use with fraudulent nucleosides;
(b) use with fraudulent nucleotides;
(c) use with thymidylate synthetase inhibitors;
(d) use with signal transduction inhibitors;
(e) use with cisplatin or platinum analogs;
(f) use with alkylating agents;
(g) use with anti-tubulin agents;
(h) use with antimetabolites;
(i) use with berberine;
(j) use with apigenin;
(k) use with colchicine or an analog thereof;
(l) use with genistein;
(m) use with etoposide;
(n) use with cytarabine;
(o) use with camptothecins;
(p) use with vinca alkaloids;
(q) use with topoisomerase inhibitors;
(r) use with 5-fluorouracil;
(s) use with curcumin;
(t) use with NF-κB inhibitors;
(u) use with rosmarinic acid;
(v) use with mitoguazone;
(w) use with meisoindigo;
(x) use with imatinib;
(y) use with dasatinib;
(z) use with nilotinib;
(aa) use with epigenetic modulators;
(ab) use with transcription factor inhibitors;
(ac) use with taxol;
(ad) use with homoharringtonine;
(ae) use with pyridoxal;
(af) use with spirogermanium;
(ag) use with caffeine;
(ah) use with nicotinamide;
(ai) use with methylglyoxalbisguanylhydrazone;
(aj) use with Rho kinase inhibitors;

(ak) use with 1,2,4-benzotriazine oxides;
(al) use with an alkylglycerol;
(am) use with an inhibitor of a Mer, Ax1, or Tyro-3 receptor kinase;
(an) use with an inhibitor of ATR kinase;
(ao) use with a modulator of Fms kinase, Kit kinase, MAP4K4 kinase, TrkA kinase, or TrkB kinase;
(ap) use with endoxifen;
(aq) use with a mTOR inhibitor;
(ar) use with an inhibitor of Mnk1a kinase, Mknl b kinase, Mnk2a kinase, or Mnk2b kinase;
(as) use with a modulator of pyruvate kinase M2;
(at) use with a modulator of phosphoinositide 3-kinases;
(au) use with a cysteine protease inhibitor;
(av) use with phenformin;
(aw) use with Sindbis virus-based vectors;
(ax) use with peptidomimetics that act as mimetics of Smac and inhibit IAPs to promote apoptosis;
(ay) use with a Raf kinase inhibitor;
(az) use with a nuclear transport modulator;
(ba) use with an acid ceramidase inhibitor and a choline kinase inhibitor;
(bb) use with tyrosine kinase inhibitors;
(bc) use with anti-CS1 antibodies;
(bd) use with inhibitors of protein kinase CK2;
(be) use with anti-guanylyl cyclase C (GCC) antibodies;
(bf) use with histone deacetylase inhibitors;
(bg) use with cannabinoids;
(bh) use with glucagon-like peptide-1 (GLP-1) receptor agonists;
(bi) use with inhibitors of Bcl-2 or Bcl-xL;
(bj) use with Stat3 pathway inhibitors;
(bk) use with inhibitors of polo-like kinase 1 (Plk1);
(bl) use with GBPAR1 activators;
(bm) use with modulators of serine-threonine protein kinase and poly(ADP-ribose) polymerase (PARP) activity;
(bn) use with taxanes;
(bo) use with inhibitors of dihydrofolate reductase;
(bp) use with inhibitors of aromatase;
(bq) use with benzimidazole-based anti-neoplastic agents;
(br) use with an O6-methylguanine-DNA-methyltransferase (MGMT) inhibitor;
(bs) use with CCR9 inhibitors;
(bt) use with acid sphingomyelinase inhibitors;
(bu) use with peptidomimetic macrocycles;
(bv) use with cholanic acid amides;
(bw) use with substituted oxazaphosphorines;
(bx) use with anti-TWEAK receptor antibodies;
(by) use with an ErbB3 binding protein;
(bz) use with a glutathione S-transferase-activated antineoplastic compound;
(ca) use with substituted phosphorodiamidates;
(cb) use with inhibitors of MEKK protein kinase;
(cd) use with COX-2 inhibitors;
(ce) use with cimetidine and a cysteine derivative;
(cf) use with anti-IL-6 receptor antibody;
(cg) use with an antioxidant;
(ch) use with an isoxazole inhibitor of tubulin polymerization;
(ci) use with PARP inhibitors;
(cj) use with Aurora protein kinase inhibitors;
(ck) use with peptides binding to prostate-specific membrane antigen;
(cl) use with CD19 binding agents;
(cm) use with benzodiazepines;
(cn) use with Toll-like receptor (TLR) agonists;
(co) use with bridged bicyclic sulfamides;
(cp) use with inhibitors of epidermal growth factor receptor kinase;
(cq) use with a ribonuclease of the T2 family having actin-binding activity;
(cr) use with myrsinoic acid A or an analog thereof;
(cs) use with inhibitors of a cyclin-dependent kinase;
(ct) use with inhibitors of the interaction between p53 and MDM2;
(cu) use with inhibitors of the receptor tyrosine kinase MET;
(cv) use with largazole or largazole analogs;
(cw) use with inhibitors of AKT protein kinase;
(cx) use with 2'-fluoro-5-methyl-β-L-arabinofuranosyluridine or L-deoxythymidine;
(cy) use with HSP90 modulators;
(cz) use with inhibitors of JAK kinases;
(da) use with inhibitors of PDK1 protein kinase;
(db) use with PDE4 inhibitors;
(de) use with inhibitors of proto-oncogene c-Met tyrosine kinase;
(df) use with inhibitors of indoleamine 2,3-dioxygenase;
(dg) use with agents that inhibit expression of ATDC (TRIM29);
(dh) use with proteomimetic inhibitors of the interaction of nuclear receptor with coactivator peptides;
(di) use with antagonists of XIAP family proteins;
(dj) use with tumor-targeted superantigens;
(dk) use with inhibitors of Pim kinases;
(dl) use with inhibitors of CHK1 or CHK2 kinases;
(dm) use with inhibitors of angiopoietin-like 4 protein;
(dn) use with Smo antagonists;
(do) use with nicotinic acetylcholine receptor antagonists;
(dp) use with farnesyl protein transferase inhibitors;
(dq) use with adenosine A3 receptor antagonists;
(dr) use with a cancer vaccine;
(ds) use with a JAK2 inhibitor;
(dt) use with a Src inhibitor;
(du) use with an agent that suppresses growth or replication of glioma or medulloblastoma cancer stem cells;
(dv) use with an agent that reduces the activity or expression of YB-1;
(dw) use with an inhibitor of Akt;
(dx) use with an inhibitor of RSK; and
(dy) use with an inhibitor of a Polo-like kinase.

Topoisomerase inhibitors include, but are not limited to, irinotecan, topotecan, camptothecin, lamellarin D, amsacrine, etoposide, etoposide phosphate, teniposide, doxorubicin, and 4-[2-(3,5-dioxo-1-piperazinyl)-1-methylpropyl] piperazine-2,6-dione (ICRF-193).

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003).

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga Calif.-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Colchicine is a tricyclic alkaloid that exerts its activity by binding to the protein tubulin. Analogs of colchicine include, but are not limited to, colchiceinamide, N-desacetylthiocolchicine, demecolcine, N-acetyliodocolchinol, trimethylcolchicinic acid (TMCA) methyl ether, N-acetylcolchinol, TMCA ethyl ether, isocolchicine, isocolchiceinamide, iso-TMCA methyl ether, colchiceine, TMCA, N-benzoyl TMCA, colchicosamide, colchicoside, colchinol and colchinoic acid (M. H. Zweig & C. F. Chignell, "Interaction of Some Colchicine Analogs, Vinblastine and Podophyllotoxin with Rat Brain Microtubule Protein," Biochem. *Pharmacol.* 22: 2141-2150 (1973) and B. Yang et al., "Syntheses and Biological Evaluation of Ring C-Modified Colchicine Analogs," *Bioorg. Med. Chem. Lett.* 20: 3831-3833 (2010)).

Genistein is an isoflavone with the systemic name 5,7-dihydroxy-3-(4-hydroxyphenyl)chromen-4-one. Genistein has a number of biological activities, including activation of PPARs, inhibition of several tyrosine kinases, inhibition of topoisomerase, antioxidative activity, activation of Nrf2 antioxidative response, activation of estrogen receptor beta, and inhibition of the mammalian hexose transporter GLUT2.

Etoposide is an anticancer agent that acts primarily as a topoisomerase II inhibitor. Etoposide forms a ternary complex with DNA and the topoisomerase II enzyme, prevents re-ligation of the DNA strands and thus induces DNA strand breakage and promotes apoptosis of the cancer cells.

Cytarabine is a nucleoside analog replacing the ribose with arabinose. It can be incorporated into DNA and also inhibits both DNA and RNA polymerases and nucleotide reductase. It is particularly useful in the treatment of acute myeloid leukemia and acute lymphocytic leukemia, but can be used for other malignancies and in various drug combinations.

Camptothecins include camptothecin, homocamptothecin, topotecan, irinotecan, DB 67, BNP 1350, exatecan, lurtotecan, ST 1481, and CKD 602. These compounds act as topoisomerase I inhibitors and block DNA synthesis in cancer cells.

Vinca alkaloids include vinblastine, vincristine, vindesine, and vinorelbine.

Topoisomerase inhibitors include topoisomerase I inhibitors and topoisomerase II inhibitors. Topoisomerase I inhibitors include the camptothecins and lamellarin D. Topoisomerase II inhibitors include, in addition to amonafide and derivatives and analogs thereof, etoposide, teniposide, doxorubicin, daunorubicin, mitoxantrone, amsacrine, ellipticines, and aurintricarboxylic acid. A number of plant-derived naturally-occurring phenolic compounds, such as genistein, quercetin, and resveratrol, exhibit inhibitory activity toward both topoisomerase I and topoisomerase II.

The compound 5-fluorouracil is a base analog that acts as a thymidylate synthase inhibitor and thereby inhibits DNA synthesis. When deprived of a sufficient supply of thymidine, rapidly dividing cancer cells die by a process known as thymineless death.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Meisoindigo is active via several, possibly novel mechanisms of action. It has cell cycle specific effects, including arrest in G(O)/G1 for AML cell lines and G2/M arrest for HT-29 colorectal cell lines. It also stimulates apoptosis through a number of mechanisms, including the upregulation of p21 and p27 and the downregulation of Bcl-2 in primary AML cells, as well as upregulation of Bak and Bax in AML cells (DKO insensitive to chemotherapy), and a novel caspase-dependent pathway in K562 cells. Meisoindigo also has effects on mitochondria, but with no change in Bcl-2, Bax, and Bid protein expression. Meisoindigo also stimulates the cleavage of pro-caspase 3, 8, 9 and PARP in HL-60 myeloid cells. Meisoindigo also is directed to multiple cellular targets, which are possibly synergistic and complementary. For example, it promotes differentiation of human myeloblastic leukemic cells, accompanied by down-regulation of c-myb gene expression. It also promotes inhibition of DNA and RNA synthesis in W256 cells, microtubule assembly, glycogen synthase kinase-3β (GSK-3β) (at 5-50 nM), CDK1/cyclin B, and CDK5/p25 (tau microtubule protein phosphorylation). Additionally, meisoindigo decreases β-catenin and c-myc (HL-60 cells, but not in K562), affects the Wnt pathway through inhibiting GSK-3β and downregulating β-catenin and c-myc protein expression. Meisoindigo also promotes upregulation of CD11b, promoting myeloid differentiation, and upregulation of Ahi-1 in Jurkat cells (inducing phosphorylation of c-Myb). Furthermore, meisoindigo exhibits antiangiogenic effects, including decreased VEGF protection, VCAM-1, tubule formulation in HUVEC, and ECV304 apoptosis.

Imatinib is an inhibitor of the receptor tyrosine kinase enzyme ABL and is used to treat chronic myelogenous leukemia, gastrointestinal stromal tumors, and other hyperproliferative disorders.

Dasatinib is an inhibitor of BCR/ABL and Src family tyrosine kinases and is used to treat chronic myelogenous leukemia and acute lymphoblastic leukemia.

Nilotinib is another tyrosine kinase inhibitor approved for the treatment of chronic myelogenous leukemia; it inhibits the kinases BCR/ABL, KIT, LCK, EPHA3, and a number of other kinases. The use of nilotinib is described in United States Patent Application Publication No. 2011/0028422 by Aloyz et al.

Epigenetic modulators include polyamine-based epigenetic modulators, such as the polyamine-based epigenetic modulators described in S. K. Sharma et al., "Polyamine-Based Small Molecule Epigenetic Modulators," *Med. Chem. Commun.* 3: 14-21 (2012), and L. G. Wang & J. W. Chiao, "Prostate Cancer Chemopreventive Activity of Phenethyl Isothiocyanate Through Epigenetic Regulation (Review), *Int. J. Oncol.* 37: 533-539 (2010).

Transcription factor inhibitors include 1-(4-hexaphenyl)-2-propane-1-one, 3-fluoro-4-[[2-hydroxy-2-(5,5,8,8-tetramethyl-5,6,7,8,-tetrahydro-2-naphthalenyl)acetyl]amino]-benzoic acid (BMS 961), 4-[5-[8-(1-methylethyl)-4-phenyl-2-quinolinyl]-1H-pyrrolo-2-benzoic acid (ER-50891), 7-ethenyl-2-(3-fluoro-4-hydroxyphenyl)-5-benzoxazolol (ERB 041), and other compounds. Trascription factor inhibitors are described in T. Berg, "Inhibition of Transcription Factors with Small Organic Molecules," *Curr. Opin. Chem. Biol.* 12: 464-471 (2008).

Tetrandrine has the chemical structure 6,6',7,12-tetramethoxy-2,2'-dimethyl-1 β-berbaman and is a calcium channel blocker that has anti-inflammatory, immunologic, and antiallergenic effects, as well as an anti-arrhythmic effect similar to that of quinidine. It has been isolated from *Stephania tetranda* and other Asian herbs.

VEGF inhibitors include bevacizumab (Avastin), which is a monoclonal antibody against VEGF, itraconazole, and suramin, as well as batimastat and marimastat, which are matrix metalloproteinase inhibitors, and cannabinoids and derivatives thereof.

Cancer vaccines are being developed. Typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, "Cancer Vaccines: Accomplishments and Challenges," *Crit. Rev. Oncol. Hematol.* 67: 93-102 (2008).

The use of methylglyoxalbisguanylhydrazone in cancer therapy has been described in D. D. Von Hoff, "MGBG: Teaching an Old Drug New Tricks," *Ann. Oncol.* 5: 487-493 (1994).

The use of Rho kinase inhibitors, such as (R)-(+)-N-(4-pyridyl)-4-(1-aminoethyl)benzamide, ethacrynic acid, 4-[2 (2,3,4,5,6-pentafluorophenyl)acryloyl]cinnamic acid, (+)-trans-4-(1-aminoethyl)-1-(4-pyridylcarbamoyl) cyclohexane, (+)-10 trans-N-(1H-pyrrolo[2,3-b]pyridin-4-yl)-4-(1-aminoethyl)cyclohexanecarboxamide, and (R)-(+)-N-(1H-pyrrolo[2,3-b]pyridin-4-yl)-4-(1-aminoethyl) benzamide, as described in U.S. Pat. No. 6,930,115 to Fujii et al.

The use of 1,2,4-benzotriazine oxides, such as 3-hydroxy-1,2,4-benzotriazine 1,4-dioxide, 3-amino-7-trifluoromethyl-1,2,4-benzotriazine 1-oxide, 3-amino-7-carbamyl-1,2,4-benzotriazine 1-oxide, 7-acetyl-3-amino-1,2,4-benzotriazine 1-oxide oxime, 3-amino-6(7)decyl-1,2,4-benzotriazine 1,4-dioxide, 1,2,4-benzotriazine dioxide, 7-chloro-3-hydroxy-1,2,4-benzotriazine 1,4-dioxide, 7-nitro-3-amino-1,2,4-benzotriazine 1,4-dioxide, 3-(3-N,N-diethylaminopropylamino)-1,2,4-benzotriazine 1,4-dioxide, 7-nitro-3-(2-N,N-diethylaminoethylamino)-1,2,4-benzotriazine 1,4-dioxide, 7-allyloxy-1,2,4-benzotriazine 1,4-dioxide, 7-(3-N-ethylacetamido-2-acetoxypropoxy) 1,2,4-benzotriazine 1,4-dioxide, 7-nitro-1,2,4-benzotriazine 1,4-dioxide. 3-propyl-1,2,4-benzotriazine 1,4-dioxide, and 3-(1-hydroxyethyl)-1,2,4-benzotriazine 1,4-dioxide, as described in U.S. Pat. No. 6,277,835 by Brown.

The use of alkylglycerols is described in U.S. Pat. No. 6,121,245 to Firshein.

The use of inhibitors of Mer, Ax1, or Tyro-3 receptor tyrosine kinase is described in United States Patent Application Publication No. 2012/0230991 by Graham et al. These inhibitors can be antibodies, including monoclonal antibodies, or fusion proteins.

The use of inhibitors of ATR kinase is described in United States Patent Application Publication No. 2012/0177748 by Charrier et al. These inhibitors of ATR kinase are substituted pyridine compounds such as 2-amino-N-phenyl-5-(3-pyridyl)pyridine-3-carboxamide, 5-(4-(methylsulfonyl)phenyl-3-(5-phenyl-1,3,4-oxadiazol-2-yl)pyridine-2-amine, and 5-(1-ethylsulfonyl-3,6-dihydro-2H-pyridin-4-yl)-3-(5-phenyl-1,3,4-oxadiazol-2-yl)pyridine-2-amine.

The use of compounds that modulate the activity of one or more of Fms kinase, Kit kinase, MAP4K4 kinase, TrkA kinase, or TrkB kinase is described in United States Patent Application Publication No. 2012/0165329 by Ibrahim et al. These compounds include (6-methoxy-pyridin-3-ylmethyl) [5-(7H-pyrrolo[2,3-d]pyrimidin-5-ylmethyl)-pyrimidin-2-yl]-amine, (5-fluoro-2-methoxy-pyridin-3-ylmethyl)-[5-(7H-pyrrolo[2,3-d]pyrimidin-5-ylmethyl)-pyrimidin-2-y]-amine, and (5-fluoro-6-methoxy-pyridin-3-ylmethyl)-[5-(7H-pyrrolo[2,3-d]pyrimidin-5-ylmethyl)-pyrimidin-2-yl]-amine. Compounds that inhibit Trk kinases, particularly TrkA, are described in United States Patent Application Publication No. 2011/0301133 by Wu et al.

The use of endoxifen is described in United States Patent Application Publication No. 2012/0164075 by Ahmad et al.

The use of a mTOR inhibitor is described in United States Patent Application Publication No. 2012/0129881 by Burke et al. Suitable mTOR inhibitors include, but are not limited to, 40-O-(2-hydroxyethyl)rapamycin. These mTOR inhibitors can be used together with Raf kinase inhibitors, as described in United States Patent Application Publication No. 2011/0301184 by Lane. Raf kinase inhibitors are also described in United States Patent Application Publication No. 2010/0286178 by Ibrahim et al.; these compounds include, but are not limited to, propane-1-sulfonic acid {2,4-difluoro-3-[5-(2-methoxy-pyrimidin-5-yl)-1H-pyrrolo [2,3-b]pyridine-3-carbonyl]-phenyl}-amide, propane-1-sulfonic acid [3-(5-cyano-1H-pyrrolo[2,3-b]pyridine-3-carbonyl)-2,4-difluoro-phenyl]-amide, propane-1-sulfonic acid

[3-(5-cyano-1H-pyrrolo[2,3-b]pyridine-3-carbonyl)-2-fluoro-phenyl]-amide, N-[3-(5-cyano-1H-pyrrolo[2,3-b]pyridine-3-carbonyl)-2,4-difluoro-phenyl]-2,5-difluoro-benzenesulfonamide, N-[3-(5-cyano-1H-pyrrolo[2,3-b]pyridine-3-carbonyl)-2,4-difluoro-phenyl]-3-fluoro-benzenesulfonamide, pyrrolidine-1-sulfonic acid [3-(5-cyano-1H-pyrrolo[2,3-b]pyridine-3-carbonyl)-2,4-difluoro-phenyl]-amide, and N,N-dimethylamino-sulfonic acid [3-(5-cyano-1H-pyrrolo[2,3-b]pyridine-3-carbonyl)-2,4-difluoro-phenyl]-amide. These mTOR inhibitors can also be used together with compounds that elevate pAkt levels in malignant cells, as described in United States Patent Application Publication No. 2009/0274698 by Bhagwat et al. A number of compounds that elevate pAkt levels are described, including chemotherapeutic agents, analogs of rapamycin, and other agents. The use of mTOR inhibitors is also described in U.S. Pat. No. 8,268,819 to Jin et al.; these mTOR inhibitors are hexahydrooxazinopterine compounds.

The use of an inhibitor of Mnk1a kinase, Mnk1b kinase, Mnk2a kinase, or Mnk2b kinase is described in United States Patent Application Publication No. 2012/0128686 by Austen et al. These compounds include thienopyrimidines. Additional thienopyrimidine inhibitors of one or more of these kinases are described in United States Patent Application Publication No. 2011/0212103 by Heckel et al. and in United States Patent Application Publication No. 2011/0212102 by Lehmann-Lintz et al.

The use of a modulator of pyruvate kinase M2 is described in United States Patent Application Publication 2012/0122885 by Salituro et al. Suitable modulators of pyruvate kinase M2 include, but are not limited to, 1-(3-chloro-5-(trifluoromethyl)pyridin-2-yl)-N-(3,5-dimethylphenyl)-1H-imidazole-5-sulfonamide; 1-(3-chloro-5-(trifluoromethyl)pyridin-2-yl)-N-(5-methoxyphenyl)-1H-imidazole-5-sulfonamide; and N-(4-methoxyphenyl)-1-(5-(trifluoromethyl)pyridine-2-yl)-H-imidazole-5-sulfonamide.

The use of a modulator of a phosphoinositide 3-kinase is described in United States Patent Application Publication No. 2012/0122838 by Ren et al. Inhibitors of phosphoinositide 3-kinase are also described in United States Patent Application Publication No. 2010/0209420 by Lamb et al. and in United States Patent Application Publication No. 2009/0209340 by Buhr et al.; these inhibitors include pyridopyrimidones. Inhibitors of phosphoinositide 3-kinase are also described in U.S. Pat. No. 8,242,104 to Blaquiere et al.; these inhibitors include benzoxazepines. Inhibitors of phosphoinositide 3-kinase are also described in U.S. Pat. No. 8,193,182 to Ren et al.; these inhibitors include isoquinolin-1(2H)-ones. Inhibitors of phosphoinositide 3-kinase are also described in U.S. Pat. No. 7,928,428 to Do et al.; these inhibitors include benzopyrans and benzoxepines.

The use of a cysteine protease inhibitor is described in United States Patent Application Publication No. 2012/0114765 by Cao et al. Suitable cysteine protease inhibitors include, but are not limited to, 1-[5-(2,4-dichlorophenylsulfanyl)-4-nitro-2-thienyl]ethanone, 1-[5-(2,4-difluorophenylsulfanyl)-4-nitro-2-thienyl]ethanone, and 1-{4-nitro-5-[2-(trifluoromethyl)phenylsulfanyl]-2-thienyl}ethanone.

The use of phenformin is described in United States Patent Application Publication No. 2012/0114676 by Thompson et al.

The use of Sindbis-based virus vectors is described in United States Patent Application Publication No. 2011/0318430 by Meruelo et al. These vectors are capable of binding to solid tumors that express higher levels of high affinity laminin receptors.

The use of peptidomimetics that act as mimetics of Smac and inhibit IAPs to promote apoptosis is described in United States Patent Application Publication No. 2011/0305777 by Condon et al.

The use of nuclear transport modulators, especially inhibitors of Crm1, is described in United States Patent Application Publication No. 2011/0275607 by Shacham et al. These inhibitors of Crm1 include, but are not limited to, (Z)-3-[3-(3-chlorophenyl)[1,2,4]-triazol-1-yl]-acrylic acid ethyl ester, (E)-3-[3-(3-chlorophenyl)[1,2,4]-triazol-1-yl]-acrylic acid ethyl ester, (Z)-3-[3-(3-chlorophenyl)-[1,2,4]-triazol-1-yl]-acrylic acid isopropyl ester, (E)-3-[3-(3-chlorophenyl)-[1,2,4]-triazol-1-yl]-acrylic acid isopropyl ester, (Z)-3-[3-(3-chlorophenyl)-[1,2,4]-triazol-1-yl]-acrylic acid t-butyl ester, (Z)-3-[3-(3-chlorophenyl)-[1,2,4]-triazol-1-yl]-acrylic acid t-butyl ester, (E)-3-[3-(3-chlorophenyl)-[1,2,4]-triazol-1-yl]-N-phenyl-acrylamide, (E)-N-(2-chlorophenyl)-3-[3-(3-chlorophenyl)-[1,2,4]-triazol-1-yl]-acrylamide, (4-{(E)-3-[3-(3-chlorophenyl)[1,2,4]-triazol-1-yl]-acryloylamino}-phenyl)-carbamic acid t-butyl ester, (E)-3-[3-(3-chlorophenyl)-[1,2,4]-triazol-1-yl]-N-(4-methoxyphenyl)-acrylamide, (E)-3-[3-(3-chlorophenyl)-[1,2,4]-triazol-1-yl]-N-methyl-N-phenyl-acrylamide, and (E)-N-(4-aminophenyl)-3-[3-(3-chlorophenyl)-[1,2,4]-triazol-1-yl]-acrylamide.

The epidermal growth factor receptor (EGFR) exists on the cell surface of mammalian cells and is activated by binding of the receptor to its specific ligands, including, but not limited to epidermal growth factor and transforming growth factor α. Upon activation by binding to its growth factor ligands, EGFR undergoes a transition from an inactive monomeric form to an active homodimer, although preformed active dimers may exist before ligand binding. In addition to forming active homodimers after ligand binding, EGFR may pair with another member of the ErbB receptor family, such as ErbB2/Her2/neu, to create an activated heterodimer. There is also evidence that clusters of activated EGFRs form, although it is uncertain whether such clustering is important for activation itself or occurs subsequent to activation of individual dimers. EGFR dimerization stimulates its intracellular intrinsic protein-tyrosine kinase activity. As a result, autophosphorylation of several tyrosine residues in the carboxyl-terminal domain of EGFR occurs. These residues include Y992, Y1045, Y1068, Y1148, and Y1171. Such autophosphorylation elicits downstream activation and signaling by several other proteins that associate with the phosphorylated tyrosine residues through their own phosphotyrosine-binding SH2 domains. The signaling of these proteins that associate with the phosphorylated tyrosine residues through their own phosphotyrosine-binding SH2 domains can then initiate several signal transduction cascades and lead to DNA synthesis and cell proliferation. The kinase domain of EGFR can also cross-phosphorylate tyrosine residues of other receptors that it is aggregated with, and can itself be activated in that manner. EGFR is encoded by the c-erbB1 proto-oncogene and has a molecular mass of 170 kDa. It is a transmembrane glycoprotein with a cysteine-rich extracellular region, an intracellular domain containing an uninterrupted tyrosine kinase site, and multiple autophosphorylation sites clustered at the carboxyl-terminal tail as described above. The extracellular portion has been subdivided into four domains: domains I and III, which have 37% sequence identity, are cysteine-poor and conformationally contain the site for ligand (EGF and transforming growing factor α (TGFα) binding. Cysteine-rich domains II and IV contain N-linked glycosylation sites and disulfide bonds, which determine the tertiary conformation of the external domain of the protein molecule. In many human cell lines, TGFα expression has a strong correlation with EGFR overexpression, and therefore TGFα was considered to act in an autocrine manner, stimulating proliferation of the cells in which it is produced via activation of EGFR. Binding of a stimulatory ligand to the EGFR extracellular domain results in receptor dimerization and initiation of intracellular signal transduction, the first step of which is activation of the tyrosine kinase. The earliest consequence of kinase activation is the phosphorylation of its own tyrosine residues (autophosphorylation) as described above. This is followed by association with activation of signal transducers leading to mitogenesis. Mutations that lead to EGFR expression or overactivity have been associated with a number of malignancies, including glioblastoma multiforme. A specific mutation of EGFR known as EGFR Variant III has frequently been observed in glioblastoma (C. T. Kuan et al., "EGF Mutant Receptor VIII as a Molecular Target in Cancer Therapy," *Endocr. Relat. Cancer* 8: 83-96 (2001)). EGFR is considered an oncogene. Inhibitors of EGFR include, but are not limited to, erlotinib, gefitinib, lapatinib, lapatinib ditosylate, afatinib, canertinib, neratinib, CP-724714, WHI-P154, TAK-285, AST-1306, ARRY-334543, ARRY-380, AG-1478, tyrphostin 9, dacomitinib, desmethylerlotinib, OSI-420, AZD8931, AEE788, pelitinib, CUDC-101, WZ8040, WZ4002, WZ3146, AG-490, XL647, PD153035 HCl, BMS-599626, BIBW 2992, CI 1033, CP 724714, OSI 420, and vandetinib. Particularly preferred EGFR inhibitors include erlotinib, afatinib, and lapatinib.

The use of tyrosine kinase inhibitors is described in United States Patent Application Publication No. 2011/0206661 by Zhang et al., which is directed to trimethoxyphenyl inhibitors of tyrosine kinase, and in United States Patent Application Publication No. 2011/0195066, which is directed to quinoline inhibitors of tyrosine kinase. The use of tyrosine kinase inhibitors is also described in United States Patent Application Publication No. 2011/053968 by Zhang et al., which is directed to aminopyridine inhibitors of tyrosine kinase. The use of tyrosine kinase inhibitors is also described in United States Patent Application Publication No. 2010/0291025 by Rao et al., which is directed to indazole inhibitors of tyrosine kinase. The use of tyrosine kinase inhibitors is also described in United States Patent Application Publication No. 2010/0190749 by Ren et al.; these tyrosine kinase inhibitors are benzoxazole compounds; compounds of this class can also inhibit mTOR and lipid kinases such as phosphoinositide 3-kinases. The use of tyrosine kinase inhibitors is also described in U.S. Pat. No. 8,242,270 by Lajeunesse et al.; these tyrosine kinase inhibitors are 2-aminothiazole-5-aromatic carboxamides.

The use of an acid ceramidase inhibitor and a choline kinase inhibitor is described in United States Patent Application Publication No. 2011/0256241 by Ramirez de Molina et al.

The use of anti-CS1 antibodies is described in United States Patent Application Publication No. 2011/0165154 by Afar.

The use of protein kinase CK2 inhibitors is described in United States Patent Application Publication No. 2011/0152240 by Haddach et al. These protein kinase CK2 inhibitors include pyrazolopyrimidines. Additional protein kinase CK2 inhibitors, including tricyclic compounds, are described in United States Patent Application Publication No. 2011/0071136 by Haddach et al.; these protein kinase CK2 inhibitors may also inhibit Pim kinases or other kinases. Additional protein kinase CK2 inhibitors, including heterocycle-substituted lactams, are also described in United States Patent Application Publication No. 2011/0071115 by Haddach et al.; these protein kinase CK2 inhibitors may also inhibit Pim kinases or other kinases.

The use of anti-guanylyl cyclase C (GCC) antibodies is described in United States Patent Application Publication No. 2011/0110936 by Nam et al.

The use of histone deacetylase inhibitors is described in United States Patent Application Publication No. 2011/0105474 by Thaler et al. These histone deacetylase inhibitors include, but are not limited to, (E)-N-hydroxy-3-{4-[(E)-3-(4-methyl-piperazin-1-yl)-3-oxo-propenyl]-phenyl}-acrylamide; (E)-N-hydroxy-3-{3-[(E)-3-(4-methyl-piperazin-1-yl)-3-oxo-propenyl]-phenyl}-acrylamide; (E)-N-hydroxy-3-{3-[(E)-3-oxo-3-(4-phenyl-piperazin-1-yl)-propenyl]-phenyl}-acrylamide; (E)-3-[3-((E)-3-[1,4']bipiperidinyl-1'-yl-3-oxo-propenyl)-phenyl]-N-hydroxy-acrylamide; (E)-N-hydroxy-3-{3-[(E)-3-oxo-3-(cis-3,4,5-trimethyl-piperazin-1-yl)-propenyl]-phenyl}-acrylamide; (E)-3-{3-[(E)-3-((1S,4S)-5-methyl-2,5-diaza-bicyclo[2.2.1]hept-2-yl)-3-oxo-propenyl]-phenyl}-N-hydroxy-acrylamide; (E)-N-hydroxy-3-{4-[(E)-3-oxo-3-(4-phenyl-piperazin-1-yl)-propenyl]-phenyl}-acrylamide; (E)-3-[4-((E)-3-[1,4']bipiperidinyl-1'-yl-3-oxo-propenyl)-phenyl]-N-hydroxy-acrylamide; (E)-N-hydroxy-3-{4-[(E)-3-oxo-3-(cis-3,4,5-trimethyl-piperazin-1-yl)-propenyl]-phenyl}-acrylamide; (E)-N-hydroxy-3-{4-[(E)-3-oxo-3-((1S,4S)-5-methyl-2,5-diaza-bicyclo[2.2.1]hept-2-yl)-propenyl]-phenyl}-acrylamide; (E)-N-hydroxy-3-{5-[(E)-3-oxo-3-(4-phenyl-piperazin-1-yl)-propenyl]-pyridin-2-yl}-acrylamide; (E)-N-hydroxy-3-{5-[(E)-3-(4-methyl-piperazin-1-yl)-3-oxo-propenyl]-pyridin-2-yl}-acrylamide; (E)-N-hydroxy-3-{6-[(E)-3-oxo-3-(4-phenyl-piperazin-1-yl)-propenyl]-pyridin-2-yl}-acrylamide; (E)-N-hydroxy-3-{6-[(E)-3-(4-methyl-piperazin-1-yl)-3-oxo-propenyl]-pyridin-2-yl}-acrylamide; (E)-3-(6-{(E)-3-[4-(3-chloro-phenyl)-piperazin-1-yl]-3-oxo-propenyl}-pyridin-2-yl)-N-hydroxy-acrylamide; (E)-3-{6-[(E)-3-(4-benzoyl-piperazin-1-yl)-3-oxo-propenyl]-pyridin-2-yl}-N-hydroxy-acrylamide hydrochloride; (E)-3-(6-{(E)-3-[4-(2-chloro-phenyl)-piperazin-1-yl]-3-oxo-propenyl}-pyridin-2-yl)-N-hydroxy-acrylamide hydrochloride; (E)-N-hydroxy-3-{6-[(E)-3-oxo-3-(4-phenyl-piperidin-1-yl)-propenyl]-pyridin-2-yl}-acrylamide hydrochloride; (E)-N-hydroxy-3-{6-[(E)-3-oxo-3-(4-pyrimidin-2-yl-piperazin-1-yl)-propenyl]-pyridin-2-yl}-acrylamide hydrochloride; (E)-3-(6-{(E)-3-[4-(4-chloro-phenyl)-piperazin-1-yl]-3-oxo-propenyl}-pyridin-2-yl)-N-hydroxy-acrylamide hydrochloride; and (E)-3-{6-[(E)-3-(4-benzyl-piperazin-1-yl)-3-oxo-propenyl]-pyridin-2-yl}-N-hydroxy-acrylamide hydrochloride. Additional histone deacetylase inhibitors, including spirocyclic derivatives, are described in United States Patent Application Publication No. 2011/039840 by Varasi et al. Prodrugs of histone deacetylase inhibitors are described in U.S. Pat. No. 8,227,636 to Miller et al. Histone deacetylase inhibitors are described in U.S. Pat. No. 8,222,451 to Kozikowski et al. Histone deacetylase inhibitors, including disubstituted aniline compounds, are also described in U.S. Pat. No. 8,119,685 to Heidebrecht et al. Histone deacetylase inhibitors, including aryl-fused spirocyclic compounds, are also described in U.S. Pat. No. 8,119,852 to Hamblett et al.

The use of cannabinoids is disclosed in United States Patent Application Publication No. 2011/0086113 by Velasco Diez et al. Suitable cannabinoids include, but are not limited to, tetrahydrocannabinol and cannabidiol.

The use of glucagon-like peptide-1 (GLP-1) receptor agonists is described in United States Patent Application Publication No. 2011/0046071 by Karasik et al. A suitable GLP-1 receptor agonist is exendin-4.

The use of inhibitors of anti-apoptotic proteins Bcl-2 or Bcl-xL is described in United States Patent Application Publication No. 2011/0021440 by Martin et al.

The use of Stat3 pathway inhibitors is described in United States Patent Application Publication No. 2010/0310503 by Li et al. These Stat3 pathway inhibitors include, but are not limited to, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, and 2-ethyl-naphtho[2,3-b]furan-4,9-dione.

The use of inhibitors of polo-like kinase 1 (Plk1) is described in United States Patent Application Publication No. 2010/0278833 by Stengel et al. These inhibitors include, but are not limited to, thiophene-imidazopyridines, including, but not limited to, 5-(6-chloro-1H-imidazo[4,5-c]pyridin-1-yl)-3-{[2-(trifluoromethyl)benzyl]oxy}thiophene-2-carboxamide, 5-(1H-imidazo[4,5-c]pyridin-1-yl)-3-{[2-(trifluoromethyl)benzyl]oxy}thiophene-2-carboxamide, 5-(3H-imidazo[4,5-c]pyridin-3-yl)-3-{[2-(trifluoromethyl)benzyl]oxy}thiophene-2-carboxamide, 1-(5-carbamoyl-4-{[2-(trifluoromethyl)benzyl]oxy}-2-thienyl)-N-(2-m ethoxyethyl)-1H-imidazo[4,5-c]pyridine-6-carboxamide, 1-(5-carbamoyl-4-{[2-(trifluoromethyl)benzyl]oxy}-2-thienyl)-N-(2-morpholin-4-ylethyl)-1H-imidazo[4,5-c]pyridine-6-carboxamide, 5-{6-[diethylamino)methyl]-1H-imidazo[4,5-c]pyridin-1-yl}-3-{[2-(trifluoromethyl)benzyl]oxy}thiophene-2-carboxamide, 5-{6-[(cyclopropylamino)methyl]-1H-imidazo[4,5-c]pyridin-1-yl}-3-{[2-(trifluoromethyl)benzyl]oxy}thiophene-2-carboxamide, 5-{6-[(4-methylpiperazin-1-yl)methyl]-1H-imidazo[4,5-c]pyridin-1-yl}-3-{[2-(trifluoromethyl)benzyl]oxy}thiophene-2-carboxamide, and 5-[6-(hydroxymethyl)-1H-imidazo[4,5-c]pyridin-1-yl]-3-{[2-(trifluoromethyl)benzyl]oxy}thiophene-2-carboxamide.

The use of GBPAR1 activators is described in United States Patent Application Publication No. 2010/0261758 by Arista et al. These GBPAR1 activators include, but are not limited to, heterocyclic amides. These compounds include, but are not limited to, N-(3,5-dichlorophenyl)-3-methyl-N-naphthalen-2-ylmethyl-isonicotinamide, (3,5-dichlorophenyl)-N-(2-methoxybenzyl)-3-methyl-isonicotinamide, 3-methyl-N-phenyl-N-pyridin-3-ylmethyl-isonicotinamide, N-naphthalen-2-ylmethyl-1-oxy-N-phenyl-isonicotinamide, N-(3,5-dichlorophenyl)-3-methyl-N-(2-trifluoromethoxybenzyl)-isonicotinamide, 4-methyl-oxazole-5-carboxylic acid benzyl-phenylamide, N-benzyl-N-phenylisonicotinamide, N-benzyl-N-p-tolylisonicotinamide, N-benzyl-2-fluoro-N-phenylisonicotinamide, N-benzyl-3,5-dichloro-N-phenyl-isonicotinamide, N-benzyl-2-chloro-N-phenyl-isonicotinamide, N-benzyl-2-chloro-6-methyl-N-phenyl-isonicotinamide, N-benzyl-3-methyl-N-phenyl-isonicotinamide, N-benzyl-3-chloro-N-phenyl-isonicotinamide, N-benzyl-2,5-dichloro-N-phenyl-isonicotinamide, N-benzyl-2-methyl-N-phenyl-isonicotinamide, N-benzyl-2-cyano-N-phenyl-isonicotinamide, N-benzyl-N-phenethyl-isonicotinamide, N-benzyl-N-(2-fluoromethoxy-phenyl)-isonicotinamide, and N-benzyl-N-(4-chlorophenyl)-isonicotinamide. Additional GBPAR1 activators are described in United States Patent Application Publication No. 2010/0048579 by Arista, including pyridazine, pyridine, and pyrane derivatives.

The use of modulators of serine-threonine protein kinase and poly(ADP-ribose) polymerase (PARP) activity is described in United States Patent Application Publication No. 2009/0105233 by Chua et al. and in United States Patent Application Publication No. 2010/0173013 by Drygin et al. The serine-threonine protein kinase can be, but is not limited to, CK2, CK2α2, Pim-1, CDK1/cyclinB, c-RAF, Mer, MELK, DYRK2, Flt3, Flt3 (D835Y), Flt4, HIPK3, HIPK2, and ZIPK.

The use of taxanes is described in United States Patent Application Publication No. 2010/0166872 by Singh et al. The taxane can be, but is not limited to, paclitaxel or docitaxel.

The use of inhibitors of dihydrofolate reductase is described in United States Patent Application Publication No. 2010/0150896 by Gant et al. These inhibitors of dihydrofolate reductase include, but are not limited to, diaminoquinazolines.

The use of inhibitors of aromatase is described in United States Patent Application Publication No. 2010/0111901 by Gant et al. These inhibitors of aromatase include, but are not limited to, triazoles.

The use of benzimidazole-based anti-neoplastic agents is described in United States Patent Application Publication No. 2010/0098691 by Goh et al. The benzimidazole-based anti-neoplastic agent can be, but is not limited to, (E)-3-[1-(3-dimethylamino-2,2-dimethyl-propyl)-2-isopropyl-1H-benzimidazol-5-yl]-N-hydroxy-acrylamide, (E)-3-[2-butyl-1-(3-dimethylamino-2,2-dimethyl-propyl)-1H-benzimidazol-5-yl]-N-hydroxy-acrylamide, (E)-3-[1-(3-dimethylamino-2,2-dimethyl-propyl)-2-(2-methylsulfanyl-ethyl)-1H-benzimidazol-5-yl]-N-hydroxy-acrylamide, (E)-3-[1-(3-dimethylamino-2,2-dimethyl-propyl)-2-ethoxymethyl-1H-benzimidazol-5-yl]-N-hydroxy-acrylamide, (E)-3-[1-(3-dimethylamino-2,2-dimethyl-propyl)-2-isobutyl-1H-benzimidazol-5-yl]-N-hydroxy-acrylamide, (E)-3-[1-(2-diethylamino-ethyl)-2-isobutyl-1H-benzimidazol-5-yl]-N-hydroxy-acrylamide, (E)-3-[2-butyl-1-(2-diethylamino-ethyl)-1H-benzimidazol-5-yl]-N-hydroxy-acrylamide, (E)-3-[2-but-3-ynyl-1-(3-dimethylamino-2,2-dimethyl-propyl)-1H-benzimidazol-5-yl]-N-hydroxy-acrylamide, (E)-3-[2-but-3-enyl-1-(3-dimethylamino-2,2-dimethyl-propyl)-1H-benzimidazol-5-yl]-N-hydroxy-acrylamide, (E)-3-[2-but-3-enyl-1-(2-diethylamino-ethyl)-1H-benzimidazol-5-yl]-N-hydroxy-acrylamide, (E)-3-[2-but-3-ynyl-1-(2-diethylamino-ethyl)-1H-benzimidazol-5-yl]-N-hydroxy-acrylamide, (E)-3-[1-(3-dimethylamino-2,2-dimethyl-propyl)-2-(3,3,3-trifluoro-propyl)-1H-benzimidazol-5-yl]-N-hydroxy-acrylamide (E)-3-[1-(2-diethylamino-ethyl)-2-(3,3,3-trifluoro-propyl)-1H-benzimidazol-5-yl]-N-hydroxy-acrylamide, (E)-3-[1-(2-diethylamino-ethyl)-2-ethoxymethyl-1H-benzimidazol-5-yl]-N-hydroxy-acrylamide, (E)-3-[1-(3-dimethylamino-2,2-dimethyl-propyl)-2-methyl-1H-benzimidazol-5-yl]-N-hydroxy-acrylamide, (E)-3-[1-(2-diethylamino-ethyl)-2-(2,2-dimethyl-propyl)-1H-benzimidazol-5-yl]-N-hydroxy-acrylamide, (E)-N-hydroxy-3-[1-(3-isopropylamino-propyl)-2-(3,3,3-trifluoro-propyl)-1-H-benzimidazol-5-yl]-acrylamide, (E)-3-[2-(2,2-dimethyl-propyl)-1-(2-isopropylamino-ethyl)-1H-benzimidazol-5-yl]-N-hydroxy-acrylamide, (E)-3-[1-(2-diisopropylamino-ethyl)-2-(2,2-dimethyl-propyl)-1H-benzimidazol-5-yl]-N-hydroxy-acrylamide, (E)-3-[1-(2-diisopropylamino-ethyl)-2-isobutyl-1H-benzimidazol-5-yl]-N-hydroxy-acrylamide, (E)-3-[1-(3-dimethylamino-2,2-dimethyl-propyl)-2-hex-3-enyl-1H-benzimidazol-5-yl]-N-hydroxy-acrylamide, (E)-3-[1-(3-dimethylamino-2,2-dimethyl-propyl)-2-(2,4,4-trimethyl-pentyl)-1H-benzimidazol-5-yl]-N-hydroxy-acrylamide, (E)-3-[2-cyclohexyl-1-(3-dimethylamino-2,2-dimethyl-propyl)-1H-benzimidazol-5-yl]-N-hydroxyacrylamide, (E)-3-[2-bicyclo[2.2.1]hept-5-en-2-yl-1-(3-dimethylamino-2,2-dimethyl-propyl)-1H-benzimidazol-5-yl]-N-hydroxy-acrylamide, (E)-3-[1-(2-diethylamino-ethyl)-2-hex-3-enyl-1H-benzimidazol-5-yl]-N-hydroxy-acrylamide, (E)-3-[1-(2-diisopropylamino-ethyl)-2-hex-3-enyl-1H-benzimidazol-5-yl]-N-hydroxy-acrylamide, (E)-3-[2-hex-3-enyl-1-(2-isopropylamino-ethyl)-1H-benzimidazol-5-yl]-N-hydroxy-acrylamide, (E)-3-[2-hex-3-enyl-1-(3-isopropylamino-propyl)-1H-benzimidazol-5-yl]-N-hydroxy-acrylamide, (E)-3-[1-(2-ethylamino-ethyl)-2-hex-3-enyl-1H-benzimidazol-5-yl]-N-hydroxy-acrylamide, (E)-3-[1-(2-diethylamino-ethyl)-2-hexyl-1H-benzimidazol-5-yl]-N-hydroxy-acrylamide, (E)-N-hydroxy-3-[1-(3-isopropylamino-propyl)-2-(2,4,4-trimethyl-pentyl)-1H-benzimidazol-5-yl]-acrylamide, (E)-3-[2-(2,2-dimethyl-propyl)-1-(3-isopropylamino-propyl)-1H-benzimidazol-5-yl]-N-hydroxy-acrylamide, (E)-3-[1-(2-diisopropylamino-ethyl)-2-(3,3,3-trifluoro-propyl)-1H-benzimidazol-5-yl]-N-hydroxy-acrylamide, and (E)-N-hydroxy-3-[2-isobutyl-1-(2-isopropylamino-ethyl)-1H-benzimidazol-5-yl]-acrylamide.

The use of $O^6$-methylguanine-DNA-methyltransferase (MGMT) inhibitors is described in United States Patent Application 2010/0093647 by Liu et al. Suitable MGMT inhibitors include, but are not limited to, $O^6$-benzylguanine, $O^6$-2-fluoropyridinylmethylguanine, $O^6$-3-iodobenzyl guanine, $O^6$-4-bromophenylguanine, $O^6$ 5-iodophenylguanine $O^6$-benzyl-8-oxoguanine, $O^6$-(p-chlorobenzyl)guanine, $O^6$-(p-methylbenzyl)guanine, $O^6$-(p-bromobenzyl)guanine, $O^6$-(p-isopropylbenzyl)guanine, $O^6$-(3,5-dimethylbenzyl)guanine, $O^6$-(p-n-butylbenzyl)guanine, $O^6$-(p-hydroxymethybenzyl)guanine, $O^6$-benzylhypoxanthine, $N^2$-acetyl-$O^6$-benzylguanine, $N^2$-acetyl-$O^6$-benzyl-8-oxo-guanine, 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, $O^6$-benzyl-7,8-dihydro-8-oxoguanine, 2,4,5-triamino-6-benzyloxyprimidine, $O^6$-benzyl-9-[(3-oxo-50-androstan-17p-yloxycarbonylmethyl]guanine, $O^6$-benzyl-9-[(3-oxo-4-androsten-17β-yloxycarbonyl)methyl(guanine, 8-amino-$O^6$-benzylguanine (8-amino-BG), 2,4-diamino-6-benzyloxy-5-nitrosopyrimidine, 2,4-diamino-6-benzyloxy-5-nitropyrimidine, and 2-amino-4-benzyloxy-5-nitropyrimidine.

The use of CCR9 inhibitors is described in United States Patent Application Publication No. 2010/0075963 by Lehr et al. These CCR9 inhibitors include, but are not limited to, benzylsulfonylindoles.

The use of acid sphingomyelinase inhibitors is described in United States Patent Application Publication No. 2010/0022482 by Baumann et al. Typically, these compounds are biphenyl derivatives.

The use of peptidomimetic macrocycles is described in United States Patent Application Publication No. 2009/0275519 by Nash et al.

The use of cholanic acid amides is described in United States Patent Application Publication No. 2009/0258847 by Schreiner et al. These cholanic acid amides include, but are not limited to, substituted 4-(3-hydroxy-10,13-hydroxymethyl-hexadecahydro-cyclopenta(a)-phenanthren-17-yl)pentanoic acid amides.

The use of substituted oxazaphosphorines is described in United States Patent Application Publication No. 2009/0202540. The oxazaphosphorine can be, but is not limited to, ifosphamide and cyclophosphamide.

The use of anti-TWEAK receptor antibodies is described in United States Patent Application Publication No. 2009/0074762 by Culp. The TWEAK receptor is a member of the tumor necrosis receptor superfamily and is expressed on the surface of cancer cells in a number of solid tumors.

The use of ErbB3 binding protein is described in United States Patent Application Publication No. 2008/0269133 by Zhang et al.

The use of a glutathione S-transferase-activated (GST-activated) anti-neoplastic compound is described in United States Patent Application Publication No. 2008/0166428 by Brown et al. A preferred GST-activated anti-neoplastic compound is canfosfamide.

The use of substituted phosphorodiamidates is described in United States Patent Application Publication No. 2008/0125398 by Ma et al., which describes 2-{[2-(substituted amino)ethyl]sulfonyl}ethyl N,N,N',N'-tetrakis(2-chloroethyl)-phosphorodiamidates, and in United States Patent Application Publication No. 2008/0125397 by Lui et al., which describes 2-({2-oxo-2-[(pyridin-3-ylmethyl)amino]ethyl}sulfonyl)ethyl N,N,N',N'-tetrakis(2-chloroethyl)phosphorodiamidate. The use of substituted phosphorodiamidates is also described in United States Patent Application Publication No. 2008/0039429 by Allen et al., which describes sulfonylethyl and thioethyl phosphorodiamidates.

The use of inhibitors of MEKK protein kinase is described in United States Patent Application Publication No. 2006/0100226 by Sikorski et al. These inhibitors include, but are not limited to, 2-thiopyrimidinones, such as 2-[3-(3,4-dichloro-benzylamino)-benzylsulfanyl]-4-(3-methoxy-phenyl)-6-oxo-1,6-dihydro-pyrimidine-5-carbonitrile, 2-[3-(3,4-dichloro-benzylamino)-benzylsulfanyl]-4-(3,4-dimethoxy-phenyl)-6-oxo-1,6-dihydro-pyrimidine-5-carbonitrile, and 2-[3-(3,4-dichloro-benzylamino)-benzylsulfanyl-4-(4-methoxy-3-thiophen-2-yl-phenyl)-6-oxo-1,6-dihydro-pyrimidine-5-carbonitrile.

The use of COX-2 inhibitors is described in United States Patent Application Publication No. 2004/0072889 by Masferrer et al. Suitable COX-2 inhibitors include, but are not limited to, celecoxib, parecoxib, deracoxib, rofecoxib, etoricoxib, valdecoxib, and meloxicam.

The use of cimetidine and N-acetylcysteine is described in United States Patent Application Publication No. 2003/0158118 by Weidner. Derivatives of cimetidine or N-acetylcysteine can also be used.

The use of an anti-IL-6 receptor antibody is described in United States Patent Application Publication No. 2002/0131967 by Nakamura et al. The antibody can be a humanized antibody.

The use of an antioxidant is described in United States Patent Application Publication No. 2001/0049349 by Chinery et al. Suitable antioxidants include, but are not limited to, pyrrolidinedithiocarbamate, probucol (4,4'-(isopropylidenedithio)bis(2,6-di-t-butylphenol), vitamin C, vitamin E, and 6-hydroxy-2,5,7,8-tetramethylchroman-2-carboxylic acid.

The use of an isoxazole inhibitor of tubulin polymerization is described in U.S. Pat. No. 8,269,017 by Sun et al. Suitable isoxazole inhibitors of tubulin polymerization include, but are not limited to, 2-amino-N-(2-methoxy-5-[5-(3,4,5-trimethoxyphenyl)-isoxazol-4-yl)-phenyl)acetamide hydrochloride; 2-amino-3-hydroxy-N-(2-methoxy-5-[5-(3,4,5-trimethoxyphenyl)isoxazol-4-yl)-phenyl)propanamide hydrochloride; 2-amino-N-(2-methoxy-5-[5-(3,4,5-trimethoxyphenyl)isoxazol-4-yl)-phenyl)propanamide; 2-amino-N-(2-methoxy-5-[5-(3,4,5-trimethoxyphenyl)-isoxazol-4-yl)-phenyl)-4-(methylthio)butanamide hydrochloride; 2-amino-N-(2-methoxy-5-[5-(3,4,5-trimethoxyphenyl)-isoxazol-4-yl)-phenyl)butanamide; 2-amino-N-(2-methoxy-5-[5-(3,4,5-trimethoxyphenyl)-isoxazol-4-yl)- phenyl)-3-phenylpropanamide hydrochloride; 2-amino-N-(2-methoxy-5-[5-(3,4,5-trimethoxyphenyl)-isoxazol-4-yl)-phenyl)-4-methylpentanamide hydrochloride; 2-amino-N-(2-methoxy-5-[5-(3,4,5-trimethoxy-phenyl)-isoxazol-4-yl)-phenyl)-3-(4-methoxyphenyl)propanamide hydrochloride; 1-{2-methoxy-5-[5-(3,4,5-trimethoxy-phenyl)-isoxazol-4-yl]-phenylcarbamoyl}-2-methyl-propyl-ammonium chloride; 1-{2-methoxy-5-[5-(3,4,5-trimethoxyphenyl)-isoxazol-4-yl]-phenylcarbamoyl}-2-methyl-butyl-ammonium chloride; 2-hydroxy-1-{2-methoxy-5-[5-(3,4,5-trimethoxy-phenyl)-isoxazol-4-yl]-phenylcarbamoyl}-propyl-ammonium chloride; 2-(4-hydroxy-phenyl)-1-{2-methoxy-5-[5-(3,4,5-trimethoxyphenyl)-isoxazol-4-yl]-phenylcarbamoyl}-ethyl-ammonium chloride; C-{2-methoxy-5-[5-(3,4,5-trimethoxyphenyl)-isoxazol-4-yl]-phenylcarbamoyl}-C-phenyl-methyl-ammonium chloride; 2-(1H-indol-2-yl)-1-{2-methoxy-5-[5-(3,4,5-trimethoxy-phenyl)-isoxazol-4-yl]-phenylcarbamoyl}-ethyl-ammonium chloride; 2-benzofuran-2-yl-1-{2-methoxy-5-[5-(3,4,5-trimethoxyphenyl)-isoxazol-4-yl]-phenylcarbamoyl}-ethyl-ammonium chloride; 2-carboxyl-1-{2-methoxy-5-[5-(3,4,5-trimethoxyphenyl)-isoxazol-4-yl]-phenylcarbamoyl}-ethyl-ammonium chloride; 3-carboxyl-1-{2-methoxy-5-[5-(3,4,5-trimethoxyphenyl)-isoxazol-4-yl]-phenylcarbamoyl}-propyl-ammonium chloride; 3-carbamoyl-1-{2-methoxy-5-[5-(3,4,5-trimethoxyphenyl)-isoxazol-4-yl]-phenylcarbamoyl}-propyl-ammonium chloride; 2-carbamoyl-1-{2-methoxy-5-[5-(3,4,5-trimethoxyphenyl)-isoxazol-4-yl]-phenylcarbamoyl}-ethyl-ammonium chloride; and 2-(3H-imidazol-4-yl)-1-{2-methoxy-5-[5-(3,4,5-trimethoxyphenyl)-isoxazol-4-yl]-phenylcarbamoyl}-ethyl-ammonium chloride.

The use of pyridazinone PARP inhibitors is described in U.S. Pat. No. 8,268,827 by Branca et al. Pyridazinone PARP inhibitors include, but are not limited to, 6-{4-fluoro-3-[(3-oxo-4-phenylpiperazin-1-yl)carbonyl]benzyl}-4,5-dimethyl-3-oxo-2,3-dihydropyridazin-1-ium trifluoroacetate; 6-{3-[(4-cyclohexyl-3-oxopiperazin-1-yl)carbonyl]-4-fluorobenzyl}-4,5-dimethyl-3-oxo-2,3-dihydropyridazin-1-ium trifluoroacetate; 6-{3-[(4-cyclopentyl-3-oxopiperazin-1-yl) carbonyl]-4-fluorobenzyl}-4,5-dimethylpyridazin-3(2H)-one; 6-{4-fluoro-3-[(3-oxo-4-phenylpiperazin-1-yl)carbonyl]benzyl}-4,5-dimethylpyridazin-3(2H)-one hydrochloride; 4-ethyl-6-{4-fluoro-3-[(3-oxo-4-phenylpiperazin-1-yl)carbonyl]benzyl}pyridazin-3(2H)-one trifluoroacetate; 6-{3-[(4-cyclohexyl-3-oxopiperazin-1-yl)carbonyl]-4-fluorobenzyl}-4-ethylpyridazin-3(2H)-one trifluoroacetate; 3-{4-fluoro-3-[(4-methyl-3-oxopiperazin-1-yl)carbonyl]benzyl}-4,5-dimethyl-6-oxo-1,6-dihydropyridazin-1-ium trifluoroacetate; 3-(4-fluoro-3-{[4-(4-fluorobenzyl)-3-oxopiperazin-1-yl]carbonyl}benzyl)-4,5-dimethyl-6-oxo-1,6-dihydropyridazin-1-ium trifluoroacetate; 6-(3-{[4-(2-chlorophenyl)-3-oxopiperazin-1-yl]carbonyl}-4-fluorobenzyl)-4,5-dimethyl-3-oxo-2,3-dihydropyridazin-1-ium trifluoroacetate; 6-(3-{[4-(3-chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate; and 6-(3-{[4-(3,4-difluorophenyl)-3-oxopiperazin-1-yl]carbonyl}-4-fluorobenzyl)-4,5-dimethyl-3-oxo-2,3-dihydropyridazin-1-ium trifluoroacetate. Other PARP inhibitors are described in U.S. Pat. No. 8,143,447 by Moore et al.; these compounds include nitrobenzamide derivatives.

The use of Aurora protein kinase inhibitors is described in U.S. Pat. No. 8,268,811 to Mortimore et al. The Aurora protein kinase inhibitors include, but are not limited to, thiazoles and pyrazoles. The use of Aurora protein kinase inhibitors is also described in U.S. Pat. No. 8,129,399 to Binch et al.; these Aurora protein kinase inhibitors include, but are not limited to, aminopyridines.

The use of peptides binding to prostate-specific membrane antigen (PSMA) is described in U.S. Pat. No. 8,258,256 to Denmeade et al.

The use of CD19 binding agents is described in U.S. Pat. No. 8,242,252 to McDonagh et al. These CD19 binding agents include, but are not limited to, anti-CD19 antibodies.

The use of benzodiazepines is described in U.S. Pat. No. 8,242,109 to Glick.

The use of Toll-like receptor (TLR) agonists is described in U.S. Pat. No. 8,242,106 to Howbert et al. Suitable TLR agonists include, but are not limited to, (1E,4E)-2-amino-N,N-dipropyl-8-(4-(pyrrolidine-1-carbonyl)phenyl)-3H-benzo[b]azepine-4-carboxamide.

The use of bridged bicyclic sulfamides is described in U.S. Pat. No. 8,242,103 to Lewis et al.

The use of inhibitors of epidermal growth factor receptor (EGFR) kinase is described in U.S. Pat. No. 8,242,080 to Kuriyan et al. Typically, these inhibitors of EGFR kinase target the asymmetric activating dimer interface.

The use of ribonucleases of the T2 family having actin-binding activity is described in U.S. Pat. No. 8,236,543 to Roiz et al. Typically, the ribonuclease binds actin in either its active or inactive ribonucleolytic form.

The use of myrsinoic acid A or an analog thereof is described in U.S. Pat. No. 8,232,318 to Lee et al.

The use of an inhibitor of a cyclin-dependent kinase is described in U.S. Pat. No. 8,227,605 to Shipps et al.; these inhibitors include, but are not limited to, 2-aminothiazole-4-carboxylic amides. Use of an inhibitor of a cyclin-dependent kinase is also described in U.S. Pat. No. 7,700,773 to Mallams et al.; these inhibitors include, but are not limited to, 4-cyano, 4-amino, and 4-aminomethyl derivatives of pyrazolo[1,5-a]pyridine, pyrazolo[1,5-c]pyrimidine, and 2H-indazole compounds and 5-cyano, 5-amino, and 5-aminomethyl derivatives of imidazo[1,2-a]pyridine and imidazo[1,5-a]pyrazine compounds.

The use of an inhibitor of the interaction between p53 and MDM2 is described in U.S. Pat. No. 8,222,288 to Wang et al.

The use of inhibitors of the receptor tyrosine kinase MET is described in U.S. Pat. No. 8,222,269 to Dinsmore et al. These inhibitors of the receptor tyrosine kinase MET include, but are not limited to, 5H-benzo[4,5]cyclohepta[1,2-b]pyridine derivatives. Inhibitors of the receptor tyrosine kinase MET are also described in U.S. Pat. No. 8,207,186 to Jewell et al. These compounds include, but are not limited to, benzocycloheptapyridines, including 5H-benzo[4,5]cyclohepta[1,2-b]pyridine derivatives.

The use of largazole or largazole analogs is described in U.S. Pat. No. 8,217,076 to Williams et al.

The use of inhibitors of the protein kinase AKT is described in U.S. Pat. No. 8,207,169 to Furuyama et al.; these inhibitors include, but are not limited to, triazolopyridopyridines, including substituted [1,2,4]triazolo[4',3':1,6]pyrido[2,3-b]pyrazines.

The use of 2'-fluoro-5-methyl-β-L-arabinofuranosyluridine or L-deoxythymidine is described in U.S. Pat. No. 8,207,143 to Cheng.

The use of compounds that modulate HSP90 activity is described in U.S. Pat. No. 8,188,075 to Ying et al. These compounds include, but are not limited to, substituted triazoles, including 3-(2-hydroxyphenyl)-4-(naphthalen-1-yl)-5-mercaptotriazole; 3-(2,4-dihydroxyphenyl)-4-[4-(2-methoxyethoxy)-naphthalen-1-yl]-5-mercaptotriazole; 3-(2, 4-dihydroxyphenyl)-4-(2-methyl-4-bromophenyl)-5-mercaptotriazole; 3-(3,4-dihydroxyphenyl)-4-(6-methoxy-naphthalen-1-yl)-5-mercaptotriazole; 3-(3,4-dihydroxyphenyl)-4-(6-ethoxy-naphthalen-1-yl)-5-mercaptotriazole; 3-(3,4-dihydroxyphenyl)-4-(6-propoxy-naphthalen-1-yl)-5-mercaptotriazole; 3-(2,4-dihydroxy-5-ethyl-phenyl)-4-(5-methoxy-naphthalen-1-yl)-5-mercaptotriazole; 3-(3,4-dihydroxyphenyl)-4-(6-isopropoxy-naphthalen-1-yl)-5-mercaptotriazole; 3-(2,4-dihydroxyphenyl)-4-(2,6-diethylphenyl)-5-mercaptotriazole; 3-(2,4-dihydroxyphenyl)-4-(2-methyl-6-ethylphenyl)-5-mercaptotriazole; 3-(2,4-dihydroxyphenyl)-4-(2,6-diisopropylphenyl)-5-mercaptotriazole; 3-(2,4-dihydroxyphenyl)-4-(1-ethyl-indol-4-yl)-5-mercaptotriazole; and 3-(2,4-dihydroxyphenyl)-4-(2,3-dihydro-benzo[1,4]dioxin-5-yl)-5-mercaptotriazole.

The use of inhibitors of a JAK kinase or PDK kinase is described in U.S. Pat. No. 8,183,245 to Guerin et al. JAK kinases include JAK1, JAK2, JAK3, and TYK2. Suitable inhibitors of these classes of kinases include, but are not limited to, 5-(1-methyl-1H-pyrazol-4-yl)-3-(6-piperazin-1-ylpyrazin-2-yl)-1H-pyrrolo[2,3-b]pyridine; 5-(1-methyl-1H-pyrazol-4-yl)-3-[6-(piperidin-4-yloxy)pyrazin-2-yl]-1H-pyrrolo[2,3-b]pyridine; 3-[6-(cyclohexyloxy)pyrazin-2-yl]-5-(1-methyl-1H-pyrazol-4-yl)-1H-pyrrolo[2,3-b]pyridine; N-methyl-6-[5-(1-methyl-1H-pyrazol-4-yl)-1H-pyrrolo[2,3-b]pyridin-3-yl]-N-piperidin-4-ylpyrazin-2-amine; 3-[6-(piperidin-4-yloxy)pyrazin-2-yl]-5-(1H-pyrazol-4-yl)-1H-pyrrolo[2,3-b]pyridine; 3-{6-[(3R)-piperidin-3-yloxy]pyrazin-2-yl}-5-(1H-pyrazol-4-yl)-1H-pyrrolo[2,3-b]pyridine; and 3-{6-[(3S)-piperidin-3-yloxy]pyrazin-2-yl}-5-(1H-pyrazol-4-yl)-1H-pyrrolo[2,3-b]pyridine.

The use of inhibitors of phosphodiesterase type IV (PDE4) is described in U.S. Pat. No. 8,158,672 to Muller et al. The inhibitors of PDE4 include fluoroalkoxy-substituted 1,3-dihydroisoindolyl compounds.

The use of inhibitors of c-Met proto-oncogene receptor tyrosine kinase is described in U.S. Pat. No. 8,143,251 to Zhuo et al., incorporated by this reference. These inhibitors include, but are not limited to, triazolotriazines, including [1,2,4]triazolo[4,3-b][1,2,4]triazines. Inhibitors of c-Met proto-oncogene receptor tyrosine kinase are also described in U.S. Pat. No. 8,106,197 to Cui et al.; these inhibitors include aminoheteroaryl compounds.

The use of inhibitors of indoleamine 2,3-dioxygenase is described in U.S. Pat. No. 8,088,803 to Combs et al.; these inhibitors include, but are not limited to, 1,2,5-oxadiazole derivatives.

The use of agents that inhibit ATDC (TRIM29) expression is described in U.S. Pat. No. 8,088,749 to Simeone et al. These agents include oligonucleotides that function via RNA interference.

The use of proteomimetic inhibitors of the interaction of nuclear receptor with coactivator peptides is described in U.S. Pat. No. 8,084,471 to Hamilton et al. These inhibitors include, but are not limited to, 2,3',3"-trisubstituted terphenyls.

The use of antagonists of XIAP family proteins is described in U.S. Pat. No. 7,910,621 to Chen et al. These antagonists include, but are not limited to, embelin.

The use of tumor-targeted superantigens is described in U.S. Pat. No. 7,763,253 to Hedlund et al.

The use of inhibitors of Pim kinases is described in U.S. Pat. No. 7,750,007 to Bearss et al. These inhibitors include, but are not limited to, imidazo[1,2-b]pyridazine and pyrazolo[1,5-a]pyrimidine compounds.

The use of inhibitors of CHK1 or CHK2 kinases is described in U.S. Pat. No. 7,732,436 to Tepe. These inhibitors include, but are not limited to, indoloazepines and acid amine salts thereof.

The use of inhibitors of angiopoietin-like 4 protein is described in U.S. Pat. No. 7,740,846 to Gerber et al. These inhibitors include, but are not limited to, antibodies, including monoclonal antibodies.

The use of inhibitors of Smo is described in U.S. Pat. No. 7,691,997 to Balkovec et al. Smo, or Smoothened, is a mediator of signaling by hedgehog proteins. Suitable inhibitors include, but are not limited to, 5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 2-(1,1-difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole; 2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and 2-(1-fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole.

The use of nicotinic acetylcholine receptor antagonists is disclosed in U.S. Pat. No. 7,652,038 to Cooke et al. Nicotinic acetylcholine receptor antagonists include, but are not limited to, mecamylamine, hexamethonium, dihydro-β-erythroidine, d-tubocurarine, pempidine, chlorisondamine, erysodine, trimethaphan camsylate, pentolinium, bungarotoxin, succinylcholine, tetraethylammonium, trimethaphan, chlorisondamine, and trimethidinium.

The use of farnesyl protein transferase inhibitors is described in U.S. Pat. No. 7,557,107 to Zhu et al. These farnesyl protein transferase inhibitors include tricyclic compounds.

The use of adenosine A3 receptor antagonists is described in U.S. Pat. No. 6,326,390 to Leung et al. These adenosine A3 receptor antagonists include tricyclic non-xanthine antagonists and triazoloquinazolines.

Additional drug combinations can include an alkylating hexitol derivative as described above with at least one agent that suppresses growth or replication of glioma cancer stem cells. Such agents include, but are not limited to: an inhibitor of tailless gene expression or tailless gene activity, as described in U.S. Pat. No. 8,992,923 to Liu et al.; an inhibitor of HDAC1, HDAC7, or phosphorylated HDAC7, as described in U.S. Pat. No. 8,912,156 to Ince et al.; Stat3 inhibitors such as naphtho derivatives, as described in U.S. Pat. No. 8,877,803 to Jiang et al.; a combination of a farnesyl transferase inhibitor and a gamma secretase inhibitor, as described in U.S. Pat. No. 8,853,274 to Wang; inhibitors of electron transport chains or the mitochondrial Krebs cycle as described in U.S. Pat. No. 8,815,844 to Clement et al.; Jak2/STAT3 pathway inhibitors such as caffeic acid derivatives as described in United States Patent Application Publication No. 2015/0094343 by Priebe et al.; inhibitors of the glycine cleavage pathway as described in United States Patent Application Publication No. 2015/0011611 by Kim et al.; and glycosylated ether lipids as described in United States Patent Application Publication No. 2015/0011486 by Arthur et al.

The Y-box binding protein-1 (YB-1) is a nucleic acid binding protein encoded by the gene YBX1. It was originally identified as a factor that bound to the Y-box (an inverted CCAAT (SEQ ID NO: 1) box) in the MHC Class II (HLA-DRA) promoter and repressed transcription. Subsequently, YB-1 has been shown to be a multitasking protein with many functions, including the regulation of both transcription and translation of several genes and proteins associated with tumor progression, cell survival, DNA replication and repair, drug resistance, and epithelial-mesenchymal transition.

YB-1 is a member of a highly conserved nucleic acid-binding polypeptide family known as the Y-box family of proteins. It has been described as a 42-50 kDa protein. Each member of the Y-box family of proteins contains a cold-shock domain which has been identified as a 66 amino acid region, is believed to be a DNA-binding domain, and is highly conserved. YB-1 has been described as a transcription factor for a number of genes associated with cell death, growth and survival in tumor cells, including epidermal growth factor receptor (EGFR) gene, proliferating cell nuclear antigen (PCNA)/cyclin gene, multidrug resistant pump (mdr1) gene and CD-95. In addition, it has also been shown to stimulate transcription of the long terminal repeats (LTRs) of both the human T-cell lymphotropic virus-1 (HTLV-1) and human immunodeficiency virus-1 (HIV-1) (United States Patent Application Publication No. 2007/0004666 by Watson et al.). Y-boxes are located on the promoter of numerous genes, such as DNA topoisomerase II alpha (Topo II alpha), proliferating cell nuclear antigen (PCNA) and multidrug resistance 1 (MDR1). YB-1 (NSEP1/DBPB) has been reported to be involved in both transcriptional and translational regulation of gene expression with its expression affecting cell proliferation, genomic instability, multidrug resistance, RNA stabilization and DNA repair. The expression of HLA class II genes is regulated by a series of cis-acting elements and trans-acting factors. Cis-acting elements include the Y box and studies have suggested that YB-1 is a negative regulator of HLA-DR beta chain mRNA expression. The expression of HLA class II genes is regulated by a series of cis-acting elements and trans-acting factors. Cis-acting elements include the Y box and studies have suggested that YB-1 is a negative regulator of HLA-DR beta chain mRNA expression. The effect of YB-1 on stabilizing mRNAs is general. It has been demonstrated that YB-1 is the major mRNA-associated protein, also termed p50, which is a potent cap-dependent mRNA stabilizer. YB-1 addition or overexpression dramatically increased mRNA stability in vitro and in vivo, whereas YB-1 depletion resulted in accelerated mRNA decay. The cold shock domain of YB-1 is responsible for the mRNA stabilizing activity, and a blocked mRNA 5' end is required for YB-1-mediated stabilization. The finding that YB-1 is necessary for JNK-induced stabilization of the IL-2 mRNA induced by T-cell activation signals is particularly interesting, as a subgroup of DLBCLs with an activated phenotype has been linked to poor prognosis. YB-1 has also been identified as a protein that interacts with a TGF-beta response element in the distal region of the collagen alpha 1(I) gene. YB-1 protein activates the collagen promoter and translocates into the nucleus during TGF-beta addition to fibroblasts, suggesting a role for this protein in TGF-beta signaling. YB-1 is overexpressed in cell lines that are resistant to the cancer treatment drug cisplatin. Subsequently YB-1 has been shown to bind to PCNA in vivo indicating that YB-1 can function as a recognition protein for cisplatin-damaged DNA and that it may be important in DNA repair or in directing the cellular response to DNA damage. YB-1 also binds directly to the p53 tumor suppressor protein (United States Patent Application Publication No. 2005/0158737 by Banham et al.). YB-1 was overexpressed in almost all cases of colorectal carcinomas compared with normal mucosa (United States Patent Application Publication No. 2003/0190602 by Pressman et al.). Diminution of YB-1 expression results in increased levels of p53 tumor suppressor protein and consequent apoptosis of tumor cells (United States Patent Application Publication No. 2003/0074684 by Graham et al.) YB-1, therefore, when overexpressed, can reduce apoptosis of malignant cells induced by agents such as anti-neoplastic drugs (United States Patent Application Publication No. 2002/0151063 by Latham et al.)

Many immunohistochemical studies have shown increased YB-1 protein levels in malignant tissues as compared with normal, non-malignant tissues. Higher levels of YB-1 have been associated with higher grades of tumors and poorer patient prognosis in a number of malignancies, including breast cancer, lung cancer, colorectal cancer, prostate cancer, and ovarian cancer. This has led to suggestions that YB-1 acts as a proto-oncogene. It has been shown that sequestration of YB-1 by transfection of cells with an oligonucleotide containing a YB-1 binding site led to the induction of apoptosis of many types of tumor cells in vitro, suggesting that the activity of YB-1 may play an important role in the survival of malignant cells.

Among the interactions of YB-1 that can have the effect of promoting tumor growth, survival, or metastasis are interactions with the epidermal growth factor receptor (EGFR) and the human epidermal growth factor receptor-2 (HER-2). Specifically, it induces expression of the gene for human epidermal growth factor receptor (her-2) along with the gene for its dimerization partner egfr by directly binding to their promoters. Increased expression of the gene encoding YB-1 has been shown to be associated with resistance to EGFR inhibitors (U.S. Pat. No. 8,148,076 to Baker et al.). Increased expression of the gene encoding YB-1 has also been shown to be associated with resistance to doxorubicin (U.S. Pat. No. 8,071,286 to Baker et al.). The promoter for the gene encoding the multiple drug resistance protein MDR also binds to YB-1 (U.S. Pat. No. 7,105,656 to Colgan). The MDR1 gene is a known gene that encodes a 170-kDa transmembrane protein, P-gp, located at the cytoplasmic surface of the cell, and its nucleotide sequence is also known. P-gp consists of two membrane-spanning domains and two nucleotide-binding domains. Of the various molecular targets, P-gp expression is responsible for cell resistance to the widest variety of anti-cancer drugs. P-gp overexpression plays an important role in the acquisition of drug resistance in various cancer cells. The enhanced expression of the MDR1 gene in malignant cancer cells has been attributed to various mechanisms, including nuclear translocation of YB-1, promoter rearrangement, and alteration of methylation status at CpG sites on the MDR1 promoter (United States Patent Application Publication No. 2006/0216738 by Wada et al.).

YB-1 is also overexpressed in a large proportion of brain tumors affecting adults and children, where it is associated with drug resistance to anti-neoplastic agents such as temozolomide. It has been shown that YB-1 is associated with the overexpression of the membrane-bound transport protein P-glycoprotein, which is a member of the ABC class of transporter proteins. The nuclear localization of YB-1 directly affects the expression of P-glycoprotein. YB-1 is transported into the nucleus by various stress conditions such as UV irradiation, administration of cytostatic agents, and hyperthermia. It is also known that the nuclear localization of YB-1 has an impact on one further ABC transporter. This ABC transporter is referred to as MRP (multidrug resistance-related protein) and is involved in the formation of the so-called atypical non-P-glycoprotein dependent multidrug resistance (U.S. Pat. No. 8,951,772 to Holm).

It has also been shown that the serine/threonine kinase Akt phosphorylates, and thus activates, YB-1 at $Ser^{102}$, and that inhibiting this phosphorylation reaction also inhibits nuclear trafficking. Additionally, the kinase p90 ribosomal S6 kinase RSK is the predominant kinase that phosphorylates YB-1 at $Ser^{102}$ and that Akt and the kinase pKCα also contribute to this phosphorylation, but to a lesser degree (J. H. Law et al., "Molecular Decoy to the Y-Box Binding Protein-1 Suppresses the Growth of Breast and Prostate Cancer Cells whilst Sparing Normal Cell Viability," *PLoS One* 5: el2661 (2010)). Therefore, as detailed below, inhibitors of Akt can be used to reduce the activity of YB-1.

In particular, YB-1 appears to promote tumor growth by modulating the expression of E2Fas and also E2F target genes. RNA interference with siRNA can be used to inhibit expression of YB-1; two siRNA molecules that can be used are 5'-GGUCCUCCACGCAAUUACCAGCAAA-3' (SEQ ID NO: 2) and 5'-GGUCCUC-CACGCAAUUACCAGCAAA-3' (SEQ ID NO: 3) (A. Lasham et al., "YB-1, the E2F Pathway, and Regulation of Tumor Cell Growth," *J. Natl. Cancer Inst.* 104: 133-146 (2012)). Similarly, it has been shown that targeting YB-1 with the siRNAs SEQ ID NO: 2 and SEQ ID NO: 3 in HER-2 overexpressing breast cancer cells induces apoptosis via the mTOR/STAT3 pathway and reduces tumor cell growth in mice (C. Lee et al., "Targeting YB-1 in HER-2 Overexpressing Breast Cancer Cells Induces Apoptosis via the mTOR/STAT3 Pathway and Suppresses Tumor Growth in Mice," *Cancer Res.* 68: 8661-8668 (2008)). When reference is made herein to siRNA or other oligonucleotides or polynucleotides, the terms refer generally to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded, unless expressly stated as either single stranded or double stranded. Nucleic acids can include DNA-RNA hybrids unless expressly excluded. When siRNA is employed, methods known in the art can be employed to modify the siRNA to increase its stability or reduce its susceptibility to hydrolysis by nucleases.

YB-1 may also play other roles in tumor survival, growth, and metastasis. For example, YB-1 can regulate non-coding RNA expression, such as miRNA, in malignancies such as glioblastoma multiforme. In particular, YB-1 preferentially recognizes a UYAUC consensus motif and binds to the majority of coding gene transcripts including pre-mRNAs and mature mRNAs. YB-1 also binds extensively to the terminal loop region of pri-/pre-miR-29b-2 and regulates the biogenesis of miR-29b-2 by blocking the recruitment of microprocessor and Dicer to its precursors. Downregulation of miR-29b by YB-1, which is up-regulated in GBM, is important for cell proliferation (S. L. Wu et al., "Genome-Wide Analysis of YB-1-RNA Interactions Reveals a Novel Role of YB-1 in miRNA Processing in Glioblastoma Multiforme," *Nucleic Acids Res.* 43: 8516-8528 (2015)).

U.S. Pat. No. 8,546,441 to Chen, discloses inhibitors of Akt including compounds of Formula (Y-I)

(Y-I)

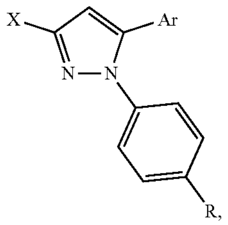

wherein: (1) X is selected from the group consisting of alkyl and haloalkyl; (2) Ar is an aryl radical selected from the group consisting of phenyl, biphenyl, naphthyl, anthryl, phenanthryl, and fluorenyl; (3) Ar is optionally substituted with one or more radicals selected from the group consisting of halo, $C_1$-$C_4$ alkyl, $C_1$-$C_4$ haloalkyl, azido, $C_1$-$C_4$ azidoalkyl, aryl, alkylaryl, haloaryl, haloalkylaryl, and combinations thereof; and (4) R is selected from the group consisting of nitrile, acetonitrile, ethylnitrile, propylnitrile, carboxamide, amidine, tetrazole, oxime, hydrazone, acetamidine, aminoacetamide, guanidine, and urea.

U.S. Pat. No. 8,319,899 to Leuschner et al., discloses fusion constructs that bind and inhibit YB-1. In one alternative, fusion construct includes a peptide first domain that includes or consists of a 12, 13, 15, 16, 17, 18, 19, 20, 22, 23, 24, 25, 26, 27 or 28 residue L- or D-amino acid sequence that includes a peptide selected from KFAKFAKKFAK-FAKK, KFAKFAKKFAKFAKKF, KFAKFAKKFAK-FAKKFA, KFAKFAKKFAKFAKKFAK, KFAKFAKK-FAKFAKKFAKF, KFAKFAKKFAKFAKKFAKFA and KFAKFAKKFAKFAKKFAKFAKKFAKFAK (SEQ ID NOs. 4, 5, 6, 7, 8, 9, and 10) having one or more of the K residues substituted with an F or L residue, one or more of the F residues substituted with a K, A or L residue, or one or more of the A residues substituted with a K, F or L residue. In another particular embodiment, a fusion construct includes a peptide first domain consisting of an L- or D-amino acid sequence selected from KFAKFAKKFAK-FAKK, KFAKFAKKFAKFAKKF, KFAKFAKKFAK-FAKKFA, KFAKFAKKFAKFAKKFAK, KFAKFAKK-FAKFAKKFAKF, KFAKFAKKFAKFAKKFAKFA and KFAKFAKKFAKFAKKFAKFAKKFAKFAK (SEQ ID NOs. 4, 5, 6, 7, 8, 9, and 10) having one or more of the K residues substituted with an F or L residue, one or more of the F residues substituted with a K, A or L residue, or one or more of the A residues substituted with a K, F or L residue; and a peptide second domain that includes or consists of a binding moiety. In further particular embodiment, a fusion construct includes or consists of a peptide first domain consisting of an L- or D-amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAKKFAKFAK (SEQ ID NOs. 4, 5, 6, 7, 8, 9, and 10) having one or more of the K residues substituted with any of an F or L residue, one or more of the F residues substituted with any of a K, A or L residue, or one or more of the A residues substituted with any of a K, F or L residue, and a peptide second domain consisting of a 1-25 L- or D-amino acid sequence (e.g., binding moiety) distinct from the first domain.

U.S. Pat. No. 8,163,507 to Mertens, discloses antibodies that specifically bind YB-1. Typically, the antibodies are monoclonal antibodies. Typically, the antibodies are chimeric antibodies or humanized antibodies.

U.S. Pat. No. 6,140,126 to Bennett et al., discloses the use of antisense compounds that are targeted to the 5'-UTR of YB-1 which specifically hybridize with and inhibit the expression of YB-1 protein. Typically, these antisense compounds are from 8 to 30 bases in length. The antisense compounds can comprise at least one modified internucleoside linkage, such as phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-aminophosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; these can be in the form of salts, mixed salts, or free acids; alternatively, the antisense compounds can be in the form of peptide nucleic acids. The antisense compounds can comprise at least one modified sugar moiety, such as a 2'-O-methoxyethyl sugar moiety, a 2'-dimethylaminooxyethoxy sugar moiety, or a 2'-dimethylaminoethoxyethoxy sugar moiety. The antisense compounds can comprise at least one modified nucleobase, such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. In another alternative, the oligonucleotides can be covalently linked to one or more moieties or conjugates that enhance the activity, cellular distribution, or cellular uptake of the oligonucleotide; these moieties can be a lipid moiety such as cholesterol, cholic acid, a thioether such as hexyl-S-trithiol, a thiocholesterol, an aliphatic chain such as one including dodecanediol or undecyl residues, a phospholipid, a polyamine, a polyethylene glycol chain, adamantane acetic acid, a palmityl moiety, an octyldecylamine moiety, or a hexylamino-carbonyl-cholesterol moiety.

United States Patent Application Publication No. 2014/0088178 by Gleave et al., discloses that YB-1 binds to the promoter for clusterin leading to increased clusterin expression after endoplasmic reticular (ER) stress responses. Therefore, it may be possible to use anti-clusterin antisense oligonucleotides such as custirsen to block this expression.

United States Patent Application Publication No. 2013/0059292 by Kim et al. discloses that Akt is associated with inactive mRNAs and that activated Akt may relieve translational repression of the YB-1 bound mRNAs. Therefore, Akt inhibitors may be useful in treating malignancies associated with overactivity of YB-1. Inhibitors of Akt are disclosed above; further Akt inhibitors are also described below.

United States Patent Application Publication No. 2012/0213801 by Gresko et al. discloses the interaction of YB-1 with Twist1 by activation of YB-1 by Twist1 acting as transcription factor. Twist1 is activated by phosphorylation at $Ser^{42}$. Therefore, inhibition of the phosphorylation of $Ser^{42}$ of Twist1 can be useful in treating malignancies associated with overactivity of YB-1. The agent that inhibits the phosphorylation of $Ser^{42}$ of Twist1 can be an anti-Twist1 antibody or a small molecule such as a peptide comprising an amino acid corresponding to $Ser^{42}$ of Twist1 which is phosphorylated by the kinase PKB.

United States Patent Application Publication No. 2010/0029003 by Bartel et al. discloses targeting of miRNA to inhibit expression of YB-1. In particular, expression of YB-1 can be inhibited by targeting miR-216

(UAAUCUCGCUGGCAACUGUG. (SEQ ID NO: 11)

Akt (protein kinase B; PKB) is a serine-threonine kinase which occupies a central place in one of the major cell signaling pathways, the PI3K/Akt pathway. Akt is in particular involved in the growth, proliferation and survival of tumor cells. Akt is activated in two steps (1) by phosphorylation of threonine 308 (P-T308) by PDK1 and (2) by phosphorylation of serine 473 (P-S473) by mTORC2 (or mTOR-Rictor complex), resulting in total activation. Akt in turn regulates a large number of proteins, including mTOR (mammalian target of Rapamycin), BAD, GSK3, p21, p27, FOXO or FKHRL1. The activation of Akt promotes the internalization of nutrients, thereby triggering an anabolic metabolization process which supports cell growth and proliferation. In particular, Akt controls the initiation of protein synthesis through a cascade of interactions which takes place by means of TSC1/2 (tuberous sclerosis complex), Rheb, and TOR so as to result in two critical targets of the signaling pathway, p70S6K and 4EBP. Akt also induces inhibitory phosphorylation of the Forkhead transcription factor and the inactivation of GSK313, which result in the inhibition of apoptosis and in progression of the cell cycle. Akt is therefore a target for anticancer therapy, and the inhibition of Akt activation by inhibition of its phosphorylation can induce apoptosis in malignant cells and thereby provide a treatment for cancer.

Akt inhibitors are described in the following patents and published patent applications: (1) U.S. Pat. No. 9,156,853 to Harrison et al. (substituted pyrimidinones including 6-(4-((1s,3s)-1-amino-3-hydroxy-3-methylcyclobutyl)phenyl)-5-phenyl-3-(2,2,2-trifluoroethyl)furo[2,3-d]pyrimidin-4(3H)-one; 6-(4-((1r,3r)-1-amino-3-hydroxycyclobutyl)phenyl)-5-phenyl-3-(2,2,2-trifluoroethyl)furo[2,3,4-pyrimidin-4(3H)-one; 6-(4-((1s,3s)-1-amino-3-hydroxycyclobutyl)phenyl)-5-phenyl-3-(2,2,2-trifluoroethyl)furo[2,3-d]pyrimidin-4(3H)-one; 6-(4-((1r,3r)-1-amino-3-hydroxy-3-methylcyclobutyl) phenyl)-5-phenyl-3-(2,2,2-trifluoroethyl)furo[2,3-d] pyrimidin-4(3H)-one; 6-(4-((1r,3r)-1-amino-3-hydroxy-3-methylcyclobutyl)phenyl)-5-phenyl-3-(2,2,2-trifluoroethyl)

thieno[2,3-d]pyrimidin-4(3H)-one; 6-(4-((1r,3r)-1-amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one; 6-(4-((1s,3s)-1-amino-3-hydroxycyclobutyl)phenyl)-7-methyl-5-phenyl-3-(2,2,2-trifluoroethyl)-3H-pyrrolo[2,3-d]pyrimidin-4(7H)-one); (2) U.S. Pat. No. 9,150,549 to Nannini et al. (ipatasertib); (3) U.S. Pat. No. 8,895,571 to Huang et al. (isoindolinone and pyrrolopyridinone derivatives, including 2-[(1S)-2-Amino-1-(3-fluorobenzyl)ethyl]-5-(1-methyl-1H-pyrazol-5-yl)isoindolin-1-one; 2-[(1S)-2-amino-1-(3-fluorobenzyl)ethyl]-5-(4-chloro-1-methyl-1H-pyrazol-5-yl)isoindolin-1-one; 2-[(1S)-2-amino-1-(3-fluorobenzyl)ethyl]-5-(4-methyl-1-methyl-1H-pyrazol-5-yl)isoindolin-1-one; 2-[(1S)-2-amino-1-(3-fluorobenzyl)ethyl]-5-(4-methoxymethyl-1-methyl-1H-pyrazol-5-yl)isoindolin-1-one; 2-[(1S)-2-amino-1-(3-fluorobenzyl)ethyl]-5-(4-ethoxymethyl-1-methyl-1H-pyrazol-5-yl)isoindolin-1-one; 2-[(1S)-2-amino-1-(3-fluorobenzyl)ethyl]-5-[4-(2-propoxymethyl)-1-methyl-1H-pyrazol-5-yl]isoindolin-1-one; 2-[(1S)-2-amino-1-(3-fluorobenzyl)ethyl]-5-[4-(1-propoxymethyl)-1-methyl-1H-pyrazol-5-yl]isoindolin-1-one; 2-[(1S)-2-amino-1-(3-fluorobenzyl)ethyl]-5-(4-cyclobutoxymethyl-1-methyl-1H-pyrazol-5-yl)isoindolin-1-one; 2-[(1S)-2-amino-1-(3-fluorobenzyl)ethyl]-5-(4-cyclopropylmethoxymethyl-1-methyl-1H-pyrazol-5-yl)isoindolin-1-one; 2-[(1S)-2-amino-1-(3-fluorobenzyl)ethyl]-5-[(methylthio)methyl-1-methyl-1H-pyrazol-5-yl]isoindolin-1-one; 2-[(1S)-2-amino-1-(3-fluorobenzyl)ethyl]-5-(4-fluoro-1-methyl-1H-pyrazol-5-yl)isoindolin-1-one; 2-[(1S)-2-amino-1-(3-fluorobenzyl)ethyl]-5-(4-bromo-1-methyl-1H-pyrazol-5-yl)isoindolin-1-one; 2-[(1S)-2-amino-1-(3-fluorobenzyl)ethyl]-5-(4-cyano-1-methyl-1H-pyrazol-5-yl)isoindolin-1-one; 2-[(1S)-2-amino-1-(3-fluorobenzyl)ethyl]-5-(4-phenyl-1-methyl-1H-pyrazol-5-yl)isoindolin-1-one); (4) U.S. Pat. No. 8,895,566 Banka et al. (5H-cyclopenta[d]pyrimidines, including (5R,7R)-4-(4-((S)-(4-chlorophenyl)(2-(dimethylamino)ethoxy)methyl)piperidin-1-yl)-5-methyl-6,7-dihydro-5H-cyclopenta[d]pyrimidin-7-ol; (5R,7R)-4-(4-((R)-(4-chlorophenyl)(2-(dimethylamino)ethoxy)methyl)piperidin-1-yl)-5-methyl-6,7-dihydro-5H-cyclopenta[d]pyrimidin-7-ol; N—((S)-1-amino-3-(2,4-dichlorophenyl)propan-2-yl)-5-((R)-5-methyl-6,7-dihydro-5H-cyclopenta[d]pyrimidin-4-yl)thiophene-2-carboxamide; N—((S)-1-amino-3-(2,4-dichlorophenyl)propan-2-yl)-5-((5R,7R)-7-hydroxy-5-methyl-6,7-dihydro-5H-cyclopenta[d]pyrimidin-4-yl)thiophene-2-carboxamide; (5R,7R)-4-(4-(4-(4-chlorophenyl)piperidin-4-yl)phenyl)-5-methyl-6,7-dihydro-5H-cyclopenta[d]pyrimidin-7-ol; N—((R)-2-(4-chlorophenyl)-2-(6((R)-5-methyl-6,7-dihydro-5H-cyclopenta[d]pyrimidin-4-yl)-1H-indol-3-yl)ethyl)propan-2-amine; (R)—N-(2-(4-chlorophenyl)-2-(4-(5-methyl-6,7-dihydro-5H-cyclopenta[d]pyrimidin-4-yl)phenoxy)ethyl)propan-2-amine; (5R,7R)-4-(3-(amino(4-chlorophenyl)methyl)-5,6-dihydro-[1,2,4]triazolo[4,3-a]pyrazin-7(8H)-yl)-5-methyl-6,7-dihydro-5H-cyclopenta[d]pyrimidin-7-ol; (5R,7R)-4-(3-(1-(4-chlorophenyl)-2-(isopropylamino)ethyl)-5,6-dihydro-[1,2,4]triazolo[4,3-a]pyrazin-7(8H)-yl)-5-methyl-6,7-dihydro-5H-cyclopenta[d]pyrimidin-7-ol); (5) U.S. Pat. No. 8,853,216 to Bencsik et al. (hydroxylated pyrimidyl cyclopentanes); (6) U.S. Pat. No. 8,853,199 to Mitchell et al. (hydroxylated and methoxylated pyrimidyl cyclopentanes); (7) U.S. Pat. No. 8,846,683 to Bencsik et al. (pyrimidyl cyclopentanes); (8) U.S. Pat. No. 8,846,681 to Mitchell et al. (pyrimidyl cyclopentanes); (9) U.S. Pat. No. 8,835,450 to Dumble et al. (N-{(1S)-2-amino-1-[(3,4-difluorophenyl)methyl]ethyl}-5-chloro-4-(4-chloro-1-methyl-1H-pyrazol-5-yl)-2-furancarboxamide); (10) U.S. Pat. No. 8,835,434 to Bencsik et al. (hydroxylated pyrimidyl cyclopentanes); (11) U.S. Pat. No. 8,828,451 to Sebti et al. (triciribine and triciribine phosphate); (12) U.S. Pat. No. 8,822,524 to Sebti et al. (non-peptide inhibitors targeting the substrate binding site); (13) U.S. Pat. No. 8,799,255 to Carry et al. ((6-oxo-1,6-dihydropyrimidin-2-yl)amide derivatives including 2-[4-(morpholin-4-yl)-6-oxo-1,6-dihydropyrimidin-2-yl]-N-phenylacetamide; N-(4-fluorophenyl)-2-[4-(morpholin-4-yl)-6-oxo-1,6-dihydropyrimidin-2-yl]acetamide; N-(3-chlorophenyl)-2-[4-(morpholin-4-yl)-6-oxo-1,6-dihydropyrimidin-2-yl]acetamide; N-[3-(dimethylamino)phenyl]-2-[4-(morpholin-4-yl)-6-oxo-1,6-dihydropyrimidin-2-yl]acetamide; N-(2,4-difluorophenyl)-2-[4-(morpholin-4-yl)-6-oxo-1,6-dihydropyrimidin-2-yl]acetamide; N-(3,4-difluorophenyl)-2-[4-(morpholin-4-yl)-6-oxo-1,6-dihydropyrimidin-2-yl]acetamide; 2-[4-(morpholin-4-yl)-6-oxo-1,6-dihydropyrimidin-2-yl]-N-(thiophen-3-yl)acetamide; N-(4-fluoro-3-methoxyphenyl)-2-[4-(morpholin-4-yl)-6-oxo-1,6-dihydropyrimidin-2-yl]acetamide; N-(2-fluorophenyl)-2[4-(morpholin-4-yl)-6-oxo-1,6-dihydropyrimidin-2-yl]acetamide; N-(2-methylphenyl)-2-[4-(morpholin-4-yl)-6-oxo-1,6-dihydropyrimidin-2-yl]acetamide; N-(2-methoxypheny)-2-[4-(morpholin-4-yl)-6-oxo-1,6-dihydropyrimidin-2-yl]acetamide); (14) U.S. Pat. No. 8,691,825 to Chen et al. (substituted fused pyrimidine compounds including 1-[4-(6-phenylimidazo[1,2-a]pyrimidin-7-yl)phenyl]cyclobutanamine; 1-[4-(3,6-diphenylimidazo[1,2-a]pyrimidin-7-yl)phenyl]cyclobutanamine; 3-amino-3-[4-(3,6-diphenylimidazo[1,2-a]pyrimidin-7-yl)phenyl]-1-methylcyclobutanol; 3-amino-1-methyl-3-[4-(2-methyl-3,6-diphenylimidazo[1,2-a]pyrimidin-7-yl)phenyl]cyclobutanol; 1-[4-(2-methyl-3,6-diphenylimidazo[1,2-a]pyrimidin-7-yl)phenyl]cyclobutanamine; 1-[4-(3,6-diphenylimidazo[1,2-a]pyrimidin-7-yl)phenyl]methanamine; 3-amino-1-cyclopropyl-3-[4-(6-phenyl-imidazo[1,2-a]pyrimidin-7-yl)-phenyl]-cyclobutanol; 1-[4-(6-phenyl-imidazo[1,2-a]pyrimidin-7-yl)-phenyl]-cyclobutylamine; 1-[4-(3-bromo-6-phenyl-imidazo[1,2-a]pyrimidin-7-yl)-phenyl]-cyclobutylamine; 1-[4-(6-phenyl-3-vinyl-imidazo[1,2-a]pyrimidin-7-yl)-phenyl]-cyclobutylamine; 1-{4-[3-(2-methoxy-phenyl)-6-phenyl-imidazo[1,2-a]pyrimidin-7-yl]-phenyl}-cyclobutylamine; 7-[4-(1-amino-cyclobutyl)-phenyl]-6-phenyl-imidazo[1,2-a]pyrimidine-3-carbonitrile; 7-[4-(1-amino-cyclobutyl)-phenyl]-6-phenyl-imidazo[1,2-a]pyrimidine-3-carboxylic acid amide; 1-[4-(3-Chloro-6-phenyl-imidazo[1,2-a]pyrimidin-7-yl)-phenyl]-cyclobutylamine; 1-[4-(3-methyl-6-phenyl-imidazo[1,2-a]pyrimidin-7-yl)-phenyl]-cyclobutylamine; 1-{4-[3-(2-cyclopropyl-vinyl)-6-phenyl-imidazo[1,2-a]pyrimidin-7-yl]-phenyl}-cyclobutylamine; 1-[4-(2,6-diphenyl-imidazo[1,2-a]pyrimidin-7-yl)-phenyl]-cyclobutylamine; 1-[4-(3-bromo-2,6-diphenylimidazo[1,2-a]pyrimidin-7-yl)-phenyl]-cyclobutylamine); (15) U.S. Pat. No. 8,618,097 to Bencsik et al. (pyrimidyl cyclopentanes); (16) U.S. Pat. No. 8,614,221 to Fan et al. (substituted fused naphthyridine derivatives including trans-3-amino-1-methyl-3-[4-(2-methyl-7-phenylpyrazolo[1,5-a]pyrido[3,2-e]pyrimidin-8-yl)phenyl]cyclobutanol; cis-3-amino-1-methyl-3-[4-(2-methyl-7-phenylpyrazolo[1,5-a]pyrido[3,2-e]pyrimidin-8-yl)phenyl]cyclobutanol; trans-3-amino-1-cyclopropyl-3-[4-(2-methyl-7-phenylpyrazolo[1,5-a]pyrido[3,2-e]pyrimidin-8-yl)phenyl]cyclobutanol; trans-3-amino-3-[4-(2-methyl-7-phenylpyrazolo[1,5-a]pyrido[3,2-e]pyrimidin-8-yl)phenyl]cyclobutanol; trans-3-methoxy-1-[4-(2-methyl-7-phenylpyrazolo[1,5-a]pyrido[3,2-e]pyrimidin- 8-yl)phenyl]cyclobutanamine; methyl {1-[4-(2-methyl-7-phenylpyrazolo[1,5-a]pyrido[3,2-e]pyrimidin-8-yl)phenyl]-3-oxocyclobutyl}carbamate; 1-[4-(2-methyl-7-phenylpyrazolo[1,5-a]pyrido[3,2-e]pyrimidin-8-yl)phenyl] methanamine; 2-methyl-7-phenyl-8-[4-(1H-pyrazol-1-ylmethyl)phenyl]pyrazolo[1,5-a]pyrido[3,2-e]pyrimidine; (1R)-1-[4-(2-methyl-7-phenylpyrazolo[1,5-a]pyrido[3,2-e] pyrimidin-8-yl)phenyl]ethanamine; trans-3-amino-1-ethyl-3-[4-(2-methyl-7-phenylpyrazolo[1,5-a]pyrido[3,2-e]pyrimidin-8-yl)phenyl]cyclobutanol; cis-3-amino-1-ethyl-3-[4-(2-methyl-7-phenylpyrazolo[1,5-a]pyrido[3,2-e] pyrimidin-8-yl)phenyl]cyclobutanol; trans-3-amino-1-ethenyl-3-[4-(2-methyl-7-phenylpyrazolo[1,5-a]pyrido[3,2-e]pyrimidin-8-yl)phenyl]cyclobutanol; 3-methylidene-1-[4-(2-methyl-7-phenylpyrazolo[1,5-a]pyrido[3,2-e]pyrimidin-8-yl)phenyl]cyclobutanamine; 3,3-difluoro-1-[4-(2-methyl-7-phenylpyrazolo[1,5-a]pyrido[3,2-e]pyrimidin-8-yl) phenyl]cyclobutanamine; 8-{4-[trans-1-amino-3-(1,2-dihydroxyethyl)-3-hydroxycyclobutyl]phenyl}-2-methyl-7-phenylpyrazolo[1,5-a]pyrido[3,2-e]pyrimidine; 8-{4-[1-amino-3-hydroxy-3-(hydroxymethyl)cyclobutyl]phenyl}-2-methyl-7-phenylpyrazolo[1,5-a]pyrido[3,2-e]pyrimidine); (17) U.S. Pat. No. 8,536,193 to Furuyama et al. (substituted [1,2,4]triazolo[4,3-a]-1,5-naphthyridine compounds including trans-3-amino-3-{4-[1-(difluoromethyl)-8-phenyl[1,2,4] triazolo[4,3-a]-1,5-naphthyridin-7-yl]phenyl}-1-methylcyclobutanol); (18) U.S. Pat. No. 8,507,483 to Certal et al. (1H-pyrimidin-2-one derivatives including 2-[(5-fluoro-1H-benzimidazol-2-yl)methyl]-6-(morpholin-4-yl)pyrimidin-4 (3H)-one; 2-(1,3-benzoxazol-2-ylmethyl)-6-(morpholin-4-yl)pyrimidin-4(3H)-one; 2-[(6-bromo-1H-benzimidazol-2-yl)methyl]-6-(morpholin-4-yl)pyrimidin-4(3H)-one; 2-[(6-methoxy-1H-benzimidazol-2-yl)methyl]-6-(morpholin-4-yl)pyrimidin-4(3H)-one; 2-[(5,6-difluoro-1H-benzimidazol-2-yl)methyl]-6-(morpholin-4-yl)pyrimidin-4(3H)-one; 2-[(6-fluoro-1,3-benzoxazol-2-yl)methyl]-6-(morpholin-4-yl)pyrimidin-4(3H)-one; 2-[(5-fluoro-1,3-benzoxazol-2-yl) methyl]-6-(morpholin-4-yl)pyrimidin-4(3H)-one); (19) U.S. Pat. No. 8,481,503 to Layton et al. (8-[4-(1-aminocyclobutyl)phenyl]-9-phenyl[1,2,4]triazolo[3,4-f]-1,6-naphthyridin-3(2H)-one); (20) U.S. Pat. No. 8,440,630 to Noguchi et al. (polypeptide inhibitors); (21) U.S. Pat. No. 8,420,690 to Seefeld et al. (heterocyclic carboxamide compounds, including N-(2-amino-1-phenylethyl)-5-(1-methyl-1H-pyrazol-5-yl)-3-thiophenecarboxamide; N[2-amino-1-(phenylmethyl)ethyl]-5-(1-methyl-1H-pyrazol-5-yl)-3-thiophenecarboxamide; N-((1S)-2-amino-1-{[2-(trifluoromethyl) phenyl]methyl}ethyl)-5-(1-methyl-1H-pyrazol-5-yl)-3-thiophenecarboxamide; N-{(1S)-2-amino-1-[(2-fluorophenyl)methyl]ethyl}-5-(1-methyl-1H-pyrazol-5-yl)-3-thiophenecarboxamide; N-{(1S)-2-amino-1-[(2-chlorophenyl)methyl]ethyl}-5-(1-methyl-1H-pyrazol-5-yl)-3-thiophenecarboxamide; N[1-(aminomethyl)-2-methyl-2-phenylpropyl]-5-(1-methyl-1H-pyrazol-5-yl)-3-thiophenecarboxamide; N[2-amino-1-(1-naphthalenypethyl]-5-(1-methyl-1H-pyrazol-5-yl)-3-thiophenecarboxamide; N[2-amino-1-(phenylmethyl)ethyl]-2-(3-furanyl)-5-(1-methyl-1H-pyrazol-5-y-l)-3-thiophenecarboxamide; N-((1S)-2-amino-1-{[2-(trifluoromethyl)phenyl]methyl}ethyl)-5-(1-methyl-1H-pyrazol-5-yl)-3-furancarboxamide; N-((1S)-2-amino-1-{[2-(trifluoromethyl)phenyl]methyl}ethyl)-1-methyl-5-(1-methyl-1H-pyrazol-5-yl)-1H-pyrrole-3-carboxamide; N-((1S)-2-amino-1-{[2-(trifluoromethyl)phenyl] methyl}ethyl)-2-chloro-1-methyl-5-(1-methyl-1H-pyrazol-5-yl)-1H-pyrrole-3-carboxamide; and N-((1S)-2-amino-1-{[2-(trifluoromethyl)phenyl]methyl}ethyl)-2-chloro-5-(4-chloro-1-methyl-1H-pyrazol-5-yl)-1-methyl-1H-pyrrole-3-carboxamide); (22) U.S. Pat. No. 8,410,158 to Seefeld et al. (N-{(1S)-2-amino-1-[(3,4-difluorophenyl)methyl]ethyl}-5-chloro-4-(4-chloro-1-methyl-1H-pyrazol-5-yl)-2-furancarboxamide); (23) U.S. Pat. No. 8,329,709 to Banka et al. (5H-cyclopenta[d]pyrimidines, including (5R,7R)-4-(4-((S)-(4-chlorophenyl)(2-(dimethylamino)ethoxy)methyl)piperidin-1-yl)-5-methyl-6,7-dihydro-5H-cyclopenta[d]pyrimidin-7-ol; (5R,7R)-4-(4-((R)-(4-chlorophenyl)(2-(dimethylamino)ethoxy)methyl)piperidin-1-yl)-5-methyl-6,7-dihydro-5H-cyclopenta[d]pyrimidin-7-ol; N—((S)-1-amino-3-(2,4-dichlorophenyl)propan-2-yl)-5-((R)-5-methyl-6,7-dihydro-5H-cyclopenta[d]pyrimidin-4-yl) thiophene-2-carboxamide; N—((S)-1-amino-3-(2,4-dichlorophenyl)propan-2-yl)-5-((5R,7R)-7-hydroxy-5-methyl-6,7-dihydro-5H-cyclopenta[d]pyrimidin-4-yl) thiophene-2-carboxamide; (5R,7R)-4-(4-(4-(4-chlorophenyl)piperidin-4-yl)phenyl)-5-methyl-6,7-dihydro-5H-cyclopenta[d]pyrimidin-7-ol; N—((R)-2-(4-chlorophenyl)-2-(6-((R)-5-methyl-6,7-dihydro-5H-cyclopenta[d]pyrimidin-4-yl)-1H-indol-3-yl)ethyl)propan-2-amine; (R)—N-(2-(4-chlorophenyl)-2-(4-(5-methyl-6,7-dihydro-5H-cyclopenta[d]pyrimidin-4-yl)phenoxy)ethyl) propan-2-amine; (5R,7R)-4-(3-(amino(4-chlorophenyl) methyl)-5,6-dihydro-[1,2,4]triazolo[4,3-a]pyrazin-7(8H)-yl)-5-methyl-6,7-dihydro-5H-cyclopenta[d]pyrimidin-7-ol; (5R,7R)-4-(3-(1-(4-chlorophenyl)-2-(isopropylamino) ethyl)-5,6-dihydro-[1,2,4]triazolo[4,3-a]pyrazin-7(8H)-yl)-5-methyl-6,7-dihydro-5H-1-cyclopenta[d]pyrimidin-7-ol; (4-chlorophenyl)(7-((R)-5-methyl-6,7-dihydro-5H-cyclopenta[d]pyrimidin-4-yl)-5,6,7,8-tetrahydro-[1,2,4]triazolo [4,3-a]pyrazin-3-yl)methanamine; (5R,7R)-4-(3-((R)-1-amino-2-(4-chlorophenyl)ethyl)-5,6-dihydro-[1,2,4]triazolo [4,3-a]pyrazin-7(8H)-yl)-5-methyl-6,7-dihydro-5H-cyclopenta[d]pyrimidin-7-ol; (5R,7R)-4-(4-(1-(4-Chlorophenyl)-2-(isopropylamino)ethylamino)phenyl)-5-methyl-6,7-dihydro-5H-cyclopenta[d]pyrimidin-7-ol hydrochloride); (24) U.S. Pat. No. 8,329,701 to Mitchell et al. (dihydrofuropyrimidines); (25) U.S. Pat. No. 8,324,221 to Banka et al. (pyrimidylcyclopentanes including (R)-5-chloro-1-(5-methyl-6,7-dihydro-5H-cyclopenta[d]pyrimidin-4-yl)spiro-[indoline-3,4'-piperidine]; (R)-5-bromo-1-(5-methyl-6,7-dihydro-5H-cyclopenta[d]pyrimidin-4-yl)spiro [indoline-3,4'-piperidine]; 5-chloro-1-((5R,7S)-7-fluoro-5-methyl-6,7-dihydro-5-1'-cyclopenta[d]pyrimidin-4-yl)spiro [indoline-3,4'-piperidine]; 5-chloro-1-45R,7R)-7-fluoro-5-methyl-6,7-dihydro-5H-cyclopenta[d]pyrimidin-4-yl)spiro [indoline-3,4'-piperidine]; (5R,7R)-4-(5-chlorospiro [indoline-3,4'-piperidine]-1-yl)-5-methyl-6,7-dihydro-5H-cyclopenta[d]pyrimidin-7-ol; (5R,7S)-4-(5-chlorospiro [indoline-3,4'-piperidine]-1-yl)-5-methyl-6,7-dihydro-5H-cyclopenta[d]pyrimidin-7-ol; (R)-5-cyclopropyl-1-(5-methyl-6,7-dihydro-5H-cyclopenta[d]pyrimidin-4-yl)spiro [indoline-3,4'-piperidine]; (R)-5-chloro-1-(5-methyl-6,7-dihydro-5H-cyclopenta[d]pyrimidin-4-yl)spiro[indoline-3,4'-piperidine]-4-carbonitrile; (R)—N-(3-chlorophenyl)-1-(5-methyl-6,7-dihydro-5H-cyclopenta[d]pyrimidin-4-yl) spiro[indoline-3,4'-piperidin]-5-amine; (R)-2-(1-(5-methyl-6,7-dihydro-5H-cyclopenta[d]pyrimidin-4-yl)spiro [indoline-3,4'-piperidine]-5-yl)acetamide; (R)-5-(3-fluorobenzyl)-1-(5-methyl-6,7-dihydro-5H-cyclopenta[d] pyrimidin-4-yl)spiro[indoline-3,4'-piperidine]; 2-(1-((R)-5-methyl-6,7-dihydro-5H-cyclopenta[d]pyrimidin-4-yl)spiro [indoline-3,4'-piperidine]-5-yloxy)-2-phenylethanamine; (R)-(1-(5-methyl-6,7-dihydro-5H-cyclopenta[d]pyrimidin-4-yl)spiro[indoline-3,4'-piperidine]-5-yl)methanamine); (26) U.S. Pat. No. 8,288,047 to Kelly, III et al. (substituted naphthyridines including 8[-4-(1-aminocyclobutyl)phenyl]-9-phenyl[1,2,4]triazolo[3,4-f]-1,6-naphthyridin-3-01); (27) U.S. Pat. No. 8,273,782 to Seefeld et al. (heterocyclic carboxamides including N-{(1S)-2-amino-1-[(3-fluorophenyl)methyl]ethyl}-5-chloro-4-(4-chloro-1-methyl-1H-pyrazol-5-yl)-2-thiophenecarboxamide); (28) U.S. Pat. No. 8,168,652 to Sanderson et al. (substituted naphthyridines including 2,2-dimethyl-3-({4-[3-phenyl-5-(1H-pyrazol-4-yl)-1,6-naphthyridin-2-yl]benzyl}amino)propan-1-ol; 3-({4-[3-phenyl-5-(1H-pyrazol-4-yl)-1,6-naphthyridin-2-yl]benzyl}amino)propan-1-ol; {1-[({4-[3-phenyl-5-(1H-pyrazol-4-yl)-1,6-naphthyridin-2-yl]benzyl}amino)methyl]cyclobutyl}methanol; {1-[({4-[3-phenyl-5-(1H-pyrazol-4-yl)-1,6-naphthyridin-2-yl]benzyl}amino)methyl]cyclopentyl}methanol; {1-[({4-[3-phenyl-5-(1H-pyrazol-4-yl)-1,6-naphthyridin-2-yl]benzyl}amino)methyl]cyclohexyl}methanol; 4-({4-[3-phenyl-5-(1H-pyrazol-4-yl)-1,6-naphthyridin-2-yl]benzyl}amino)butan-1-ol; 2,2-dimethyl-N-{4-[3-phenyl-5-(1H-pyrazol-4-yl)-1,6-naphthyridin-2-yl]benzyl}propan-1-amine; 2-({4-[3-phenyl-5-(1H-pyrazol-4-yl)-1,6-naphthyridin-2-yl]benzyl}amino)ethanol; [(1R,2S)-2-({4-[3-phenyl-5-(1H-pyrazol-4-yl)-1,6-naphthyridin-2-yl]-benzyl}amino)cyclohexyl]methanol; (2S)-1-methoxy-3-({4-[3-phenyl-5-(1H-pyrazol-4-yl)-1,6-naphthyridin-2-yl]benzyl}amino)propan-2-ol); (29) U.S. Pat. No. 8,063,050 to Mitchell et al. (hydroxylated and methoxylated pyrimidylcyclopentanes including 2-(4-chlorophenyl)-1-(4((5R,7R)-7-hydroxy-5-methyl-6,7-dihydro-5H-cyclopenta[d]pyrimidin-4-yl)piperazin-1-yl)-3-(isopropylamino)propan-1-one; (R)-2-amino-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one; (R)-2-amino-3-(4-chloro-3-fluorophenyl)-1 ((S)-4-((5R,7R)-7-hydroxy-5-methyl-6,7-dihydro-5H-cyclopenta[d]pyrimidin-4-yl)-3-methylpiperazin-1-yl)propan-1-one; (R)-2-amino-3-(4-chloro-3-fluorophenyl)-1-((S)-4-((5R,7R)-7-methoxy-5-methyl-6,7-dihydro-5H-cyclopenta[d]pyrimidin-4-yl)-3-methylpiperazin-1-yl)propan-1-one; (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one; (R)-2-amino-3-(4-chlorophenyl)-1-((S)-4-((S)-7-hydroxy-6,7-dihydro-5H-cyclopenta[d]pyrimidin-4-yl)-3-methylpiperazin-1-yl)propan-1-one; (R)-2-amino-3-(4-chloro-3-fluorophenyl)-1-((S)-4((S)-7-hydroxy-6,7-dihydro-5H-cyclopenta[d]pyrimidin-4-yl)-3-methylpiperazin-1-yl)propan-1-one; (2R)-2-amino-3-(4-chloro-3-fluorophenyl)-1-((3S)-4-((5R)-7-hydroxy-5-methyl-6,7-dihydro-5H-cyclopenta[d]pyrimidin-4-yl)-3-methylpiperazin-1-yl)propan-1-one); (30) U.S. Pat. No. 8,008,317 to Armstrong et al. (substituted naphthyridines including 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-amine; 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol; 9-phenyl-8-(4-{[4-(4-pyridin-2-yl-1H-imidazol-1-yl)piperidin-1-yl]methyl}phenyl) [1,2,4]triazolo[3,4-f]-1,6-naphthyridin-3-amine; 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-thiol; 3-methyl-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine; 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine; 3-(chloromethyl)-9-phenyl-8-(4-{[4-(4-pyridin-2-yl-1H-imidazol-1-yl)piperidin-1-yl]methyl}phenyl)[1,2,4]triazolo[3,4-f]-1,6-naphthyridine; 3-[(4-methylpiperazin-1-yl)methyl]-9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridine; 2-({[9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-yl]methyl}amino)ethanol; 8-(4-aminomethyl-phenyl)-9-phenyl-[1,2,4]triazolo[3,4-f][1,6]naphthyridin-3-ol; 1-[4-(9-phenyl[1,2,4]triazolo[3,4-f]-1,6-naphthyridin-8-yl)phenyl]methanamine; 4-(3-methyl-9-phenyl-[1,2,4]triazolo[3,4-f][1,6]naphthyridin-8-yl)-benzylamine); (31) U.S. Pat. No. 8,003,651 to Mitchell et al. (pyrimidylcyclopentanes including 2-(4-chlorophenyl)-3-(isopropylamino)-1-(4-((R)-5-methyl-6,7-dihydro-5H-cyclopenta[d]pyrimidin-4-yl)piperazin-1-yl)propan-1-one dihydrochloride; (R)-2-amino-3-(4-chlorophenyl)-1-((S)-3-methyl-4-((R)-5-methyl-6,7-dihydro-5H-cyclopenta[d]pyrimidin-4-yl)piperazin-1-yl)propan-1-one dihydrochloride; (R)-2-amino-3-(4-chloro-3-fluorophenyl)-1-((S)-3-methyl-4-((R)-5-methyl-6,7-dihydro-5H-cyclopenta[d]pyrimidin-4-yl)piperazin-1-yl)propan-1-one dihydrochloride; 2-(aminomethyl)-3-(4-chloro-3-fluorophenyl)-1-((S)-3-methyl-4-((R)-5-methyl-6,7-dihydro-5H-cyclopenta[d]pyrimidin-4-yl)piperazin-1-yl)propan-1-one dihydrochloride; (R,S)-2-(2,4-dichlorophenyl)-3-(isopropylamino)-1-(4-((R)-5-methyl-6,7-dihydro-5H-cyclopenta[d]pyrimidin-4-yl)piperazin-1-yl)propan-1-one dihydrochloride; (R,S)-2-(4-chlorophenyl)-3-(cyclopropylmethylamino)-1-(4((R)-5-methyl-6,7-dihydro-5H-cyclopenta[d]pyrimidin-4-yl)piperazin-1-yl)propan-1-one dihydrochloride); (32) U.S. Pat. No. 8,003,643 to Bilodeau et al. (substituted pyridazines and pyrimidines including 5-phenyl-2-pyridin-2-yl-4-(4-{[4-(5-pyridin-2-yl-1H-1,2,4-triazol-3-yl)piperidin-1-yl]methyl}phenyl)pyrimidine; 1-{4-[5-phenyl-2-(pyridine-3-ylamino)pyrimidin-4-yl]benzyl}-4-(5-pyridin-2-yl-4H-1,2,4-triazol-3-yl)piperidine; 1-{4-[2-(5-amino-1,3,4-thiadiazol-2-yl)-5-phenylpyrimidin-4-yl]benzyl}-4-(5-pyridin-2-yl-4H-1,2,4-triazol-3-yl)piperidine; 1-methyl-4-(2-{[5-phenyl-4-(4-{[4-(5-pyridin-2-yl-4H-1,2,4-triazol-3-yl)piperidin-1-yl]methyl}phenyl)pyrimidin-2-yl]amino}ethyl)piperazine; 1-[4-(2-amino-5-phenylpyrimidin-4-yl)benzyl]-4-(5-pyridin-2-yl-4H-1,2,4-triazol-3-yl)piperidine; 1-{4-[2-(methylthio)-5-phenylpyrimidin-4-yl]benzyl}-4-(5-pyridin-2-yl-4H-1,2,4-triazol-3-yl)piperidine; 1-{4-[2-(4-acetylpiperazin-1-yl)-5-phenylpyrimidin-4-yl]benzyl}-4-(5-pyridin-2-yl-4H-1,2,4-triazol-3-yl)piperidine; 1-[4-(2-{[1-(ethoxycarbonyl)piperidin-4-yl]amino}-5-phenylpyrimidin-4-yl)benzyl]-4-(5-pyridin-2-yl-4H-1,2,4-triazol-3-yl)piperidine); (33) U.S. Pat. No. 7,998,977 to Joseph et al. (4-[5-(2-amino-ethanesulfonyl)-isoquinolin-7-yl]-phenol); (34) U.S. Pat. No. 7,910,561 to Arruda et al. (substituted naphtyridines including 3-phenyl-2-(4-{[4-(5-pyridin-2-yl-1H-1,2,4-triazol-3-yl)piperidin-1-yl]methyl}phenyl)-1,6-naphthyridin-5(6H)-one; 2-(4-{[4-(4-amino-1H-pyrazolo[3,4-d]pyrimidin-1-yl)piperidin-1-yl]methyl}phenyl)-3-phenyl-1,6-naphthyridin-5(6H)-one; 6-methyl-3-phenyl-2-(4-{[4-(5-pyridin-2-yl-1H-1,2,4-triazol-3-yl)piperidin-1-yl]-methyl}phenyl)-1,6-naphthyridin-5(6H)-one; 6-(2-hydroxyethyl)-3-phenyl-2-(4-{[4-(5-pyridin-2-yl-1H-1,2,4-triazol-3-yl)piperidin-1-yl]methyl}phenyl)-1,6-naphthyridin-5(6H)-one; 3-phenyl-2-(4-{[4-(5-pyridin-2-yl-1H-1,2,4-triazol-3-yl)piperidin-1-yl]methyl}phenyl)-1,7-naphthyridin-8(7H)-one; 2-(4-{[4-(1,3-benzoxazol-2-yl)piperidin-1-yl]methyl}phenyl)-3-phenyl-1,6-naphthyridin-5(6H)-one; 3-phenyl-2-(4-{[445-pyridin-2-yl-2H-tetrazol-2-yl)piperidin-1-yl]methyl}phenyl)-1,6-naphthyridin-5(6H)-one; 3-phenyl-2-(4-{[4-(4-pyridin-2-yl-1H-1,2,3-triazol-1- yl)piperidin-1-yl]methyl}phenyl)-1,6-naphthyridin-5(6H)-one; 3-phenyl-2-(4-{[4-(1-pyridin-2-yl-1H-pyrrol-3-yl)piperidin-1-yl]methyl}phenyl)-1,6-naphthyridin-5(6H)-one; 3-phenyl-2-(4-{[4-(5-pyridin-2-yl-1,2,4-oxadiazol-3-yl)piperidin-1-yl]methyl}phenyl)-1,6-naphthyridin-5(6H)-one; 3-phenyl-2-(4-{[4-(5-pyridin-2-yl-1,3-thiazol-2-yl)piperidin-1-yl]methyl}phenyl)-1,6-naphthyridin-5(6H)-one; 3-phenyl-2-(4-{[4-(3-pyridin-3-yl-1,2,4-oxadiazol-5-yl)piperidin-1-yl]methyl}phenyl)-1,6-naphthyridin-5(6H)-one; 3-phenyl-2-(4-{[4-(3-pyrimidin-4-yl-1,2,4-oxadiazol-5-yl) piperidin-1-yl]methyl}phenyl)-1,6-naphthyridin-5(6H)-one; 3-phenyl-2-(4-{[4-(5-phenyl-1,3,4-oxadiazol-2-yl)piperidin-1-yl]methyl}phenyl)-1,6-naphthyridin-5(6H)-one; 2-(4-{[4-(1H-benzimidazol-2-yl)piperidin-1-yl]methyl}phenyl)-3-phenyl-1,6-naphthyridin-5(6H)-one; 2-(4-{[4-fluoro-4-(5-pyridin-2-yl-4H-1,2,4-triazol-3-yl)piperidin-1-yl] methyl}phenyl)-3-phenyl-1,6-naphthyridin-5(6H)-one); (35) U.S. Pat. No. 7,750,151 to Bilodeau et al. (substituted napthyridines including 3-[(3-hydroxyphenyl)amino]-3-oxo-N--[4-(5-oxo-3-phenyl-5,6-dihydro-1,6-naphthyridin-2-yl)benzyl]propane; [4-(5-oxo-3-phenyl-5,6-dihydro-1,6-naphthyridin-2-yl)phenyl]-N-{[5-(1H-pyrazol-1-yl)pyridin-2-yl]methyl}methane; (6-chloropyridin-3-yl)-N-[4-(5-oxo-3-phenyl-5,6-dihydro-1,6-naphthyridin-2-yl)benzyl] methane; [4-(5-oxo-3-phenyl-5,6-dihydro-1,6-naphthyridin-2-yl)phenyl]-N-(pyridin-3-ylmethyl)methane; (6-methoxypyridin-3-yl)-N—[4-(5-oxo-3-phenyl-5,6-dihydro-1,6-naphthyridin-2-yl)benzyl]methane; (6-oxo-1,6-dihydropyridin-3-yl)-N-[4-(5-oxo-3-phenyl-5,6-dihydro-1,6-naphthyridin-2-yl)benzyl]methane; 3-[(2-hydroxyphenyl) amino]-3-oxo-N-[4-(5-oxo-3-phenyl-5,6-dihydro-1,6-naphthyridin-2-yl)benzyl]propane; 3-[(3-hydroxyphenyl) amino]-3-oxo-N—[4-(5-oxo-3-phenyl-5,6-dihydro-1,6-naphthyridin-2-yl)benzyl]propane; 3-[(4-hydroxyphenyl) amino]-3-oxo-N-[4-(5-oxo-3-phenyl-5,6-dihydro-1,6-naphthyridin-2-yl)benzyl]propane; 3-[(2-m ethoxyphenyl) amino]-3-oxo-N-[4-(5-oxo-3-phenyl-5,6-dihydro-1,6-naphthyridin-2-yl)benzyl]propane; 3-[(2-methoxyphenyl) (methyl)amino]-3-oxo-N-[4-(5-oxo-3-phenyl-5,6-dihydro-1,6-naphthyridin-2-yl)benzyl]propane; 3-[(3-hydroxypyridin-2-yl)amino]-3-oxo-N-[4-(5-oxo-3-phenyl-5,6-dihydro-1,6-naphthyridin-2-yl)benzyl]propane; 3-phenyl-2-[4-({[4-(1H-pyrazol-1-yl)benzyl] amino}methyl)phenyl]-1,6-naphthyridin-5(6H)-one; 2,2,2-trifluoro-N-[4-(6-methyl-5-oxo-3-phenyl-5,6-dihydro-1,6-naphthyridin-2-yl)benzyl]ethanesulfonamide); (36) U.S. Pat. No. 7,705,014 to Chen et al. (substituted naphthyridines including 2-{4-[(3-hydroxy-4,7-dihydroisoxazolo[5,4-c] pyridin-6(5H)-yl)methyl]phenyl}-3-phenyl-1,6-naphthyridin-5(6H)-one; 3-phenyl-2-(4-{[7-(trifluoromethyl)-3,4-dihydroisoquinolin-2(1H)-yl]methyl}phenyl)-1,6-naphthyridin-5(6H)-one; methyl 2-[4-(5-oxo-3-phenyl-5,6-dihydro-1,6-naphthyridin-2-yl)benzyl]-1,2,3,4-tetrahydroisoquinoline-6-carboxylate; methyl 2-[4-(5-oxo-3-phenyl-5,6-dihydro-1,6-naphthyridin-2-yl)benzyl]-1,2,3,4-tetrahydroisoquinoline-7-carboxylate; 2-{4-[(6-amino-3,4-dihydroisoquinolin-2(1H)-yl)methyl]phenyl}-3-phenyl-1,6-naphthyridin-5(6H)-one; 3-phenyl-2-[4-(1,4,6,7-tetrahydro-5H-pyrazolo[4,3-c]pyridin-5-ylmethyl)phenyl]-1,6-naphthyridin-5(6H)-one); (37) U.S. Pat. No. 7,655,649 to Bilodeau et al. (substituted pyridazines and pyrimidines including N,N-dimethyl-5-phenyl-6-(4-{[4-(5-pyridin-2-yl-1H-pyrazol-3-yl)piperidin-1-yl]methyl}phenyl) pyridazin-3-amine; N-methyl-5-phenyl-6-(4-{[4-(5-pyridin-2-yl-1H-pyrazol-3-yl)piperidin-1-yl]methyl}phenyl)pyridazin-3-amine; 4-[5-phenyl-6-(4-{[4-(5-pyridin-2-yl-1H-1,2,4-triazol-3-yl)-piperidin-1-yl]methyl}phenyl)pyridazin-3-yl] morpholine; tert-butyl 4-[5-phenyl-6-(4-{[4-(5-pyridin-2-yl-1H-1,2,4-triazol-3-yl)piperidin-1-yl]methyl}phenyl) pyridazin-3-yl]piperazine-1-carboxylate; 4-phenyl-6-piperazin-1-yl-3-(4-{[4-(5-pyridin-2-yl-1H-1,2,4-triazol-3-yl)-piperidin-1-yl]methyl}phenyl)pyridazine; 4-[5-phenyl-6-(4-{[4-(5-pyridin-2-yl-1H-1,2,4-triazol-3-yl)piperidin-1-yl]methyl}phenyl)pyridazin-3-yl]thiomorpholine); (38) U.S. Pat. No. 7,638,530 to Bilodeau et al. (compounds that contain a five-membered heterocyclic ring fused to a substituted pyridine moiety including 1-{1-[4-(3-amino-5-phenyl-1H-pyrazolo[3,4-b]pyridin-6-yl)benzyl]piperidin-4-yl}-1,3-dihydro-2H-benzimidazol-2-one; 1-{1-[4-(3-amino-1-methyl-5-phenyl-1H-pyrazolo[3,4-b]pyridin-6-yl)benzyl] piperidin-4-yl}-1,3-dihydro-2H-benzimidazol-2-one; 1-(1-{4-[3-amino-1-(2-morpholin-4-ylethyl)-5-phenyl-1H-pyrazolo[3,4-b]pyridin-6-yl]benzyl}piperidin-4-yl)-1,3-dihydro-2H-benzimidazol-2-one; 1-(1-{4-[3-amino-1-(2-hydroxyethyl)-5-phenyl-1H-pyrazolo[3,4-b]pyridin-6-yl] benzyl}piperidin-4-yl)-1,3-dihydro-2H-benzimidazol-2-one; 1-[1-(4-{3-amino-1-[2-(1H-imidazol-4-yl)ethyl]-5-phenyl-1H-pyrazolo[3,4-b]pyridin-6-yl}benzyl)piperidin-4-yl]-1,3-dihydro-2H-benzimidazol-2-one; 1-methyl-6-(4-{[4-(2-methyl-1H-benzimidazol-1-yl)piperidin-1-yl] methyl}phenyl)-5-phenyl-1H-pyrazolo[3,4-b]pyridin-3-amine; 9-{1-[4-(3-amino-1-methyl-5-phenyl-1H-pyrazolo [3,4-b]pyridin-6-yl)benzyl]piperidin-4-yl}-9H-purin-6-amine); (39) U.S. Pat. No. 7,625,890 to Heerding et al. (1H-imidazo[4,5-c]pyridin-2-yl compounds including 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol; 4-(2-(4-amino-1,2,5-oxadiazol-3-yl)-1-ethyl-7-{[(2S)-2-thiomorpholinylmethyl]oxy}-1H-imidazo[4,5-c] pyridin-4-yl)-2-methyl-3-butyn-2-ol; 4-(2-(4-amino-1,2,5-oxadiazol-3-yl)-1-ethyl-7-{[(2S)-2-morpholinylmethyl] oxy}-1H-imidazo[4,5-c]pyridin-4-yl)-2-methyl-3-butyn-2-ol; and 4-[2-(4-amino-1,2,5-oxadiazol-3-yl)-1-ethyl-7-({[(2R)-6-methyl-2-morpholinyl]methyl}oxy)-1H-imidazo [4,5-c]pyridin-4-yl]-2-methyl-3-butyn-2-ol); (40) U.S. Pat. No. 7,625,890 to Heerding et al. (1H-imidazo[4,5-c]pyridin-2-yl compounds including 4-(2-(4-amino-1,2,5-oxadiazol-3-yl)-1-ethyl-7-{[(3S)-3-piperidinylmethyl]oxy}-1H-imidazo [4,5-c]pyridin-4-yl)-2-methyl-3-butyn-2-ol; 4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol; 4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol; and 4-[2-(4-amino-1,2,5-oxadiazol-3-yl)-1-ethyl-7-({[(2R)-6-methyl-2-morpholinyl]methyl}oxy)-1H-imidazo[4,5-c] pyridin-4-yl]-2-methyl-3-butyn-2-ol); (41) U.S. Pat. No. 7,589,068 to Cosford et al. (substituted naphthyridines including 5-methoxy-2(4-{[4-5-pyridin-2-yl-4H-1,2,4-triazol)piperidin-1-yl]methyl}phenyl)-3-(2-thienyl)-1,6-naphthyridine; 2-(4-{[4-(5-pyridin-2-yl-4H-1,2,4-4triazol-3-yl) piperidin-1-yl]methyl}phenyl)-3-(2-thienyl)-1,6-naphthyridin-5(6H)-one; 1-{4-[4-(3-pyrimidin-5-ylquinoxalin-2-yl)benzyl]cyclohexyl}-1,3-dihydro-2H-benimidazol-2-one; 3-[3-(4-{[4-2-oxo-2,3-dihydro-1H-benimidazol-1-yl)cyclohexyl]methyl}phenyl)quinoxalin-2-yl]thiophene-2-carbaldehyde; 1-(4{4-[3(H-pyrazol-5-yl) quinoxalin-2-yl]benzyl}cyclohexyl)-1,3-dihydro-2H-benzimidazol-2-one; and 2-[4-(1-amino-1-methylethyl) phenyl]-3-(2-thienyl)-1,6-naphthyridin-5(6H)-one); (42) U.S. Pat. No. 7,579,355 to Bilodeau et al. (substituted pyridines including 1-(1-{4-[5-(5-amino-1,3,4-thiadiazol-2-yl)-3-phenylpyridin-2-yl]benzyl}piperidin-4-yl)-1H-pyrazolo[3,4-d]pyrimidin-4-amine; 1-(1-{4-[5-(1,2,4-oxadiazol- 3-yl)-3-phenylpyridin-2-yl]benzyl}piperidin-4-yl)-1H-pyrazolo[3,4-d]pyrimidin-4-amine; 1-(1-{4-[3-phenyl-5-(1H-1,2,4-triazol-5-yl)pyridin-2-yl]benzyl}piperidin-4-yl)-1H-pyrazolo[3,4-d]pyrimidin-4-amine; 1-{1-[4-(3-phenyl-5-pyrimidin-2-ylpyridin-2-yl)benzyl]piperidin-4-yl}-1H-pyrazolo[3,4-d]pyrimidin-4-amine; 1-{1-[4-(5'-phenyl-2,3'-bipyridin-6'-yl)benzyl]piperidin-4-yl}-1H-pyrazolo[3,4-d]pyrimidin-4-amine); (43) U.S. Pat. No. 7,576,209 to Kelly, III et al. (substituted naphthyridines including 8-[4-(1-aminocyclobutyl)phenyl]-9-phenyl[1,2,4]triazolo[3,4-f]-1,6-naphthyridin-3(2H)-one); (44) U.S. Pat. No. 7,544,677 to Bilodeau et al. (substituted 5-deazapteridines including 2-(methylthio)-6-phenyl-7-(4-{[4-(5-pyridin-2-yl-4H-1,2,4-triazol-3-yl)piperidin-1-yl]methyl}phenyl)pyrido[2,3-d]pyrimidine; 2-(methylthio)-6-phenyl-7-(4-{[4-(3-pyridin-3-yl-1,2,4-oxadiazol-5-yl)piperidin-1-yl]methyl}phenyl)pyrido[2,3-d]pyrimidine; 2-(methylthio)-6-phenyl-7-(4-{[4-(5-pyridin-4-yl-1H-pyrazol-3-yl)piperidin-1-yl]methyl}phenyl)pyrido[2,3-d]pyrimidine; 5-(1-{4-[2-(methylthio)-6-phenylpyrido[2,3-d]pyrimidin-7-yl]benzyl}piperidin-4-yl)-1,3,4-thiadiazol-2-amine; 1-{4-[2-(methylthio)-6-phenylpyrido[2,3-d]pyrimidin-7-yl]benzyl}-N-pyridin-4-ylpiperidine-4-carboxamide; 1-(1-{4-[2-(methylthio)-6-phenylpyrido[2,3-d]pyrimidin-7-yl]benzyl}piperidin-4-yl)-1H-pyrazolo[3,4-d]pyrimidin-4-amine; 6-phenyl-7-(4-{[4-(5-pyridin-2-yl-4H-1,2,4-triazol-3-yl)piperidin-1-yl]methyl}phenyl)pyrido[2,3-d]pyrimidine-2-carboxamide); (45) U.S. Pat. No. 7,524,850 to Duggan et al. (substituted pyrazines including 1-{1-[4-(5-hydroxy-6-isobutyl-3-phenylpyrazin-2-yl)benzyl]piperidin-4-yl-}-1,3-dihydro-2H-benzimidazol-2-one; 1-{1-[4-(6-hydroxy-5-isobutyl-3-phenylpyrazin-2-yl)benzyl]piperidin-4-yl-}-1,3-dihydro-2H-benzimidazol-2-one; 1-{1-[4-(5-hydroxy-3-phenylpyrazin-2-yl)benzyl]piperidin-4-yl-}-1,3-dihydro-2H-benzimidazol-2-one; 1-{1-[4-(6-hydroxy-3-phenylpyrazin-2-yl)benzyl]piperidin-4-yl-}-1,3-dihydro-2H-benzimidazol-2-one; 1-{1-[4-(6-benzyl-5-hydroxy-3-phenylpyrazin-2-yl)benzyl]piperidin-4-yl-}-1,3-dihydro-2H-benzimidazol-2-one; 1-{1-[4-(5-benzyl-6-hydroxy-3-phenylpyrazin-2-yl)benzyl]piperidin-4-yl-}-1,3-dihydro-2H-benzimidazol-2-one; 1-{1-[4-(6-sec-butyl-5-hydroxy-3-phenylpyrazin-2-yl)benzyl]piperidin-4-yl-}-1,3-dihydro-2H-benzimidazol-2-one; 1-{1-[4-(5-sec-butyl-6-hydroxy-3-phenylpyrazin-2-yl)benzyl]piperidin-4-yl}-1,3-dihydro-2H-benzimidazol-2-one); (46) U.S. Pat. No. 7,504,410 to Bryant et al. (pyrimidine derivatives including N-[3-[[5-bromo-4-[[3-[[[1-(trifluoromethyl)cyclobutyl]carbonyl]amino]propyl]amino]-2-pyrimidinyl]amino]phenyl]-1-pyrrolidinecarboxamide, N-[3-[[5-bromo-4-[[3-[[1-oxo-3-(phenylsulfonyl)propyl]amino]propyl]amino]-2-pyrimidinyl]amino]phenyl]-1-pyrrolidinecarboxamide, N-[3-[[5-bromo-2-[[3-[(1-pyrrolidinylcarbonyl)amino]phenyl]amino]-4-pyrimidinyl]amino]propyl]-2,2-dimethyl-propanediamide, N-[3-[[4-[[3-[[(1-aminocyclopentyl)carbonyl]amino]propyl]amino]-5-bromo-2-pyrimidinyl]amino]phenyl]-1-pyrrolidinecarboxamide, N-[3-[[4-[[3-[[(1-aminocyclobutyl)carbonyl]amino]propyl]amino]-5-iodo-2-pyrimidinyl]amino]phenyl]-1-pyrrolidinecarboxamide, $N^1$-[3-[[5-bromo-2-[[3-[(1-pyrrolidinylcarbonyl)amino]phenyl]amino]-4-pyrimidinyl]amino]propyl]-1,1-cyclopentanedicarboxamide, (4R)—N-[3-[[5-bromo-2-[[3-(2,5-dioxo-1-imidazolidinyl)phenyl]amino]-4-pyrimidinyl]amino]propyl]-2-oxo-4-thiazolidinecarboxamide, (4R)—N-[3-[[5-bromo-2-[[3-(3-methyl-2,5-dioxo-1-imidazolidinyl)phenyl]amino])-4-pyrimidinyl]amino]propyl]-2-oxo-4-thiazolidinecarboxamide, 3-[3-[[5-bromo-4-[[2-(1H-imidazol-4-yl)ethyl]amino]-2-pyrimidinyl]amino]phenyl]-2,4-imidazolidinedione, 3-[3-[[5-bromo-4-[[2-(1H-imidazol-4-yl)ethyl]amino]-2-pyrimidinyl]amino-]phenyl]-1-methyl-2,4-imidazolidinedione, N'-[3-[[5-bromo-4-[[2-(1H-imidazol-4-yl)ethyl]amino]-2-pyrimidinyl]amino]phenyl]-N-ethyl-N-8-(1-piperidinyl)ethyl]-urea); (47) U.S. Pat. No. 7,449,477 to Barda et al. (7-phenyl-isoquinoline-5-sulfonylamino derivatives including 7-phenyl-isoquinoline-5-sulfonic acid (2-amino-ethyl)-amide; 7-(3-difluoromethylphenyl)-isoquinoline-5-sulfonic acid (2-amino-ethyl)-amide; 7-(4-aminophenyl)-isoquinoline-5-sulfonic acid (2-amino-ethyl)-amide; 7-(3-aminophenyl)-isoquinoline-5-sulfonic acid (2-amino-ethyl)-amide; 7-(3-fluorophenyl)-isoquinoline-5-sulfonic acid (2-amino-ethyl)-amide; 7-(4-methylsulfonamido)-isoquinoline-5-sulfonic acid (2-amino-ethyl)-amide; 7-(3-hydroxyphenyl)-isoquinoline-5-sulfonic acid (2-amino-ethyl)-amide; 7-(4-hydroxyphenyl)-isoquinoline-5-sulfonic acid (2-amino-ethyl)-amide; 7-(4-hydroxyphenyl)-isoquinoline-5-sulfonic acid {2-[3-(4-nitro-phenyl)-propylamino]-ethyl}-amide, dihydrochloride salt; and 7-phenyl-isoquinoline-5-sulfonic acid {2-[3-(4-nitro-phenyl)-propylamino]-ethyl}-amide dimesylate); (48) U.S. Pat. No. 7,414,055 to Duggan et al. (substituted pyridines including 5-phenyl-6-[4-({[4-(1,2,3-thiadiazol-4-yl)benzyl]amino}methyl)phenyl]nicotinonitrile; 5-phenyl-6-[4-({[(1S,2R)-2-phenylcyclopropyl]amino}methyl)phenyl]nicotinonitrile; 6-(4-{[(3,4-difluorobenzyl)amino]methyl}phenyl)-5-phenylnicotinonitrile; 6-[4-({[2-(3-fluorophenyl)ethyl]amino}methyl)phenyl]-5-phenylnicotinonitrile; 6-[4-({[2-(4-fluorophenyl)ethyl]amino}methyl)phenyl]-5-phenylnicotinonitrile; 5-phenyl-6-[4-({[(4-phenylmorpholin-2-yl)methyl]amino}methyl)phenyl]nicotinonitrile; and 6-[4-({[(4-benzylmorpholin-2-yl)methyl]amino}methyl)phenyl]-5-phenylnicotinonitrile); (49) U.S. Pat. No. 7,399,764 to Duggan et al. (compounds with a five-membered heterocyclic ring fused to a substituted pyrazine moiety including 1-{1-[4-(3-phenylthieno[3,4-b]pyrazin-2-yl)benzyl]piperidin-4-yl}-1,3-dihydro-2H-benzimidazol-2-one; N-ethyl-N'-{(3R)-1-[4-(3-phenylthieno[3,4-b]pyrazin-2-yl)benzyl]pyrrolidin-3-yl}urea; N-{(3R)-1-[4-(3-phenylthieno[3,4-b]pyrazin-2-yl)benzyl]pyrrolidin-3-yl}-1,3-thiazole-5-carboxamide; 9-{1-[4-(3-phenylthieno[3,4-b]pyrazin-2-yl)benzyl]piperidin-4-yl}-9H-purin-6-amine; 2-(4-{[4-(3H-imidazo[4,5-b]pyridin-3-yl)piperidin-1-yl]methyl}phenyl)-3-phenylthieno[3,4-b]pyrazine; 9-{(1-[4-(3-phenylthieno[3,4-b]pyrazin-2-yl)benzyl]piperidin-4-yl}-9H-purine; {1-[4-(3-phenylthieno[3,4-b]pyrazin-2-yl)benzyl]-1H-benzimidazol-2-yl}methanol); (50) U.S. Pat. No. 7,396,832 to Lindsley et al. (substituted 2,3-diphenylquinoxalines including N-[4-(3-phenylquinoxalin-2-yl)benzyl]propane-1-sulfonamide); (51) U.S. Pat. No. 7,304,063 to Bilodeau et al. (heterocyclic triazine derivatives including 1-(1-{4-[3-(1,3-oxazol-2-yl)-6-phenyl-1,2,4-triazin-5-yl]benzyl}piperidin-4-yl)-1,3-dihydro-2H-benzimidazol-2-one; 1-{1-[4-(6-phenyl-3-pyrimidin-2-yl-1,2,4-triazin-5-yl)benzyl]piperidin-4-yl}-1,3-dihydro-2H-benzimidazol-2-one; 1-(1-{4-[3-(1H-imidazol-2-yl)-6-phenyl-1,2,4-triazin-5-yl]benzyl}piperidin-4-yl)-1,3-dihydro-2H-benzimidazol-2-one; 1-(1-{4-[3-(1-methyl-1H-pyrazol-5-yl)-6-phenyl-1,2,4-triazin-5-yl]benzyl}piperidin-4-yl)-1,3-dihydro-2H-benzimidazol-2-one; 1-(1-{4-[6-phenyl-3-(1H-pyrazol-5-yl)-1,2,4-triazin-5-yl]benzyl}piperidin-4-yl)-1,3-dihydro-2H-benzimidazol-2-one; 1-(1-{4-[6-phenyl-3-(1H-pyrazol-5-yl)-1,2,4-triazin-5-yl]benzyl}piperidin-4-yl)-1,3-dihydro-2H-benzimidazol-2-one; 1-(1-{4-[3-(1-methyl-1H-pyrazol-4-yl)-6-phenyl-1,2,4-triazin-5-yl]benzyl}piperidin-4-yl)-1,3-dihydro-2H-benzimidazol-2-one; 1-(1-{4-[3-(1-methyl-1H-imidazol-2- yl)-6-phenyl-1,2,4-triazin-5-yl]benzyl}piperidin-4-yl)-1,3-dihydro-2H-benzimidazol-2-one); (52) U.S. Pat. No. 7,263,869 to Lindsley et al. (ring-fused quinoxalinyl derivatives including 1-{1-[4-(7-phenyl-1H-imidazo[4,5-g]quinoxalin-6-yl)benzyl]piperidin-4-yl}-1,3-dihydro-2H-benzimidazol-2-one; N,N-dimethyl-1-[4-(6-phenyl-1H-imidazo[4,5-g]quinoxalin-7-yl)phenyl]methanamine; 1-{1-[4-(3-phenylbenzo[g]quinoxalin-2-yl)benzyl]piperidin-4-yl}-1,3-dihydro-2H-benzimidazol-2-one); (53) U.S. Pat. No. 7,223,738 to Bilodeau et al. (substituted 2,3-diphenylquinoxalines including 1-{1-[4-(3-phenylquinoxalin-2-yl)benzyl]piperidin-4-yl}-1,3-dihydro-2H-benzimidazol-2-one; 3-(4-{[4-(2-oxo-2,3-dihydro-1H-benzimidazol-1-yl)piperdin-1-yl]methyl}phenyl)-2-phenylquinaxoline-6-carboxylic acid; 2-(4-{[4-(2-oxo-2,3-dihydro-1H-benzimidazol-1-yl)piperdin-1-yl]methyl}phenyl)-3-phenylquinaxoline-6-carboxylic acid; N-[3-(1H-imidazol-1-yl)propyl]-3-(4-{[4-(2-oxo-2,3-dihydro-1H-benzimidazol-1-yl)piperdin-1-yl]methyl}phenyl)-2-phenylquinaxoline-6-carboxamide; 1-{1-[4-(3-phenylpyrido[3,4-b]pyrazin-2-yl)benzyl]piperidin-4-yl}-1,3-dihydro-2H-benzimidazol-2-one; 1-{1-[4-(2-phenylpyrido[3,4-b]pyrazin-3-yl)benzyl]piperidin-4-yl}-1,3-dihydro-2H-benzimidazol-2-one; 1-{1-[4-(2-phenylquinolin-3-yl)benzyl]piperdin-4-yl}-1,3-dihydro-2H-benzimidazol-2-one; 1-{1-[4-(6,7-diamino-3-phenylquinoxalin-2-yl)benzyl]piperidin-4-yl}-1,3-dihydro-2H-benzimidazol-2-one; 2-(4-{[3-(1H-indol-3-yl)pyrrolidin-1-yl]methyl}phenyl)-3-phenylquinoxaline); (54) U.S. Pat. No. 7,098,208 to Owens et al. (substituted triazolo[4,3-b]pyridazines including N'-(7-cyclobutyl-3-phenyl-[1,2,4]triazolo[4,3-b]pyridazin-6-yl)-2,2, N, N-tetramethyl-propane-1,3-diamine; N'-(7-cyclobutyl-3-(3,5-difluoro-phenyl)-[1,2,4]triazolo[4,3-b]pyridazin-6-yl)-2,2,N,N-tetramethyl-propane-1,3-diamine; N'-(7-cyclobutyl-3-(3,4-difluoro-phenyl)-[1,2,4]triazolo[4,3-b]pyridazin-6-yl)-2,2,N,N-tetramethyl-propane-1,3-diamine; N'-(7-Cyclobutyl-3-(4-fluoro-phenyl)-[1,2,4]triazolo[4,3-b]pyridazin-6-yl)-2,2, N, N-tetramethyl-propane-1,3-diamine; and N'-(7-cyclobutyl-3-(3-fluoro-phenyl)-[1,2,4]triazolo[4,3-b]pyridazin-6-yl)-2,2, N, N-tetramethyl-propane-1,3-diamine); and U.S. Pat. No. 6,958,334 to Owens et al. (substituted triazolo[4,3-b]pyridazines including 2,2,N,N-tetramethyl-N-(3-phenyl-[1,2,4]triazolo[3,4-a]phthalazin-6-yl)-propane-1,3-diamine N'-[3-(4-methoxy-phenyl)-[1,2,4]triazolo[4,3-a]phthalazin-6-yl)-2,2, N, N-tetramethyl-propane-1,3-diamine).

Additional Akt inhibitors are described in U.S. Pat. No. 9,133,168 to Brollo et al., including compounds of Formula (A-I), (A-II), and (A-III). Formula (A-I) is:

(A-I)

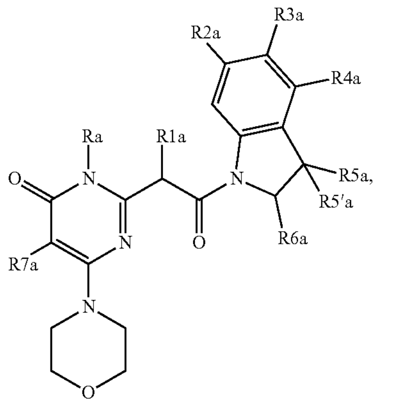

wherein:

(1) Ra is hydrogen or alkyl;

(2) R1a is hydrogen or methyl;

(3) R2a is hydrogen or fluorine;

(4) R3a is hydrogen or halogen;

(5) R4a is hydrogen, a halogen, a hydroxyl, an alkyl group, or an alkoxy group, wherein the alkyl group is optionally substituted with one or more groups, which may be identical or different and that are halogen or hydroxyl, and wherein the alkoxy group is optionally substituted with one or more halogens;

(6) R5a and R5'a are identical or different and are hydrogen or alkyl;

(7) R6a is hydrogen or an alkyl group that is optionally substituted with one or more groups, which may be identical or different and that are halogen or hydroxyl; and (8) R7 is halogen.

Formula (A-III) is:

(A-II)

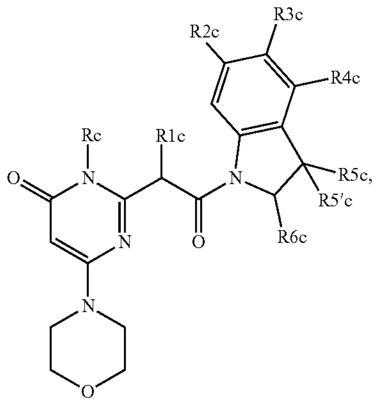

wherein:

(1) Rc is hydrogen or alkyl;

(2) R1c is hydrogen or methyl;

(3) R2c is hydrogen or fluorine;

(4) R3c is hydrogen or halogen;

(5) R4c is hydrogen, a halogen, a hydroxyl, an alkyl group, or an alkoxy group, wherein the alkyl group is optionally substituted with one or more groups, which may be identical or different and that are halogen or hydroxyl, and wherein the alkoxy group is optionally substituted with one or more halogens;

(6) R5c and R5'c are identical or different and are hydrogen or alkyl; and (7) R6 is hydrogen or an alkyl group, wherein the alkyl group is optionally substituted with one or more halogens, hydroxyl groups, and alkoxy groups.

Formula (A-III) is:

(A-III)

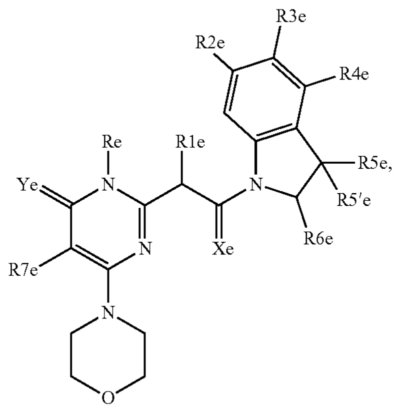

wherein:

(1) Xe and Ye can be identical or different, wherein Xe is O or S and Ye is $^P$S;

(2) Re is hydrogen or alkyl;

(3) R1e is hydrogen or methyl;

(4) R2e is hydrogen or fluorine;

(5) R3e is hydrogen or halogen;

(6) R4e is hydrogen, a halogen, a hydroxyl, an alkyl group, or an alkoxy group, wherein the alkyl group is optionally substituted with one or more groups, which may be identical or different and that are halogen or hydroxyl, and wherein the alkoxy group is optionally substituted with one or more halogens;

(7) R5e and R5'e are identical or different and are hydrogen or alkyl;

(8) R6e is hydrogen or an alkyl group, wherein the alkyl group is optionally substituted with one or more halogens, hydroxyl groups, and alkoxy groups; and (9) R7e is hydrogen or halogen.

Additional Akt inhibitors are described in U.S. Pat. No. 8,993,565 to Carry et al., including compounds of Formula (A-IV). Formula (A-IV) is:

(A-IV)

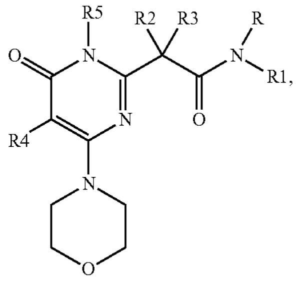

wherein:

(1) R1 represents an aryl or heteroaryl radical optionally substituted with one or more radicals, which may be identical or different, chosen from halogen atoms and hydroxyl, CN, nitro, —COOH, —COOalk, —NRxRy, —CONRxRy, —NRxCORy, —CORy, —$NRxCO_2Rz$, alkoxy, phenoxy, alkylthio, alkyl, alkenyl, alkynyl, cycloalkyl, O-cycloalkyl, heterocycloalkyl, aryl and heteroaryl radicals; the latter alkoxy, phenoxy, alkylthio, alkyl, alkenyl, alkynyl, heterocycloalkyl, aryl and heteroaryl radicals being themselves optionally substituted with one or more radicals, which may be identical or different, chosen from halogen atoms and hydroxyl, alkoxy, NRvRw, heterocycloalkyl or heteroaryl radicals; the aryl and heteroaryl radicals being, in addition, optionally substituted with one or more alkyl and alkoxy radicals, themselves optionally substituted with one or more halogen atoms; it being possible for the heterocycloalkyl and heteroaryl radicals to additionally contain an oxo radical;

(2) R represents a hydrogen atom or else forms, with R1, a saturated or partially or totally unsaturated 5- or 6-membered ring fused to an aryl or heteroaryl residue and optionally containing one or more other heteroatoms chosen from O, S, N, NH and Nalk, this bicyclic radical being optionally substituted with one or more radicals, which may be identical or different, chosen from halogen atoms and CO—$NH_2$, hydroxyl, alkyl and alkoxy radicals; the latter alkyl radical being itself optionally substituted with a hydroxyl, alkoxy, $NH_2$, NHalk or $N(alk)_2$ radical;

(3) R2 and R3, which may be identical or different, independently represent a hydrogen atom, a halogen atom or an alkyl radical optionally substituted with one or more halogen atoms;

(4) R4 represents a hydrogen atom; R5 represents a hydrogen atom or an alkyl radical optionally substituted with one or more halogen atoms;

(5) NRvRw being such that Rv represents a hydrogen atom or an alkyl radical and Rw represents a hydrogen atom or a cycloalkyl radical, $CO_2$alk, or an alkyl radical optionally substituted with one or more radicals, which may be identical or different, chosen from hydroxyl, alkoxy, NRvRw and heterocycloalkyl radicals; or (6) Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted; NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or (7) Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;

(8) the cyclic radicals that Rx and Ry or Rv and Rw, respectively, can form, with the nitrogen atom to which they are attached, being optionally substituted with one or more radicals, which may be identical or different, chosen from halogen atoms and alkyl, hydroxyl, oxo, alkoxy, $NH_2$; NHalk and $N(alk)_2$ radicals;

(9) Rz represents the values of Ry except for hydrogen; Rx, Ry and Rz in the —NRxCORy, —CORy and $NRxCO_2Rz$ radicals being chosen from the meanings indicated above for Rx, Ry and Rz; and

(10) all the above alkyl (alk), alkoxy and alkylthio radicals being linear or branched and containing from 1 to 6 carbon atoms.

Additional Akt inhibitors are disclosed in U.S. Pat. No. 8,946,278 to Seefeld et al., including compounds of Formula (A-V). Formula (A-V) is:

wherein:

(A-V)

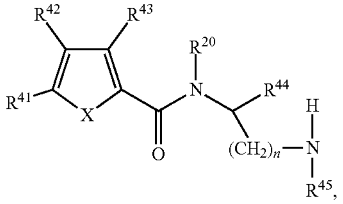

(1) $R^{41}$ and $R^{42}$ are each independently selected from a moiety of Subformula (A-V(a))

(A-V(a))

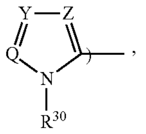

halogen, $C_1$-$C_4$ alkyl, substituted $C_1$-$C_4$ alkyl, $C_1$-$C_4$ alkoxy, substituted $C_1$-$C_4$ alkoxy, furan, substituted furan, thiophene, and substituted thiophene;

(2) wherein Q and Y are independently selected from nitrogen and —$C(R^{70})$—; and (3) Z is selected from nitrogen and —$C(R^{48})$—, provided that at least one and at most two of Q, Y, and Z are nitrogen, and $R^{30}$ is selected from $C_1$-$C_4$ alkyl and $C_1$-$C_4$ alkyl substituted with from one to three fluorine atoms;

(4) $R^{70}$ is selected from hydrogen and halogen;

(5) $R^{48}$ is selected from hydrogen, $C_1$-$C_4$ alkyl, substituted $C_1$-$C_4$ alkyl, aryl, substituted aryl, heteroaryl, substituted heteroaryl, cycloalkyl, substituted cycloalkyl, heterocycloalkyl, substituted heterocycloalkyl, and halogen;

(6) $R^{43}$ is selected from hydrogen, halogen, $C_1$-$C_4$ alkyl, substituted $C_1$-$C_4$ alkyl, $C_1$-$C_4$ alkoxy, substituted $C_1$-$C_4$ alkoxy, furan, and thiophene;

(7) $R^{44}$ is absent or selected from —$(CR^{60}R^{61})_m$AR wherein the AR is unsubstituted, —$(CR^{60}R^{61})_m$AR wherein the AR is substituted, and $C_1$-$C_6$ alkyl;

(8) where m is 0 to 3 and AR is a cyclic or polycyclic aromatic or saturated or unsaturated non-aromatic ring containing from 3 to 16 carbon atoms and optionally containing from one to three heteroatoms, provided that when the ring is aromatic and the number of carbon atoms is 3 the ring contains at least two heteroatoms and when the ring is aromatic and the number of carbon atoms is 4 the ring contains at least one heteroatom, and $R^{60}$ and $R^{61}$ are independently selected from hydrogen and $C_1$-$C_4$ alkyl, provided that when m is 3 no more than 4 of $R^{60}$ and $R^{61}$ when added together are $C_1$-$C_4$ alkyl;

(9) $R^{45}$ is selected from hydrogen and $C_1$-$C_4$ alkyl;

(10) $R^{20}$ is selected from hydrogen, $C_1$-$C_4$ alkyl, and alkoxy;

(11) X is selected from O, S, and $R^{49}$, where $R^{49}$ is selected from hydrogen and $C_1$-$C_4$ alkyl; and

(12) n is 0 to 2 and this moiety is optionally, if applicable, substituted by hydroxy$C_1$-$C_4$ alkyl;

(13) provided that only one of $R^{41}$ and $R^{42}$ is from a moiety of Formula (A-V(a)).

Additional Akt inhibitors are described in U.S. Pat. No. 8,592,475 to Rouse et al., including compounds of Formula (A-VI). Formula (A-VI) is:

(A-VI)

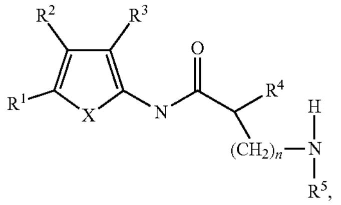

wherein:

(1) $R^1$ and $R^2$ are independently selected from a moiety of Subformula (A-VI(a))

(A-VI(a))

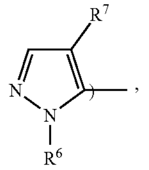

halogen, and $C_1$-$C_4$ alkyl, wherein $R^6$ is $C_1$-$C_4$ alkyl and $R^7$ is selected from hydrogen, $C_1$-$C_4$ alkyl, and halogen;

(2) $R^3$ is selected from hydrogen, $C_1$-$C_4$ alkyl, and halogen;

(3) $R^4$ is selected from —$(CH_2)_m$aryl and —$(CH_2)_m$aryl wherein the aryl is substituted, where m is 0 to 2;

(4) $R^5$ is selected from hydrogen and $C_1$-$C_4$ alkyl;

(5) X is selected from O and S; and (6) n is 0 to 2;

(7) provided that only one of $R^1$ and $R^2$ is a moiety of Formula (A-VI(a)); and (8) further provided that at least one of $R^1$, $R^2$, and $R^3$ is hydrogen.

Additional Akt inhibitors are described in U.S. Pat. No. 8,436,002 to Beight et al., including compounds of Formula (A-VII). Formula (A-VII) is:

(A-VII)

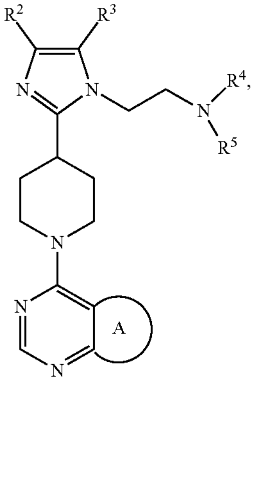

wherein:

(1) A is a moiety of Subformula (A-VII(a)) or (A-VII(b)), (A-VII(a))

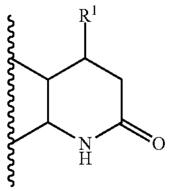

(A-VII(b))

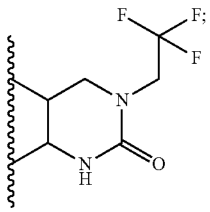

(2) $R^1$ is $CH_3$, $CH_2CH_3$ or $CF_3$;

(3) $R^2$ is H, $CF_3$, $CH_2CF_3$, $CH_2CH_2CF_3$, $C_1$-$C_4$ alkyl, $C_3$-$C_6$ cycloalkyl, CN, Cl, Br, CH═$CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H; or (4) $R^2$ and $R^3$ are both Cl; and $R^4$ is H and $R^5$ is $CH_3$, $C(CH_3)_3$, $CH(CH_3)_2$, cyclobutyl, cyclopentyl, $CH_2$-cyclopropyl, $C(CH_3)_2CH_2CH_3$ or tetrahydropyran-4-yl; or (5) $R^4$ and $R^5$ are both $CH_3$; or $R^4$ and $R^5$ together with the N to which they are attached form a pyrrolidine, optionally substituted by hydroxy at the 3-position, or an azetidine.

Additional Akt inhibitors are described in U.S. Pat. No. 8,377,937 to Bencsik et al., including compounds of Formula (A-VIII). Formula (A-VIII) is:

(A-VIII)

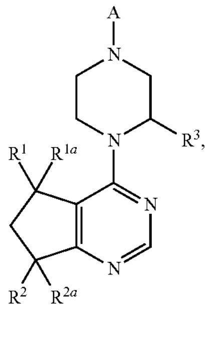

wherein:

(1) $R^1$ and $R^{1a}$ are independently selected from hydrogen, methyl, ethyl, vinyl, trifluoromethyl, $CHF_2$, or $CH_2F$;

(2) $R^2$ is hydrogen, hydroxy, methoxy, or fluoro;

(3) $R^{2a}$ is hydrogen, methyl, or fluoro;

(4) $R^3$ is hydrogen, methyl, ethyl, or trifluoromethyl;

(5) A is a moiety of Subformula (A-VIII(a))

(A-VIII(a))

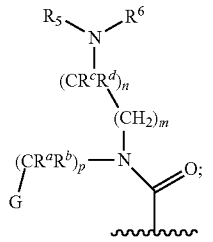

(6) G is phenyl optionally substituted by one to four $R^e$ groups or a 5-6 membered heteroaryl optionally substituted by a halogen;

(7) $R^5$ and $R^6$ are independently H, $OCH_3$, $C_3$-$C_6$-cycloalkyl optionally substituted with F, OH, $C_1$-$C_3$ alkyl or O($C_1$-$C_3$ alkyl), 4-6 membered heterocycle optionally substituted with F, OH, $C_1$-$C_3$ alkyl, cyclopropylmethyl or C(═O)($C_1$-$C_3$ alkyl), or $C_1$-$C_6$ alkyl optionally substituted with one or more groups independently selected from OH, oxo, O($C_1$-$C_6$ alkyl), CN, F, $NH_2$, NH($C_1$-$C_6$ alkyl), N($C_1$-$C_6$ alkyl)$_2$, cyclopropyl, phenyl, imidazolyl, piperidinyl, pyrrolidinyl, morpholinyl, tetrahydropyranyl, oxetanyl or tetrahydropyranyl; or (8) or $R^5$ and $R^6$ together with the nitrogen to which they are attached form a 4-7 membered heterocyclic ring optionally substituted with one or more groups independently selected from OH, halogen, oxo, trifluoromethyl, $CH_2CF_3$, $CH_2CH_2OH$, O($C_1$-$C_3$ alkyl), C(═O)$CH_3$, $NH_2$, NHMe, $N(Me)_2$, $S(O)_2CH_3$, cyclopropylmethyl, and $C_1$-$C_3$ alkyl; or (9) $R^c$ is hydrogen and $R^d$ and $R^6$ together with the atoms to which they are attached form a 4 to 6 membered heterocyclic ring having one nitrogen atom;

(10) $R^a$ and $R^b$ are H; or

(11) $R^a$ is H, and $R^b$ and $R^6$ together with the atoms to which they are attached form a 5-6 membered heterocyclic ring having one or two ring nitrogen atoms;

(12) $R^c$ and $R^d$ are hydrogen or methyl; or

(13) $R^c$ and $R^d$ together with the atom to which they are attached from a cyclopropyl ring;

(14) each $R^e$ is independently halogen, $C_1$-$C_6$ alkyl, $C_3$-$C_6$-cycloalkyl, O—($C_1$-$C_6$ alkyl), $CF_3$, $OCF_3$, S($C_1$-$C_6$ alkyl), CN, $OCH_2$-phenyl, $NH_2$, NO2, N—($C_1$-$C_6$ alkyl)$_2$, piperidine, pyrrolidine, $CH_2F$, $CHF_2$, $OCH_2F$, $OCHF_2$, OH, $SO_2$($C_1$-$C_6$ alkyl), C(O)$NH_2$, C(O)NH($C_1$-$C_6$ alkyl), and C(O)N($C_1$-$C_6$ alkyl)$_2$;

(15) m and n are independently 0, 1, 2 or 3 with the proviso that (m+n) must equal 2, 3 or 4; and

(16) p is 0 or 1.

Additional Akt inhibitors are disclosed in U.S. Pat. No. 8,338,434 to Seefeld et al., including compounds of Formula (A-IX) and Formula (A-X). Formula (A-IX) is:

(A-IX)

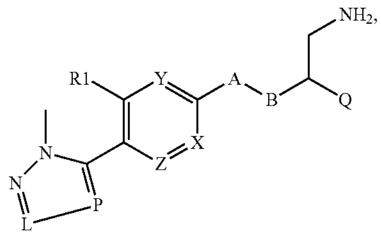

wherein:

(1) Q is selected from: phenyl, substituted phenyl, benzyl, and benzyl wherein the aromatic ring is substituted;

(2) $R^1$ is selected from: hydrogen, trifluoromethyl, hydroxy, $C_1$-$C_2$ alkyl, and halogen;

(3) L is selected from: nitrogen and —C(H)—;

(4) P is selected from: nitrogen and —C($R^{40}$)—, where $R^{40}$ is selected from: hydrogen, $C_1$-$C_4$ alkyl, and halogen;

(5) A is selected from: —C(O)— and —N(H)—;

(6) B is selected from: —C(O)— and —N(H)—; and (7) X, Y and Z are independently selected from: nitrogen, —C(H)—, and —C($R^2$)—, wherein $R^2$ is selected from halogen, trifluoromethyl, hydroxy, and $C_1$-$C_4$ alkyl; provided: A and B are not the same; and provided: X, Y and Z are not all nitrogen; and provided: that at most one of P and L are nitrogen.

Formula (A-X) is:

(A-X)

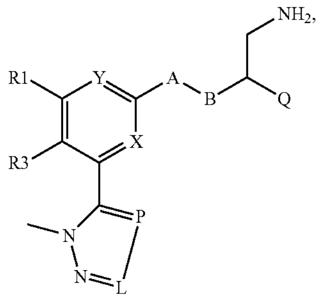

wherein:

(1) Q is selected from: phenyl, substituted phenyl, benzyl, and benzyl wherein the aromatic ring is substituted;

(2) $R^1$ is selected from: hydrogen, trifluoromethyl, hydroxy, $C_1$-$C_2$ alkyl, and halogen;

(3) $R^3$ is selected from: hydrogen, trifluoromethyl, hydroxy, $C_1$-$C_2$ alkyl, and halogen;

(4) L is selected from: nitrogen and —C(H)—;

(5) P is selected from: nitrogen and —C($R^{45}$)—, where $R^{45}$ is selected from: hydrogen, $C_1$-$C_4$ alkyl, and halogen;

(6) A is selected from: —C(O)— and —N(H)—;

(7) B is selected from: —C(O)— and —N(H)—; and (8) X and Y are independently selected from: nitrogen, —C(H)—, and —C($R^2$)—, wherein $R^2$ is selected from halogen, trifluoromethyl, hydroxy, and $C_1$-$C_4$ alkyl; provided: A and B are not the same; and provided: that at most one of P and L are nitrogen.

Additional Akt inhibitors are disclosed in U.S. Pat. No. 8,148,387 to Shepherd et al., including compounds of Formula (A-XI).] Formula (A-XI) is:

(A-XI)

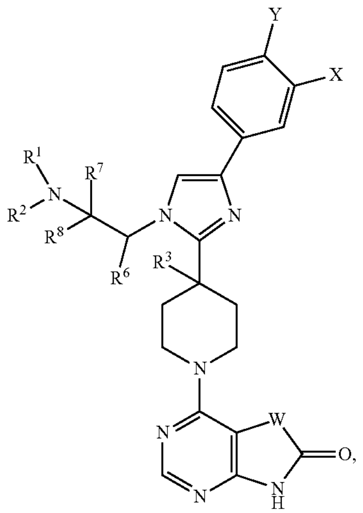

wherein:

(1) X is F, Cl, $CF_3$, CN or H;

(2) Y is F, H or Cl; $R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position, or an azetidine ring substituted with hydroxy at the 3-position;

(3) $R^3$ is H or OH;

(4) $R^6$ is H; or $R^6$ and $R^2$ together with the nitrogen atom to which $R^2$ is attached form a piperidine ring; $R^7$ and $R^8$ are independently H or $CH^3$; or $R^7$ and $R^1$ together with the nitrogen atom to which $R^1$ is attached form a pyrrolidine ring;

(5) W is $CR^4R^5$, $NR^{10}$, C═O or C═CH—$R^9$;

(6) $R^4$ and $R^5$ are independently H, $CH_3$, or $CH_2CH_3$; $R^4$ and $R^5$ together with the carbon atom to which they are attached form a cyclopentane ring; or one of $R^4$ and $R^5$ is benzyl and the other is H;

(7) $R^9$ is 2-thiazolyl, 4-pyridyl, 2-methyl-4-thiazolyl, 2-imidazolyl, 5-thiazolyl, or 4-imidazolyl; and (8) $R^{10}$ is H or $C_1$-$C_3$ alkyl.

Additional Akt inhibitors are disclosed in U.S. Pat. No. 7,414,063 to El-Awar et al., including compounds of Formula (A-XII). Formula (A-XII) is:

(A-XII)

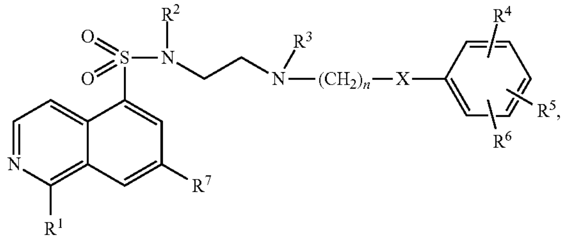

wherein:

(1) $R^1$ is hydrogen, halo, amino or hydroxy;

(2) $R^2$ is hydrogen, $C_1$-$C_4$ alkyl, or $C_2$-$C_4$ alkenyl, wherein said $C_1$-$C_4$ alkyl is optionally substituted with carboxyl, trifluoro, benzyl, acetamide, $C_1$-$C_4$ alkoxycarbonyl, substituted $C_1$-$C_4$ alkoxycarbonyl, wherein the substitution is $C_1$-$C_4$ alkyl, or —$NR^9R^{10}$, wherein $R^9$ and $R^{10}$ are each independently hydrogen or $C_1$-$C_4$ alkyl;

(3) $R^3$ is hydrogen, or $C_1$-$C_4$ alkyl;

(4) $R^4$ is hydrogen, halo, $C_1$-$C_4$ alkyl, or $C_1$-$C_4$ alkoxy;

(5) $R^5$ is hydrogen, halo, $C_1$-$C_4$ alkyl, $C_1$-$C_4$ alkoxy, trifluoromethyl, or nitro, or $R^4$ and $R^5$, together with the carbon atoms to which they are attached, form a benzo-fused ring;

(6) $R^6$ is selected from the group consisting of hydrogen, halo, $C_1$-$C_4$ alkyl, $C_2$-$C_4$ alkenyl, $C_1$-$C_4$ alkoxy, trifluoromethyl, nitro, cyano, $C_3$-$C_6$ cycloalkyl, phenyl, phenoxy, phenethyl, benzyl, benzoyl, isoxazolyl, furyl, thienyl, and methylsulfonyl; wherein said $C_1$-$C_4$ alkyl group may be substituted by N-morpholino, piperidine, pyrrolidine, or $NR^9R^{10}$; wherein said thienyl group may be substituted by halo or $C_1$-$C_4$ alkyl; and wherein said phenyl, benzoyl or benzyl group may be substituted with one to two substituents independently selected from the group consisting of halo, $C_1$-$C_4$ alkyl, $C_1$-$C_4$ alkoxy, $CF_3$, amino, nitro, hydroxy, methylsulfonylamino, sulfonamido, and $C(O)R^{11}$; wherein $R^{11}$ is selected from the group comprising N-morpholino, hydroxy or $NR^9R^{10}$;

(7) X is —O—, —$S(O)_p$—, or —$NR^8$—;

(8) n is 2 or 3;

(9) p is 0, 1, or 2;

(10) $R^7$ is hydrogen, methyl, ethynyl, phenyl, thienyl or pyrazole; wherein said phenyl, thienyl or pyrazole may be substituted by hydroxy, halo or amino; and

(11) $R^8$ is hydrogen, $C_1$-$C_4$ alkyl, benzyl or tert-butyl ester.

Additional Akt inhibitors are disclosed in U.S. Pat. No. 7,378,403 to Kozikowski et al., including compounds of Formula (A-XIII). Formula (A-XIII) is:

(A-XIII)

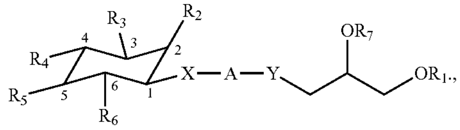

wherein:

(1) X and Y are independently selected from the group consisting of O, $CF_2$, $CH_2$, and CHF;

(2) A is independently selected from the group consisting of P(O)OH, CHCOOH, and $C(COOH)_2$;

(3) $R_2$ is selected from the group consisting of H, OH, isosteres of OH, $C_1$-$C_{25}$ alkyloxy, $C_6$-$C_{10}$ aryloxy, $C_3$-$C_8$ cycloalkyloxy, $C_3$-$C_8$ cycloalkyl $C_1$-$C_6$ alkoxy, $C_2$-$C_{22}$ alkenyloxy, $C_3$-$C_8$ cycloalkenyloxy, $C_7$-$C_{32}$ aralkyloxy, $C_7$-$C_{32}$ alkylaryloxy, $C_9$-$C_{32}$ aralkenyloxy, and $C_9$-$C_{32}$ alkenylaryloxy;

(4) $R_3$-$R_6$ are independently selected from the group consisting of H, OH, isosteres of OH; and (5) $R_1$ and $R_7$ are independently selected from the group consisting of $C_1$-$C_{25}$ alkyl, $C_6$-$C_{10}$ aryl, $C_3$-$C_8$ cycloalkyl, $C_2$-$C_{22}$ alkenyl, $C_3$-$C_8$ cycloalkenyl, $C_7$-$C_{32}$ aralkyl, $C_7$-$C_{32}$ alkylaryl, $O_8$—$O_{32}$ aralkenyl, and $C_8$-$C_{32}$ alkenylaryl;

with the provisos that (i) when X is O, Y is O or $CH_2$, and $R_3$ is H, at least one of $R_2$ and $R_4$-$R_6$ is not OH; (ii) when A is CHCOOH or $C(COOH)_2$, X and Y cannot be simultaneously O; and (iii) all of $R_2$-$R_6$ are not simultaneously H.

Additional Akt inhibitors are disclosed in U.S. Pat. No. 7,034,026 to Barnett et al., including compounds of Formula (A-XIV). Formula (A-XIV) is:

(A-XIV)

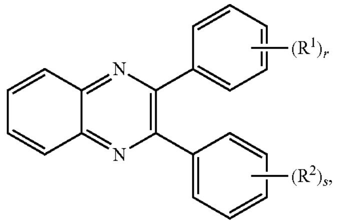

wherein:

(1) $R^1$ independently represents amino, $C_1$-$C_4$ alkylamino, di-$C_1$-$C_6$-alkylamino, amino-$C_1$, alkyl, $C_1$-$C_6$ alkylamino-($C_1$-$C_6$)alkyl, di($C_1$-$C_6$)amino-($C_1$-$C_6$)alkyl, $C_3$-$C_7$ cycloalkylamino, di-$C_3$-$C_7$ cycloalkylamino, —$C_3$-$C_7$ cycloalkylamino, N-pyrrolidinyl-$C_1$-$C_6$ alkyl, N-piperidinyl-$C_1$-$C_6$ alkyl, piperidinyl or pyrrolidinyl; and (2) $R^2$ independently represents hydrogen, amino, $C_1$-$C_6$-alkyl amino, di-$C_1$-$C_6$-alkylamino, amino-$C_1$-$C_6$ alkyl, $C_1$-$C_6$ alkylamino-($C_1$-$C_6$)alkyl or di($C_1$-$C_6$ alkyl)amino-($C_1$-$C_6$)alkyl;

(3) r is 1 to 3; and (4) s is 1 to 3.

Additional Akt inhibitors are described in U.S. Pat. No. 6,960,584 to Carling et al., including compounds of Formula (A-XV). Formula (A-XV) is:

(A-XV)

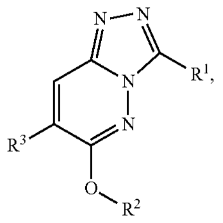

wherein:

(1) $R^1$ is phenyl, furyl, thienyl or pyridinyl, any of which groups may be optionally substituted with one, two or three substituents, independently selected from: (a) halogen; (b) $C_1$-$C_4$ alkyl; (c) $C_1$-$C_4$ alkoxy; (d) cyano; (e) di($C_1$-$C_4$ alkyl)amino; and (f) hydroxy;

(2) $R^2$ is amino-$C_1$-$C_6$ alkyl, $C_1$-$C_4$ alkylamino-($C_1$-$C_4$) alkyl, di($C_1$-$C_4$ alkyl)amino-($C_1$-$C_6$)alkyl, hydroxy-($C_1$-$C_6$) alkyl or $C_1$-$C_4$ alkoxy-($C_1$-$C_6$)alkyl, any of which groups may be optionally substituted; and (3) $R^3$ is $C_3$-$C_7$ cycloalkyl or aryl, any of which groups may be optionally substituted.

The kinase RSK (ribosomal S6 kinase) is also known as MAPK-activated protein kinase I (MAPKAP-K1) and acts as a signal transducer. Its substrates include the enzyme glycogen synthase kinase 3 (GSK3), also involved in regulation of cellular proliferation.

RSK inhibitors are disclosed in the following patents and patent publications: (1) U.S. Pat. No. 9,150,577 to Boyer et al. (substituted diazepinoindole carboxamides, including N-(2-methoxypyridin-4-yl)-1-oxo-2,3,4,5-tetrahydro-1H-[1,4]diazepino[1,2-a]indole-8-carboxamide; N-(1-ethyl-1H-benzimidazol-2-yl)-4,4-dimethyl-1-oxo-1,2,3,4-tetrahydropyrazino[1,2-a]indole-7-carboxamide; N-(1-ethyl-1H-benzimidazol-2-yl)-cis-3,4-dimethyl-1-oxo-1,2,3,4-tetrahydropyrazino[1,2-a]indole-7-carboxamide; (4R)—N-{1-[3-(dimethylamino)propyl]-1H-benzimidazol-2-yl}-4-methyl-1-oxo-1,2,3,4-tetrahydropyrazino[1,2-a]indole-7-carboxamide; N-(1-ethyl-1H-benzimidazol-2-yl)-5-methyl-1-oxo-2,3,4,5-tetrahydro-1H-[1,4]diazepino[1,2-a]indole-8-carboxamide; 5-methyl-1-oxo-N-[1-(propan-2-yl)-1H-benzimidazol-2-yl]-2,3,4,5-tetrahydro-1H-[1,4]diazepino[1,2-a]indole-8-carboxamide); (2) U.S. Pat. No. 9,073,926 Boyer et al. (substituted pyrrolodiazepine carboxamides, including 10-methyl-6-oxo-N-[1-(pyridin-4-ylmethyl)-1H-pyrazol-4-yl]-7,8,9,10-tetrahydro-6H-pyrido[3',2':4,5]pyrrolo[1,2-a][1,4]diazepine-2-carboxamide; N-(1-benzyl-1H-pyrazol-4-yl)-trans-8,9-dimethyl-6-oxo-6,7,8,9-tetrahydropyrido[3',2':4,5]pyrrolo[1,2-a]pyrazine-2-carboxamide; (9R)—N-(1-benzyl-1H-pyrazol-4-yl)-9-methyl-6-oxo-6,7,8,9-tetrahydropyrido[3',2':4,5]pyrrolo[1,2-a]pyrazine-2-carboxamide; N-(1-benzyl-1H-pyrazol-4-yl)-10-methyl-6-oxo-7,8,9,10-tetrahydro-6H-pyrid-o[3',2':4,5]pyrrolo[1,2-a][1,4]diazepine-2-carboxamide; (9S)—N-(1-benzyl-1H-pyrazol-4-yl)-9-methyl-6-oxo-6,7,8,9-tetrahydropyrido[3',2':4,5]pyrrolo[1,2-a]pyrazine-2-carboxamide; (9R)-9-methyl-N-(5-methyl-1,2-oxazol-3-yl)-6-oxo-6,7,8,9-tetrahydropyrido[3',2':4,5]pyrrolo[1,2-a]pyrazine-2-carboxamide; (9R)-9-methyl-6-oxo-N-[1-(propan-2-yl)-1H-pyrazolo[3,4-b]pyridin-5-yl]-6,7,8,9-tetrahydropyrido[3',2':4,5]pyrrolo[1,2-a]pyrazine-2-carboxamide); (3) U.S. Pat. No. 8,829,185 to Dixon et al. (substituted 4-amino-pyrrolotriazine derivatives); (4) U.S. Pat. No. 8,765,802 to Shoemaker et al. (guanidinyl hydrazone-substituted compounds); (5) U.S. Pat. No. 8,748,601 to Taunton et al. (substituted pyrrolopyrimidines and oxindoles having an electrophilic substituent); (6) U.S. Pat. No. 8,648,069 to Akritopoulou-Zanze et al. (triazolylindazole derivatives including 5-(1-benzyl-1H-1,2,3-triazol-4-yl)-1H-indazole; 5-[1-(2-methylbenzyl)-1H-1,2,3-triazol-4-yl]-1H-indazole; 5-[1-(3-methylbenzyl)-1H-1,2,3-triazol-4-yl]-1H-indazole; 5-[1-(4-methylbenzyl)-1H-1,2,3-triazol-4-yl]-1H-indazole; 5-[1-(3-methoxybenzyl)-1H-1,2,3-triazol-4-yl]-1H-indazole; 5-[1-(2-fluorobenzyl)-1H-1,2,3-triazol-4-yl]-1H-indazole; 5-[1-(3-fluorobenzyl)-1H-1,2,3-triazol-4-yl]-1H-indazole; 5-[1-(4-fluorobenzyl)-1H-1,2,3-triazol-4-yl]-1H-indazole; 5-[1-(2-chlorobenzyl)-1H-1,2,3-triazol-4-yl]-1H-indazole; 5-[1-(3-chlorobenzyl)-1H-1,2,3-triazol-4-yl]-1H-indazole; 5-[1-(4-chlorobenzyl)-1H-1,2,3-triazol-4-yl]-1H-indazole; 5-[1-(2-bromobenzyl)-1H-1,2,3-triazol-4-yl]-1H-indazole; 5-[1-(2-nitrobenzyl)-1H-1,2,3-triazol-4-yl]-1H-indazole; 5-[1-(3-nitrobenzyl)-1H-1,2,3-triazol-4-yl]-1H-indazole; 5-[1-(4-nitrobenzyl)-1H-1,2,3-triazol-4-yl]-1H-indazole; 2-{[4-(1H-indazol-5-yl)-1H-1,2,3-triazol-1-yl]methyl}benzonitrile; 3-{[4-(1H-indazol-5-yl)-1H-1,2,3-triazol-1-yl]methyl}benzonitrile; 4-{[4-(1H-indazol-5-yl)-1H-1,2,3-triazol-1-yl]methyl}benzonitrile; 5-{1-[2-(trifluoromethyl)benzyl]-1H-1,2,3-triazol-4-yl}-1H-indazole; 5-{1-[3-(trifluoromethyl)benzyl]-1H-1,2,3-triazol-4-yl}-1H-indazole); (7) United States Patent No. U.S. Pat. No. 8,426,404 to Zhang et al. (pyrimidine-substituted benzimidazole derivatives including 3-[1-(6-amino-pyrimidin-4-yl)-1H-benzoimidazol-2-ylamino]-4-methyl-N-[4-(2-methyl-imidazol-1-yl)-3-trifluoromethyl-phenyl]-benzamide, N-{3-[1-(6-amino-pyrimidin-4-yl)-1H-benzoimidazol-2-ylamino]-4-methyl-phenyl}-3-morpholin-4-yl-5-trifluoromethyl-benzamide, N-(3-{1-[6-(4-diethylamino-butylamino)-pyrimidin-4-yl]-1H-benzoimidazol-2-ylamino}-4-methyl-phenyl)-3-trifluoromethyl-benzamide, N-(3-{1-[6-(4-diethylamino-butylamino)-pyrimidin-4-yl]-1H-benzoimidazol-2-ylamino}-4-methyl-phenyl)-4-(2-methyl-imidazol-1-yl)-3-trifluoromethyl-benzamide, N-(3-{1-[6-(4-diethylamino-butylamino)-pyrimidin-4-yl]-1H-benzoimidazol-2-ylamino}-4-methyl-phenyl)-3-(4-methyl-imidazol-1-yl)-5-trifluoromethyl-benzamide, N-(3-{1-[6-(4-diethylamino-butylamino)-pyrimidin-4-yl]-1H-benzoimidazol-2-ylamino}-4-methyl-phenyl)-4-(4-ethyl-piperazin-1-yl-methyl)-3-trifluoromethyl-benzamide, N-{3-[1-(6-amino-pyrimidin-4-yl)-1H-benzoimidazol-2-ylamino]-4-methyl-phenyl}-3-trifluoromethyl-benzamide, N-{3-[1-(6-amino-pyrimidin-4-yl)-1H-benzoimidazol-2-ylamino]-4-methyl-phenyl}-4-(2-methyl-imidazol-1-yl)-3-trifluoromethyl-benzamide); (8) U.S. Pat. No. 8,329,722 Siu et al. (pyridonaphthyridinone derivatives including 6-{[(1R)-2-methyl-1-(trifluoromethyl)propyl]amino}pyrido[4,3-c]-1,6-naphthyridin-1(2H)-one; 6-{[1-(2,4-dichloro-5-fluorophenyl)ethyl]amino}pyrido[4,3-c]-1,6-naphthyridin-1(2H)-one; 6-[(2,2,2-trifluoroethyl)amino]pyrido[4,3-c]-1,6-naphthyridin-1(2H)-one; 6-[(3-thienylmethyl)amino]pyrido[4,3-c]-1,6-naphthyridin-1(2H)-one; 6-[(1,3-thiazol-2-ylmethyl)amino]pyrido[4,3-c]-1,6-naphthyridin-1(2H)-one; 6-[(pyridin-2-ylmethyl)amino]pyrido[4,3-c]-1,6-naphthyridin-1(2H)-one; 6-{[(5-methylisoxazol-3-yl)methyl]amino}pyrido[4,3-c]-1,6-naphthyridin-1(2H)-one; tert-butyl (3S)-3-[(1-oxo-1,2-dihydropyrido[4,3-c]-1,6-naphthyridin-6-yl)amino]piperidine-1-carboxylate; 6-(benzylamino)pyrido[4,3-c]-1,6-naphthyridin-1(2H)-one; 6-(methylamino)pyrido[4,3-c]-1,6-naphthyridin-1(2H)-one; 6-(dimethylamino)pyrido[4,3-c]-1,6-naphthyridin-1(2H)-one; 6-(benzylamino)pyrido[4,3-c]-1,6-naphthyridin-1(2H)-one); (9) U.S. Pat. No. 8,143,393 to Dixon et al. (substituted 4-amino-pyrrolotriazine derivatives including N-{4-[4-amino-7-(morpholin-4-ylmethyl)pyrrolo[2,1-f][1,2,4]triazin-5-yl]-2-fluorophenyl}-N'-[2-fluoro-5-(trifluoromethyl)phenyl]urea; N-{4-[4-amino-7-(morpholin-4-ylmethyl)pyrrolo[2,1-f][1,2,4]triazin-5-yl]phenyl}-N'-(3-tert-butylisoxazol-5-yl)urea; N-{4-[4-amino-7-(morpholin-4-ylmethyl)pyrrolo[2,1-f][1,2,4]triazin-5-yl]phenyl}-N'-[4-(trifluoromethyl)pyridin-2-yl]urea; N-{4-[4-amino-7-(morpholin-4-ylmethyl)pyrrolo[2,1-f][1,2,4]triazin-5-yl]phenyl}-N'-[2-fluoro-5-(trifluoromethyl)phenyl]urea; N-{4-[4-amino-7-(morpholin-4-ylmethyl)pyrrolo[2,1-f][1,2,4]triazin-5-yl]phenyl}-N'-[3-(trifluoromethyl)phenyl]urea; N-{4-[4-amino-7-(morpholin-4-ylmethyl)pyrrolo[2,1-f][1,2,4]triazin-5-yl]phenyl}-N'-[4-fluoro-3-(trifluoromethyl)phenyl]urea; N-{4-[4-amino-7-(morpholin-4-ylmethyl)pyrrolo[2,1-f][1,2,4]triazin-5-yl]-2,6-difluorophenyl}-N'-[2-fluoro-5-(trifluoromethyl)phenyl]urea; N-{4-[4-amino-7-(morpholin-4-ylmethyl)pyrrolo[2,1-f][1,2,4]triazin-5-yl]-2-fluorophenyl}-N'-[4-(trifluoromethyl)pyridin-2-yl]urea; N-{5-[4-amino-7-(morpholin-4-ylmethyl)pyrrolo[2,1-f][1,2,4]triazin-5-yl]pyridin-2-yl}-N'-[2-fluoro-5-(trifluoromethyl)phenyl]urea; N-{4-[4-amino-7-(morpholin-4-ylmethyl)pyrrolo[2,1-f][1,2,4]triazin-5-yl]-2-fluorophenyl}-N'-[3-(trifluoromethyl)phenyl]urea; N-{4-[4-amino-7-(morpholin-4-ylmethyl)pyrrolo[2,1-f][1,2,4]triazin-5-yl]-3-fluorophenyl}-N'-[4-(trifluoromethyl)pyridin-2-yl]urea; N-{5-[4-amino-7-(morpholin-4-ylmethyl)pyrrolo[2,1-f][1,2,4]triazin-5-yl]pyridin-2-yl}-N'-[4-(trifluoromethyl)pyridin-2-yl]urea); (10) U.S. Pat. No. 8,133,995 to Dixon et al. (substituted 4-amino-pyrrolotriazine derivatives including 4-amino-5-{4-[({[2-fluoro-5-(trifluoromethyl)phenyl]amino}carbonyl)-amino]-phenyl}-7-(morpholin-4-ylmethyl)-N-(2,2,2-trifluoroethyl)-pyrrolo[2,1-f][1,2,4]-triazine-6-carboxamide; 4-amino-5-{4-[({[2-fluoro-5-(trifluoromethyl)phenyl]amino}carbonyl)-amino]phenyl}-

7-[(4-methylpiperazin-1-yl)methyl]-N-(2,2,2-trifluoroethyl)-pyrrolo[2,1-f][1,2,4]triazine-6-carboxamide; N-{4-[4-amino-6-(methoxymethyl)-7-(morpholin-4-ylmethyl)-pyrrolo[2,1-f][1,2,4]triazin-5-yl]phenyl}-N'-[2-fluoro-5-(trifluoromethyl)phenyl]urea; N-(4-[4-amino-6-(methoxymethyl)-7-[(4-methylpiperazin-1-yl)methyl]-pyrrolo[2,1-f][1,2,4]triazin-5-yl]phenyl)-N'-[2-fluoro-5-(trifluoromethyl)-phenyl]urea; N-{4-[4-amino-7-{[(2-methoxyethyl)amino]methyl}-6-(methoxymethyl)-pyrrolo[2,1-f][1,2,4]triazin-5-yl]phenyl}-N'-[2-fluoro-5-(trifluoromethyl)-phenyl]urea; N-{4-[4-amino-7-[(2,6-dimethylmorpholin-4-yl)methyl]-6-(methoxymethyl)-pyrrolo[2,1-f][1,2,4]triazin-5-yl]phenyl}-N'-[2-fluoro-5-(trifluoromethyl)-phenyl]urea; N-(4-[4-amino-6-(methoxymethyl)-7-[(3-oxopiperazin-1-yl)methyl]-pyrrolo[2,1-f][1,2,4]triazin-5-yl]phenyl)-N'-[2-fluoro-5-(trifluoromethyl)-phenyl]urea; N-{4-[4-amino-7-{[(2-methoxyethyl)(methyl)amino]methyl}-6-(methoxymethyl)pyrrolo[2,1-f][1,2,4]triazin-5-yl]phenyl}-N'-[2-fluoro-5-(trifluoromethyl)phenyl]urea); (11) U.S. Pat. No. 7,642,255 Sim et al. (pyridopyrimidinyl compounds including N-{3-[7-(3-diethylamino-propylamino)-1-methyl-2-oxo-1,4-dihydro-2H-pyrido[4,3-d]pyrimidin-3-yl]-4-methyl-phenyl}-3-trifluoromethyl-benzamide; N-{4-methyl-3-[1-methyl-2-oxo-7-(pyridin-3-ylamino)-1,4-dihydro-2H-pyrido[4,3-d]pyrimidin-3-yl]-phenyl}-3-trifluoromethyl-benzamide; N-{4-methyl-3-[1-methyl-7-(6-methyl-pyridin-3-ylamino)-2-oxo-1,4-dihydro-2H-pyrido[4,3-d]pyrimidin-3-yl]-phenyl}-3-trifluoromethyl-benzamide; N-{3-[7-(2,5-dimethyl-2H-pyrazol-3-ylamino)-1-methyl-2-oxo-1,4-dihydro-2H-pyrido[4,3-d]pyrimidin-3-yl]-4-methyl-phenyl}-3-trifluoromethyl-benzamide; N-{4-methyl-3-[1-methyl-2-oxo-7-(pyrazin-2-ylamino)-1,4-dihydro-2H-pyrido[4,3-d]pyrimidin-3-yl]-phenyl}-3-trifluoromethyl-benzamide; N-{4-methyl-3-[1-methyl-7-(3-morpholin-4-yl-propylamino)-2-oxo-1,4-dihydro-2H-pyrido[4,3-d]pyrimidin-3-yl]-phenyl}-3-trifluoromethyl-benzamide; N-{3-[7-(3-diethylamino-propylamino)-1-methyl-2-oxo-1,4-dihydro-2H-pyrido[4,3-d]pyrimidin-3-yl]-4-methyl-phenyl}-3-trifluoromethyl-benzamide; N-{3-[7-(4-diethylamino-butylamino)-1-methyl-2-oxo-1,4-dihydro-2H-pyrido[4,3-d]pyrimidin-3-yl]-4-methyl-phenyl}-3-trifluoromethyl-benzamide); (12) U.S. Pat. No. 7,605,241 to Hecht et al. (kaempferol glycoside and analogs thereof); (13) U.S. Pat. No. 7,521,446 to Albers et al. (4-[[9-[(3S)-Tetrahydro-3-furanyl]-8-[(2,4,6-trifluorophenyl)amino]-9H-purin-2-yl]amino]cyclohexanol); (14) U.S. Pat. No. 7,470,709 to Barsanti et al. (benzimidazole quinolinones); (15) U.S. Pat. No. 7,442,700 to Mastalerz et al. (pyrrolotriazine derivatives including N-[4-({4-[(5-methyl-1H-pyrazol-3-yl)amino]pyrrolo[2,1f][1,2,4]triazin-2-yl}sulfanyl)phenyl]cyclopropanecarboxamide; N-(3-cyclopropyl-1H-pyrazol-5-yl)-2-{[3-(methyloxy)phenyl]sulfanyl}pyrrolo[2,1-f][1,2,4]triazin-4-amine; N-[4-({4-[(3-cyclopropyl-1H-pyrazol-5-yl)amino]pyrrolo[2,1-f][1,2,4]triazin-2-yl}sulfanyl)phenyl]acetamide; 3-({4-[(3-cyclopropyl-1H-pyrazol-5-yl)amino]pyrrolo[2,1-f][1,2,4]triazin-2-yl}sulfanyl)-N-methylbenzamide; N-(5-methyl-1H-pyrazol-3-yl)-2-(phenylsulfanyl)pyrrolo[2,1-f][1,2,4]triazin-4-amine; and N-(4-((4-((5-methyl-1H-pyrazol-3-yl)amino)pyrrolo[2,1f][1,2,4]triazin-2-yl)sulfanyl)phenyl)benzamide); (16) U.S. Pat. No. 7,405,213 to Chen et al. (pyrrolotriazine compounds including 3-chloro-4-fluoro-N-(5-{[6-({3-[4-(hydroxymethyl)piperidin-1-yl]propyl}oxy)-5-methylpyrrolo[2,1-f][1,2,4]triazin-4-yl]amino}pyrimidin-2-yl)benzamide; 3-chloro-4-fluoro-N-(5-{[6-({3-[(2S)-2-(hydroxymethyl)pyrrolidin-1-yl]propyl}oxy)-5-methylpyrrolo[2,1-f][1,2,4]triazin-4-yl]amino}pyrimidin-2-yl)-benzamide 3-chloro-4-fluoro-N-(5-{[6-({3-[(2S)-2-(hydroxymethyl)morpholin-4-yl]propyl}oxy)-5-methylpyrrolo[2,1-f][1,2,4]triazin-4-yl]amino}pyrimidin-2-yl)benzamide; 3-chloro-4-fluoro-N-(5-{[6-({3-[3-(hydroxymethyl)morpholin-4-yl]propyl}oxy)-5-methylpyrrolo[2,1-f][1,2,4]triazin-4-yl]amino}pyrimidin-2-yl)benzamide; N-(5-{[6-({3-[4-(hydroxymethyl)piperidin-1-yl]propyl}oxy)-5-methylpyrrolo[2,1-f][1,2,4]triazin-4-yl]amino}pyrimidin-2-yl)benzamide; N-(5-{[6-({3-[(2S)-2-(hydroxymethyl)pyrrolidin-1-yl]propyl}oxy)-5-methylpyrrolo[2,1-f][1,2,4]triazin-4-yl]amino}pyrimidin-2-yl)benzamide); (17) U.S. Pat. No. 7,402,582 Gavai et al. (pyrrolotriazine compounds including 2-(2-{[6-({3-[4-(hydroxymethyl)piperidin-1-yl]propyl}oxy)-5-methylpyrrolo[2,1-f][1,2,4]triazin-4-yl]amino}1,3-thiazol-5-yl)-N-(3-methylphenyl)acetamide; N-(3-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-chloro-4-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(4-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)pyrrolo[2,1-f][1,2,4]triazin-4-yl]amino}-1,3-thiazol-5-yl)acetamide; 2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-phenylacetamide; N-(3-fluorophenyl)-2-(2-{[6-({3-[(2S)-2-(hydroxymethyl)pyrrolidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[(2S)-2-(hydroxymethyl)pyrrolidin-1-yl]propyl}oxy)pyrrolo[2,1-][1,2,4]triazin-4-yl]amino}-1,3-thiazol-5-yl)acetamide); and (18) U.S. Pat. No. 7,371,750 to Sim et al. (pyrimidopyrimidinyl compounds including N-{3-[7-(3-dimethylamino-phenylamino)-1-methyl-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide; N-{3-[7-(3-amino-phenylamino)-1-methyl-2-oxo-1,4-dihydro-2H-pyrimido[4,5-d]pyrimidin-3-yl]-4-methyl-phenyl}-3-trifluoromethyl-benzamide; N-[4-methyl-3-(1-methyl-7-methylamino-2,4-dioxo-1,4-dihydro-2H-pyrimido[4,5-d]pyrimidin-3-yl)-phenyl]-3-trifluoromethyl-benzamide; N-[3-(7-benzylamino-1-methyl-2-oxo-1,4-dihydro-2H-pyrimido[4,5-d]pyrimidin-3-yl)-4-methyl-phenyl]-3-trifluoromethyl-benzamide; N-{4-methyl-3-[1-methyl-2-oxo-7-(3-ureido-phenylamino)-1,4-dihydro-2H-pyrimido[4,5-d]pyrimidin-3-yl]-phenyl}-3-trifluoromethyl-benzamide; N-{3-[7-(3-hydroxymethyl-phenylamino)-1-methyl-2-oxo-1,4-dihydro-2H-pyrimido[4,5-d]pyrimidin-3-yl]-4-methyl-phenyl}-3-trifluoromethyl-benzamide; N-(4-methyl-3-{1-methyl-7-[3-(4-methyl-piperazin-1-ylmethyl)-phenylamino]-2-oxo-1,4-dihydro-2H-pyrimido[4,5-d]pyrimidin-3-yl}-phenyl)-3-trifluoromethyl-benzamide; N-{4-methyl-3-[1-methyl-2-oxo-7-(3-sulfamoyl-phenylamino)-1,4-dihydro-2H-pyrimido[4,5-d]pyrimidin-3-yl]-phenyl}-3-trifluoromethyl-benzamide).

Additional RSK inhibitors are described in U.S. Pat. No. 7,759,342 Bennett et al. including compounds of Formula (R-I). Formula (R-I) is:

(R-I)

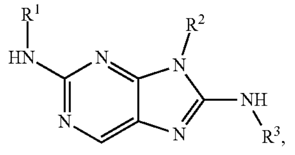

wherein:

(1) $R^1$ is substituted or unsubstituted $C_1$-$C_6$ alkyl, substituted or unsubstituted aryl, substituted or unsubstituted $C_3$-$C_{10}$ cycloalkyl, substituted or unsubstituted $C_3$-$C_{10}$ heterocycle or substituted or unsubstituted $C_3$-$C_{10}$ heteroaryl;

(2) $R^2$ is H, substituted or unsubstituted $C_1$-$C_6$ alkyl, substituted or unsubstituted aryl, substituted or unsubstituted $C_3$-$C_{10}$ cycloalkyl, substituted or unsubstituted $C_3$-$C_{10}$ heterocycle or substituted or unsubstituted $C_3$-$C_{10}$ heteroaryl; and (3) $R^3$ is aryl substituted with one or more halogens or $C_3$-$C_{10}$ heteroaryl substituted with one or more halogens, wherein the aryl or $C_3$-$C_{10}$ heteroaryl group is optionally further substituted with one or more $C_1$-$C_6$ alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

Additional RSK inhibitors are described in United States Patent Application Publication No. 2005/0233985 by Smith et al., including compounds of Formula (R-II). Formula (R-II) is:

(R-II)

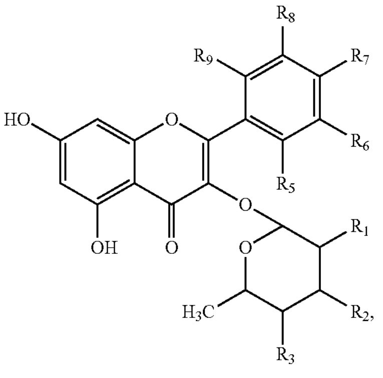

wherein:

(1) $R_1$, $R_2$, and $R_3$ are independently selected from the group consisting of hydroxy, —$OCOR_4$, —$COR_4$, $C_1$-$C_4$ alkoxy, —O-glucoside and —O-rhamnoside;

(2) $R_5$, $R_6$, $R_7$, $R_8$ and $R_9$ are independently selected from the group consisting of H, hydroxy, —$OCOR_4$, —$COR_4$, $C_1$-$C_4$ alkoxy, —O-glucoside and —O-rhamnoside; and (3) $R_4$ is H or $C_1$-$C_4$ alkyl;

with the proviso that $R_1$, $R_2$ and $R_3$ are not all hydroxy.

Polo-like kinase 1 (PLK1) is a serine/threonine protein kinase that plays a critical role in cell division and replication. PLK1 is a 66-kDa protein of 603 amino acid residues. In addition to the N-terminus kinase domain, there are two conserved polo-box regions of 30 amino acids at the C-terminus. Kinase activity is regulated at least in part, by the polo-boxes that are functionally important for both auto-inhibition and subcellular localization. PLK1 is an early trigger for G2/M transition in the cell cycle. It is frequently overexpressed in malignant cells and is regarded as a proto-oncogene (U. Holtrich et al., "Induction and Down-Regulation of PLK, a Human Serine/Threonine Kinase Expressed in Proliferating Cells and Tumors," *Proc. Natl. Acad. Sci. USA* 91: 1736-1740 (1994).

PLK1 inhibitors include BI2536 ((R)-4-(8-cyclopentyl-7-ethyl-5-methyl-6-oxo-5,6,7,8-tetrahydropteridin-2-ylamino)-3-methoxy-N-(1-methylpiperidin-4-yl)benzamide), volasertib (BI6727), rigosertib, GSK461364 (5-(6-((4-methylpiperazin-1-yl)methyl)-1H-benzo[d]imidazol-1-yl)-3-((R)-1-(2-(trifluoromethyl)phenyl)ethoxy)thiophene-2-carboxamide), HMN-214 (N-[(4-methoxyphenyl) sulfonyl]-N-[2-[(1E)-2-(1-oxido-4-pyridinyl)ethenyl] phenyl]-acetamide), SBE 13 hydrochloride (N-(4-((6-chloropyridin-3-yl)methoxy)-3-methoxybenzyl)-2-(3,4-dimethoxyphenyl)ethanamine hydrochloride), NMS-P937 (4,5-dihydro-1-(2-hydroxyethyl)-8-[[5-(4-methyl-1-piperazinyl)-2-(trifluoromethoxy)phenyl]amino]-1H-pyrazolo[4,3-h]quinazoline-3-carboxamide), and MLN0905 (2-[[5-[3-(dimethylamino)propyl]-2-methyl-3-pyridinyl]amino]-5,7-dihydro-9-(trifluoromethyl)-6H-pyrimido[5,4-d][1] benzazepine-6-thione). A particularly preferred PLK1 inhibitor is volasertib.

Additional PKL1 inhibitors are known in the art. U.S. Pat. No. 7,977,336 to Hashihayata et al. discloses aminopyrimidine PLK1 inhibitors, including 2-[((1S)-1-{4-[2-(tert-butylamino)-1-hydroxyethyl]phenyl}ethyl)amino]-4-(8-ethylimidazo[1,2-a]pyridin-3-yl)-pyrimidine-5-carbonitrile; (1R)-1-[4-((1S)-1-{[5-bromo-4-(8-ethylimidazo[1,2-a]pyridin-3-yl)pyrimidin-2-yl]amino}ethyl)phenyl]-2-(tert-butylamino)ethanol; 2-[((1S)-1-{4-[hydroxy(pyridin-2-yl) methyl]phenyl}ethyl)amino]-4-(8-methylimidazo[1,2-a] pyridin-3-yl)pyrimidine-5-carbonitrile; 4-(8-ethylimidazo [1,2-a]pyridin-3-yl)-2-({(1S)-1-[4-(4-hydroxy-1-methylpiperidin-4-yl)phenyl]ethyl}amino)pyrimidine-5-carbonitrile; 4-(8-ethylimidazo[1,2-a]pyridin-3-yl)-2-[((1S)-1-{4-[hydroxy(1-isopropylpiperidin-4-yl)methyl] phenyl}ethyl)amino]pyrimidine-5-carbonitrile; 4-(8-cyclopropylimidazo[1,2-a]pyridin-3-yl)-2-[((1S)-1-{4-[hydroxy(1-methylpiperidin-4-yl)methyl]phenyl}ethyl) amino]pyrimidine-5-carbonitrile; 4-(8-chloroimidazo[1,2-a] pyridin-3-yl)-2-[((1S)-1-{4-[(1-cyclopropylpiperidin-4-yl) (hydroxy)methyl]phenyl}ethyl)amino]pyrimidine-5-carbonitrile; 4-(8-ethylimidazo[1,2-a]pyridin-3-yl)-2-[((1S)-1-{4-[hydroxy(1-methyl-piperidin-3-yl)methyl] phenyl}ethyl)amino]pyrimidine-5-carbonitrile; and 2-{[(1S)-1-(4-{hydroxy[1-methylpyrrolidin-2-yl] methyl}phenyl)ethyl]amino}-4-(8-methylimidazo[1,2-a] pyridin-3-yl)pyrimidine-5-carbonitrile). U.S. Pat. No. 8,514,418 to Galemmo et al., discloses dihydropterinone inhibitors of PLK1, including (7R)-7-ethyl-5-methyl-8-(tetrahydrofuran-3-yl)-2-(5-(thiazol-2-yl)-1H-pyr-azol-4-yl)-7,8-dihydropteridin-6(5H)-one, (R)-7-ethyl-2-(2-(4-fluorophenyl)-1H-imidazol-1-yl)-5-methyl-8-(1-methyl-1H-pyrazol-4-yl)-7,8-dihydropteridin-6(5H)-one, (R)-7-ethyl-2-(2-(4-fluorophenyl)-1H-imidazol-1-yl)-5-methyl-8-(1-methyl-1H-pyrazol-3-yl)-7,8-dihydropteridin-6(5H)-one, (R)-7-ethyl-5-methyl-8-(1-methyl-1H-pyrazol-4-yl)-2-(2-phenyl-1H-imidazol-1-yl)-7,8-dihydropteridin-6(5H)-one, (R)-7-ethyl-5-methyl-8-(1-methyl-1H-pyrazol-4-yl)-2-(1-methyl-3-(thiazol-2-yl)-1H-pyrazol-4-yl)-7,8-dihydropteridin-6 (5H)-one, (R)-2-(3-(2,4-difluorophenyl)-1H-pyrazol-4-yl)-7-ethyl-5-methyl-8-(1-methyl-1H-pyrazol-4-yl)-7,8-dihydropteridin-6(5H)-one, and (R)-7-ethyl-5-methyl-8-(1-methyl-1H-pyrazol-3-yl)-2-(1-methyl-3-(thiazol-2-yl)-1H-pyrazol-4-yl)-7,8-dihydropteridin-6(5H)-one. U.S. Pat. No. 8,445,503 to Galemmo et al. discloses pyrazinopteridinone inhibitors of PLK1, including 6a-ethyl-5-methyl-2-(2-phenyl-1H-imidazol-1-yl)-6a,7,9,10-tetrahydro-[1,4]oxazino[3,4-h]pteridin-6(5H)-one, (S)-6a-ethyl-5-methyl-2-(5-(thiazol-2-yl)-1H-pyrazol-4-yl)-6a,7,9,10-tetrahydro-[1,4]oxazino[3,4-h]pteridin-6(5H)-one, (S)-6a-ethyl-5,8-dimethyl-2-(2-phenyl-1H-imidazol-1-yl)-7,8,9,10-tetrahydro-5H-pyrazino[2,1-h]pteridin-6(6aH)-one, (S)-2-(2-(2,4-difluorophenyl)-1H-imidazol-1-yl)-6a-ethyl-5-methyl-6a,7,9,10-tetrahydro-[1,4]oxazino[3,4-h]pteridin-6(5H)-one, and (S)-6a-ethyl-2-(2-(5-fluoropyridin-2-yl)-1H-imidazol-1-yl)-5-methyl-6a,7,9,10-tetrahydro-[1,4]oxazino[3,4-h]pteridin-6(5H)-one. U.S. Pat. No. 8,318,727 to Cao et al. discloses inhibitors of PLK1 including 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide. U.S. Pat. No. 7,956,185 to Diebold et al. discloses cyclobut-3-ene-1,2-dione inhibitors of PLK1.

As used herein, unless further defined or limited, the term "antibody" encompasses both polyclonal and monoclonal antibodies, as well as genetically engineered antibodies such as chimeric or humanized antibodies of the appropriate binding specificity. As used herein, unless further defined, the term "antibody" also encompasses antibody fragments such as sFv, Fv, Fab, Fab' and $F(ab)'_2$ fragments. In many cases, it is preferred to use monoclonal antibodies. This applies to antibodies or compositions including antibodies as described above as well as additional antibodies described herein.

In one alternative, when the drug combination is use with an alkylating agent, the alkylating agent can be selected from the group consisting of BCNU, BCNU wafers (Gliadel), ACNU, CCNU, bendamustine (Treanda), lomustine, and temozolimide (Temodar).

When the improvement is made by chemosensitization, the chemosensitization can comprise, but is not limited to, the use of a substituted hexitol derivative as a chemosensitizer in combination with an agent selected from the group consisting of:

(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) topoisomerase inhibitors;
(t) 5-fluorouracil;
(u) curcumin;
(v) NF-κB inhibitors;
(w) rosmarinic acid;
(x) mitoguazone;
(y) tetrandrine;
(z) a tyrosine kinase inhibitor;
(aa) an inhibitor of EGFR; and
(ab) an inhibitor of PARP.

When the improvement is made by chemopotentiation, the chemopotentiation can comprise, but is not limited to, the use of a substituted hexitol derivative as a chemopotentiator in combination with an agent selected from the group consisting of:

(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) 5-fluorouracil;
(t) curcumin;
(u) NF-κB inhibitors;
(v) rosmarinic acid;
(w) mitoguazone;
(x) tetrandrine;
(y) a tyrosine kinase inhibitor;
(z) an inhibitor of EGFR; and
(aa) an inhibitor of PARP.

In one alternative, when the chemopotentiation involves chemopotentiation of an alkylating agent by the activity of dianhydrogalactitol, the alkylating agent can be selected from the group consisting of BCNU, BCNU wafers (Gliadel), CCNU, bendamustine (Treanda), lomustine, ACNU, and temozolimide (Temodar).

When the improvement is made by post-treatment management, the post-treatment management can be, but is not limited to, a method selected from the group consisting of:

(a) a therapy associated with pain management;
(b) administration of an anti-emetic;
(c) an anti-nausea therapy;
(d) administration of an anti-inflammatory agent;
(e) administration of an anti-pyretic agent; and
(f) administration of an immune stimulant.

When the improvement is made by alternative medicine/post-treatment support, the alternative medicine/post-treatment support can be, but is not limited to, use of a herbal medication created either synthetically or through extraction.

In one alternative, when the method is a herbal medication created either synthetically or through extraction, the herbal medication created either synthetically or through extraction can be selected from the group consisting of:

(a) a NF-κB inhibitor;
(b) a natural anti-inflammatory;
(c) an immunostimulant;
(d) an antimicrobial; and
(e) a flavonoid, isoflavone, or flavone.

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an antimicrobial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

When the improvement is made by a bulk drug product improvement, the bulk drug product improvement can be, but is not limited to, a bulk drug product improvement selected from the group consisting of:

(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

When the improvement is made by use of a diluent, the diluent can be, but is not limited to, a diluent selected from the group consisting of:

(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

When the improvement is made by use of a solvent system, the solvent system can be, but is not limited to, a solvent system selected from the group consisting of:

(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

When the improvement is made by use of an excipient, the excipient can be, but is not limited to, an excipient selected from the group consisting of:

(a) mannitol;
(b) albumin;
(c) EDTA;
(d) sodium bisulfite;
(e) benzyl alcohol;
(f) carbonate buffers;
(g) phosphate buffers;
(h) PEG;
(i) vitamin A;
(j) vitamin D;
(k) vitamin E;
(l) esterase inhibitors;
(m) cytochrome P450 inhibitors;
(n) multi-drug resistance (MDR) inhibitors;
(o) organic resins;
(p) detergents;
(q) perillyl alcohol or an analog thereof; and
(r) activators of channel-forming receptors.

Suitable esterase inhibitors include, but are not limited to, ebelactone A and ebelactone B.

Suitable cytochrome P450 inhibitors include, but are not limited to, 1-aminobenzotriazole, N-hydroxy-N'-(4-butyl-2-methylphenyl)formamidine, ketoconazole, methoxsalen, metyrapone, roquefortine C, proadifen, 2,3',4,5'-tetramethylstilbene, and troleandomycin.

Suitable MDR inhibitors include, but are not limited to, 5'-methoxyhydnocarpin, INF 240, INF 271, INF 277, INF 392, INF 55, reserpine, and GG918. MDR inhibitors are described in M. Zloh & S. Gibbons, "Molecular Similarity of MDR9 Inhibitors," *Int. J. Mol. Sci.* 5: 37-47 (2004).

Suitable organic resins include, but are not limited to, a partially neutralized polyacrylic acid, as described in U.S. Pat. No. 8,158,616 to Rodgers et al.

Suitable detergents include, but are not limited to, nonionic detergents such as a polysorbate or a poloxamer, and are described in PCT Patent Application Publication No. WO/1997/039768 by Bjorn et al.

The use of perillyl alcohol or an analog thereof to improve transport of anti-neoplastic agents is described in United States Patent Application 2012/0219541 by Chen et al.

The use of activators of channel-forming receptors is described in United States Patent Application Publication No. 2010/0311678 by Bean et al. Such activators of channel-forming receptors include, but are not limited to, capsaicin, lidocaine, eugenol, arvanil (N-arachidonoylvanillamine), anandamide, 2-aminoethoxydiphenyl borate, resiniferatoxin, phorbol 12-phenylacetate 13-acetate 20-homovanillate (PPAHV), olvanil, N-oleoyldopamine, N-arachidonyldopamine, 6'-iodoresiniferatoxin (6'-IRTX), $C_{18}$ N-acylethanolamines, lipoxygenase derivatives such as 12-hydroperoxyeicosatetraenoic acid, inhibitor cysteine knot (ICK) peptides (vanillotoxins), piperine, N-[2-(3,4-dimethylbenzyl)-3-(pivaloyloxy)propyl]-2-[4-(2-aminoethoxy)-3-methoxyphenyl]acetamide, N-[2-(3,4-dimethylbenzyl)-3-(pivaloyloxy)propyl]-N'-(4-hydroxy-3-methoxybenzyl)thiourea, SU200 N-(4-t-butylbenzyl)-N'-(4-hydroxy-3-methoxybenzyl)thiourea), transacin, cinnamaldehyde, allyl-isothiocyanate, diallyl disulfide, icilin, cinnamon oil, wintergreen oil, clove oil, acrolein, mustard oil, ATP, 2-methylthio-ATP, 2' and 3'-O-(4-benzoylbenzoyl)-ATP, ATP-5'-O-(3-thiotriphosphate), menthol, eucalyptol, linalool, geraniol, and hydroxycitronellal.

When the improvement is made by use of a dosage form, the dosage form can be, but is not limited to, a dosage form selected from the group consisting of:

(a) tablets;
(b) capsules;
(c) topical gels;
(d) topical creams;
(e) patches;
(f) suppositories;
(g) lyophilized dosage fills;
(h) immediate-release formulations;
(i) slow-release formulations;
(j) controlled-release formulations; and
(k) liquid in capsules.

Formulation of pharmaceutical compositions in tablets, capsules, and topical gels, topical creams or suppositories is well known in the art and is described, for example, in United States Patent Application Publication No. 2004/0023290 by Griffin et al.

Formulation of pharmaceutical compositions as patches such as transdermal patches is well known in the art and is described, for example, in U.S. Pat. No. 7,728,042 to Eros et al.

Lyophilized dosage fills are also well known in the art. One general method for the preparation of such lyophilized dosage fills, applicable to dianhydrogalactitol and derivatives thereof and to diacetyldianhydrogalactitol and derivatives thereof, comprises the following steps:

(1) Dissolve the drug in water for injection precooled to below 10° C. Dilute to final volume with cold water for injection to yield a 40 mg/mL solution.

(2) Filter the bulk solution through an 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

Immediate-release formulations are described in U.S. Pat. No. 8,148,393 to van Dalen et al. Immediate-release formulations can include, for example, conventional film-coated tablets.

Slow-release formulations are described in U.S. Pat. No. 8,178,125 to Wen et al. Slow-release formulations can include, for example, microemulsions or liquid crystals.

Controlled-release formulations are described in U.S. Pat. No. 8,231,898 to Oshlack et al. Controlled-release formulations can include, for example, a matrix that includes a controlled-release material. Such a controlled-release material can include hydrophilic and/or hydrophobic materials, such as gums, cellulose ethers, acrylic resins, protein derived materials, waxes, shellac, and oils such as hydrogenated castor oil or hydrogenated vegetable oil.

However, any pharmaceutically acceptable hydrophobic or hydrophilic controlled-release material which is capable of imparting controlled-release of the mustard-based alkylating agent may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (e.g., hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer, poly(methyl methacrylate), poly(methacrylic acid) (anhydride), polymethacrylate, polyacrylamide, poly(methacrylic acid anhydride), and glycidyl methacrylate copolymers.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability.

When the improvement is made by use of a drug delivery system, the drug delivery system can be, but is not limited to, a drug delivery system selected from the group consisting of:

(a) oral dosage forms;
(b) nanocrystals;
(c) nanoparticles;
(d) cosolvents;
(e) slurries;
(f) syrups;
(g) bioerodible polymers;
(h) liposomes;
(i) slow-release injectable gels;
(j) microspheres; and
(k) targeting compositions with epidermal growth factor receptor-binding peptides.

Nanocrystals are described in U.S. Pat. No. 7,101,576 to Hovey et al.

Nanoparticles for drug delivery are described in U.S. Pat. No. 8,258,132 to Bosch et al. Typically, such nanoparticles have an average particle size of the active ingredient of less than about 1000 nm, more preferably, less than about 400 nm, and most preferably, less than about 250 nm. The nanoparticles can be coated with a surface stabilizer, such as, but not limited to, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxes 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)), dioctyl sodium sulfosuccinate (DOSS), docusate sodium (Ashland Chem. Co., Columbus, Ohio); Duponol P®, which is a sodium lauryl sulfate (DuPont); Triton X-200®, which is an alkyl aryl polyether sulfonate (Rohm and Haas); Crodestas F-110®, which is a mixture of sucrose stearate and sucrose distearate (Croda Inc.); p-isononylphenoxy-poly-(glycidol), also known as Olin-IOG® or Surfactant 10-G® (Olin Chemicals, Stamford, Conn.); Crodestas SL-40® (Croda, Inc.); and SA9OHCO, which is $C_{18}H_{37}CH_2(CON(CH_3)$—$OCH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-nonanoyl β-D-glucopyranoside; octanoyl-N-methylglucamide; n-octyl β-D-glucopyranoside; and octyl β-D-thioglucopyranoside. Nanoparticles for drug delivery are also described in United States Patent Application Publication No. 2010/209479 by Carroll et al. These nanoparticles include carbon nanoparticles such as carbon nanotubes.

Pharmaceutically acceptable cosolvents are described in U.S. Pat. No. 8,207,195 to Navratil et al., and include, but are not limited to, water, methanol, ethanol, 1-propanol, isopropanol, 1-butanol, isobutanol, t-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether.

Slurries for use in pharmaceutical formulations are described in United States Patent Application Publication No. 2006/0229277 by Laxminarayan.

Syrups for use in pharmaceutical formulations are described in U.S. Pat. No. 8,252,930 to Stoit et al. Such syrups can include the active ingredient and a syrup-forming component such as sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents.

Bioerodible polymers are described in U.S. Pat. No. 7,318,931 to Okumu et al. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutryate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al. Liposomes can incorporate short oligopeptide sequences capable of targeting the EGFR receptor, as described in United States Patent Application Publication 2012/0213844 by Huang et al. Alternatively, liposomes can include nuclear localization signal/fusogenic peptide conjugates and form targeted liposome complexes, as described in United States Patent Application Publication 2012/0183596 to Boulikas.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000).

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995).

The use of targeting compositions with epidermal growth factor receptor-binding peptides is described in United States Patent Application Publication No. 2010/0151003 by Trikha et al.

When the improvement is made by use of a drug conjugate form, the drug conjugate form can be, but is not limited to, a drug conjugate form selected from the group consisting of:

(a) a polymer system;
(b) polylactides;
(c) polyglycolides;
(d) amino acids;
(e) peptides;
(f) multivalent linkers;
(g) immunoglobulins;
(h) cyclodextrin polymers;
(i) modified transferrin;
(j) hydrophobic or hydrophobic-hydrophilic polymers;
(k) conjugates with a phosphonoformic acid partial ester;
(l) conjugates with a cell-binding agent incorporating a charged cross-linker; and
(m) conjugates with β-glucuronides through a linker.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010).

Polyglycolide conjugates are also well known in the art and are described, for example, in PCT Patent Application Publication No. WO 2003/070823 by Elmaleh et al.

Multivalent linkers are known in the art and are described, for example, in United States Patent Application Publication No. 2007/0207952 by Silva et al. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Conjugates with immunoglobulins are disclosed in U.S. Pat. No. 4,925,662 to Oguchi et al. The conjugates are prepared by use of a cross-linking agent such as carbodiimide, glutaraldehyde, or diethyl malonimidate.

Cyclodextrin polymers, their conjugates with therapeutically active agents, and their administration together with particles are described in United States Patent Application Publication Serial No. 2012/0213854 by Fetzer.

Conjugates with modified transferrin are described in United States Patent Application Publication Serial No. 2011/0288023 by Kamei et al.

Conjugates with hydrophobic or hydrophobic-hydrophilic polymers are described in United States Patent Application Publication No. 2011/0268658 by Crawford et al. These polymers can include mono-, di-, or tripeptides. These polymers can also include polylactic acid (PLA), polyglycolic acid (PGA), poly (lactic-co-glycolic) acid (PLGA), polycaprolactone (PCL), polydioxanone (PDO), polyanhydrides, polyorthoesters, or chitosan.

Conjugates with a phosphonoformic acid partial ester are described in United States Patent Application Publication No. 2010/227831 by Saha et al.

Conjugates with a cell-binding agent incorporating a charged cross-linker are described in U.S. Pat. No. 8,236,319 to Chari et al.

Conjugates with β-glucuronides through a linker are described in U.S. Pat. No. 8,039,273 to Jeffrey.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146. Additionally, electrophilic reagents are known that will react with carboxylate side chains such as those of aspartate and glutamate, such as diazoalkanes and diazoacetyl compounds, carbonydilmidazole, and carbodiimides. These are described in G. T. Hermanson, "Bioconjugate Techniques" (Academic Press, San Diego, 1996), pp. 152-154. Furthermore, electrophilic reagents are known that will react with hydroxyl groups such as those in the side chains of serine and threonine, including reactive haloalkane derivatives. These are described in G. T. Hermanson, "Bioconjugate Techniques" (Academic Press, San Diego, 1996), pp. 154-158. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996).

When the improvement is made by use of a compound analog, the compound analog can be, but is not limited to, a compound analog selected from the group consisting of:

(a) alteration of side chains to increase or decrease lipophilicity;
(b) addition of an additional chemical functionality to alter a property selected from the group consisting of reactivity, electron affinity, and binding capacity; and
(c) alteration of salt form.

When the improvement is made by use of a prodrug system, the prodrug system can be, but is not limited to, a prodrug system selected from the group consisting of:

(a) the use of enzyme sensitive esters;
(b) the use of dimers;
(c) the use of Schiff bases;
(d) the use of pyridoxal complexes;
(e) the use of caffeine complexes; and
(f) the use of nitric oxide-releasing prodrugs;
(g) the use of prodrugs with fibroblast activation protein α-cleavable oligopeptides;
(h) the use of prodrugs that are products of reaction with an acetylating or carbamylating agent;
(i) the use of prodrugs that are hexanoate conjugates;
(j) the use of prodrugs that are polymer-agent conjugates; and
(k) the use of prodrugs that are subject to redox activation.

As used herein, the term "prodrug" refers to compounds that are transformed in vivo to yield a disclosed compound or a pharmaceutically acceptable form of the compound. In some embodiments, a prodrug is a compound that may be converted under physiological conditions or by solvolysis to a biologically active compound as described herein. Thus, the term "prodrug" refers to a precursor of a biologically active compound that is pharmaceutically acceptable. A prodrug can be inactive when administered to a subject, but is then converted in vivo to an active compound, for example, by hydrolysis (e.g., hydrolysis in blood or a tissue). In certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24). A discussion of prodrugs is provided in T. Higuchi et al., "Pro-Drugs as Novel Delivery Systems," *ACS Symposium Series*, Vol. 14 and in E. B. Roche, ed., *Bioreversible Carriers in Drug Design* (American Pharmaceutical Association & Pergamon Press, 1987). Exemplary advantages of a prodrug can include, but are not limited to, its physical properties, such as enhanced water solubility for parenteral administration at physiological pH compared to the parent compound, enhanced absorption from the digestive tract, or enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ is alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$))alkanoyloxy)ethyl, 1-methyl-1-(($C_1$-$C_6$)alkanoyloxy)ethyl ($C_1$-$C_6$)alkoxycarbonyloxymethyl, N($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, $P(O)(O(C_1$-$C_6)alkyl)_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, $C(OH)C(O)OY^1$ wherein $Y^1$ is H, ($C_1$-$C_6$)alkyl or benzyl, $C(OY^2)Y^3$ wherein $Y^2$ is ($C_1$-$C_4$) alkyl and $Y^3$ is ($C_1$-$C_6$)alkyl, carboxy($C_1$-$C_6$)alkyl, amino($C_1$-$C_4$)alkyl or mono-N or di-N,N($C_1$-$C_6$)alkylaminoalkyl, $C(Y^4)Y^5$ wherein $Y^4$ is H or methyl and $Y^5$ is mono-N or di-N,N($C_1$-$C_6$)alkylamino, morpholino, piperidin-1-yl or pyrrolidin-1-yl.

The use of prodrug systems is described in T. Järvinen et al., "Design and Pharmaceutical Applications of Prodrugs" *in Drug Discovery Handbook* (S. C. Gad, ed., Wiley-Interscience, Hoboken, N.J., 2005), ch. 17, pp. 733-796. This publication describes the use of enzyme sensitive esters as prodrugs. The use of dimers as prodrugs is described in U.S. Pat. No. 7,879,896 to Allegretti et al. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007). The use of Schiff bases as prodrugs is described in U.S. Pat. No. 7,619,005 to Epstein et al. The use of caffeine complexes as prodrugs is described in U.S. Pat. No. 6,443,898 to Unger et al. The use of nitric oxide-releasing prodrugs is described in N. Nath et al., "JS-K, a Nitric Oxide-Releasing Prodrug, Modulates β-Catenin/TCF Signaling in Leukemic Jurkat Cells: Evidence of an S-Nitrosylated Mechanism," *Biochem. Pharmacol.* 80: 1641-1649 (2010). The use of prodrugs with fibroblast activation protein α-cleavable oligopeptides is described in United States Patent Application Publication No. 2002/0155565 by Garin-Chesa et al. The use of prodrugs that are products of reaction with an acetylating or carbamylating agent is described in J. H. Lin & J. Y. H. Lu, "Role of Pharmacokinetics and Metabolism in Drug Discovery and Development," *Pharmacol. Rev.* 4: 403-449 (1997). The use of hexanoate conjugates is described in U.S. Pat. No. 8,101,661 to Mickle. The use of polymer-agent conjugates is described in R. Satchi et al., "PDEPT: Polymer-Directed Enzyme Prodrug Therapy," *Br. J. Cancer* 85: 1070-1076 (2001). The use of prodrugs that are subject to redox activation is described in S. H. van Rijt & P. J. Sadler, "Current Applications and Future Potential for Bioinorganic Chemistry in the Development of Anticancer Drugs," *Drug Discov. Today* 14: 1089-1097 (2009).

When the improvement is made by use of a multiple drug system, the multiple drug system can be, but is not limited to, a multiple drug system selected from the group consisting of:

(a) inhibitors of multi-drug resistance;
(b) specific drug resistance inhibitors;
(c) specific inhibitors of selective enzymes;
(d) signal transduction inhibitors;
(e) meisoindigo;
(f) imatinib;
(g) hydroxyurea;
(h) dasatinib;
(i) capecitabine;
(j) nilotinib;
(k) repair inhibition agents; and
(l) topoisomerase inhibitors with non-overlapping side effects.

Multi-drug resistance inhibitors are described in U.S. Pat. No. 6,011,069 to Inomata et al.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001).

Selective inhibitors of specific enzymes are described in D. Leung et al., "Discovering Potent and Selective Reversible Inhibitors of Enzymes in Complex Proteomes," *Nature Biotechnol.* 21: 687-691 (2003).

Repair inhibition is described in N. M. Martin, "DNA Repair Inhibition and Cancer Therapy," *J. Photochem. Photobiol. B* 63: 162-170 (2001).

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:

(a) cytokines;
(b) lymphokines;
(c) therapeutic antibodies;
(d) antisense therapies;
(e) gene therapies;
(f) ribozymes;
(g) RNA interference; and
(h) vaccines.

Antisense therapies are described, for example, in B. Weiss et al., "Antisense RNA Gene Therapy for Studying and Modulating Biological Processes," *Cell. Mol. Life Sci.* 55: 334-358 (1999).

Ribozymes are described, for example, in S. Pascolo, "RNA-Based Therapies" *in Drug Discovery Handbook* (S. C. Gad, ed., Wiley-Interscience, Hoboken, N.J., 2005), ch. 27, pp. 1273-1278.

RNA interference is described, for example, in S. Pascolo, "RNA-Based Therapies" *in Drug Discovery Handbook* (S. C. Gad, ed., Wiley-Interscience, Hoboken, N.J., 2005), ch. 27, pp. 1278-1283.

As described above, typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, (2008), supra.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by use of biotherapeutic resistance modulation, the biotherapeutic resistance modulation can be, but is not limited to, use against glioblastoma multiforme tumors resistant to a therapeutic agent or technique selected from the group consisting of:

(a) biological response modifiers;
(b) cytokines;
(c) lymphokines;
(d) therapeutic antibodies;
(e) antisense therapies;
(f) gene therapies;
(g) ribozymes;
(h) RNA interference; and
(i) vaccines.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:

(a) hypoxic cell sensitizers;
(b) radiation sensitizers/protectors;
(c) photosensitizers;
(d) radiation repair inhibitors;
(e) thiol depleters;
(f) vaso-targeted agents;
(g) DNA repair inhibitors;
(h) radioactive seeds;
(i) radionuclides;
(j) radiolabeled antibodies; and
(k) brachytherapy.

A substituted hexitol derivative such as dianhydrogalactitol can be used in combination with radiation for the treatment of glioblastoma multiforme or other malignancies as described herein.

Hypoxic cell sensitizers are described in C. C. Ling et al., "The Effect of Hypoxic Cell Sensitizers at Different Irradiation Dose Rates," *Radiation Res.* 109: 396-406 (1987). Radiation sensitizers are described in T. S. Lawrence, "Radiation Sensitizers and Targeted Therapies," *Oncology* 17 (Suppl. 13) 23-28 (2003). Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008). Photosensitizers are described in R. R. Allison & C. H. Sibata, "Oncologic Photodynamic Therapy Photosensitizers: A Clinical Review," *Photodiaqnosis Photodynamic Ther.* 7: 61-75 (2010). Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008). Thiol depleters are described in K. D. Held et al., "Postirradiation Sensitization of Mammalian Cells by the Thiol-Depleting Agent Dimethyl Fumarate," *Radiation Res.* 127: 75-80 (1991). Vaso-targeted agents are described in A. L. Seynhaeve et al., "Tumor Necrosis Factor c Mediates Homogeneous Distribution of Liposomes in Murine Melanoma that Contributes to a Better Tumor Response," *Cancer Res.* 67: 9455-9462 (2007). As described above, radiation therapy is frequently employed for the treatment of GBM, so radiation therapy enhancement is significant for this malignancy.

When the improvement is by use of a novel mechanism of action, the novel mechanism of action can be, but is not limited to, a novel mechanism of action that is a therapeutic interaction with a target or mechanism selected from the group consisting of:

(a) inhibitors of poly-ADP ribose polymerase;
(b) agents that affect vasculature or vasodilation;
(c) oncogenic targeted agents;
(d) signal transduction inhibitors;
(e) EGFR inhibition;
(f) protein kinase C inhibition;
(g) phospholipase C downregulation;
(h) Jun downregulation;
(i) histone genes;
(j) VEGF;
(k) ornithine decarboxylase;
(l) ubiquitin C;
(m) Jun D;
(n) v-Jun;
(o) GPCRs;
(p) protein kinase A;

(q) protein kinases other than protein kinase A;

(r) prostate specific genes;

(s) telomerase;

(t) histone deacetylase; and (u) tyrosine kinase inhibitors.

EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005). Protein kinase C inhibition is described in H. C. Swannie & S. B. Kaye, "Protein Kinase C Inhibitors," *Curr. Oncol. Rep.* 4: 37-46 (2002). Phospholipase C downregulation is described in A. M. Martelli et al., "Phosphoinositide Signaling in Nuclei of Friend Cells: Phospholipase C β Downregulation Is Related to Cell Differentiation," *Cancer Res.* 54: 2536-2540 (1994). Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," Oncogene 22: 2296-2308 (2003). The role of histone genes as a target for therapeutic intervention is described in B. Calabretta et al., "Altered Expression of G1-Specific Genes in Human Malignant Myeloid Cells," *Proc. Natl. Acad. Sci. USA* 83: 1495-1498 (1986). The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," *Surgery* 132: 1056-1063 (2002). The role of ornithine decarboxylase as a target for therapeutic intervention is described in J. A. Nilsson et al., "Targeting Ornithine Decarboxylase in Myc-Induced Lymphomagenesis Prevents Tumor Formation," *Cancer Cell* 7: 433-444 (2005). The role of ubiquitin C as a target for therapeutic intervention is described in C. Aghajanian et al., "A Phase I Trial of the Novel Proteasome Inhibitor PS341 in Advanced Solid Tumor Malignancies," *Clin. Cancer Res.* 8: 2505-2511 (2002). The role of Jun D as a target for therapeutic intervention is described in M. M. Caffarel et al., "JunD Is Involved in the Antiproliferative Effect of $\Delta^9$-Tetrahydrocannibinol on Human Breast Cancer Cells," *Oncogene* 27: 5033-5044 (2008). The role of v-Jun as a target for therapeutic intervention is described in M. Gao et al., "Differential and Antagonistic Effects of v-Jun and c-Jun," *Cancer Res.* 56: 4229-4235 (1996). The role of protein kinase A as a target for therapeutic intervention is described in P. C. Gordge et al., "Elevation of Protein Kinase A and Protein Kinase C in Malignant as Compared With Normal Breast Tissue," *Eur. J. Cancer* 12: 2120-2126 (1996). The role of telomerase as a target for therapeutic intervention is described in E. K. Parkinson et al., "Telomerase as a Novel and Potentially Selective Target for Cancer Chemotherapy," *Ann. Med.* 35: 466-475 (2003). The role of histone deacetylase as a target for therapeutic intervention is described in A. Melnick & J. D. Licht, "Histone Deacetylases as Therapeutic Targets in Hematologic Malignancies," *Curr. Opin. Hematol.* 9: 322-332 (2002).

When the improvement is made by use of selective target cell population therapeutics, the use of selective target cell population therapeutics can be, but is not limited to, a use selected from the group consisting of:

(a) use against radiation sensitive cells;

(b) use against radiation resistant cells; and (c) use against energy depleted cells.

The improvement can also be made by use of dianhydrogalactitol, diacetyldianhydrogalactitol, or a derivative or analog of dianhydrogalactitol or diacetyldianhydrogalactitol in combination with ionizing radiation.

When the improvement is made by use with an agent to enhance the activity of an alkylating hexitol derivative such as dianhydrogalactitol or diacetyldianhydrogalactitol, the agent to enhance the activity of the alkylating hexitol derivative can be, but is not limited to, an agent selected from the group consisting of:

(a) nicotinamide;

(b) caffeine;

(c) tetandrine; and (d) berberine.

When the improvement is made by use of an agent that counteracts myelosuppression, the agent that counteracts myelosuppression can be, but is not limited to, a dithiocarbamate.

U.S. Pat. No. 5,035,878 to Borch et al., discloses dithiocarbamates for treatment of myelosuppression; the dithiocarbamates are compounds of the formula $R^1R^2NCS(S)M$ or $R^1R^2NCSS$—$SC(S)NR^3R^4$, wherein $R^1$, $R^2$, $R^3$, and $R^4$ are the same or different, and $R^1$, $R^2$, $R^3$, and $R^4$ are aliphatic, cycloaliphatic, or heterocycloaliphatic groups that are unsubstituted or substituted by hydroxyl; or wherein one of $R^1$ and $R^2$ and one of $R^3$ and $R^4$ can be hydrogen; or wherein $R^1$, $R^2$, $R^3$, and $R^4$ taken together with the nitrogen atom upon which the pair of R groups is substituted, can be a 5-membered or 6-membered N-heterocyclic ring which is aliphatic or aliphatic interrupted by a ring oxygen or a second ring nitrogen, and M is hydrogen or one equivalent or a pharmaceutically acceptable cation, in which case the rest of the molecule is negatively charged.

U.S. Pat. No. 5,294,430 to Borch et al., discloses additional dithiocarbamates for treatment of myelosuppression. In general, these are compounds of Formula (D-I):

(D-I)

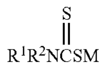

wherein:

(i) $R^1$ and $R^2$ are the same or different $C_1$-$C_6$ alkyl groups, $C_3$-$C_6$ cycloalkyl groups, or $C_5$-$C_6$ heterocycloalkyl groups; or (ii) one of $R^1$ and $R^2$, but not both, can be H; or (iii) $R^1$ and $R^2$ taken together with the nitrogen atom can be a 5-membered or 6-membered N-heterocyclic ring which is aliphatic or aliphatic interrupted by a ring oxygen or a second ring nitrogen; and (iv) M is hydrogen or one equivalent of a pharmaceutically acceptable cation, in which case the rest of the molecule is negatively charged; or (v) M is a moiety of Formula (D-II):

(D-II)

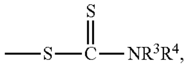

wherein $R^3$ and $R^4$ are defined in the same manner as $R^1$ and $R^2$. Where the group defined by Formula (D-I) is an anion, the cation can be an ammonium cation or can be derived from a monovalent or divalent metal such as an alkali metal or an alkaline earth metal, such as $Na^+$, $K^+$, or $Zn^{+2}$. In the case of the dithiocarbamic acids, the group defined by Formula (D-I) is linked to an ionizable hydrogen atom; typically, the hydrogen atom will dissociate at a pH above about 5.0. Among dithiocarbamates that can be used are: N-methyl, N-ethyldithiocarbamates, hexamethylenedithiocarbamic acid, sodium di(P3-hydroxyethyl)dithiocarbamate, various dipropyl, dibutyl and diamyl dithiocarbamates, sodium N-methyl,N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, α-furfuryl dithiocarbamates and imidazoline dithiocarbamates. Another alternative is a compound where $R^1$ of Formula (D-I) is a hydroxy-substituted or, preferably, a (bis to penta) polyhydroxy-substituted lower alkyl group having up to 6 carbon atoms. For example, $R^1$ can be HO—$CH_2$—CHOH—CHOH—CHOH—CHOH—$CH_2$—. In such compounds, $R^2$ can be H or lower alkyl (unsubstituted or substituted with one or more hydroxyl groups). Steric problems can be minimized when $R^2$ is H, methyl, or ethyl. Accordingly, a particularly preferred compound of this type is an N-methyl-glucamine dithiocarbamate salt, the most preferred cations of these salts being sodium or potassium. Other preferred dithiocarbamates include the alkali or alkaline earth metal salts wherein the anion is di-n-butyldithiocarbamate, di-n-propyldithiocarbamate, pentamethylenedithiocarbamate, or tetramethylene dithiocarbamate.

When the improvement is made by use with an agent that increases the ability of the substituted hexitol to pass through the blood-brain barrier, the agent that increases the ability of the substituted hexitol to pass through the blood-brain barrier can be, but is not limited to, an agent selected from the group consisting of:

(a) a chimeric peptide of the structure of Formula (D-III):

(D-III)

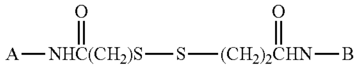

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

A-NH$(CH_2)_2$S—S—B (cleavable linkage) (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

A-NH═CH$(CH_2)_3$CH═NH—B (non-cleavable linkage) (D-III(b)), wherein the bridge is formed using glutaraldehyde as the bridge reagent;

(b) a composition comprising either avidin or an avidin fusion protein bonded to a biotinylated substituted hexitol derivative to form an avidin-biotin-agent complex including therein a protein selected from the group consisting of insulin, transferrin, an anti-receptor monoclonal antibody, a cationized protein, and a lectin;

(c) a neutral liposome that is pegylated and incorporates the substituted hexitol derivative, wherein the polyethylene glycol strands are conjugated to at least one transportable peptide or targeting agent;

(d) a humanized murine antibody that binds to the human insulin receptor linked to the substituted hexitol derivative through an avidin-biotin linkage; and (e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the substituted hexitol by a covalent link to biotin.

Agents that improve penetration of the blood-brain barrier are disclosed in W. M. Pardridge, "The Blood-Brain Barrier: Bottleneck in Brain Drug Development," *NeuroRx* 2: 3-14 (2005).

One class of these agents is disclosed in U.S. Pat. No. 4,801,575 to Pardridge, which discloses chimeric peptides for delivery of agents across the blood-brain barrier. These chimeric peptides include peptides of the general structure of Formula (D-IV):

(D-IV)

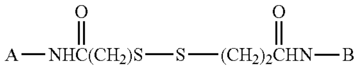

wherein:

(i) A is somatostatin, thyrotropin releasing hormone (TRH), vasopressin, alpha interferon, endorphin, muramyl dipeptide or ACTH 4-9 analogue; and (ii) B is insulin, IGF-I, IGF-II, transferrin, cationized (basic) albumin or prolactin.

In another alternative, the disulfide conjugating bridge between A and B is replaced with a bridge of Subformula (D-IV(a)):

A-NH$(CH_2)_2$S—S—B (cleavable linkage) (D-IV(a));

the bridge of Subformula (D-III(a)) is formed when cysteamine and EDAC are employed as the bridge reagents. In yet another alternative, the disulfide conjugating bridge between A and B is replaced with a bridge of Subformula (D-IV(b)):

A-NH═CH$(CH_2)_3$CH═NH—B (non-cleavable linkage) (D-IV(b));

the bridge of Subformula (D-III(b)) is formed when glutaraldehyde is employed as the bridge reagent.

U.S. Pat. No. 6,287,792 to Pardridge et al., discloses methods and compositions for delivery of agents across the blood-brain barrier comprising either avidin or an avidin fusion protein bonded to a biotinylated agent to form an avidin-biotin-agent complex. The avidin fusion protein can include the amino acid sequences of proteins such as insulin or transferrin, an anti-receptor monoclonal antibody, a cationized protein, or a lectin.

U.S. Pat. No. 6,372,250 to Pardridge, discloses methods and compositions for delivery of agents across the blood-brain barrier employing liposomes. The liposomes are neutral liposomes. The surface of the neutral liposomes is pegylated. The polyethylene glycol strands are conjugated to transportable peptides or other targeting agents. Suitable targeting agents include insulin, transferrin, insulin-like growth factor, or leptin. Alternatively, the surface of the liposome could be conjugated with 2 different transportable peptides, one peptide targeting an endogenous BBB receptor and the other targeting an endogenous BCM (brain cell plasma membrane) peptide. The latter could be specific for particular cells within the brain, such as neurons, glial cells, pericytes, smooth muscle cells, or microglia. Targeting peptides may be endogenous peptide ligands of the receptors, analogues of the endogenous ligand, or peptidomimetic MAbs that bind the same receptor of the endogenous ligand. Transferrin receptor-specific peptidomimetic monoclonal antibodies can be used as transportable peptides. Monoclonal antibodies to the human insulin receptor can be used as transportable peptides. The conjugation agents which are used to conjugate the blood-barrier targeting agents to the surface of the liposome can be any of the well-known polymeric conjugation agents such as sphingomyelin, polyethylene glycol (PEG) or other organic polymers, with PEG preferred. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol. The transportable peptide is linked to the liposome as follows: A transportable peptide such as insulin or an HIRMAb is thiolated and conjugated to a maleimide group on the tip of a small fraction of the PEG strands; or, surface carboxyl groups on a transportable peptide such as transferrin or a TfRMAb are conjugated to a hydrazide (Hz) moiety on the tip of the PEG strand with a carboxyl activator group such as N-methyl-N'-3(dimethylaminopropyl)carbodiimide hydrochloride (EDAC); a transportable peptide is thiolated and conjugated via a disulfide linker to the liposome that has been reacted with N-succinimidyl 3-(2-pyridylthio)propionate (SPDP); or a transportable peptide is conjugated to the surface of the liposome with avidin-biotin technology, e.g., the transportable peptide is mono-biotinylated and is bound to avidin or streptavidin (SA), which is attached to the surface of the PEG strand.

U.S. Pat. No. 7,388,079 to Pardridge et al., discloses the use of a humanized murine antibody that binds to the human insulin receptor; the humanized murine antibody can be linked to the agent to be delivered through an avidin-biotin linkage.

U.S. Pat. No. 8,124,095 to Pardridge et al., discloses monoclonal antibodies that are capable of binding to an endogenous blood-brain barrier receptor-mediated transport system and are thus capable of serving as a vector for transport of a therapeutic agent across the BBB. The monoclonal antibody can be, for example, an antibody specifically binding the human insulin receptor on the human BBB.

United States Patent Application Publication No. 2005/0085419 by Morrison et al., discloses a fusion protein for delivery of a wide variety of agents to a cell via antibody-receptor-mediated endocytosis comprises a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative. Typically, the antigen is a protein. Typically, the protein antigen on the surface of the cell is a receptor such as a transferrin receptor-or an insulin receptor. The invention also includes an antibody construct incorporating the fusion protein that is either a heavy chain or a light chain together with a complementary light chain or heavy chain to form an intact antibody molecule. The therapeutic agent can be a non-protein molecule and can be linked covalently to biotin.

Inhibitors of the enzyme poly-ADP ribose polymerase (PARP) have been developed for multiple indications, especially for treatment of malignancies. Several forms of cancer are more dependent on the activity of PARP than are non-malignant cells.

The enzyme PARP catalyzes the polymerization of poly-ADP ribose chains, typically attached to a single-strand break in cellular DNA. The coenzyme NAD is required as a substrate for generating ADP-ribose monomers to be polymerized; nicotinamide is the leaving group during polymerization, in contrast to pyrophosphate which is the leaving group during normal DNA or RNA synthesis, which leaves a pyrophosphate as the linking group between adjacent ribose sugars in the chain rather than phosphate as occurs in normal DNA or RNA. The PARP enzyme comprises four domains: a DNA-binding domain, a caspase-cleaved domain, an auto-modification domain, and a catalytic domain. The DNA-binding domain comprises two zinc finger motifs. In the presence of damaged DNA, the DNA-binding domain will bind the DNA and induce a conformational shift. PARP can be inactivated by caspase-3 cleavage, which is a step that occurs in programmed cell death (apoptosis).

Several PARP enzymes are known, including PARP1 and PARP2. Of these two enzymes, PARP1 is responsible for most cellular PARP activity. The binding of PARP1 to single-strand breaks in DNA through the amino-terminal zinc finger motifs recruits XRCC1, DNA ligase III, DNA polymerase β, and a kinase to the nick. This is known as base excision repair (BER). PARP2 has been shown to oligomerize with PARP1, and the oligomerization stimulates catalytic activity. PARP2 is also therefore implicated in BER.

PARP1 inhibitors inhibit the activity of PARP1 and thus inhibit the repair of single-strand breaks in DNA. When such breaks are unrepaired, subsequent DNA replication can induce double-strand breaks. The proteins BRCA1, BRCA2, and PALB2 can repair double-strand breaks in DNA by the error-free homologous recombinational repair (HRR) pathway. In tumors with mutations in the genes BRCA1, BRCA2, or PALB1, these double-strand breaks cannot be efficiently repaired, leading to cell death. Normal cells do not replicate their DNA as frequently as tumor cells, and normal cells that lack mutated BRCA1 or BRCA2 proteins can still repair these double-strand breaks through homologous repair. Therefore, normal cells are less sensitive to the activity of PARP inhibitors than tumor cells.

Some tumor cells that lack the tumor suppressor PTEN may be sensitive to PARP inhibitors because of downregulation of, a critical homologous recombination component. Tumor cells that are low in oxygen are also sensitive to PARP inhibitors.

PARP inhibitors are also considered potential treatments for other life-threatening diseases, including stroke and myocardial infarction, as well as for long-term neurodegenerative diseases (G. Graziani & C. Szabó, "Clinical Perspectives of PARP Inhibitors," *Pharmacol. Res.* 52: 109-118 (2005)).

A number of PARP inhibitors are known in the art. PARP inhibitors include, but are not limited to, iniparib, talazoparib, olaparib, rucaparib, veliparib, CEP-9722 (a prodrug of CEP-8983 (11-methoxy-4,5,6,7-tetrahydro-1H-cyclopenta[a]pyrrolo[3,4-c]carbazole-1,3(2H)-dione), MK 4827 ((S)-2-(4-(piperidin-3-yl)phenyl)-2H-indazole-7-carboxamide), and BGB-290.

U.S. Pat. No. 9,073,893 to Papeo et al., discloses 3-oxo-2,3-dihydro-1H-indazole-4-carboxamide derivatives as PARP inhibitors, including: 3-oxo-2-(piperidin-4-yl)-2,3-dihydro-1H-indazole-4-carboxamide; 2-(1-cyclopentylpiperidin-4-yl)-3-oxo-2,3-dihydro-1H-indazole-4-carboxamide; 2-(1-cyclohexylpiperidin-4-yl)-3-oxo-2,3-dihydro-1H-indazole-4-carboxamide; 2-[1-(4,4-difluorocyclohexyl)piperidin-4-yl]-3-oxo-2,3-dihydro-1H-indazole-4-carboxamide; 2-(1-cyclohexylpiperidin-4-yl)-1-methyl-3-oxo-2,3-dihydro-1H-indazole-4-carboxamide; 2-[1-(4,4-difluorocyclohexyl)piperidin-4-yl]-1-methyl-3-oxo-2,3-dihydro-1-H-indazole-4-carboxamide; 2-(1-cyclopentylpiperidin-4-yl)-1-methyl-3-oxo-2,3-dihydro-1H-indazole-4-carboxamide; 2-(1-methylpiperidin-4-yl)-3-oxo-2,3-dihydro-1H-indazole-4-carboxamide; 1-methyl-3-oxo-2-(piperidin-4-yl)-2,3-dihydro-1H-indazole-4-carboxamide; 1-methyl-2-(1-methylpiperidin-4-yl)-3-oxo-2,3-dihydro-1H-indazole-4-carboxamide; 2-(1-ethylpiperidin-4-yl)-3-oxo-2,3-dihydro-1H-indazole-4-carboxamide; 3-oxo-2-(1-propylpiperidin-4-yl)-2,3-dihydro-1H-indazole-4-carboxamide; 2-(1-ethylpiperidin-4-yl)-1-methyl-3-oxo-2,3-dihydro-1H-indazole-4-carboxamide; 1-methyl-3-oxo-2-[1-(propan-2-yl)piperidin-4-yl]-2,3-dihydro-1H-indazole-4-carboxamide; 3-oxo-2-[1-(propan-2-yl)piperidin-4-yl]-2,3-dihydro-1H-indazole-4-carboxamide; 2-(1-cyclobutylpiperidin-4-yl)-3-oxo-2,3-dihydro-1H-indazole-4-carboxamide; 2-(1-cyclobutylpiperidin-4-yl)-6-fluoro-3-oxo-2,3-dihydro-1H-indazole-4-carboxamide; 2-(1-cyclobutylpiperidin-4-yl)-1-methyl-3-oxo-2,3-dihydro-1H-indazole-4-carboxamide; 2-(1-cyclobutylpiperidin-4-yl)-6-fluoro-1-methyl-3-oxo-2,3-dihydro-1H-indazole-4-carboxamide; 6-fluoro-3-oxo-2-(piperidin-4-yl)-2,3-dihydro-1H-indazole-4-carboxamide; 6-fluoro-1-methyl-3-oxo-2-(piperidin-4-yl)-2,3-dihydro-1H-indazole-4-carboxamide; 2-(1-cyclohexylpiperidin-4-yl)-6-fluoro-1-methyl-3-oxo-2,3-dihydro-1H-indazole-4-carboxamide; 2-(1-cyclohexylpiperidin-4-yl)-6-fluoro-3-oxo-2,3-dihydro-1H-indazole-4-carboxamide; 2-[1-(4,4-difluorocyclohexyl)piperidin-4-yl]-6-fluoro-1-methyl-3-oxo-2,3-dihydro-1H-indazole-4-carboxamide; and 2-[1-(4,4-dichlorocyclohexyl)piperidin-4-yl]-1-methyl-3-oxo-2,3-dihydro-1H-indazole-4-carboxamide.

U.S. Pat. No. 9,062,061 by Honda et al. discloses a PARP inhibitor of Formula (P-I):

(P-I)

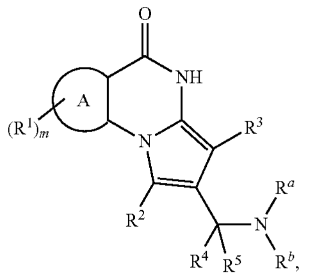

wherein:

(1) $R^1$ represents a halogen atom, a lower alkyl group, a hydroxy group, a lower alkoxy group, an amino group, a nitro group or a cyano group;

(2) $R^2$ and $R^3$ may be the same or different and each represent a hydrogen atom, a halogen atom or a lower alkyl group;

(3) $R^4$ and $R^5$ may be the same or different and each represent a hydrogen atom, a deuterium atom or a lower alkyl group, or $R^4$ and $R^5$ may form an oxo group; $R^a$ and $R^b$ may be the same or different and each represent a hydrogen atom, a lower alkyl group optionally having a substituent or an aryl group optionally having a substituent; $R^a$ and $R^b$ may bind to each other to form a nitrogen-containing heterocyclic ring which may be substituted by one or plural $R^c$;

(4) $R^c$ represents a lower alkyl group optionally having a substituent, a lower cycloalkyl group optionally having a substituent, an aryl group optionally having a substituent, a heterocyclic group optionally having a substituent, a hydroxy group, a lower alkoxy group optionally having a substituent, a lower alkylcarbonyl group optionally having a substituent, a lower cycloalkylcarbonyl group optionally having a substituent, a lower alkylaminocarbonyl group optionally having a substituent, a lower cycloalkylaminocarbonyl group optionally having a substituent, a lower alkoxycarbonyl group optionally having a substituent, an amino group, a lower alkylamino group or a carboxyl group;

(5) ring A represents a benzene ring or an unsaturated heteromonocyclic ring; and (6) m represents 0, 1 or 2.

U.S. Pat. No. 9,062,043 to Chua et al. discloses fused tricyclic PARP inhibitors, including a compound of Formula (P-III):

(P-II)

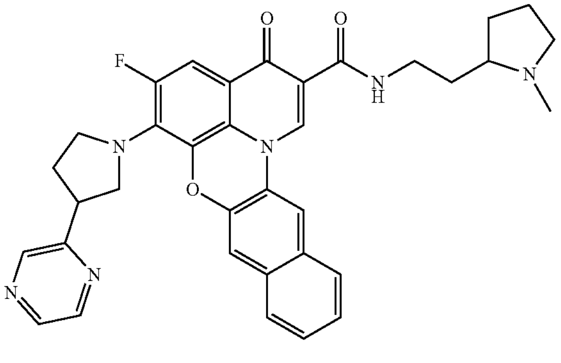

U.S. Pat. No. 9,018,201 to Chu et al. discloses dihydropyridophthalazinone inhibitors of PARP.

U.S. Pat. No. 8,993,594 to Papeo et al. discloses substituted isoquinolin-1(2H)-one derivatives as inhibitors of PARP.

U.S. Pat. No. 8,980,902 to Brown et al., discloses substituted benzamide PARP inhibitors, including: N-ethyl-4-(4-((6-oxo-5,6-dihydropyrido[2,3-e]pyrrolo[1,2-c]pyrimidin-3-yl)methyl)piperazin-1-yl)benzamide; N-methyl-4-(4-((6-oxo-5,6-dihydropyrido[2,3-e]pyrrolo[1,2-c]pyrimidin-3-yl)methyl)piperazin-1-yl)benzamide; N-cyclopropyl-4-(4-((6-oxo-5,6-dihydropyrido[2,3-e]pyrrolo[1,2-c]pyrimidin-3-yl)methyl)piperazin-1-yl)benzamide; 3-chloro-N-methyl-4-(4-((6-oxo-5,6-dihydropyrido[2,3-e]pyrrolo[1,2-c]pyrimidin-3-yl)methyl)piperazin-1-yl)benzamide; 3-chloro-N-ethyl-4-(4-((6-oxo-5,6-dihydropyrido[2,3-e]pyrrolo[1,2-c]pyrimidin-3-yl)methyl)piperazin-1-yl)benzamide; N,3-dimethyl-4-(4-((6-oxo-5,6-dihydropyrido[2,3-e]pyrrolo[1,2-c]pyrimidin-3-yl)methyl)piperazin-1-yl)benzamide; N-ethyl-3-methyl-4-(4-((6-oxo-5,6-dihydropyrido[2,3-e]pyrrolo[1,2-c]pyrimidin-3-yl)methyl)piperazin-1-yl)benzamide; 3-fluoro-N-methyl-4-(4-((6-oxo-5,6-dihydropyrido[2,3-e]pyrrolo[1,2-c]pyrimidin-3-yl)methyl)piperazin-1-yl)benzamide; and N-ethyl-3-fluoro-4-(4-((6-oxo-5,6-dihydropyrido[2,3-e]pyrrolo[1,2-c]pyrimidin-3-yl)methyl)piperazin-1-yl)benzamide.

U.S. Pat. No. 8,946,221 to Mevellec et al., discloses phthalazine derivatives as PARP inhibitors.

U.S. Pat. No. 8,894,989 to Xu et al., discloses tetraazaphenalen-3-one derivatives as PARP inhibitors.

U.S. Pat. No. 8,889,866 to Angibaud et al., discloses tetrahydrophenanthridinones and tetrahydrocyclopentaquinolinones as PARP inhibitors.

U.S. Pat. No. 8,883,787 to Xu et al., discloses diazabenzo[de]anthracen-3-one derivatives as PARP inhibitors.

U.S. Pat. No. 8,877,944 to Papeo et al., discloses substituted 3-oxo-2,3-dihydro-1H-isoindole-4-carboxamide derivatives as PARP inhibitors, including 2-[1-(cis-4-methoxycyclohexyl)piperidin-4-yl]-3-oxo-2,3-dihydro-1H-isoindole-4-carboxamide; 2-[1-(trans-4-methoxycyclohexyl)piperidin-4-yl]-3-oxo-2,3-dihydro-1H-isoindole-4-carboxamide; 2-{1-[cis-4-(hydroxymethyl)cyclohexyl]piperidin-4-yl}-3-oxo-2,3-dihydro-1H-isoindole-4-carboxamide; 2-{1-[trans-4-(hydroxymethyl)cyclohexyl]piperidin-4-yl}-3-oxo-2,3-dihydro-1H-isoindole-4-carboxamide; 2-{1-[cis-4-(methoxymethyl)cyclohexyl]piperidin-4-yl}-3-oxo-2,3-dihydro-1H-isoindole-4-carboxamide; 2-{1-[trans-4-(methoxymethyl)cyclohexyl]piperidin-4-yl}-3-oxo-2,3-dihydro-1H-isoindole-4-carboxamide; 2-[1-(4,4-difluorocyclohexyl)piperidin-4-yl]-3-oxo-2,3-dihydro-1H-isoindole-4-carboxamide; 2-[1-(1,4-dioxaspiro[4.5]dec-8-yl)piperidin-4-yl]-3-oxo-2,3-dihydro-1H-isoindole-4-carboxamide; 2-{1-[4-(dimethylamino)benzyl]piperidin-4-yl}-3-oxo-2,3-dihydro-1H-isoindole-4-carboxamide; 2-[1-(4-fluorobenzyl)piperidin-4-yl]-3-oxo-2,3-dihydro-1H-isoindole-4-carboxamide; 2-[1-(2-fluorobenzyl)piperidin-4-yl]-3-oxo-2,3-dihydro-1H-isoindole-4-carboxamide; 2-[1-(3-fluorobenzyl)piperidin-4-yl]-3-oxo-2,3-dihydro-1H-isoindole-4-carboxamide; 2-{1-[(1-methyl-1H-pyrrol-2-yl)methyl]piperidin-4-yl}-3-oxo-2,3-dihydro-1H-isoindole-4-carboxamide; 3-oxo-2-{1-[4-(trifluoromethylbenzyl]piperidin-4-yl}-2,3-dihydro-1H-isoindole-4-carboxamide; 3-oxo-2-[1-(quinolin-2-ylmethyl)piperidin-4-yl]-2,3-dihydro-1H-isoindole-4-carboxamide; 2-[1-(2,4-difluorobenzyl)piperidin-4-yl]-3-oxo-2,3-dihydro-1H-isoindole-4-carboxamide; 2-[1-(3,4-dimethylbenzyl)piperidin-4-yl]-3-oxo-2,3-dihydro-1H-isoindole-4-carboxamide; 2-[1-(2-methylbenzyl)piperidin-4-yl]-3-oxo-2,3-dihydro-1H-isoindole-4-carboxamide; 2-[1-(2-bromobenzyl)piperidin-4-yl]-3-oxo-2,3-dihydro-1H-isoindole-4-carboxamide; 2-[1-(3-bromobenzyl)piperidin-4-yl]-3-oxo-2,3-dihydro-1H-isoindole-4-carboxamide; 2-[1-(4-bromobenzyl)piperidin-4-yl]-3-oxo-2,3-dihydro-1H-isoindole-4-carboxamide; and 3-oxo-2-{1-[3-(trifluoromethyl)benzyl]piperidin-4-yl}-2,3-dihydro-1H-isoindole-4-carboxamide.

U.S. Pat. No. 8,778,966 to Vialard et al., discloses substituted quinolinone derivatives as PARP inhibitors.

U.S. Pat. No. 8,697,736 to Penning et al., discloses 1H-benzimidazole-4-carboxamides as PARP inhibitors.

U.S. Pat. No. 8,669,249 to Brown et al., discloses PARP inhibitors including: 2-methyl-6-((4-phenylpiperidin-1-yl)methyl)-2H-benzo[b][1,4]oxazin-3(4H)-one; 2-methyl-6-((4-phenylpiperazin-1-yl)methyl)-2H-benzo[b][1,4]oxazin-3(4H)-one; 6-((4-(4-fluorophenyl)-5,6-dihydropyridin-1(2H)-yl)methyl)-2-methyl-2H-benzo[b][1,4]oxazin-3(4H)-one; 6-((4-(4-chlorophenyl)-5,6-dihydropyridin-1(2H)-yl)methyl)-2-methyl-2H-benzo[b][1,4]oxazin-3(4H)-one; 2-methyl-6-((4-p-tolylpiperidin-1-yl)methyl)-2H-benzo[b][1,4]oxazin-3(4H)-one; 6-((4-(4-fluorophenyl)piperidin-1-yl)methyl)-2-methyl-2H-benzo[b][1,4]oxazin-3(4H)-one; 6-((4-(4-chlorophenyl)piperidin-1-yl)methyl)-2-methyl-2H-benzo[b][1,4]oxazin-3(4H)-one; 2-methyl-6-((4-(3-phenyl-1,2,4-thiadiazol-5-yl)piperazin-1-yl)methyl)-2H-benzo[b][1,4]oxazin-3(4H)-one; 6-((4-cyclopentylpiperazin-1-yl)methyl)-2-methyl-2H-benzo[b][1,4]oxazin-3-(4H)-one; 6-((4-(1-benzo[d]imidazol-2-yl)piperazin-1-yl)methyl)-2-methyl-2H-benzo[b][1,4]oxazin-3(4H)-one; (S)-2-methyl-6-((4-phenylpiperidin-1-yl)methyl)-2H-benzo[b][1,4]oxazin-3(4H)-one; (R)-2-methyl-6-((4-phenylpiperidin-1-yl)methyl)-2H-benzo[b][1,4]oxazin-3(4H)-one; 6-((4-(1H-benzo[d]imidazol-2-yl)piperidin-1-yl)methyl)-2-methyl-2H-benzo[b][1,4]oxazin-3(4H)-one; 2-methyl-6-((4-(4-nitrophenyl)piperazin-1-yl)methyl)-2H-benzo[b][1,4]oxazin-3(4H)-one; 4-(4-((2-methyl-3-oxo-3,4-dihydro-2H-benzo[b][1,4]oxazin-6-yl)methyl)piperazin-1-yl)benzoic acid; 6-((4-cycloheptylpiperazin-1-yl)methyl)-2-methyl-2H-benzo[b][1,4]oxazin-3-(4H)-one; 1,3,7-trimethyl-8-(4-((2-methyl-3-oxo-3,4-dihydro-2H-benzo[b][1,4]oxazin-6-yl)methyl)piperazin-1-yl)-1H-purine-2,6(3H,7H)-dione; 6-((4-(4-aminophenyl)piperazin-1-yl)methyl)-2-methyl-2H-benzo[b][1,4]oxazin-3(4H)-one; 6-((4-(6-fluorobenzo[d]isoxazol-3-yl)piperidin-1-yl)methyl)-2-methyl-2H-benzo[b][1,4]oxazin-3(4H)-one; 6-((4-(2-hydroxyphenyl)piperazin-1-yl)methyl)-2-methyl-2H-benzo[b][1,4]oxazin-3(4H)-one; 2-methyl-6-((4-phenyl-5,6-dihydropyridin-1(2H)-yl)methyl)-2H-benzo[b][1,4]oxazin-3(4H)-one; 2-methyl-6-((4-phenyl-5,6-dihydropyridin-1(2H)-yl)methyl)-2H-benzo[b][1,4]oxazin-3(4H)-one; 6-((4-(2-methoxyphenyl)piperazin-1-yl)methyl)-2-methyl-2H-benzo[b][1,4]ox-azin-3(4H)-one; 6-((4-(5-chloropyridin-2-yl)piperazin-1-yl)methyl)-2-methyl-2H-benzo[b][1,4]oxazin-3(4H)-one; (S)-6-((4-(4-chlorophenyl)-5,6-dihydropyridin-1(2H)-yl)methyl)-2-methyl-2H-benzo[b][1,4]oxazin-3(4H)-one; (R)-6-((4-(4-chlorophenyl)-5,6-dihydropyridin-1(2H)-yl)methyl)-2-methyl-2H-benzo[b][1,4]oxazin-3(4H)-one; and 2-methyl-6-((3-oxo-4-phenylpiperazin-1-yl)methyl)-2H-benzo[b][1,4]oxazin-3(4H)-one.

U.S. Pat. No. 8,663,884 to Kennis et al., discloses quinazolinedione derivatives as PARP inhibitors.

U.S. Pat. No. 8,623,872 to Guillemont et al., discloses quinazolinone derivatives as PARP inhibitors.

U.S. Pat. No. 8,546,368 to Penning et al., discloses pyrazoquinolones as PARP inhibitors, including 7,9-dimethyl-1,2,3,4,6,7-hexahydro-5H-pyrazolo[3,4-h]-1,6-naphthyridin-5-one.

U.S. Pat. No. 8,541,417 to Brown et al., discloses PARP inhibitors, including: 3-(hydroxymethyl)pyrido[2,3-e]pyrrolo[1,2-c]pyrimidin-6(5H)-one; N-ethyl-4-(4-((6-oxo-5,6-dihydropyrido[2,3-e]pyrrolo[1,2-c]pyrimidin-3-yl)methyl) piperazin-1-yl)benzamide; N-methyl-4-(4-((6-oxo-5,6-dihydropyrido[2,3-e]pyrrolo[1,2-c]pyrimidin-3-yl)methyl) piperazin-1-yl)benzamide; N-cyclopropyl-4-(4-((6-oxo-5,6-dihydropyrido[2,3-e]pyrrolo[1,2-c]pyrimidin-3-yl)methyl) piperazin-1-yl)benzamide; 3-chloro-N-methyl-4-(4-((6-oxo-5,6-dihydropyrido[2,3-e]pyrrolo[1,2-c]pyrimidin-3-yl) methyl)piperazin-1-yl)benzamide; 3-chloro-N-ethyl-4-(4-((6-oxo-5,6-dihydropyrido[2,3-e]pyrrolo[1,2-c]pyrimidin-3-yl)methyl)piperazin-1-yl)benzamide; N,3-dimethyl-4-(4-((6-oxo-5,6-dihydropyrido[2,3-e]pyrrolo[1,2-c]pyrimidin-3-yl)methyl)piperazin-1-yl)benzamide; N-ethyl-3-methyl-4-(4-((6-oxo-5,6-dihydropyrido[2,3-e]pyrrolo[1,2-c] pyrimidin-3-yl)methyl)piperazin-1-yl)benzamide; 3-fluoro-N-methyl-4-(4-((6-oxo-5,6-dihydropyrido[2,3-e]pyrrolo[1,2-c]pyrimidin-3-yl)methyl)piperazin-1-yl)benzamide; N-ethyl-3-fluoro-4-(4-((6-oxo-5,6-dihydropyrido[2,3-e]pyrrolo[1,2-c]pyrimidin-3-yl)methyl)piperazin-1-yl)benzamide; N-isopropyl-4-(4-((6-oxo-5,6-dihydropyrido[2,3-e] pyrrolo[1,2-c]pyrimidin-3-yl)methyl)piperazin-1-yl) benzamide; N-isopropyl-3-methyl-4-(4-((6-oxo-5,6-dihydropyrido[2,3-e]pyrrolo[1,2-c]pyrimidin-3-yl)methyl) piperazin-1-yl)benzamide; 3-fluoro-N-isopropyl-4-(4-((6-oxo-5,6-dihydropyrido[2,3-e]pyrrolo[1,2-c]pyrimidin-3-yl) methyl)piperazin-1-yl)benzamide; 3-chloro-N-isopropyl-4-(4-((6-oxo-5,6-dihydropyrido[2,3-e]pyrrolo[1,2-c] pyrimidin-3-yl)methyl)piperazin-1-yl)benzamide; 3-bromo-N-isopropyl-4-(4-((6-oxo-5,6-dihydropyrido[2,3-e]pyrrolo [1,2-c]pyrimidin-3-yl)methyl)piperazin-1-yl)benzamide; N-isopropyl-3-methoxy-4-(4-((6-oxo-5,6-dihydropyrido[2,3-e]pyrrolo[1,2-c]pyrimidin-3-yl)methyl)piperazin-1-yl) benzamide; N-isopropyl-3-(methylamino)-4-(4-((6-oxo-5,6-dihydropyrido[2,3-e]pyrrolo[1,2-c]pyrimidin-3-yl)methyl) piperazin-1-yl)benzamide; 3-ethyl-N-isopropyl-4-(4-((6-oxo-5,6-dihydropyrido[2,3-e]pyrrolo[1,2-c]pyrimidin-3-yl) methyl)piperazin-1-yl)benzamide; N-isopropyl-3-(methylthio)-4-(4-((6-oxo-5,6-dihydropyrido[2,3-e]pyrrolo [1,2-c]pyrimidin-3-yl)methyl)piperazin-1-yl)benzamide; 3-bromo-N-methyl-4-(4-((6-oxo-5,6-dihydropyrido[2,3-e] pyrrolo[1,2-c]pyrimidin-3-yl)methyl)piperazin-1-yl)benzamide; 3-methoxy-N-methyl-4-(4-((6-oxo-5,6-dihydropyrido[2,3-e]pyrrolo[1,2-c]pyrimidin-3-yl)methyl) piperazin-1-yl)benzamide; and N-methyl-3-(methylamino)-4-(4-((6-oxo-5,6-dihydropyrido[2,3-e]pyrrolo[1,2-c] pyrimidin-3-yl)methyl)piperazin-1-yl)benzamide.

U.S. Pat. No. 8,541,403 to Chu et al., discloses dihydropyridophthalazinone derivatives as PARP inhibitors, including: 8,9-diphenyl-8,9-dihydro-2H-pyrido[4,3,2-de]phtalazin-3(7H)-one; 8,9bis(4-methylamino)methyl)phenyl-8,9-dihydro-2H-pyrido[4,3,2-de]phtalazin-3(7H)-one; 8,9-di (pyridin-4-yl)-8,9-dihydro-2H-pyrido[4,3,2-de]phthalazin-3 (7H)-one; 8,9-di(pyridin-3-yl)-8,9-dihydro-2H-pyrido[4,3,2-de]phthalazin-3(7H)-one; 8,9-di(pyridin-2-yl)-8,9-dihydro-2H-pyrido[4,3,2-de]phthalazin-3(7H)-one; 9-isopropyl-8-phenyl-8,9-dihydro-2H-pyrido[4,3,2-de] phthalazin-3(7H)-one; 9-(4-((methylamino)methyl)phenyl)-8-phenyl-8,9-dihydro-2H-pyrido[4,3,2-de]phthalazin-3 (7H)-one; 9-(4-((dimethylamino)methyl)phenyl)-8-phenyl-8,9-dihydro-2H-pyrido[4,3,2-de]phthalazin-3(7H)-one; 9-(3-((methylamino)methyl)phenyl)-8-phenyl-8,9-dihydro-2H-pyrido[4,3,2-de]phthalazin-3(7H)-one; 8-(4((methylamino)methyl)phenyl)-9-phenyl-8,9-dihydro-2Hpyrido[4,3,2-de]phthalazin-3(7H)-one, 8,9-bi(3-((methylamino) methyl)phenyl)-8,9-dihydro)-2H-pyrido[4,3,2-de] phthalazin-3(7H)-one; 9-4-(hydroxymethyl)phenyl)-8-phenyl-8,9-dihydro-2H-pyrido[4,3,2-de]phthalazin-3(7H)-one; 9-(3-(4-isobutyrylpiperazine-1-carbonyl)phenyl)-8-phenyl-8,9-dihydro-2H-pyrido[4,3,2-de]phthalazin-3(7H)-one; 8,9-bis(3-(4-(isobutyrylpiperazine-1-carbonyl)phenyl)-8,9-dihydro-2H-pyrido[4,3,2-de]pthalazin-3(7H)-one; 9-(piperidin-3-yl)-8-(pyridin-3-yl)-8,9-dihydro-2H-pyrido [4,3,2-de]phthalazin-3(7H)-one; 9-(piperidin-4-yl)-8-(pyridin-4-yl)-8,9-dihydro-2H-pyrido[4,3,2-de]phthal-azin-3 (7H)-one; 8,9-bis(4-((dimethylamino)methyl)phenyl)-8,9-dihydro-2H-pyrido[4,3,2-de]phthalazin-3(7H)-one; 9-(4-(4-(cyclopropanecarbonyl)piperazine-1-carbonyl)phenyl)-8(4-((methylamino)methyl)phenyl)-8,9-dihydro-2H-pyrido[4,3,2-de]phthalazin-3(7H)-one; and 9-(4-(4-(cyclopropanecarbonyl)piperazine-1-carbonyl)phenyl)-8-(4-((dimethylamino)methyl)phenyl)-8,9-dihydro-2H-pyrido [4,3,2-de]phthalazin-3(7H)-one.

U.S. Pat. No. 8,513,433 to Panicker et al., discloses inhibitors of PARP, including benzyl 2-(4-carbamoyl-1H-benzo[d]imidazol-2-yl)indoline-1-carboxylate; 2-(indolin-2-yl)-1H-benzo[d]imidazole-4-carboxamide; tert-butyl 2-(4-carbamoyl-1H-benzo[d]imidazol-2-yl)-3,4-dihydroquinoline-1(2H)-carboxylate; 2-(1,2,3,4-tetrahydroquinolin-2-yl)-1H-benzo[d]imidazole-4-carboxamide; benzyl 1-(4-carbamoyl-1H-benzo[d]imidazol-2-yl)isoindoline-2-carboxylate; 2-(isoindolin-1-yl)-1H-benzo[d]imidazole-4-carboxamide; benzyl 1-(4-carbamoyl-1H-benzo[d]imidazol-2-yl)-3,4-dihydroisoquinoline-2(1H)-carboxylate; 2-(1,2,3,4-tetrahydroisoquinolin-1-yl)-1H-benzo[d]imidazole-4-carboxamide; benzyl 3-(4-carbamoyl-1H-benzo[d]imidazol-2-yl)-3,4-dihydroisoquinoline-2(1H)-carboxylate; 2-(1,2,3,4-tetrahydroisoquinolin-3-yl)-1H-benzo[d]imidazole-4-carboxamide; benzyl 3-(4-carbamoyl-1H-benzo[d]imidazol-2-yl)-3-methyl-3,4-dihydroisoquinoline-2(1H)-carboxylate; 2-(3-methyl-1,2,3,4-tetrahydroisoquinolin-3-yl)-1H-benzo [d]imidazole-4-carboxamide; tert-butyl 7-((tert-butoxycarbonyl)amino)-3-(4-carbamoyl-1H-benzo[d]imidazol-2-yl)-3,4-dihydroisoquinoline-2(1H)-carboxylate; tert-butyl 7-amino-3-(4-carbamoyl-1H-benzo[d]imidazol-2-yl)-3,4-dihydroisoquinoline-2(1H)-carboxylate; tert-butyl (3-(4-carbamoyl-1H-benzo[d]imidazol-2-yl)-1,2,3,4-tetrahydroisoquinolin-7-yl)carbamate; and 2-(7-amino-1,2,3,4-tetrahydroisoquinolin-3-yl)-1H-benzo[d]imidazole-4-carboxamide.

U.S. Pat. No. 8,470,825 to Xu et al., discloses substituted diazabenzo[de]anthracen-3-one compounds as PARP inhibitors.

U.S. Pat. No. 8,420,650 to Wang et al., discloses dihydropyridophthalazinone inhibitors of PARP, including: 8,9-di(pyridin-4-yl)-8,9-dihydro-2H-pyrido[4,3,2-de]phthalazin-3(7H)-one; 8,9-di(pyridin-3-yl)-8,9-dihydro-2H-pyrido[4,3,2-de]phthalazin-3(7H)-one; 8,9-di(pyridin-2-yl)-8,9-dihydro-2H-pyrido[4,3,2-de]phthalazin-3(7H)-one; 5-fluoro-9-(1-methyl-1H-imidazol-2-yl)-8-phenyl-8,9-dihydro-2H-pyrido[4,3,2-de]phthalazin-3(7H)-one; 5-fluoro-8-(4-fluorophenyl)-9-(1-methyl-1H-imidazol-2-yl)-8,9-dihydro-2H-pyrido[4,3,2-de]phthalazin-3(7H)-one; 8-(4-((dimethylamino)methyl)phenyl)-9-(1-methyl-1H-imidazol-2-yl)-8,9-dihydro-2H-pyrido[4,3,2-de]phthalazin-3(7H)-one; 9-(1-isopropyl-1H-imidazol-5-yl)-8-phenyl-8,9-dihydro-2H-pyrido[4,3,2-de]phthalazin-3(7H)-one; 9-(4-methyl-1H-imidazol-2-yl)-8-phenyl-8,9-dihydro-2H-pyrido [4,3,2-de]phthalazin-3(7H)-one; 8-phenyl-9-(thiazol-5-yl)-

8,9-dihydro-2H-pyrido[4,3,2-de]phthalazin-3(7H)-one; 9-(furan-3-yl)-8-phenyl-8,9-dihydro-2H-pyrido[4,3,2-de] phthalazin-3(7H)-one; 9-(1-methyl-1H-imidazol-2-yl)-8-phenyl-8,9-dihydro-2H-pyrido[4,3,2-de]phthalazin-3(7H)-one; 8,9-bis(1-methyl-1H-imidazol-2-yl)-8,9-dihydro-2H-pyrido[4,3,2-de]phthalazin-3(7H)-one; 9-(1H-imidazol-2-yl)-8-phenyl-8,9-dihydro-2H-pyrido[4,3,2-de]phthalazin-3 (7H)-one; 9-(1-ethyl-1H-imidazol-2-yl)-8-phenyl-8,9-dihydro-2H-pyrido[4,3,2-de]phthalazin-3(7H)-one; 8-phenyl-9-(1-propyl-1H-imidazol-2-yl)-8,9-dihydro-2H-pyrido[4,3,2-de]phthalazin-3(7H)-one; 9-(1-methyl-1H-imidazol-5-yl)-8-phenyl-8,9-dihydro-2H-pyrido[4,3,2-de] phthalazin-3(7H)-one; 8-(4-fluorophenyl)-9-(1-methyl-1H-imidazol-2-yl)-8,9-dihydro-2H-pyrido[4,3,2-de]phthalazin-3(7H)-one; 9-(1-methyl-1H-1,2,4-triazol-5-yl)-8-phenyl-8,9-dihydro-2H-pyrido[4,3,2-de]phthalazin-3(7H)-one; and 8-(4-((dimethylamino)methyl)phenyl)-9-(1-methyl-1H-1,2,4-triazol-5-yl)-8,9-dihydro-2H-pyrido[4,3,2-de]phthalazin-3(7H)-one.

U.S. Pat. No. 8,362,030 to Ingenito et al., discloses tricyclic PARP inhibitors, including: N-methyl[4-(6-oxo-3,4,5,6-tetrahydro-2H-azepino[5,4,3-cd]indazol-2-yl)phenyl] methanaminium trifluoroacetate; N,N-dimethyl[4-(6-oxo-3,4,5,6-tetrahydro-2H-azepino[5,4,3-cd]indazol-2-yl)phenyl] methanaminium trifluoroacetate; $N^2$,$N^2$-dimethyl-N-[4-(1-oxo-1,2,3,4-tetrahydroazepino[3,4,5-hi]indolizin-5-yl) phenyl]glycinamide; 3-[4-(8-fluoro-6-oxo-3,4,5,6-tetrahydro-2H-azepino[5,4,3-cd]indazol-2-yl)phenyl] piperidinium trifluoroacetate; 8-fluoro-2-{4-[(3R)-piperidin-3-yl]phenyl}-2,3,4,5-tetrahydro-6H-azepino[5,4,3-cd]indazol-6-one; 8-fluoro-2-{4-(3S)-piperidin-3-yl] phenyl}-2,3,4,5-tetrahydro-6H-azepino[5,4,3-cd]indazol-6-one; 2-[4-(6-oxo-3,4,5,6-tetrahydro-2H-azepino[5,4,3-cd] indazol-2-yl)benzyl]-2,7-diazoniaspiro[4.5]decane bis (trifluoroacetate); [4-(8-fluoro-6-oxo-3,4,5,6-tetrahydro-2H-azepino[5,4,3-cd]indazol-2-yl)phenyl]-N,N-dimethylmethanaminium trifluoroacetate; 5-phenyl-3,4-dihydroazepino[3,4,5-hi]indolizin-1(2H)-one; ethyl 4-(1-oxo-1,2,3,4-tetrahydroazepino[3,4,5-hi]indolizin-5-yl) benzoate; 5-(4-nitrophenyl)-3,4-dihydroazepino[3,4,5-hi] indolizin-1(2H)-one; 5-[4-(hydroxymethyl)phenyl]-3,4-dihydroazepino[3,4,5-hi]indolizin-1(2H)-one; N-[4-(1-oxo-1,2,3,4-tetrahydroazepino[3,4,5-hi]indolizin-5-yl)phenyl] nicotinamide; N-[4-(1-oxo-1,2,3,4-tetrahydroazepino[3,4,5-hi]indolizin-5-yl)phenyl]pyridine-2-carboxamide; and N-[4-(1-oxo-1,2,3,4-tetrahydroazepino[3,4,5-hi]indolizin-5-yl) phenyl]-2-pyrrolidin-1-ylacetamide.

U.S. Pat. No. 8,354,413 to Jones et al., discloses quinolin-4-one and 4-oxodihydrocinnoline derivatives as PARP inhibitors, including: 1-[3-(8-aza-1-azoniaspiro[4.5]dec-8-ylcarbonyl)-4-fluorobenzyl]-4-oxo-1,4-dihydroquinolinium bis(trifluoroacetate); 1-[4-fluoro-3-({4-[2-(4-fluorobenzyl) prolyl]piperazin-1-yl}carbonyl)benzyl]quinolin-4(1H)-one; 1-[3-(8-aza-1-azoniaspiro[4.5]dec-8-ylcarbonyl)-4-fluorobenzyl]-4-oxo-1,4-dihydrocinnolin-1-ium bis(trifluoroacetate); 1-[3-(1,4-diazepan-1-ylcarbonyl)-4-fluorobenzyl] quinolin-4(1H)-one; 1-{4-fluoro-3-[(4-propionylpiperazin-1-yl)carbonyl]benzyl}quinolin-4(1H)-one; 1-(4-fluoro-3-{[3-(trifluoromethyl)-5,6-dihydro[1,2,4]triazolo[4,3-a] pyrazin-7(8H)-yl]carbonyl}benzyl)quinolin-4(1H)-one; 1-[3-(1,8-diazaspiro[4.5]dec-8-ylcarbonyl)-4-fluorobenzyl] quinolin-4(1H)-one; 1-[4-fluoro-3-(piperazin-1-ylcarbonyl) benzyl]quinolin-4(1H)-one; 1-[3-(2,6-diazaspiro[3.5]non-2-ylcarbonyl)-4-fluorobenzyl]quinolin-4(1H)-one; 1-[3-(2,5-diazabicyclo[2.2.2]oct-2-ylcarbonyl)-4-fluorobenzyl] quinolin-4(1H)-one; 1-(4-fluoro-3-{[4-(2-methylprolyl) piperazin-1-yl]carbonyl}benzyl)quinolin-4(1H)-one; 1-(4-fluoro-3-{[4-(3,3,3-trifluoro-N,N-dimethylalanyl)piperazin-1-yl]carbonyl}benzyl)quinolin-4(1H)-one; (2R)-2-[(4-{2-fluoro-5-[(4-oxoquinolin-1 (4H)-yl)methyl] benzoyl}piperazin-1-yl)carbonyl]-2-methylazetidinium trifluoroacetate; 1-{4-fluoro-3-[(4-propionylpiperazin-1-yl) carbonyl]benzyl}-4-oxo-1,4-dihydrocinnolin-1-ium trifluoroacetate; 1-{3-[(3-ethyl-5,6-dihydro[1,2,4]triazolo[4,3-a] pyrazin-2-ium-7(8H)-yl)carbonyl]-4-fluorobenzyl}-4-oxo-1,4-dihydrocinnolin-1-ium bis(trifluoroacetate); 1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate; and 8-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate.

U.S. Pat. No. 8,268,827 to Branca et al., discloses pyridazinone derivatives as PARP inhibitors, including: 6-{4-fluoro-3-[(3-oxo-4-phenylpiperazin-1-yl)carbonyl] benzyl}-4,5-dimethyl-3-oxo-2,3-dihydropyridazin-1-ium trifluoroacetate; 6-{3-[(4-cyclohexyl-3-oxopiperazin-1-yl) carbonyl]-4-fluorobenzyl}-4,5-dimethyl-3-oxo-2,3-dihydropyridazin-1-ium trifluoroacetate; 6-{3-[(4-cyclopentyl-3-oxopiperazin-1-yl)carbonyl]-4-fluorobenzyl}-4,5-dimethylpyridazin-3(2H)-one; 6-{4-fluoro-3-[(3-oxo-4-phenylpiperazin-1-yl)carbonyl]benzyl}-4,5-dimethylpyridazin-3(2H)-one hydrochloride; 4-ethyl-6-{4-fluoro-3-[(3-oxo-4-phenylpiperazin-1-yl)carbonyl] benzyl}pyridazin-3(2H)-one trifluoroacetate; 6-{3-[(4-cyclohexyl-3-oxopiperazin-1-yl)carbonyl]-4-fluorobenzyl}-4-ethylpyridazin-3(2H)-one trifluoroacetate; 3-{4-fluoro-3-[(4-methyl-3-oxopiperazin-1-yl)carbonyl]benzyl}-4,5-dimethyl-6-oxo-1,6-dihydropyridazin-1-ium trifluoroacetate; 3-(4-fluoro-3-{[4-(4-fluorobenzyl)-3-oxopiperazin-1-yl]carbonyl}benzyl)-4,5-dimethyl-6-oxo-1,6-dihydropyridazin-1-ium trifluoroacetate; 6-(3-{[4-(2-chlorophenyl)-3-oxopiperazin-1-yl]carbonyl}-4-fluorobenzyl)-4,5-dimethyl-3-oxo-2,3-dihydropyridazin-1-ium trifluoroacetate; 6-(3-{[4-(3-chloro-4-fluorophenyl)-3-oxopiperazin-1-yl]carbonyl}-4-fluoro-benzyl)-4,5-dimethyl-3-oxo-2,3-dihydropyridazin-1-ium trifluoroacetate; 6-(3-{[4-(3,4-difluorophenyl)-3-oxopiperazin-1-yl]carbonyl}-4-fluorobenzyl)-4,5-dimethyl-3-oxo-2,3-dihydropyridazin-1-ium trifluoroacetate; and 6-(3-{[4-(3,5-difluorophenyl)-3-oxopiperazin-1-yl]carbonyl}-4-fluorobenzyl)-4,5-dimethyl-3-oxo-2,3-dihydropyridazin-1-ium trifluoroacetate.

U.S. Pat. No. 8,217,070 to Zhu et al., discloses 2-substituted-1H-benzimidazole-4-carboxamides as PARP inhibitors, including: 2-(1-aminocyclopropyl)-1H-benzimidazole-4-carboxamide; 2-[1-(isopropylamino)cyclopropyl]-1H-benzimidazole-4-carboxamide; 2-[1-(cyclobutylamino) cyclopropyl]-1H-benzimidazole-4-carboxamide; 2-{1-[(3,5-dimethylbenzyl)amino]cyclopropyl}-1H-benzimidazole-4-carboxamide; 2-{1-[(pyridin-4-ylmethyl)amino] cyclopropyl}-1H-benzimidazole-4-carboxamide; 2-[1-(dipropylamino)cyclopropyl]-1H-benzimidazole-4-carboxamide; 2-{1-[bis(cyclopropylmethy)amino] cyclopropyl}-1H-benzimidazole-4-carboxamide; 2-(1-aminocyclobutyl)-1H-benzimidazole-4-carboxamide; 2-[1-(propylamino)cyclobutyl]-1H-benzimidazole-4-carboxamide; 2-{1-[(cyclopropylmethyl)amino] cyclobutyl}-1H-benzimidazole-4-carboxamide; 2-[1-(isopropylamino)cyclobutyl]-1H-benzimidazole-4-carboxamide; 2-[1-(dipropylamino)cyclobutyl]-1H-benzimidazole-4-carboxamide; 2-[1-(dibutylamino) cyclobutyl]-1H-benzimidazole-4-carboxamide; 2-(1-aminocyclohexyl)-1H-benzimidazole-4-carboxamide;

9H-fluoren-9-ylmethyl 4-[4-(aminocarbonyl)-1H-benzimidazol-2-yl]piperidin-4-ylcarbamate; benzyl 4-amino-4-[4-(aminocarbonyl)-1H-benzimidazol-2-yl]piperidine-1-carboxylate; [2-(4-amino-piperidin-4-yl]-1H-benzoimidazole-4-carboxylic acid amide; 2-(2-amino-1,2,3,4-tetrahydronaphthalen-2-yl)-1H-benzimidazole-4-carboxamide; and 2-(2-amino-2,3-dihydro-1H-inden-2-yl)-1H-benzimidazole-4-carboxamide.

U.S. Pat. No. 8,188,103 to Van der Aa et al., discloses substituted 2-alkyl quinazolinone derivatives as PARP inhibitors.

U.S. Pat. No. 8,173,682 to Weintraub et al., discloses 2,3,5-substituted pyridone derivatives as PARP inhibitors, including: 5-(5-ethyl-2-methyl-6-oxo-1,6-dihydro-pyridin-3-yl)-thiophene-2-sulfonic acid [3-(3-hydroxy-pyrrolidin-1-yl)-propyl]-amide hydrochloride; 5-(5-ethyl-2-methyl-6-oxo-1,6-dihydropyridin-3-yl)thiophene-2-sulfonic acid [2-(1-methylpyrrolidin-2-yl)ethyl]amide hydrochloride; 5-(5-ethyl-2-methyl-6-oxo-1,6-dihydro-pyridin-3-yl)-thiophene-2-sulfonic acid [3-(3,3-difluoro-pyrrolidin-1-yl)-propyl]-amide hydrochloride; 5-[5-ethyl-2-methyl-6-oxo-1,6-dihydropyridin-3-yl]thiophene-2-sulfonic acid [3-(2-oxopyrrolidin-1-yl)propyl]amide; 5-[5-ethyl-2-methyl-6-oxo-1,6-dihydropyridin-3-yl]thiophene-2-sulfonic acid methyl (1-methylpyrrolidin-3-yl)amide hydrochloride; 3-ethyl-5-[5-(3-hydroxypyrrolidine-1-sulfonyl)thiophen-2-yl]-6-methyl-1H-pyridin-2-one; 5-(5-ethyl-2-methyl-6-oxo-1,6-dihydropyridin-3-yl)thiophene-2-sulfonic acid (2-pyrrolidin-1-yl)ethylamide hydrochloride; 5-(5-ethyl-2-methyl-6-oxo-1,6-dihydropyridin-3-yl)-thiophene-2-sulfonic acid (1-ethyl-pyrrolidin-2-ylmethyl)amide hydrochloride; 3-ethyl-6-methyl-5-[5-((S)-2-phenylaminomethylpyrrolidine-1-sulfonyl)-thiophen-2-yl]-1H-pyridin-2-one hydrochloride; 5-(5-ethyl-2-methyl-6-oxo-1,6-dihydro-pyridin-3-yl)-thiophene-2-sulfonic acid [3-(2R-hydroxymethyl-pyrrolidin-1-yl)-propyl]-amide hydrochloride; 5-(5-ethyl-2-methyl-6-oxo-1,6-dihydro-pyridin-3-yl)-thiophene-2-sulfonic acid [2-(2R-hydroxymethyl-pyrrolidin-1-yl)-ethyl]-amide hydrochloride; 5-(5-ethyl-2-methyl-6-oxo-1,6-dihydro-pyridin-3-yl)-thiophene-2-sulfonic acid [2-(3,3-difluoro-pyrrolidin-1-yl)-ethyl]-amide; and 1-{2-[5-(5-ethyl-2-methyl-6-oxo-1,6-dihydro-pyridin-3-yl)-thiophene-2-sulfonylamino]-ethyl}-pyrrolidine-2-carboxylic acid.

U.S. Pat. No. 8,129,382 to Kalish et al., discloses PARP inhibitors of Formula (P-III)

(P-III)

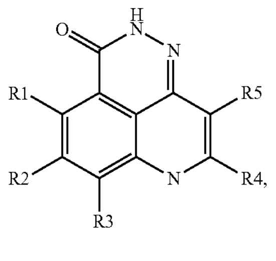

wherein:

(1) $R^1$ is H, halogen, alkoxy, or lower alkyl;

(2) $R^2$ is H, halogen, alkoxy, or lower alkyl;

(3) $R^3$ is independently H, amino, hydroxy, —N—N, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl;

(4) R4 is independently H, amino, hydroxy, —N—N, —CO—N—N, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl; and (5) R5 is independently H, amino, hydroxy, —N—N, —CO—N—N, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl.

U.S. Pat. No. 8,088,760 to Chu et al., discloses benzoxazole carboxamide inhibitors of PARP, including: 2-(4-((methylamino)methyl)phenyl)benzo[d]oxazole-4-carboxamide; 2-(2-methylpyrrolidin-2-yl)benzo[d]oxazole-4-carboxamide; 2-(4-((methylamino)methyl)phenyl)benzo[d]oxazole-7-carboxamide; 2-(2-methylpyrrolidin-2-yl)benzo[d]oxazole-7-carboxamide; 2-(pyrrolidin-2-yl)benzo[d]oxazole-4-carboxamide; 2-(pyrrolidin-2-yl)benzo[d]oxazole-7-carboxamide; 2-(7-azabicyclo[2.2.1]heptan-1-yl)benzo[d]oxazole-4-carboxamide; 2-(7-azabicyclo[2.2.1]heptan-1-yl)benzo[d]oxazole-7-carboxamide; 2-(2-methyl-7-azabicyclo[2.2.1]heptan-1-yl)benzo[d]oxazole-4-carboxamide; 2-(2-methyl-7-azabicyclo[2.2.1]heptan-1-yl)benzo[d]oxazole-7-carboxamide; 2-(2-azabicyclo[2.1.1]hexan-1-yl)benzo[d]oxazole-4-carboxamide; 2-(2-azabicyclo[2.1.1]hexan-1-yl)benzo[d]oxazole-7-carboxamide; 2-(6-azabicyclo[3.2.1]octan-5-yl)benzo[d]oxazole-4-carboxamide; 2-(6-azabicyclo[3.2.1]octan-5-yl)benzo[d]oxazole-7-carboxamide; 2-((1S,5R)-6-azabicyclo[3.2.1]octan-5-yl)benzo[d]oxazole-4-carboxamide; 2-((1S,5R)-6-azabicyclo[3.2.1]octan-5-yl)benzo[d]oxazole-7-carboxamide; 2-((1R,5S)-6-azabicyclo[3.2.1]octan-5-yl)benzo[d]oxazole-4-carboxamide; 2-((1R,5S)-6-azabicyclo[3.2.1]octan-5-yl)benzo[d]oxazole-7-carboxamide; 2-(2-benzyl-2-azabicyclo[2.2.2]octan-1-yl)benzo[d]oxazole-4-carboxamide; 2-(2-benzyl-2-azabicyclo[2.2.2]octan-1-yl)benzo[d]oxazole-7-carboxamide; 2-(2-azabicyclo[2.2.2]octan-1-yl)benzo[d]oxazole-4-carboxamide; 2-(2-azabicyclo[2.2.2]octan-1-yl)benzo[d]oxazole-7-carboxamide; 2-(4-azaspiro[2.4]heptan-5-yl)benzo[d]oxazole-4-carboxamide; 2-(4-azaspiro[2.4]heptan-5-yl)benzo[d]oxazole-7-carboxamide; 2-((1R,4S)-2-methyl-2-azabicyclo[2.2.1]heptan-1-yl)benzo[d]oxazole-4-carboxamide; and 2-((1R,4S)-2-methyl-2-azabicyclo[2.2.1]heptan-1-yl)benzo[d]oxazole-7-carboxamide.

U.S. Pat. No. 8,071,623 to Jones et al., discloses amide-substituted indazoles as PARP inhibitors, including: 2-(4-piperidin-3-ylphenyl)-2H-indazole-7-carboxamide; 2-{4-[(3R)-piperidin-3-yl]phenyl}-2H-indazole-7-carboxamide; 2-{4-[(3S)-piperidin-3-yl]phenyl}-2H-indazole-7-carboxamide; 5-fluoro-2-(4-piperidin-3-ylphenyl)-2H-indazole-7-carboxamide; 5-fluoro-2-{4-[(3S)-piperidin-3-yl]phenyl}-2H-indazole-7-carboxamide; 5-fluoro-2-{4-[(3R)-piperidin-3-yl]phenyl}-2H-indazole-7-carboxamide; 5-fluoro-2-(3- fluoro-4-piperidin-3-ylphenyl)-2H-indazole-7-carboxamide; 5-fluoro-2-{3-fluoro-4-[(3R)-piperidin-3-yl]phenyl}-2H-indazole-7-carboxamide; and 5-fluoro-2-{3-fluoro-4-[(3S)-piperidin-3-yl]phenyl}-2H-indazole-7-carboxamide.

U.S. Pat. No. 8,058,275 to Xu et al., discloses diazabenzo[de]anthracen-3-one compounds as PARP inhibitors.

U.S. Pat. No. 8,012,976 to Wang et al., discloses dihydropyridophthalazinone compounds as PARP inhibitors, including 5-fluoro-8-(4-fluorophenyl)-9-(1-methyl-1H-1,2,4-triazol-5-yl)-8,9-dihydro-2H-pyrido[4,3,2-de]phthalazin-3(7H)-one.

U.S. Pat. No. 8,008,491 to Jiang et al., discloses substituted aza-indole derivatives as PARP inhibitors, including: 1-phenyl-2-(piperazin-1-yl)-1,3-dihydropyrrolo[2,3-b]pyridine-3-carboxaldehyde, 1-phenyl-2-(piperazin-1-yl)-1H-pyrrolo[2,3-c]pyridine-3-carboxaldehyde, 2-[1,4]diazepan-1-yl-1-phenyl-1H-pyrrolo[2,3-b]pyridine-3-carbaldehyde trifluoroacetic acid salt, and 2-piperazin-1-yl-1-pyridin-3-yl-1H-pyrrolo[2,3-b]pyridine-3-carbaldehyde bis-trifluoroacetic acid salt.

U.S. Pat. No. 7,999,117 to Giranda et al., discloses 1H-benzimidazole-4-carboxamides as PARP inhibitors, including: 6-fluoro-2-[4-((S)-2-hydroxymethylpyrrolidin-1-ylmethyl)phenyl]-1H-benzimidazole-4-carboxamide; 6-fluoro-2-[4-(2-trifluoromethylpyrrolidin-1-ylmethyl)phenyl]-1H-benzimidazole-4-carboxamide; 6-fluoro-2-[4-((R)-2-hydroxymethylpyrrolidin-1-ylmethyl)phenyl]-1H-benzimidazole-4-carboxamide; 2-[4-((S)-2-hydroxymethylpyrrolidin-1-ylmethyl)phenyl]-1H-benzimidazole-4-carboxamide; 2-[4-(2-trifluoromethylpyrrolidin-1-ylmethyl)phenyl]-1H-benzimidazole-4-carboxamide; 2-[4-((R)-2-hydroxymethylpyrrolidin-1-ylmethyl)phenyl]-1H-benzimidazole-4-carboxamide; 6-chloro-2-[4-(2-trifluoromethylpyrrolidin-1-ylmethyl)phenyl]-1H-benzimidazole-4-carboxamide; 6-chloro-2-[4-((S)-2-hydroxymethylpyrrolidin-1-ylmethyl)phenyl]-1H-benzimidazole-4-carboxamide; 6-chloro-2-[4-((R)-2-hydroxymethylpyrrolidin-1-ylmethyl)phenyl]-1H-benzimidazole-4-carboxamide; 2-[2-fluoro-4-((S)-2-hydroxymethylpyrrolidin-1-ylmethyl)phenyl]-1H-benzimidazole-4-carboxamide; 2-{4-[(3-aminopyrrolidin-1-yl)methyl]phenyl}-1H-benzimidazole-4-carboxamide; and 2-(4-{[3-(dimethylamino)pyrrolidin-1-yl]methyl}phenyl)-1H-benzimidazole-4-carboxamide.

U.S. Pat. No. 7,994,182 to Sumegi et al., discloses quinazolinone derivatives as PARP inhibitors of Formula (P-IV):

(P-IV)

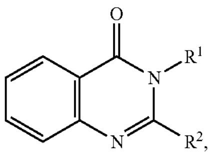

wherein:

(1) $R^1$ is hydrogen or a moiety of Subformula (P-IV(a)):

(P-IV(a))

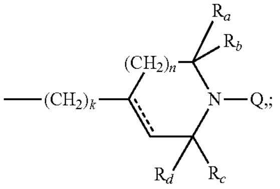

(2) k is 1, 2, 3, or 4;

(3) n is 0 or 1;

(4) Q is an oxyl group or hydrogen;

(5) $R_a$ and $R_b$ are independently hydrogen or $C_1$-$C_6$ alkyl;

(6) $R_b$ and $R_d$ are independently $C_1$-$C_6$ alkyl;

(7) the broken line in the six-membered ring is an optional valence bond (the bond is either a single or a double bond);

(8) $R^2$ is either:

(8a) if $R^1$ is other than hydrogen, hydrogen or $C_1$-$C_6$ alkyl;

(8b) if $R^1$ is hydrogen, a group of Subformula (P-IV(b)), Subformula (P-IV(c)), or Subformula (P-IV(d)):

(P-IV(b))

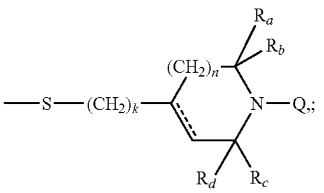

(P-IV(c)

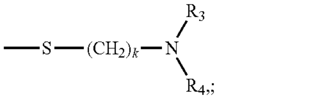

(P-IV(d))

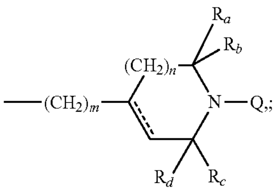

wherein:

(9) in Subformula (P-IV(b)), k, n, $R_a$, $R_b$, $R_c$, $R_d$, and the broken line are as defined above in (2), (3), (5), (6), and (7);

(10) in Subformula (P-IV(c)), k is 1, 2, or 3, and $R^3$ and $R^4$ are independently $C_1$-$C_6$ alkyl;

(11) or together with the attached nitrogen form a group of Subformula (P-IV(e)), wherein p is 0 or 1 and $R_{a'}$, $R_{b'}$, $R_{c'}$, and $R_{d'}$ are independently hydrogen or $C_1$-$C_6$ alkyl;

(P-IV(e))

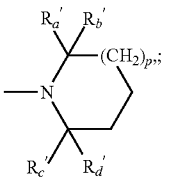

and

(11) in Subformula (P-IV(d), n, $R_a$, $R_b$, $R_c$, $R_d$, and the broken line are as defined above in (3), (5), (6), and (7).

U.S. Pat. No. 7,834,015 to Jones et al., discloses pyrrolo [1,2-a]pyrazin-1(2H)-one and pyrrolo[1,2-d][1,2,4]triazin-1 (2H)-one derivatives as PARP inhibitors.

U.S. Pat. No. 7,825,129 to Pellicciari et al., discloses thieno[2,3-c]quinolones as PARP inhibitors, including compounds of Formula (P-V):

(P-V)

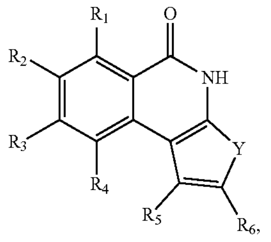

wherein:

(1) Y is selected from sulfur, nitrogen, and oxygen;

(2) $R_1$, $R_2$, $R_3$, $R_4$, $R_5$ and $R_6$ are the same or different, and each represent hydrogen, hydroxy, $OR_7$, $COOR_7$, carboxy, amino, $NHR_7$ or halogen, or $R_5$ and $R_6$ taken together form a fused non-aromatic 5- or 6-membered carbocylic ring; and (3) $R_7$ is $C_1$-$C_6$ alkyl, $C_2$-$C_6$ alkenyl or $C_3$-$C_7$ cycloalkyl optionally substituted with one or more group selected from hydroxyl, $C_1$-$C_4$ alkoxy, carboxy, $C_1$-$C_6$ alkoxycarbonyl, amino, $C_1$-$C_6$ mono-alkylamino, $C_1$-$C_6$ di-alkylamino and halogen.

U.S. Pat. No. 7,820,668 to Xu et al., discloses diazabenzo [de]anthracen-3-one compounds as PARP inhibitors.

U.S. Pat. No. 7,732,491 to Sherman et al., discloses 4-iodo-3-nitrobenzamide as a PARP inhibitor.

U.S. Pat. No. 7,728,026 to Zhu et al., discloses 2-substituted 1H-benzimidazole-4-carboxamides as PARP inhibitors, including 2-(1-amino-1-methylethyl)-1H-benzimidazole-4-carboxamide; 2-[1-methyl-1-(propylamino)ethyl]-1H-benzimidazole-4-carboxamide; 2-[1-(butylamino)-1-methylethyl]-1H-benzimidazole-4-carboxamide; 2-{1-methyl-1-[(2-phenylethyl)amino]ethyl}-1H-benzimidazole-4-carboxamide; 2-[1-(isopropylamino)-1-methylethyl]-1H-benzimidazole-4-carboxamide; 2-{1-[(cyclopropylmethyl) amino]-1-methylethyl}-1H-benzimidazole-4-carboxamide; 2-[1-(cyclobutylamino)-1-methylethyl]-1H-benzimidazole-4-carboxamide; 2-[1-(cyclopentylamino)-1-methylethyl]-1H-benzimidazole-4-carboxamide; 2-(1-{[(cyclopentylamino)carbonyl]amino}-1-methylethyl)-1H-benzimidazole-4-carboxamide; 2-(1-{[(ethylamino) carbonyl]amino}-1-methylethyl)-1H-benzimidazole-4-carboxamide; 2-(1-{[(dimethylamino)sulfonyl]amino}-1-methylethyl)-1H-benzimidazole-4-carboxamide; 2-(3-amino-1-methylpropyl)-1H-benzimidazole-4-carboxamide; 2-[3-(cyclopentylamino)-1-methylpropyl]-1H-benzimidazole-4-carboxamide; 2-[3-(cyclohexylamino)-1-methylpropyl]-1H-benzimidazole-4-carboxamide; 2-(1-aminoethyl)-1H-benzimidazole-4-carboxamide; 2-[1-(propylamino) ethyl]-1H-benzimidazole-4-carboxamide; 2-[1-(butylamino)ethyl]-1H-benzimidazole-4-carboxamide; 2-{1-[(cyclopropylmethyl)amino]ethyl}-1H-benzimidazole-4-carboxamide; 2-[1-(isobutylamino)ethyl]-1H-benzimidazole-4-carboxamide; 2-[1-(isopropylamino)ethyl]-1H-benzimidazole-4-carboxamide; 2-[1-(cyclopentylamino) ethyl]-1H-benzimidazole-4-carboxamide; 2-[1-(cyclohexylamino)ethyl]-1H-benzimidazole-4-carboxamide; 2-{1-[(2-phenylethyl)amino]ethyl}-1H-benzimidazole-4-carboxamide; 2-[1-(dipropylamino)ethyl]-1H-benzimidazole-4-carboxamide; 2-{1-[butyl(pentyl) amino]ethyl}-1H-benzimidazole-4-carboxamide; 2-{1-[bis (cyclopropylmethyl)amino]ethyl}-1H-benzimidazole-4-carboxamide; 2-(1-{[(dimethylamino)sulfonyl] amino}ethyl)-1H-benzimidazole-4-carboxamide; 2-(1-aminopropyl)-1H-benzimidazole-4-carboxamide; 2-[(1R)-1-(dimethylamino)-2-phenylethyl]-1H-benzimidazole-4-carboxamide; and 2-(1-amino-1-methylethyl)-5-chloro-1H-benzimidazole-7-carboxamide.

U.S. Pat. No. 7,595,406 to Penning et al., discloses substituted 1H-benzimidazole-4-carboxamides as PARP inhibitors, including 2-{4-[1-(cyclohexylmethylamino) ethyl]phenyl}-1H-benzimidazole-4-carboxamide; 2-[4-(1-cyclobutylaminoethyl)phenyl]-1H-benzimidazole-4-carboxamide; 2-[3-(2-cyclopropylaminoethyl)phenyl]-1H-benzimidazole-4-carboxamide; 2-(4-cyclopropylaminomethylphenyl)-1H-benzimidazole-4-carboxamide; 2-(4-cyclobutylaminomethylphenyl)-1H-benzimidazole-4-carboxamide; 2-(4-cyclopentylaminomethylphenyl)-1H-benzimidazole-4-carboxamide; 6-chloro-2-{4-[(1,2,3,4-tetrahydronaphthalen-1-ylamino)methyl]phenyl}-1H-benzimidazole-4-carboxamide; 2-(4-cyclopropylaminomethylphenyl)-6-fluoro-1H-benzimidazole-4-carboxamide; 2-(4-cyclobutylaminomethylphenyl)-6-fluoro-1H-benzimidazole-4-carboxamide; 2-(4-cyclopentylaminomethylphenyl)-6-fluoro-1H-benzimidazole-4-carboxamide; 2-[4-(2-cyclopropylaminoethyl)phenyl]-1H-benzimidazole-4-carboxamide; 2-[4-(2-cyclobutylaminoethyl)phenyl]-1H-benzimidazole-4-carboxamide; 2-(4-cyclopropylaminomethyl-2-fluorophenyl)-1H-benzimidazole-4-carboxamide; 2-[4-(1-cyclopropylaminoethyl)phenyl]-1H-benzimidazole-4-carboxamide; 2-(4-cyclobutylaminomethyl-2-fluorophenyl]-1H-benzimidazole-4-carboxamide; 2-(4-cyclohexylaminomethyl-2-fluorophenyl)-1H-benzimidazole-4-carboxamide; and 2-(4-cyclopentylaminomethyl-2-fluorophenyl)-1H-benzimidazole-4-carboxamide.

U.S. Pat. No. 7,550,603 to Zhu et al., discloses 1H-benzimidazole-4-carboxamides substituted with a quaternary carbon at the 2-position as PARP inhibitors, including 2-(2-methylpyrrolidin-2-yl)-1H-benzimidazole-4-carboxamide; 2-[(2R)-2-methylpyrrolidin-2-yl]-1H-benzimidazole-4-carboxamide; 2-[(2S)-2-methylpyrrolidin-2-yl]-1H-benzimidazole-4-carboxamide; 2-(1,2-dimethylpyrrolidin-2-yl)-1H-benzimidazole-4-carboxamide; 2-(1-ethyl-2-methylpyrrolidin-2-yl)-1H-benzimidazole-4-carboxamide; 2-(2-methyl-1-propylpyrrolidin-2-yl)-1H-benzimidazole-4-carboxamide; 2-(1-isopropyl-2-methylpyrrolidin-2-yl)-1H-benzimidazole-4-carboxamide; 2-(1-cyclobutyl-2-methylpyrrolidin-2-yl)-1H-benzimidazole-4-carboxamide; 2-(3-methylpyrrolidin-3-yl)-1H-benzimidazole-4-carboxamide; 2-(3-methyl-1-propylpyrrolidin-3-yl)-1H-benzimidazole-4-carboxamide; 2-[1-(cyclopropylmethyl)-3-methylpyrrolidin-3-yl]-1H-benzimidazole-4-carboxamide; 2-(1-isobutyl-3-methylpyrrolidin-3-yl)-1H-benzimidazole-4-carboxamide; 2-(1-isopropyl-3-methylpyrrolidin-3-yl)-1H-benzimidazole-4-carboxamide; 2-(1-cyclobutyl-3-methylpyrrolidin-3-yl)-1H-benzimidazole-4-carboxamide; 2-(1-cyclopentyl-3-methylpyrrolidin-3-yl)-1H-benzimidazole-4-carboxamide; 2-(1-cyclohexyl-3-methylpyrrolidin-3-yl)-1H-benzimidazole-4-carboxamide; 2-(3-methyl-1-tetrahydro-2H-pyran-4-ylpyrrolidin-3-yl)-1H-benzimidazole-4-carboxamide; 2-[3-methyl-1-(pyridin4-ylmethyl)pyrrolidin-3-yl]-1H-benzimidazole-4-carboxamide; 2-[3-methyl-1-(2-phenylethyl)pyrrolidin-3-yl]-1H-benzimidazole-4-carboxamide; 2-[3-methyl-1-(1-methyl-3-phenylpropyl) pyrrolidin-3-yl]-1H-benzimidazole-4-carboxamide; 2-(2-methylazetidin-2-yl)-1H-benzimidazole-4-carboxamide; 2-(1-isopropyl-2-methylazetidin-2-yl)-1H-benzimidazole-4-carboxamide; 2-(1-cyclobutyl-2-methylazetidin-2-yl)-1H-benzimidazole-4-carboxamide; 2-(1-cyclopentyl-2-methylazetidin-2-yl)-1H-benzimidazole-4-carboxamide; 2-(1-cyclohexyl-2-methylazetidin-2-yl)-1H-benzimidazole-4-carboxamide; 2-(3-methylazetidin-3-yl)-1H-benzimidazole-4-carboxamide; 2-(3-methyl-1-propylazetidin-3-yl)-1H-benzimidazole-4-carboxamide; 2-[1-(cyclopropylmethyl)-3-methylazetidin-3-yl]-1H-benzimidazole-4-carboxamide; 2-(1-isobutyl-3-methylazetidin-3-yl)-1H-benzimidazole-4-carboxamide; 2-(1-cyclobutyl-3-methylazetidin-3-yl)-1H-benzimidazole-4-carboxamide; 2-(1-cyclopentyl-3-methylazetidin-3-yl)-1H-benzimidazole-4-carboxamide; 2-(1-cyclohexyl-3-methylazetidin-3-yl)-1H-benzimidazole-4-carboxamide; 2-(3-methyl-1-tetrahydro-2H-pyran-4-ylazetidin-3-yl)-1H-benzimidazole-4-carboxamide; 2-{1-[(dimethylamino)sulfonyl]-3-methylazetidin-3-yl}-1H-benzimidazole-4-carboxamide; and 2-(2-methylpiperidin-2-yl)-1H-benzimidazole-4-carboxamide.

U.S. Pat. No. 7,405,300 to Jiang et al., discloses substituted indoles as PARP inhibitors, including 2-(piperazin-1-yl)-1-(3-nitrophenyl)-1H-indole-3-carboxaldehyde; 2-(piperazin-1-yl)-1-(4-methoxyphenyl)-1H-indole-3-carboxaldehyde; 2-(piperazin-1-yl)-1-(4-tert-butylphenyl)-1H-indole-3-carboxaldehyde; 2-(piperazin-1-yl)-1-(4-bromophenyl)-1H-indole-3-carboxaldehyde; 2-(piperazin-1-yl)-1-(4-chlorophenyl)-1H-indole-3-carboxaldehyde; 2-(piperazin-1-yl)-1-(3-chloro-4-fluorophenyl)-1H-indole-3-carboxaldehyde, 2-(piperazin-1-yl)-1-(3-methoxyphenyl)-1H-indole-3-carboxaldehyde; 2-(piperazin-1-yl)-1-(4-thiomethylphenyl)-1H-indole-3-carboxaldehyde; 2-(piperazin-1-yl)-1-(3-fluorophenyl)-1H-indole-3-carboxaldehyde; 2-(piperazin-1-yl)-1-(3-methylphenyl)-1H-indole-3-carboxaldehyde; 1-(4-tert-butylphenyl)-2-piperazin-1-yl-1H-indole-3-carboxaldehyde, 1-(4-tert-butylphenyl)-2-piperidin-1-yl-1H-indole-3-carboxaldehyde; 1-(3-formylphenyl)-2-(piperazin-2-yl)-1H-indole-3-carboxaldehyde; 1-(biphenyl-4-yl)-2-(piperazin-1-yl)-1H-indole-3-carboxaldehyde hydrochloride; 1-(4-ethylphenyl)-2-(piperazin-1-yl)-1H-indole-3-carboxaldehyde hydrochloride; and 1-(3-bromophenyl)-2-piperazin-1-yl-1H-indole-3-carboxaldehyde.

U.S. Pat. No. 7,087,637 to Grandel et al., discloses indole derivatives as PARP inhibitors, including: 2-(4(4-n-propyl-piperazin-1-yl)-phenyl)-1H-indol-4-carboxamide; 2-(4-piperazin-1-yl-phenyl)-1H-indol-4-carboxamide; 2-(4(4-Isopropyl-piperazin-1-yl)-phenyl)-1H-indol-4-carboxamide; 2-(4(4-benzyl-piperazin-1-yl)-phenyl)-1H-indol-4-carboxam id; 2-(4(4-n-butyl-piperazin-1-yl)-phenyl)-1H-indol-4-carboxamid; 2-(4(4-ethyl-piperazin-1-yl)-phenyl)-1H-indol-4-carboxamide; 2-(4-(2-N,N-dimethylamino-eth-1-yloxy)-phenyl)-1H-indol-4-carboxamide; 2-(4-(2-pyrrolidinl-yl-eth-1-yloxy)-phenyl)-1H-indol-4-carboxamide; 2-(4-(2-piperidin-yl-eth-1-yloxy)-phenyl)-1H-indol-4-carboxamide; 2-(4-(2-piperazin-1-yl-eth-1-yloxy)-phenyl)-1H-indol-4-carboxamide; 2-(4-(2-(4-methyl-piperazin-1-yl)-eth-1-yloxy)-phenyl)-1H-indol-4-carboxamide; 2-(4-(2-(4-propyl-piperazin-1-yl)-eth-1-yloxy)-phenyl)-1H-indol-4-carboxamide; 2-(4-(2-(4-ethyl-piperazin-1-yl)-eth-1-yloxy)-phenyl)-1H-indol-4-carboxamide; and 2-(4-(2-(4-benzyl-piperazin-1-yl)-eth-1-yloxy)-phenyl)-1H-indol-4-carboxamide.

U.S. Pat. No. 7,041,675 to Lubisch et al., discloses substituted pyridine carboxamides as PARP inhibitors, including 2-phenylimidazo[1,2-a]pyridine-8-carboxamide; 2-(4-nitrophenyl)imidazo[1,2-a]pyridine-8-carboxamide; 2-(4-aminophenyl)imidazo[1,2-a]pyridine-8-carboxamide; 2-(2-benzothienyl)imidazo[1,2-a]pyridine-8-carboxamide; 2-(4-bromophenyl)-imidazo[1,2-a]pyridine-8-carboxamide; and 2-(4-imidazol-1-ylphenyl)imidazo[1,2-a]pyridine-8-carboxamide.

U.S. Pat. No. 6,924,284 to Beaton et al., discloses substituted bicyclic aryl PARP inhibitors, including: N-[3-(4-oxo-3,4-dihydro-phthalazin-1-ylamino)-propyl]-3-[3-(1H-pyrrol-2-yl)-[1,2,4]oxadiaol-5-yl]propionamide; N-[3-(4-oxo-3,4-dihydro-phthalazin-1-ylamino)-propyl]-3-(3-thiophen-3-yl-[1,2,4]oxadiazol-5-yl)propionamide; 3-(3-furan-2-yl-[1,2,4]oxadiazol-5-yl)-N-[3-(4-oxo-3,4-dihydro-phthalazin-1-ylamino)-propyl]-propionamide; N-[3-(4-oxo-3,4-dihydro-phthalazin-1-ylamino)-propyl]-3-(3-thiophen-2-yl-[1,2,4]oxadiazol-5-yl)-propionamide; 3-[3-(2-methyl-thiophen-3-yl)-[1,2,4]oxadiazol-5-yl]-N-[3-(4-oxo-3,4-dihydro-phthalazin-1-ylamino)-propyl]-propionamide; 3-[3-(3,5-dihydroxy-phenyl)-[1,2,4]oxadiazol-5-yl]-N-[3-(4-oxo-3,4-dihydro-phthalazin-1-ylamino)-propyl]-propionamide; 3-[3-(3-hydroxy-phenyl)-[1,2,4]oxadiazol-5-yl]-N-[3-(4-oxo-3,4-dihydro-phthalazin-1-ylamino)-propyl]-propionamide; and 3-[3-(5-amino-3H-imidazol-4-yl)-[1,2,4]oxadiazol-5-yl]-N-[3-(4-oxo-3,4-dihydro-phthalazin-1-ylamino)-propyl]-propionamide.

U.S. Pat. No. 6,635,642 to Jackson et al., discloses phthalazinone derivatives as PARP inhibitors, including 4-(3-nitro-4-(piperidin-1-yl)phenyl-phthalazin-1(2H)-one; 4-(4-(dimethylamino)-3-nitrophenyl)-phthalazin-1(2H)-one; 4-(3-amino-4-(dimethylamino)phenyl)-phthalazin-1(2H)-one; 4-(4-phenylpiperazin-1-yl)-phthalazin-1(2H)-one; and 4-(4-(4-chlorophenyl)-piperazin-1-yl)-phthalazin-1(2H)-one.

U.S. Pat. No. 6,448,271 to Lubisch et al., discloses substituted benzimidazoles as PARP inhibitors, including 2-(piperidin-4-yl)benzimidazole-4-carboxamide dihydrochloride; 2-(N-acetylpiperidin-4-yl)benzimidazole-4-carboxamide; 2-(N-propylpiperidin-4-yl)benzimidazole-4-carboxamide; 2-piperidin-3-ylbenzimidazole-4-carboxamide dihydrochloride; 2-(N—(O-t-butoxycarbonyl)piperidin-3-yl)benzimidazole-4-carboxamide; 2-(N-benzylpiperidin-3-yl)benzimidazole-4-carboxamide; 2-(N-methylpiperidin-3-yl)benzimidazole-4-carboxamide dihydrochloride; 2-piperazin-4-yl-benzimidazole-4-carboxamide; 2-(N-propylpiperidin-3-yl)benzimidazole-4-carboxamide dihydrochloride; 2-(N-(3-phenylprop-1-yl)-piperidin-3-yl)benzimidazole-4-carboxamide dihydrochloride; 2-(N-benzoylpiperidin-3-yl)benzimidazole-4-carboxamide; 2-(N-benzylpiperidin-4-yl)benzimidazole-4-carboxamide dihydrochloride; 2-(1-(1-methylpiperidin-4-yl)piperidin-4-yl)benzimidazole-4-carboxamide trihydrochloride; 2-(N-n-pentylpiperidin-4-yl)benzimidazole-4-carboxamide; 2-(N-isobut-1-yl-piperidin-4-yl)benzimidazole-4-carboxamide; 2-(N-n-butylpiperidin-4-yl)benzimidazole-4-carboxamide hydrochloride; 2-(N-(3-methyl-but-1-yl)piperidin-4-yl)benzimidazole-4-carboxamide hydrochloride; 2-(1,4-dimethylpiperazin-2-yl)benzimidazole-4-carboxamide dihydrochloride; 2-piperazin-2-yl-benzimidazole-4-carboxamide dihydrochloride; 2-(N-isopropylpiperidin-4-yl)benzimidazole-4-carboxamide hydrochloride; 2-(4-(2-ethyl-prop-1-yl) piperidin-4-yl)benzimidazole-4-carboxamide; 2-(1,4-dibenzylpiperazin-2-yl)benzimidazole-4-carboxamide dihydrochloride; and 2-(N-benzylpiperidin-4-yl)-1-(1-benzylpiperidin-4-ylcarbonyl)benzimidazole-4-carboxamide.

U.S. Pat. No. 6,426,415 to Jackson et al., discloses alkoxy-substituted PARP inhibitors, including 1-(benzyloxy)-5-methylphthalazine; 1-(methoxy)-5-methyl-phthalazine; 1-(ethoxy)-5-methylphthalazine; 1-(propoxy)-5-methylphthalazine; 1-(butoxy)-5-methyl-phthalazine; 1-(methoxy)-5-hydroxyphthalazine; 1-(ethoxy)-5-hydroxyphthalazine; 1-(propoxyoxy)-5-hydroxy-phthalazine; 1-(butoxy)-5-hydroxyphthalazine; 1-(benzyloxy)-5-methyl-isoquinoline; 1-(methoxy)-5-methyl-isoquinoline; 1-(ethoxy)-5-methylisoquinoline; 1-(propoxy)-5-methylisoquinoline; 1-(butoxy)-5-methylisoquinoline; 1-(ethoxy)-5-hydroxyisoquinoline; 1-(propoxy)-5-hydroxyisoquinoline; and 1-(butoxy)-5-hydroxy-isoquinoline.

U.S. Pat. No. 6,395,749 to Li et al., discloses substituted carboxamides as PARP inhibitors, including 5-carbamoylquinoline-4-carboxylic acid.

U.S. Pat. No. 6,387,902 to Zhang et al., discloses substituted phenazines as PARP inhibitors, including compounds of Formula (P-VI):

(P-VI)

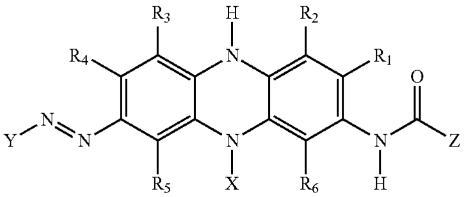

wherein:

(1) $R_1$-$R_9$ and Z are independently hydrogen, hydroxy, halo, haloalkyl, thiocarbonyl, cyano, nitro, amino, imino, alkylamino, aminoalkyl, sulfhydryl, thioalkyl, alkylthio, sulfonyl, alkylsulfonyl, $C_1$-$C_9$ straight or branched chain alkyl, $C_2$-$C_9$ straight or branched chain alkenyl, $C_2$-$C_9$ straight or branched chain alkynyl, $C_1$-$C_6$ straight or branched chain alkoxy, $C_2$-$C_6$ straight or branched chain alkenoxy, $C_2$-$C_6$ straight or branched chain alkynoxy, aryl, carbocycle, heterocycle, aralkyl, alkylaryl, alkylaryloxy, aryloxy, aralkyloxy, aralkylsulfonyl, aralkylamino, arylamino, arylazo, arylthio, or aralkylthio; or (2) Z is a moiety of Subformula (P-VI(a))

(P-VI(a)

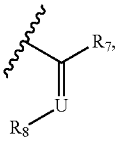

wherein U is C or N; $R_7$ and $R_8$ are as defined in (1); and X and Y are independently aryl, carbocycle, or heterocycle.

U.S. Pat. No. 6,380,211 to Jackson et al., discloses alkoxy-substituted PARP inhibitors, including 1-(methoxy)-5-methylisoquinoline, 1-(ethoxy)-5-methyl-isoquinoline, 1-(propoxy)-5-methylisoquinoline, 1-(butoxy)-5-methylisoquinoline, 1-(ethoxy)-5-hydroxy-isoquinoline, 1-(propoxy)-5-hydroxyisoquinoline, 1-(butoxy)-5-hydroxyisoquinoline, 1-(benzyloxy)-5-methylphthalazine and 1-(benzyloxy)-5-methylisoquinoline.

U.S. Pat. No. 6,358,975 to Eliasson et al., discloses PARP inhibitors, including 6(5H)-phenanthridinone, 2-nitro-6(5H)-phenanthridinone, 4-hydroxyquinazoline, 2-methyl-4(3H)-quinazoline, 2-mercapto-4(3H)-quinazoline, benzoyleneurea, 6-amino-1,2-benzopyrone, trp-P-1(3-amino-1,4-dimethyl-5H-pyrido[4,3-b]indole), juglone, luminol, 1(2H)-phthalazinone, phthalhydrazide, and chlorothenoxazin.

U.S. Pat. No. 6,235,748 to Li et al., discloses oxo-substituted compounds containing at least one ring nitrogen as PARP inhibitors.

U.S. Pat. No. 6,201,020 to Zhang et al., discloses ortho-diphenol compounds as PARP inhibitors, including compounds of Formula (P-VII):

(P-VII)

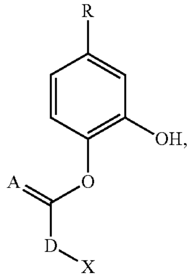

wherein:

(1) A is O or S;

(2) R is $C_1$-$C_{10}$ straight or branched chain alkyl, $C_2$-$C_{10}$ straight or branched chain alkenyl, $C_2$-$C_{10}$ straight or branched chain alkynyl, aryl, heteroaryl, carbocycle, or heterocycle;

(3) D is a bond, or a $C_1$-$C_3$ straight or branched chain alkyl, $C_2$-$C_3$ straight or branched chain alkenyl, $C_2$-$C_3$ straight or branched chain alkynyl, wherein any of the carbon atoms of said alkyl, alkenyl, or alkynyl of D are optionally replaced with oxygen, nitrogen, or sulfur; and (4) X is aryl, heteroaryl, carbocycle, or heterocycle.

U.S. Pat. No. 5,756,510 to Griffin et al., discloses benzamide analogs that are PARP inhibitors, including: 3-benzyloxybenzamide; 3-(4-methoxybenzyloxy)benzamide; 3-(4-nitrobenzyloxy)benzamide; 3-(4-azidobenzyloxy)benzamide; 3-(4-bromobenzyloxy)benzamide; 3-(4-fluorobenzyloxy)benzamide; 3-(4-aminobenzyloxy)benzamide; 3-(3-nitrobenzyloxy)benzamide; 3-(3,4-methylenedioxyphenylmethyloxy)benzamide; 3-(piperonyloxy)benzamide; 3-(N-acetyl-4-aminobenzyloxy)benzamide; 3-(4-trifluoromethylbenzyloxy)benzamide; 3-(4-cyanobenzyloxy)benzamide; 3-(4-carboxymethylbenzyloxy)benzamide; 3-(2-nitrobenzyloxy)benzamide; 3-(4-carboxybenzyloxy)benzamide; 3-(8-adenos-9-yloctyloxy)benzamide; 3-[5-(6-chloropurin-9-yl)pentyloxy]benzamide; 3-(5-adenos-9-ylpentyloxy)benzamide; 3-[8-(6-chloropurin-9-yl)octyloxy]benzamide; 3-[12-(6-chloropurin-9-yl)dodecyloxy]benzamide; and 3-(12-adenos-9-yldodecyloxy)benzamide.

United States Patent Application Publication No. 2015/0175617 by Zhou et al., discloses fused tetra or penta-cyclic dihydrodiazepinocarbazolones as PARP inhibitors, including: 2,3,5,10-tetrahydro-[1,2]diazepino[3,4:5,6-def]carbazol-6(1H)-one; 5,6,7,8-tetrahydro-4H-4,9,10-triazaindeno[2,1,7-kla]heptalen-11(10H)-one; 2-methyl-2,3,5,10-tetrahydro-[1,2]diazepino[3,4:5,6-def]carbazol-6(1H)-one; 3,3-dimethyl-2,3,5,10-tetrahydro-[1,2]diazepino[3,4:5,6-def]carbazol-6(1H)-one; 2-phenyl-2,3,5,10-tetrahydro-[1,2]

diazepino[3,4:5,6-def]carbazol-6(1H)-one; and 2-isopropyl-2,3,5,10-tetrahydro-[1,2]diazepino[3,4:5,6-def]carbazol-6(1H)-one.

United States Patent Application Publication No. 2015/0152118 by Jana et al., discloses tetrahydroquinazolinone derivatives as PARP inhibitors, including: 2'-(3-(4-(4-fluorophenyl)piperazin-1-yl)propyl)-6',7'-dihydro-3'H-spiro[cyclopropane-1,8'-quinazolin]-4'(5'H)-one; 2'-(3-(4-(4-chlorophenyl)piperazin-1-yl)propyl)-6',7'-dihydro-3'H-spiro[cyclopropane-1,8'-quinazolin]-4'(5'H)-one; 2'-(3-(4-phenyl-5,6-dihydropyridin-1(2H)-yl)propyl)-6',7'-dihydro-3'H-spiro[cyclopropane-1,8'-quinazolin]-4'(5'H)-one; 2'-(3-(3-(4-fluorophenyl)-3,8-diazabicyclo[3.2.1]octan-8-yl)propyl)-4a',5',6',7'-tetrahydro-3'H-spiro[cyclopropane-1,8'-quinazolin]-4'(8a'H)-one; 2'-(3-(4-(4-fluorophenyl)piperazin-1-yl)propyl)-7',8'-dihydro-3'H-spiro[cyclopropane-1,6'-quinazolin]-4'(5'H)-one; 2'-(3-(4-(4-chlorophenyl)piperazin-1-yl)propyl)-7',8'-dihydro-3'H-spiro[cyclopropane-1,6'-quinazolin]-4'(5'H)-one; 2'-(3-(3-(4-fluorophenyl)-3,8-diazabicyclo[3.2.1]octan-8-yl)propyl)-7',8'-dihydro-3'H-spiro[cyclopropane-1,6'-quinazolin]-4'(5'H)-one; 2'-(3-(8-(4-fluorophenyl)-3,8-diazabicyclo[3.2.1]octan-3-yl)propyl)-7',8'-dihydro-3'H-spiro[cyclopropane-1,6'-quinazolin]-4'(5'H)-one; 2'-(3-(4-(4-fluorophenyl)-5,6-dihydropyridin-1(2H)-yl)propyl)-7',8'-dihydro-3'H-spiro[cyclopropane-1,6'-quinazolin]-4'(5'H)-one; and 2'-(3-(4-(3,4-dichlorophenyl)piperazin-1-yl)propyl)-7',8'-dihydro-3'H-spiro[cyclopropane-1,6'-quinazolin]-4'(5'H).

United States Patent Application Publication No. 2015/0031652 by Gangloff et al., discloses substituted 1,2,3,4-tetrahydropyrido[2,3-b]pyrazines as PARP inhibitors, including (S)-3-((4-(4-chlorophenyl)piperazin-1-yl)methyl)-6a,7,8,9-tetrahydropyrido[3,2-e]pyrrolo[1,2-a]pyrazin-6(5H)-one; (S)-3-((4-(4-chlorophenyl)-5,6-dihydropyridin-1(2H)-yl)methyl)-6a,7,8,9-tetrahydropyrido[3,2-e]pyrrolo[1,2-a]pyrazin-6(5H)-one; (S)-3-((4-(4-chlorophenyl)piperidin-1-yl)methyl)-6a,7,8,9-tetrahydropyrido[3,2-e]pyrrolo[1,2-a]pyrazin-6(5H)-one; (S)-4-(4-((6-oxo-5,6,6a,7,8,9-hexahydropyrido[3,2-e]pyrrolo[1,2-a]pyrazin-3-yl)methyl)piperazin-1-yl)benzonitrile; (S)-6-(4-((6-oxo-5,6,6a,7,8,9-hexahydropyrido[3,2-e]pyrrolo[1,2-a]pyrazin-3-yl)methyl)piperazin-1-yl)nicotinonitrile; (S)—N-methyl-6-(4-((6-oxo-5,6,6a,7,8,9-hexahydropyrido[3,2-e]pyrrolo[1,2-a]pyrazin-3-yl)methyl)piperazin-1-yl)nicotinamide; (S)-ethyl 6-(4-((6-oxo-5,6,6a,7,8,9-hexahydropyrido[3,2-e]pyrrolo[1,2-a]pyrazin-3-yl)methyl)piperazin-1-yl)nicotinate; (S)-6-(4-((6-oxo-5,6,6a,7,8,9-hexahydropyrido[3,2-e]pyrrolo[1,2-a]pyrazin-3-yl)methyl)piperazin-1-yl)nicotinic acid; (S)—N-ethyl-6-(4-((6-oxo-5,6,6a,7,8,9-hexahydropyrido[3,2-e]pyrrolo[1,2-a]pyrazin-3-yl)methyl)piperazin-1-yl)nicotinamide; (S)—N-cyclopropyl-6-(4-((6-oxo-5,6,6a,7,8,9-hexahydropyrido[3,2-e]pyrrolo[1,2-a]pyrazin-3-yl)methyl)piperazin-1-yl)nicotinamide; (S)—N-isopropyl-6-(4-((6-oxo-5,6,6a,7,8,9-hexahydropyrido[3,2-e]pyrrolo[1,2-a]pyrazin-3-yl)methyl)piperazin-1-yl)nicotinamide; (S)—N-ethyl-4-(4-((6-oxo-5,6,6a,7,8,9-hexahydropyrido[3,2-e]pyrrolo[1,2-a]pyrazin-3-yl)methyl)piperazin-1-yl)benzamide; (S)-ethyl 4-(4-((6-oxo-5,6,6a,7,8,9-hexahydropyrido[3,2-e]pyrrolo[1,2-a]pyrazin-3-yl)methyl)piperazin-1-yl)benzoate; (S)-4-(4-((6-oxo-5,6,6a,7,8,9-hexahydropyrido[3,2-e]pyrrolo[1,2-a]pyrazin-3-yl)methyl)piperazin-1-yl)benzoic acid; (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzamide; (S)—N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide; (S)—N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide; (S)-3-fluoro-4-(4-((6-oxo-5,6,66a, 7,8,9-hexahydropyrido[3,2-e]pyrrolo[1,2-a]pyrazin-3-yl)methyl)piperazin-1-yl)benzonitrile; and (S)-3-((4-(2,4-difluorophenyl)piperazin-1-yl)methyl)-6a,7,8,9-tetrahydropyrido[3,2-e]pyrrolo[1,2-a]pyrazin-6(5H)-one.

United States Patent Application Publication No. 2015/0025071 by Buchstaller et al., discloses tetrahydroquinazolinone derivatives as PARP inhibitors, including: 2-[4-(4-methoxy-phenyl)-piperazin-1-yl]-5,6,7,8-tetrahydro-3H-quinazolin-4-one; 2-[4-(3-fluorophenyl)piperazin-1-yl]-5,6,7,8-tetrahydro-3H-quinazolin-4-one; 2-[4-(4-fluorophenyl)piperazin-1-yl]-5,6,7,8-tetrahydro-3H-quinazolin-4-one; 2-[4-(3-methoxyphenyl)piperazin-1-yl]-5,6,7,8-tetrahydro-3H-quinazolin-4-one; 2-[4-(4-chlorophenyl)piperazin-1-yl]-5,6,7,8-tetrahydro-3H-quinazolin-4-one; 2-[4-(2-chlorophenyl)piperazin-1-yl]-5,6,7,8-tetrahydro-3H-quinazolin-4-one; 2-(4-trifluoromethylpiperidin-1-yl)-5,6,7,8-tetrahydro-3H-quinazolin-4-one; 2-[4-(3-chlorophenyl)piperazin-1-yl]-5,6,7,8-tetrahydro-3H-quinazolin-4-one; 2-[4-(2-methoxyphenyl)piperazin-1-yl]-5,6,7,8-tetrahydro-3H-quinazolin-4-one; 2-(4-tert-butylpiperazin-1-yl)-5,6,7,8-tetrahydro-3H-quinazolin-4-one; 2-[4-(4-methoxyphenyl)-3-oxopiperazin-1-yl]-5,6,7,8-tetrahydro-3H-quinazolin-4-one; 2-[4-(piperidine-1-carbonyl)piperazin-1-yl]-5,6,7,8-tetrahydro-3H-quinazolin-4-one; 2-[4-(6-hydroxypyridin-2-yl)piperazin-1-yl]-5,6,7,8-tetrahydro-3H-quinazolin-4-one; 2-(4-benzoylpiperazin-1-yl)-5,6,7,8-tetrahydro-3H-quinazolin-4-one; N-pyridin-2-yl-2-[4-(4-oxo-3,4,5,6,7,8-hexahydroquinazolin-2-yl)piperazin-1-yl]acetamide; 2-(4-acetylpiperazin-1-yl)-5,6,7,8-tetrahydro-3H-quinazolin-4-one; 2-[4-(morpholine-4-carbonyl)piperazin-1-yl]-5,6,7,8-tetrahydro-3H-quinazolin-4-one; 2-[4-(3-aminopropanoyl)piperazin-1-yl]-5,6,7,8-tetrahydro-3H-quinazolin-4-one; 2-[4-(4-oxo-5,6,7,8-tetrahydro-3H-quinazolin-2-yl)piperazin-1-yl]pyridine-3-carboxamide; 2-[4-(4-oxo-3,4,5,6,7,8-hexahydroquinazolin-2-yl)piperazin-1 yl]-N-pyridin-3-ylacetamide; 2-[4-(2,2-dimethylpropanoyl)piperazin-1-yl]-5,6,7,8-tetrahydro-3H-quinazolin-4-one; 2-[4-(2-hydroxyethyl)piperazin-1-yl]-5,6,7,8-tetrahydro-3H-quinazolin-4-one; 2-[4-[2-(2-pyridyl)ethyl]piperazin-1-yl]-5,6,7,8-tetrahydro-3H-quinazolin-4-one; 2-[4-(piperidine-2-carbonyl)piperazin-1-yl]-5,6,7,8-tetrahydro-3H-quinazolin-4-one; 4-(4-oxo-5,6,7,8-tetrahydro-3H-quinazolin-2-yl)piperazine-2-carboxamide; 2-[3-(hydroxymethyl)piperazin-1-yl]-5,6,7,8-tetrahydro-3H-quinazolin-4-one; (2R)-1-(4-oxo-5,6,7,8-tetrahydro-3H-quinazolin-2-yl)piperazine-2-carboxamide; and 2-[(2R)-2-(hydroxymethyl)piperazin-1-yl]-5,6,7,8-tetrahydro-3H-quinazolin-4-one.

United States Patent Application Publication No. 2015/0018356 by Zhou et al., discloses fused tetra- or pentacyclic pyridophthalazinones as PARP inhibitors.

United States Patent Application Publication No. 2014/0336192 to Papeo et al., discloses substituted 3-phenyl-isoquinolin-1(2H)-one derivatives as PARP inhibitors, including: 4-(2-amino-ethoxy)-3-(4-bromo-phenyl)-7-fluoro-2H-isoquinolin-1-one; 4-(2-amino-ethoxy)-7-fluoro-3-(3-trifluoromethyl-phenyl)-2H-isoquinolin-1-one; 4-(2-amino-ethoxy)-7-fluoro-3-(4-morpholin-4-yl-phenyl)-2H-isoquinolin-1-one; 4-(2-amino-ethoxy)-3-(3-bromo-4-morpholin-4-yl-phenyl)-7-fluoro-2H-isoquinolin-1-one; 4-(2-amino-ethoxy)-3-(3-bromo-phenyl)-7-fluoro-2H-isoquinolin-1-one; 4-[4-(2-amino-ethoxy)-7-fluoro-1-oxo-1,2-dihydro-isoquinolin-3-yl]-benzonitrile; 4-(2-aminoethoxy)-7-fluoro-3-(4-pyrrolidin-1-yl-phenyl)-2H-isoquinolin-1-one; 4-(2-amino-ethoxy)-3-(4-chloro-phenyl)-7-fluoro-2H- isoquinolin-1-one; 4-(2-amino-ethoxy)-7-fluoro-3-(4-methanesulfonyl-phenyl)-2H-isoquinolin-1-one; 4-(2-amino-ethoxy)-7-fluoro-3-(4-fluoro-phenyl)-2H-isoquinolin-1-one; 3-[4-(2-amino-ethoxy)-7-fluoro-1-oxo-1,2-dihydro-isoquinolin-3-yl]-benzonitrile; 4-(2-amino-ethoxy)-3-(4-bromo-phenyl)-7,8-difluoro-2H-isoquinolin-1-one; 4-(2-amino-ethoxy)-3-(4-chloro-3-methyl-phenyl)-7-fluoro-2H-isoquinolin-1-one; 4-(2-amino-ethoxy)-3-(3,4-dichloro-phenyl)-7-fluoro-2H-isoquinolin-1-one; 4-(2-amino-ethoxy)-3-(3,4-difluoro-phenyl)-7-fluoro-2H-isoquinolin-1-one; 5-[4-(2-amino-ethoxy)-7-fluoro-1-oxo-1,2-dihydro-isoquinolin-3-yl]-2-morpholin-4-yl-benzonitrile; 5-[4-(2-amino-ethoxy)-7-fluoro-1-oxo-1,2-dihydro-isoquinolin-3-yl]-2-pyrrolidin-1-yl-benzonitrile; 4-(2-amino-ethoxy)-3-(3-bromo-4-pyrrolidin-1-yl-phenyl)-7-fluoro-2H-isoquinolin-1-one; 4-(2-amino-ethoxy)-3-(2,3-dihydro-benzo[1,4]dioxin-6-yl)-7-fluoro-2H-isoquinolin-1-one; 4-(2-amino-ethoxy)-3-benzo[1,3]dioxol-5-yl-7-fluoro-2H-isoquinolin-1-one; 4-(2-amino-ethoxy)-7-fluoro-3-(3-fluoro-4-methoxy-phenyl)-2H-isoquinolin-1-one; 4-(2-amino-ethoxy)-7-fluoro-3-(4-trifluoromethoxy-phenyl)-2H-isoquinolin-1-one; and 4-(2-amino-ethoxy)-3-(3,4-dihydro-2H-benzo[b][1,4]dioxepin-7-yl)-7-fluoro-2H-isoquinolin-1-one.

United States Patent Application Publication No. 2014/0235675 by Papeo et al., discloses 3-oxo-2,3-dihydro-1H-indazole-4-carboxamide derivatives as PARP inhibitors, including: 3-oxo-2-(piperidin-4-yl)-2,3-dihydro-1H-indazole-4-carboxamide; 2-(1-cyclopentylpiperidin-4-yl)-3-oxo-2,3-dihydro-1H-indazole-4-carboxamide; 2-(1-cyclohexylpiperidin-4-yl)-3-oxo-2,3-dihydro-1H-indazole-4-carboxamide; 2-[1-(4,4-difluorocyclohexyl)piperidin-4-yl]-3-oxo-2,3-dihydro-1H-indazole-4-carboxamide; 2-(1-cyclohexylpiperidin-4-yl)-1-methyl-3-oxo-2,3-dihydro-1H-indazole-4-carboxamide; 2-[1-(4,4-difluorocyclohexyl)piperidin-4-yl]-1-methyl-3-oxo-2,3-dihydro-1H-indazole-4-carboxamide; 2-(1-cyclopentylpiperidin-4-yl)-1-methyl-3-oxo-2,3-dihydro-1H-indazole-4-carboxamide; 2-(1-methylpiperidin-4-yl)-3-oxo-2,3-dihydro-1H-indazole-4-carboxamide; 1-methyl-3-oxo-2-(piperidin-4-yl)-2,3-dihydro-1H-indazole-4-carboxamide; 1-methyl-2-(1-methylpiperidin-4-yl)-3-oxo-2,3-dihydro-1H-indazole-4-carboxamide; 2-(1-ethylpiperidin-4-yl)-3-oxo-2,3-dihydro-1H-indazole-4-carboxamide; 3-oxo-2-(1-propylpiperidin-4-yl)-2,3-dihydro-1H-indazole-4-carboxamide; 2-(1-ethylpiperidin-4-yl)-1-methyl-3-oxo-2,3-dihydro-1H-indazole-4-carboxamide; 1-methyl-3-oxo-2-[1-(propan-2-yl)piperidin-4-yl]-2,3-dihydro-1H-indazole-4-carboxamide; 3-oxo-2-[1-(propan-2-yl)piperidin-4-yl]-2,3-dihydro-1H-indazole-4-carboxamide; 2-(1-cyclobutylpiperidin-4-yl)-3-oxo-2,3-dihydro-1H-indazole-4-carboxamide; 2-(1-cyclobutylpiperidin-4-yl)-6-fluoro-3-oxo-2,3-dihydro-1H-indazole-4-carboxamide; 2-(1-cyclobutylpiperidin-4-yl)-1-methyl-3-oxo-2,3-dihydro-1H-indazole-4-carboxamide; 2-(1-cyclobutylpiperidin-4-yl)-6-fluoro-1-methyl-3-oxo-2,3-dihydro-1H-indazole-4-carboxamide; 6-fluoro-3-oxo-2-(piperidin-4-yl)-2,3-dihydro-1H-indazole-4-carboxamide; 6-fluoro-1-methyl-3-oxo-2-(piperidin-4-yl)-2,3-dihydro-1H-indazole-4-carboxamide; 2-(1-cyclohexylpiperidin-4-yl)-6-fluoro-1-methyl-3-oxo-2,3-dihydro-1H-indazole-4-carboxamide; 2-(1-cyclohexylpiperidin-4-yl)-6-fluoro-3-oxo-2,3-dihydro-1H-indazole-4-carboxamide; and 2-[1-(4,4-difluorocyclohexyl)piperidin-4-yl]-6-fluoro-1-methyl-3-oxo-2,3-dihydro-1H-indazole-4-carboxamide.

United States Patent Application Publication No. 2014/0023642 by Cai et al., discloses 1-(arylmethyl)quinazoline-2,4(1H,3H)-diones as PARP inhibitors, including: 1-(3-methoxycarbonylbenzyl)quinazoline-2,4(1H,3H)-dione; 1-(3-carboxybenzyl)quinazoline-2,4(1H,3H)-dione; 1-(3-(4-(pyridin-2-yl)piperazine-1-carbonyl)benzyl)quinazoline-2,4(1H,3H)-dione; 1-(3-(4-(pyrimidin-2-yl)piperazine-1-carbonyl)benzyl)quinazoline-2,4(1H,3H)-dione; 1-(3-(4-cyclohexylpiperazine-1-carbon yl)benzyl)quinazoline-2,4(1H,3H)-dione; 1-(3-(4-([1,2,4]triazolo[4,3-b]pyridazin-6-yl)piperazine-1-carbonyl)benzyl)quinazoline-2,4(1H,3H)-dione; 1-(3-(4-ethylpiperazine-1-carbonyl)benzyl)quinazoline-2,4(1H,3H)-dione; 1-(3-(4-benzoylpiperazine-1-carbonyl)benzyl)quinazoline-2,4(1H,3H)-dione; 1-(3-(4-(4-fluorobenzoyl)piperazine-1-carbonyl)benzyl)quinazoline-2,4(1H,3H)-dione; 1-(3-(4-(4-chlorobenzoyl)piperazine-1-carbonyl)benzyl)quinazoline-2,4(1H,3H)-dione; 1-(3-(4-(4-bromobenzoyl)piperazine-1-carbonyl)benzyl)quinazoline-2,4(1H,3H)-dione; 1-(3-(4-(4-methoxybenzoyl)piperazine-1-carbonyl)benzyl)quinazoline-2,4(1H,3H)-dione; 1-(3-(4-(tetrahydro-2H-pyran-4-yl)carbonylpiperazine-1-carbonyl)benzyl)quinazoline-2,4(1H,3H)-dione; 1-(3-(4-(cyclopentylcarbonyl)piperazine-1-carbonyl)benzyl)quinazoline-2,4-(1H,3H)-dione; 1-(3-(4-(cyclopropylcarbonyl)piperazine-1-carbonyl)benzyl)quinazoline-2,4-(1H,3H)-dione; 1-(3-(4-(ethylsulfonyl)piperazine-1-carbonyl)benzyl)quinazoline-2,4(1H,3H)-dione; 1-(3-(4-acetylpiperazine-1-carbonyl)benzyl)quinazoline-2,4(1H,3H)-dione; 1-(3-(4-phenylpiperidine-1-carbonyl)benzyl)quinazoline-2,4(1H,3H)-dione; 1-(3-(4-phenylpiperazine-1-carbonyl)benzyl)quinazoline-2,4(1H,3H)-dione; and 1-(3-(4-(pyrazin-2-yl)piperazine-1-carbonyl)benzyl)quinazoline-2,4(1H,3H)-dione.

United States Patent Application Publication No. 2013/0225647 by Donawho et al., discloses PARP inhibitors of Formula (P-VIII):

(P-VIII)

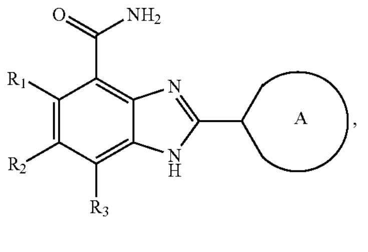

wherein:

(1) $R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

(2) A is a nonaromatic 4, 5, 6, 7, or 8-membered ring that contains 1 or 2 nitrogen atoms and, optionally, one sulfur or oxygen atom, wherein the nonaromatic ring is optionally substituted with 1, 2, or 3 substituents selected from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, heterocycle, heterocyclealkyl, heteroaryl, heteroarylalkyl, hydroxy, hydroxyalkyl, nitro, $NR_CR_D$, $(NR_CR_D)$alkyl, $(NR_CR_D)$carbonyl, $(NR_CR_D)$carbonylalkyl, and $(NR_CR_D)$sulfonyl; and;

(3) $R_A$, $R_B$, $R_C$, and $R_D$ are independently selected from the group consisting of hydrogen, alkyl, and alkycarbonyl.

United States Patent Application Publication No. 2013/0129841 by Ciavolella et al., disclosed PARP inhibitors including 2-[1-(4,4-difluorocyclohexyl)piperidin-4-yl]-3-oxo-2,3-dihydro-1H-isoindole-4-carboxamide; 2-[1-(4,4-difluorocyclohexy)piperidin-4-yl]-6-fluoro-3-oxo-2,3-dihydro-1H-isoindole-4-carboxamide; 6-fluoro-3-oxo-2-[1-(4-oxocyclohexy)piperidin-4-yl]-2,3-dihydro-1H-isoindole-4-carboxamide, and 2-[1-(4,4-dichlorocyclohexyl)piperidin-4-yl]-6-fluoro-3-oxo-2,3-dihydro-1-H-isoindole-4 carboxamide.

The gene PTEN encodes a protein, PTEN, that acts as a tumor suppressor. The protein encoded by PTEN is a phosphatidylinositol-3,4,5-trisphosphate 3-phosphatase. It contains a tensin-like domain as well as a catalytic domain similar to that of the dual specificity protein tyrosine phosphatases. Unlike most of the protein tyrosine phosphatases, this protein preferentially dephosphorylates phosphoinositide substrates. It negatively regulates intracellular levels of phosphatidylinositol-3,4,5-trisphosphate in cells and functions as a tumor suppressor by negatively regulating the Akt/PKB signaling pathway. The PTEN gene is frequently mutated, lost, or its expression downregulated in cancer. As such, the loss or inactivation of PTEN function is increasingly viewed as a target for therapeutic intervention (L. M. Dillon & T. W. Miller, "Therapeutic Targeting of Cancers with Loss of PTEN Function," *Curr. Drug Targets* 15: 65-79 (2014)). PTEN deficiency can be caused by inherited germline mutations, somatic mutations, epigenetic and transcriptional silencing, post-translational modifications, and protein-protein interactions.

The germline mutations can include, but are not limited to, mutations in Exon 5 encoding the PTEN phosphatase domain. Other mutations have been shown to occur in the PTEN promoter or in splice donor and acceptor sites.

Missense, nonsense, insertion, and deletion mutations occur throughout PTEN and contribute to loss of PTEN expression and/or function. Although the distribution of these mutations is generally sporadic and such mutations can occur throughout the genome, there are a number of mutational hotspots, including $Arg^{130}$, $Arg^{173}$, and $Arg^{233}$.

PTEN loss of function can also result from epigenetic and transcriptional silencing. Several studies have shown that CpG islands in the PTEN promoter are hypermethylated in cancer, leading to silencing of PTEN transcription. Transcription of PTEN can be repressed by the epigenetic repressor complex Mi-2/NuRD that contains a chromatin-remodeling ATPase and a histone deacetylase (HDAC). This repression occurs when the transcription factor Sal-Like Protein 4 (SALL4) binds to the PTEN promoter and recruits Mi-2/NuRD. PTEN transcription can also be repressed by the transcription factors NF-κB, c-JUN, and BM1.

The tumor suppressor p53, which can act as a transcription factor, promotes PTEN expression; therefore, loss of function for p53 can have the effect of reducing PTEN expression. The ubiquitous transcription factor Specificity Protein 1 (Sp1) can also inhibit PTEN expression: acetylated Sp1 binds to the PTEN promoter and recruits HDAC1 to repress PTEN transcription. Accordingly, Sp1 overexpression upregulated PI3K pathway activation (assessed by AKT phosphorylation), and promoted migration and invasion of human salivary adenoid cystic cancer cells. MicroRNAs (miRNAs), have been shown to repress translation of PTEN mRNA by interacting with the 3' untranslated region. In particular, the miRNA miR-21 represses PTEN expression in many cancer subtypes and metabolic diseases; this miRNA may also repress PTEN expression by increasing the expression of other miRNAs that are known to repress the expression of PTEN. The transcription factor transforming growth factor beta (TGF-β), which inhibits PTEN expression in some models, upregulates miR-21 expression. Post-translational modifications including phosphorylation, acetylation, oxidation, and ubiquitylation have been shown to cause loss of PTEN function. The phosphatase activity of PTEN can be inhibited by phosphorylation of several serine and threonine resides in its C-terminal tail. This phosphorylation may be driven by the activity of the kinase CK2. While such phosphorylation stabilizes PTEN, it reduces PTEN localization to the plasma membrane, thereby limiting its interaction with $PIP_3$. PTEN can be also inhibited by oxidation and acetylation. PTEN contains a residue characteristic of protein tyrosine phosphatases termed a catalytic cysteine nucleophile which is prone to oxidation at Cys124; Cys124 can form a disulfide bond with Cys71, inhibiting the catalytic activity of PTEN. Additionally, PTEN is subject to acetylation at residues Lys125-128, which also inhibits the catalytic activity of PTEN. PTEN monoubiquitination at Lys13 and Lys289 promotes its nuclear localization and suppresses its phosphatase activity.

Several proteins have been shown to interact with PTEN to repress its tumor suppressive functions. Parkinson Protein 7 (PARK7, DJ-1) binds PTEN under conditions of oxidative stress, and this interaction is associated with increased AKT activation and poor clinical outcome in different cancer subtypes. $PIP_3$-dependent Rac Exchange Factor 2a (P-REX2a), Shank-Interacting Protein-Like 1 (SIPL1) and α-Mannosidase 2C1 (MAN2C1) have also been shown to bind PTEN and inhibit its phosphatase activity, leading to increased activation of AKT. Other proteins can stabilize PTEN, but mutations in these proteins can, therefore, reduce the activity of PTEN and promote tumorigenesis. The membrane-localized proteins E-cadherin and MAGI-2, which are lost in some cancers, promote PTEN stability. The p85 subunit of PI3K binds PTEN to promote stability. The genes encoding p85 isoforms (PIK3R1, PIK3R2) are frequently mutated in endometrial cancer, and some mutations destabilize PTEN and promote PI3K pathway activation.

There is also an interaction between PTEN and p53 that may repress or promote tumorigenesis. Nuclear PTEN binds p53 in a phosphatase-independent manner to promote p53 stabilization, thus promoting PTEN transcription. PTEN complexes with p300/CBP acetyltransferase to promote p53 acetylation in response to DNA damage, and p53 acetylation enhances PTEN-p53 interaction. Therefore, in cells expressing wild-type p53, PTEN inhibits cell proliferation and increases apoptosis. In contrast, PTEN promotes proliferation and suppresses apoptosis in cells expressing mutant p53.

Among agents that are potentially useful for countering loss of PTEN function are temsirolimus, everolimus, and other inhibitors of the AKT/mTOR pathway, including AZD6482 ((R)-2-(1-(7-methyl-2-morpholino-4-oxo-4H-pyrido[1,2-a]pyrimidin-9-yl)ethylamino)benzoic acid), which is a PI3K/p110p inhibitor, MK-2206 (8-(4-(1-aminocyclobutyl)phenyl)-9-phenyl-[1,2,4]triazolo[3,4-f][1,6] naphthyridin-3(2H)-one), which is an allosteric AKT inhibitor, and 17-AAG ([(3S,5S,6R,7S,8E,10R,11S,12E,14E)-21-(allylamino)-6-hydroxy-5,11-dimethoxy-3,7,9,15-tetramethyl-16,20,22-trioxo-17-azabicyclo[16.3.1]docosa-8,12,14,18,21-pentaen-10-yl]carbamate), which is a Hsp90 chaperonin inhibitor that induces degradation of many proteins including $HER^2$ and AKT.

Loss of or inhibition of PTEN can drive resistance to a large range of anti-neoplastic therapies.

A large number of drugs have been proposed for use in the treatment of PTEN-deficient malignancies. These drugs include: (1) buparlisib; (2) XL-147 (N-[3-(2,1,3-benzothiadiazol-5-ylamino)quinoxalin-2-yl]-4-methylbenzenesulfonamide); (3) PX-866 ((1E,4S,4aR,5R,6aS,9aR)-5-(acetyloxy)-1-[(di-2-propen-1-ylamino)methylene]-4,4a,5,6,6a,8,9,9a-octahydro-11-hydroxy-4-(methoxymethyl)-4a,6a-dimethylcyclopenta[5,6]naphtho[1,2-c]pyran-2,7,10(1H)-trione); (4) pictilisib dimethanesulfonate; (5) copanlisib; (6) CH5132799 (5-(7-(methylsulfonyl)-2-morpholino-6,7-dihydro-5H-pyrrolo[2,3-d]pyrimidin-4-yl)pyrimidin-2-amine); (7) GDC-0084; (8) SZTK474 (2-(difluoromethyl)-1-(4,6-dimorpholino-1,3,5-triazin-2-yl)-1H-benzo[d]imidazole); (9) GDC-0032 (2-methyl-2-[4-[2-(5-methyl-2-propan-2-yl-1,2,4-triazol-3-yl)-5,6-dihydroimidazo[1,2-d][1,4]benzoxazepin-9-yl]pyrazol-1-yl]propanamide); (10) alpelisib; (11) MLN1117 (6-(2aminobenzo[d]oxazol-5-yl(1,2-a]pyridine-3-yl(morpholinomethanone); (12) GSK2636771 (2-methyl-1-[[2-methyl-3-(trifluoromethyl)phenyl]methyl]-6-(4-morpholinyl)-1H-benzimidazole-4-carboxylic acid; (13) rigosertib; (14) CUDC-097 (N-hydroxy-2-(((2-(6-methoxypyridin-3-yl)-4-morpholinothieno[3,2-d]pyrimidin-6-yl)methyl)(methyl)amino)pyrimidine-5-carboxamide); (15) gedatolisib; (16) dactolisib; (17) BGT226 (8-(6-methoxypyridin-3-yl)-3-methyl-1-(4-(piperazin-1-yl)-3-(trifluoromethyl)phenyl)-1H-imidazo[4,5-c]quinolin-2(3H)-one maleic acid); (18) apitolisib; (19) voxtalisib; (20) SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate); (21) LY3023414; (22) everolimus; (23) temsirolimus; (24) ridaforolimus; (25) MLN0128 (3-(2-aminobenzo[d]oxazol-5-yl)-1-isopropyl-1H-pyrazolo[3,4-d]pyrimidin-4-amine); (26) AZD-2014 (3-(2,4-bis((S)-3-methylmorpholino)pyrido[2,3-d]pyrimidin-7-yl)-N-methylbenzamide); (27) CC-223; (28) AZD-5313 (5-[(4-bromo-2-chlorophenyl)amino]-4-fluoro-N-(2-hydroxyethoxy)-1-methyl-1H-benzimidazole-6-carboxamide); (29) LY2780301; (30) ipatasertib; (31) afuresertib; (32) MK-2206 (8-(4-(1-aminocyclobutyl)phenyl)-9-phenyl-[1,2,4]triazolo[3,4-f][1,6]naphthyridin-3(2H)-one); (33) olaparib; (34) veliparib; (35) iniparib; (36) rucaparib; (37) CEP-9722 (11-methoxy-4,5,6,7-tetrahydro-1H-cyclopenta[a]pyrrolo[3,4-c]carbazole-1,3(2H)dione; (38) E7016 (10-((4-Hydroxypiperidin-1-yl)methyl)chromeno[4,3,2-de]phthalazin-3(2H)-one); and (39) E7449 (9-isoindolin-2ylmethyl-1,2-dihydro-3H-pyridazino[3,4,5-de]quinazolin-3-one). Other therapeutic agents are known in the art.

U.S. Pat. No. 8,933,070 to Pan et al., discloses treatment of malignancies characterized by a PTEN gene mutation by administration of a PLK4 antagonist.

United States Patent Application Publication No. 2015/0159161 by Krieg et al., discloses single-stranded oligonucleotides for enhancing or activating expression of PTEN, such as oligonucleotides having a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length, wherein the single stranded oligonucleotide is complementary with at least 8 consecutive nucleotides of a PRC2-associated region of a PTEN gene.

United States Patent Application Publication No. 2014/0378525 by Ashworth et al., discloses the use of inhibitors of mitotic kinases for the treatment of cancers that are characterized by mutated or deficient PTEN. The mitotic kinases include AURKA, TTK, CDK4, PLK4, BUB1B, PLK1, CDC2, PLK3, and AURKB. The inhibitors can be small molecule inhibitors, such as small molecule inhibitors of TTK, such as AZ3146 (9-cyclopentyl-2-(2-methoxy-4-(1-methylpiperidin-4-yloxy)phenylamino)-7-methyl-7H-purin-8(9H)-one) or CCT132774. Antibodies, peptide fragments, antisense nucleic acids, or interfering RNA molecules can also be used.

United States Patent Application Publication No. 2014/0112917 by Yu et al., discloses use of an ErbB2-targeting agent such as trastuzumab, LY294002, Wortmannin, demethoxyviridin, Perifosine, SAR245408 (XL147), BKM120, BEZ235, GS-1101 (CAL-101), PX-866, IPI-145, and BAY 80-6946 when PTEN transcription is reduced or when at least one allele of PTEN is lost.

United States Patent Application Publication No. 2012/0165340 by Furnari et al., discloses that phosphorylation of the Y240 residue in PTEN is associated with poorer prognosis and increased resistance to antineoplastic agents. The resistance can be driven by src family kinase-mediated phosphorylation of Y240.

United States Patent Application Publication No. 2012/0107299 by Morishita et al., discloses a protein, NDRG2, that inhibits phosphorylation of residues T382, T383, and S380 of PTEN or induces dephosphorylation of these amino acid residues of PTEN; the activity of this protein can be used to inhibit the activation of the PI3K/Akt pathway.

United States Patent Application Publication No. 2011/0189169 by Abounader et al., discloses administration of an agonist for PTEN together with an inhibitor of hepatocyte growth factor (HGF). The agonist for PTEN can be an mTOR inhibitor (see WO 00/00388), which can be rapamycin, sirolimus, temsirolimus, everolimus, monoclonal antibodies, zinc fingers, or other agonists.

United States Patent Application Publication No. 2010/0286141 by Durden, is relevant for the following description of the PTEN protein. The crystal structure of PTEN, solved in 1999, revealed that the 403 amino acid protein comprises three domains of known function. These are the N terminal catalytic domain (residues 1-185), the C2 domain (residues 186-349) that participates in membrane binding and catalysis and the C terminal tail region (residues 350-403). Each of these domains provide suitable targets for the rational design of therapeutic agents which modulate PTEN activity. Particularly preferred regions are the N terminal and C2 domains, specifically regions including certain unique residues within and adjacent to the P loop, the WPD loop and the TI loop. It is these residues that participate in specific PIP3 substrate recognition and catalysis thereof. Another suitable region includes the C terminal tail which participates in PTEN regulatory and degradation in vivo. Small peptide molecules corresponding to these regions may be used to advantage in the design of therapeutic agents which effectively modulate the activity of PTEN, PI-3 kinase cascades, AKT cascades, as well as p53-mediated transcription and cell death. PTEN is phosphorylated on tyrosine, serine and threonine residues. Agents which affect the phosphorylation state of the protein will also be screened as those small molecules which affect phosphorylation of PTEN should also modulate PTEN interactions with other proteins. The DLDLTYIYP motif (residues 22-30; SEQ ID NO: 12) at the extreme N terminus of PTEN contains a YXXP motif (SEQ ID NO: 13), a possible docking site for adapter proteins like crk and crkl via SH2 interactions. Another motif, YFSPN (SEQ ID NO: 14) in the C terminus has been identified as the binding site for crk and crkl. The YLVLTL motif (SEQ ID NO: 15) in the extreme C terminus is a site for SH2 interactions with Shc or SHP-1. The YSYL motif (SEQ ID NO: 16), which contains a tyrosine at position 178, is 100% conserved from *Drosophila* to man. Other tyrosine phosphorylated motifs include: YRNNIDD (SEQ ID NO: 17), Y at position 46, a sequence present in the catalytic domain identified as a binding site for Grb2 via its SH2 domain.

United States Patent Application Publication No. 2009/0019558 by Song et al., discloses agents that modulate the activity of PGD to restore function of PTEN.

Substituted hexitol derivatives as described above, including dianhydrogalactitol, diacetyldianhydrogalactitol, and derivatives or analogs of dianhydrogalactitol or diacetyldianhydrogalactitol, can be used together with other DNA-damaging anti-neoplastic agents by administration of a therapeutically effective quantity of another DNA-damaging anti-neoplastic agent. DNA-damaging anti-neoplastic agents are disclosed in K. Cheung-Ong et al., "DNA-Damaging Agents in Cancer Chemotherapy: Serendipity and Chemical Biology," *Chem. Biol.* 20: 648-659 (2013). DNA-damaging anti-neoplastic agents are also disclosed in the following patents or published patent applications, all of which are incorporated herein by this reference: U.S. Pat. No. 9,097,722 to Yu; U.S. Pat. No. 9,096,602 to Everitt et al.; U.S. Pat. No. 8,840,898 to Goldmakher; U.S. Pat. No. 8,735,590 to Adejare et al.; U.S. Pat. No. 8,415,357 to Kawabe et al.; U.S. Pat. No. 8,476,025 to Clifford; U.S. Pat. No. 7,902,165 to Kim; U.S. Pat. No. 7,875,586 to Kovbasnjuk et al.; U.S. Pat. No. 7,652,042 to Kawabe et al.; U.S. Pat. No. 7,465,542 to Chu et al.; U.S. Pat. No. 7,070,968 to Kufe et al.; United States Patent Application Publication No. 2011/0028422 by Aloyz et al.; and United States Patent Application Publication No. 2007/0032502 by Mallams et al. DNA-damaging anti-neoplastic agents can act by a variety of mechanisms, including modification of DNA bases such as by alkylation, intercalation into the DNA structure, formation of crosslinks in DNA, prevention of unwinding or replication of DNA to induce double-strand breaks, incorporation into DNA in place of normal nucleosides, and other mechanisms. DNA-damaging anti-neoplastic agents include, but are not limited to: cisplatin, carboplatin, oxaliplatin, picoplatin, nedaplatin, satraplatin, tetraplatin, doxorubicin, daunorubicin, methotrexate, 5-fluorouracil, gemcitabine, podophyllotoxin, etoposide, teniposide, cyclophosphamide, chlorambucil, melphalan, carmustine, lomustine, estramustine, semustine, bendamustine, prednamustine, uramustine, chlornaphazine, dacarbazine, altretamine, temozolomide, mitomycin C, streptozotocin, chlorozotocin, capecitabine, floxuridine, 6-mercaptopurine, 8-azaguanine, azathiopurine, 5-ethynyluracil, thioguanine, fludarabine, cytarabine, cladribine, 2-fluoro-arabinosyl-adenine, aminopterin, pemetrexed, ralitrexed, camptothecin, epirubicin, idarubicin, methylnitronitrosoguanidine, topotecan, irinotecan, mechlorethamine, ifosfamide, trofosfamide, busulfan, procarbazine, mitoxantrone, actinomycin, calicheamicin, Tegafur (R,S-1-(tetrahydro-2-furanyl)-5-fluorouracil), 2',2'-difluoro-2'-deoxycytidine, bischloroethylsulfide, thiotepa, aziridinylbenzoquinone, BCNU, CCNU, 4-methyl CCNU, ACNU, rebeccamycin, bleomycin, pepleomycin, ethylmethanesulfonate, methylmethanesulfonate, dimethylnitrosamine, dimethyl sulfate, and N'-[2-[2-(4-methoxyphenyl)ethenyl]-4-quinazolinyl]-N,N-dimethyl-1,3-propanediamine dihydrochloride.

Substituted hexitol derivatives as described above, including dianhydrogalactitol, diacetyldianhydrogalactitol, and derivatives or analogs of dianhydrogalactitol or diacetyldianhydrogalactitol, can be used together with an agent modulating at least one of the following pathways: γH2AX, p-RPA32 (S4/8, S33), ATR, ATM, Rad51, CtIP, BRCA1, and LEDGF by administration of a therapeutically effective quantity of an agent modulating at least one of those pathways. Modulation of one or more of these pathways can be useful for the prevention or reduction of resistance to anti-neoplastic agents, including, but not limited to, substituted hexitol derivatives.

When more than one agent is administered in a method according to the present invention, the agents can be administered simultaneously or substantially simultaneously. In an alternative, the agents can be administered in sequence. When the agents are administered simultaneously, they can be administered in a single pharmaceutical composition if the agents can be combined in such a composition without an adverse interaction of the agents and if the agents can be administered by a suitable route of administration for the single pharmaceutical composition. Alternatively, the agents can be administered in separate pharmaceutical compositions, either by the same route of administration or by different routes of administration, as appropriate for the agents involved.

Another aspect of the present invention is a composition to improve the efficacy and/or reduce the side effects of suboptimally administered drug therapy employing a substituted hexitol as described above for the treatment of malignancies of the central nervous system such as glioblastoma multiforme or medulloblastoma in pediatric patients comprising an alternative selected from the group consisting of:

(i) a therapeutically effective quantity of a modified hexitol derivative or a derivative, analog, or prodrug of a hexitol derivative or a modified hexitol derivative, wherein the modified hexitol derivative or the derivative, analog or prodrug of the modified hexitol derivative possesses increased therapeutic efficacy or reduced side effects for treatment of malignancies of the central nervous system such as glioblastoma multiforme or medulloblastoma in pediatric patients as compared with an unmodified hexitol derivative;

(ii) a composition comprising:
  (a) a therapeutically effective quantity of a hexitol derivative, a modified hexitol derivative, or a derivative, analog, or prodrug of a hexitol derivative or a modified hexitol derivative; and
  (b) at least one additional therapeutic agent, therapeutic agent subject to chemosensitization, therapeutic agent subject to chemopotentiation, diluent, excipient, solvent system, drug delivery system, agent for counteracting myelosuppression, or agent for increasing the ability of the hexitol derivative, the modified hexitol derivative, or the derivative, analog, or prodrug of the hexitol derivative or the modified hexitol derivative to pass through the blood-brain barrier, wherein the composition possesses increased therapeutic efficacy or reduced side effects for treatment of malignancies of the central nervous system such as glioblastoma multiforme or medulloblastoma in pediatric patients as compared with an unmodified hexitol derivative;

(iii) a therapeutically effective quantity of a hexitol derivative, a modified hexitol derivative, or a derivative, analog, or prodrug of a hexitol derivative or a modified hexitol derivative that is incorporated into a dosage form, wherein a hexitol derivative, a modified hexitol derivative, or a derivative, analog, or prodrug of a hexitol derivative or a modified hexitol derivative incorporated into the dosage form possesses increased therapeutic efficacy or reduced side effects for treatment of malignancies of the central nervous system such as glioblastoma multiforme or medulloblastoma in pediatric patients as compared with an unmodified hexitol derivative;

(iv) a therapeutically effective quantity of a hexitol derivative, a modified hexitol derivative, or a derivative, analog, or prodrug of an hexitol derivative or a modified hexitol derivative that is incorporated into a dosage kit and packaging, wherein a hexitol derivative, a modified hexitol derivative, or a derivative, analog, or prodrug of a hexitol derivative or a modified hexitol derivative incorporated into the dosage kit and packaging possesses increased therapeutic efficacy or reduced side effects for treatment of malignancies of the central nervous system such as glioblastoma multiforme or medulloblastoma in pediatric patients as compared with an unmodified hexitol derivative; and (v) a therapeutically effective quantity of a hexitol derivative, a modified hexitol derivative, or a derivative, analog, or prodrug of a hexitol derivative or a modified hexitol derivative that is subjected to a bulk drug product improvement, wherein the hexitol derivative, the modified hexitol derivative, or the derivative, analog, or prodrug of the hexitol derivative or the modified hexitol derivative subject to the bulk drug product improvement possesses increased therapeutic efficacy or reduced side effects for treatment of malignancies of the central nervous system such as glioblastoma multiforme or medulloblastoma in pediatric patients as compared with an unmodified alkylating hexitol derivative.

As described above, the alkylating hexitol derivative can be, but is not limited to, dianhydrogalactitol, a derivative or analog of dianhydrogalactitol, diacetyldianhydrogalactitol, or a derivative or analog of diacetyldianhydrogalactitol.

In one alternative, the pharmaceutical composition is formulated to exert a cytotoxic effect against cancer stem cells.

In one alternative, the composition comprises a drug combination comprising:

(i) an alkylating hexitol derivative, a modified alkylating hexitol derivative, or a derivative, analog, or prodrug of an alkylating hexitol derivative or a modified alkylating hexitol derivative; and (ii) an additional therapeutic agent selected from the group consisting of:

(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone; and
(s) tetrandrine.

In these alternatives, when the additional therapeutic agent is an alkylating agent, the alkylating agent can be, but is not limited to, an alkylating agent selected from the group consisting of BCNU, BCNU wafers, CCNU, bendamustine (Treanda), and temozolimide (Temodar). In another alternative, the drug composition comprises one or more additional agents that are described above with respect to methods according to the present invention employing drug combinations. In drug combinations according to the present invention, both the alkylating hexitol derivative and the additional agent are present in a therapeutically effective quantity. More than one additional agent can be present in a drug combination according to the present invention, subject to the condition that the at least one additional agent does not interact deleteriously with either the alkylating hexitol derivative present in the composition or other additional agent or agents present in the composition.

In another alternative, the composition comprises:

(i) an alkylating hexitol derivative, a modified alkylating hexitol derivative, or a derivative, analog, or prodrug of an alkylating hexitol derivative or a modified alkylating hexitol derivative; and (ii) a therapeutic agent subject to chemosensitization selected from the group consisting of:

(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) colchicine or an analog of colchicine;
(m) genistein;
(n) etoposide;
(o) cytarabine;
(p) camptothecin;
(q) vinca alkaloids;
(r) 5-fluorouracil;
(s) curcumin;
(t) NF-κB inhibitors;
(u) rosmarinic acid; and
(v) mitoguazone;

wherein the alkylating hexitol derivative, a modified alkylating hexitol derivative, or a derivative, analog, or prodrug of an alkylating hexitol derivative or a modified alkylating hexitol derivative acts as a chemosensitizer.

In still another alternative, the composition comprises:

(i) an alkylating hexitol derivative, a modified alkylating hexitol derivative, or a derivative, analog, or prodrug of an alkylating hexitol derivative or a modified alkylating hexitol derivative; and (ii) a therapeutic agent subject to chemopotentiation selected from the group consisting of:

(a) fraudulent nucleosides;
(b) fraudulent nucleotides;
(c) thymidylate synthetase inhibitors;
(d) signal transduction inhibitors;
(e) cisplatin or platinum analogs;
(f) alkylating agents;
(g) anti-tubulin agents;
(h) antimetabolites;
(i) berberine;
(j) apigenin;
(k) colchicine or analogs of colchicine;
(l) genistein;
(m) etoposide;
(n) cytarabine;

(o) camptothecins;
(p) vinca alkaloids;
(q) topoisomerase inhibitors;
(r) 5-fluorouracil;
(s) curcumin;
(t) NF-κB inhibitors;
(u) rosmarinic acid;
(v) mitoguazone; and
(w) a biotherapeutic;

wherein the alkylating hexitol derivative, a modified alkylating hexitol derivative, or a derivative, analog, or prodrug of an alkylating hexitol derivative or a modified alkylating hexitol derivative acts as a chemopotentiator.

In these alternatives, wherein the additional therapeutic agent is a biotherapeutic, the biotherapeutic can be, but is not limited to, a biotherapeutic selected from the group consisting of Avastin, Herceptin, Rituxan, and Erbitux.

In yet another alternative, the alkylating hexitol derivative, a modified alkylating hexitol derivative, or a derivative, analog, or prodrug of the alkylating hexitol derivative or the modified alkylating hexitol derivative of the composition is subjected to a bulk drug product improvement, wherein the bulk drug product improvement is selected from the group consisting of:

(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

In still another alternative, the composition comprises an alkylating hexitol derivative, a modified alkylating hexitol derivative, or a derivative, analog, or prodrug of an alkylating hexitol derivative or a modified alkylating hexitol derivative and a diluent, wherein the diluent is selected from the group consisting of:

(a) an emulsion;
(b) dimethylsulfoxide (DMSO);
(c) N-methylformamide (NMF)
(d) dimethylformamide (DMF)
(e) dimethylacetamide (DMA);
(f) ethanol;
(g) benzyl alcohol;
(h) dextrose-containing water for injection;
(i) Cremophor;
(j) cyclodextrins; and
(k) PEG.

In still another alternative, the composition comprises an alkylating hexitol derivative, a modified alkylating hexitol derivative, or a derivative, analog, or prodrug of an alkylating hexitol derivative or a modified alkylating hexitol derivative and a solvent system, wherein the solvent system is selected from the group consisting of:

(a) an emulsion;
(b) DMSO;
(c) NMF;
(d) DMF;
(e) DMA;
(f) ethanol;
(g) benzyl alcohol;
(h) dextrose-containing water for injection;
(i) Cremophor;
(j) PEG; and
(k) salt systems.

In yet another alternative, the composition comprises an alkylating hexitol derivative, a modified alkylating hexitol derivative, or a derivative, analog, or prodrug of an alkylating hexitol derivative or a modified alkylating hexitol derivative and an excipient, wherein the excipient is selected from the group consisting of:

(a) mannitol;
(b) albumin;
(c) EDTA;
(d) sodium bisulfite;
(e) benzyl alcohol;
(f) carbonate buffers;
(g) phosphate buffers;
(h) PEG;
(i) vitamin A;
(j) vitamin D;
(k) vitamin E;
(l) esterase inhibitors;
(m) cytochrome P450 inhibitors;
(n) multi-drug resistance (MDR) inhibitors;
(o) organic resins;
(p) detergents;
(q) perillyl alcohol or an analog thereof; and
(r) activators of channel-forming receptors.

In still another alternative, the alkylating hexitol derivative, modified alkylating hexitol derivative, or derivative, analog, or prodrug of the alkylating hexitol derivative or modified alkylating hexitol derivative is incorporated into a dosage form selected from the group consisting of:

(a) tablets;
(b) capsules;
(c) topical gels;
(d) topical creams;
(e) patches;
(f) suppositories;
(g) lyophilized dosage fills;
(h) immediate-release formulations;
(i) slow-release formulations;
(j) controlled-release formulations; and
(k) liquid in capsules.

In still another alternative, the alkylating hexitol derivative, modified alkylating hexitol derivative, or derivative, analog, or prodrug of an alkylating hexitol derivative or modified alkylating hexitol derivative is incorporated into a dosage kit and packaging selected from the group consisting of amber vials to protect from light and stoppers with specialized coatings to improve shelf-life stability.

In still another alternative, the composition comprises: (i) an alkylating hexitol derivative, modified alkylating hexitol derivative, or derivative, analog, or prodrug of an alkylating hexitol derivative or modified alkylating hexitol derivative; and (ii) a drug delivery system, wherein the drug delivery system is selected from the group consisting of:

(a) oral dosage forms;
(b) nanocrystals;
(c) nanoparticles;
(d) cosolvents;
(e) slurries;
(f) syrups;
(g) bioerodible polymers;
(h) liposomes;
(i) slow-release injectable gels;
(j) microspheres; and
(k) targeting compositions with epidermal growth factor receptor-binding peptides.

In still another alternative of a composition according to the present invention, the therapeutic agent is a modified alkylating hexitol derivative, and the modification is selected from the group consisting of:

(a) alteration of side chains to increase or decrease lipophilicity;
(b) addition of an additional chemical functionality to alter a property selected from the group consisting of reactivity, electron affinity, and binding capacity; and
(c) alteration of salt form.

In still another alternative of a composition according to the present invention, the therapeutic agent is an alkylating hexitol derivative, modified alkylating hexitol derivative, or derivative or analog of an alkylating hexitol derivative or modified alkylating hexitol derivative and the therapeutic agent is present in the composition in a drug conjugate form, wherein the drug conjugate form is a drug conjugate form selected from the group consisting of:
(a) a polymer system;
(b) polylactides;
(c) polyglycolides;
(d) amino acids;
(e) peptides;
(f) multivalent linkers;
(g) immunoglobulins;
(h) cyclodextrin polymers;
(i) modified transferrin;
(j) hydrophobic or hydrophobic-hydrophilic polymers;
(k) conjugates with a phosphonoformic acid partial ester;
(l) conjugates with a cell-binding agent incorporating a charged cross-linker; and
(m) conjugates with β-glucuronides through a linker.

In still another alternative of a composition according to the present invention, the therapeutic agent is an alkylating hexitol derivative, modified alkylating hexitol derivative, or derivative or analog of an alkylating hexitol derivative or modified alkylating hexitol derivative and the therapeutic agent is in the form of a prodrug system, wherein the prodrug system is selected from the group consisting of:
(a) enzyme sensitive esters;
(b) dimers;
(c) Schiff bases;
(d) pyridoxal complexes;
(e) caffeine complexes;
(f) nitric oxide-releasing prodrugs;
(g) prodrugs with fibroblast activation protein α-cleavable oligopeptides;
(h) products of reaction with an acylating or carbamylating agent;
(i) hexanoate conjugates;
(j) polymer-agent conjugates; and
(k) prodrugs that are subject to redox activation.

In still another alternative of a composition according to the present invention, the therapeutic agent is an alkylating hexitol derivative, modified alkylating hexitol derivative, or derivative, analog, or prodrug of an alkylating hexitol derivative or modified alkylating hexitol derivative and the composition further comprises at least one additional therapeutic agent to form a multiple drug system, wherein the at least one additional therapeutic agent is selected from the group consisting of:
(a) an inhibitor of multi-drug resistance;
(b) a specific drug resistance inhibitor;
(c) a specific inhibitor of a selective enzyme;
(d) a signal transduction inhibitor;
(e) an inhibitor of a repair enzyme; and
(f) a topoisomerase inhibitor with non-overlapping side effects.

In still another alternative of a composition according to the present invention, the therapeutic agent is an alkylating hexitol derivative, modified alkylating hexitol derivative, or derivative, analog, or prodrug of an alkylating hexitol derivative or modified alkylating hexitol derivative and the composition further comprises an agent for counteracting myelosuppression. Typically, the agent that counteracts myelosuppression is a dithiocarbamate.

In still another alternative of a composition according to the present invention, the therapeutic agent is an alkylating hexitol derivative, modified alkylating hexitol derivative, or derivative, analog, or prodrug of an alkylating hexitol derivative or modified alkylating hexitol derivative and the composition further comprises an agent that increases the ability of the substituted hexitol to pass through the blood-brain barrier, wherein the agent that increases the ability of the substituted hexitol to pass through the blood-brain barrier is selected from the group consisting of:
(a) a chimeric peptide of the structure of Formula (D-III):

(D-III)

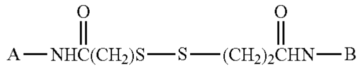

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

A-NH$(CH_2)_2$S—S—B (cleavable linkage) (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

A-NH—CH$(CH_2)_3$CH═NH—B (non-cleavable linkage) (D-III(b)), wherein the bridge is formed using glutaraldehyde as the bridge reagent;
(b) a composition comprising either avidin or an avidin fusion protein bonded to a biotinylated substituted hexitol derivative to form an avidin-biotin-agent complex including therein a protein selected from the group consisting of insulin, transferrin, an anti-receptor monoclonal antibody, a cationized protein, and a lectin;
(c) a neutral liposome that is pegylated and incorporates the substituted hexitol derivative, wherein the polyethylene glycol strands are conjugated to at least one transportable peptide or targeting agent;
(d) a humanized murine antibody that binds to the human insulin receptor linked to the substituted hexitol derivative through an avidin-biotin linkage; and
(e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the substituted hexitol by a covalent link to biotin.

In one alternative, when the alkylating hexitol derivative is dianhydrogalactitol, the composition is formulated for administration of dianhydrogalactitol by dosing once daily for three consecutive days every 21 days.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, 221rabic221, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, P3-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent, such as dianhydrogalactitol or an analog or derivative of dianhydrogalactitol as described above, that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., $20^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg.

Plasma concentrations in the subjects may be between about 100 μM to about 1000 μM. In some embodiments, the plasma concentration may be between about 200 μM to about 800 μM. In other embodiments, the concentration is about 300 μM to about 600 μM. In still other embodiments the plasma concentration may be between about 400 to about 800 μM. Administration of prodrugs is typically dosed at weight levels, which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum 226rabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-α-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Dianhydrogalactitol, diacetyldianhydrogalactitol, and pharmaceutical compositions comprising dianhydrogalactitol or diacetyldianhydrogalactitol, are typically administered orally or intravenously.

Pharmaceutical compositions according to the present invention can be prepared in accordance with methods well known and routinely practiced in the art. See, e.g., Remington: *The Science and Practice of Pharmacy*, Mack Publishing Co., $20^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated, as described above.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" *in Controlled Drug Delivery: Fundamentals and Applications* (J. R. Robinson & V. H. L. Lee, eds, 2d ed., Marcel Dekker, New York, 1987), ch. 5, pp. 213-251.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" *in Controlled Drug Delivery: Fundamentals and Applications* (J. R. Robinson & V. H. L. Lee, eds, 2d ed., Marcel Dekker, New York, 1987), ch. 1, pp. 3-94. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

Typically, the therapeutically effective quantity of dianhydrogalactitol is about 40 $mg/m^2$. The therapeutically effective quantity of diacetyldianhydrogalactitol is similar taking into account differences in molecular weight. Other dosages can be employed, including up to 50 $mg/m^2$ for dianhydrogalactitol. Higher dosages may also be used, particularly when steps are taken to prevent myelosuppression.

Another aspect of the present invention is a method of treating a central nervous system malignancy in a pediatric patient comprising the step of administering a therapeutically effective quantity of a substituted hexitol derivative to a patient suffering from the malignancy. As detailed above, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

Typically, when the substituted hexitol derivative is dianhydrogalactitol, the therapeutically effective quantity of dianhydrogalactitol is a dosage from about 1 mg/$m^2$ to about 40 mg/$m^2$. Preferably, the therapeutically effective quantity of dianhydrogalactitol is a dosage from about 5 mg/$m^2$ to about 25 mg/$m^2$. The therapeutically effective quantity of diacetyldianhydrogalactitol is similar taking into account differences in molecular weight. Other dosages can be employed, including up to 50 mg/$m^2$ for dianhydrogalactitol. Higher dosages may also be used, particularly when steps are taken to prevent myelosuppression.

Typically, the substituted hexitol derivative, such as dianhydrogalactitol, is administered by a route selected from the group consisting of intravenous and oral. Similar routes of administration can be used for diacetyldianhydrogalactitol. Other potential routes of administration are described above.

The method can further comprise the step of administering a therapeutically effective dose of ionizing radiation. The method can further comprise the step of administering a therapeutically effective quantity of temozolomide, bevacizumab, or a corticosteroid.

The method can further comprise the administration of a therapeutically effective quantity of a tyrosine kinase inhibitor as described above.

The method can further comprise the administration of a therapeutically effective quantity of an epidermal growth factor receptor (EGFR) inhibitor as described below. The EGFR inhibitor can affect either wild-type binding sites or mutated binding sites, including Variant III, as described above.

Another aspect of the present invention is a kit comprising, separately packaged, two or more different doses of a hexitol derivative as described above for treatment of a malignancy, in particular, a central nervous system malignancy in a pediatric patient. Typically, the hexitol derivative is dianhydrogalactitol or diacetyldianhydrogalactitol. When the alkylating hexitol derivative is dianhydrogalactitol, the kit can comprise, but is not limited to, the following combinations of doses: (i) 1.5 mg/$m^2$ and 3.0 mg/$m^2$; (ii) 1.5 mg/$m^2$, 3.0 mg/$m^2$, and 5.0 mg/$m^2$; (iii) 1.5 mg/$m^2$, 3.0 mg/$m^2$, 5.0 mg/$m^2$, and 10 mg/$m^2$; (iv) 1.5 mg/$m^2$, 3.0 mg/$m^2$, 5.0 mg/$m^2$, 10 mg/$m^2$, and 15 mg/$m^2$; (v) 10 mg/$m^2$; (iv) 1.5 mg/$m^2$, 3.0 mg/$m^2$, 5.0 mg/$m^2$, 10 mg/$m^2$, 15 mg/$m^2$, and 20 mg/$m^2$; (vi) 1.5 mg/$m^2$, 3.0 mg/$m^2$, 5.0 mg/$m^2$, 10 mg/$m^2$, 15 mg/$m^2$, 20 mg/$m^2$, and 25 mg/$m^2$; (vii) 1.5 mg/$m^2$, 3.0 mg/$m^2$, 5.0 mg/$m^2$, 10 mg/$m^2$, 15 mg/$m^2$, 20 mg/$m^2$, 25 mg/$m^2$, and 30 mg/$m^2$; (viii) 1.5 mg/$m^2$, 3.0 mg/$m^2$, 5.0 mg/$m^2$, 10 mg/$m^2$, 15 mg/$m^2$, 20 mg/$m^2$, 25 mg/$m^2$, 30 mg/$m^2$, and 40 mg/$m^2$; and (ix) 1.5 mg/$m^2$, 3.0 mg/$m^2$, 5.0 mg/$m^2$, 10 mg/$m^2$, 15 mg/$m^2$, 20 mg/$m^2$, 25 mg/$m^2$, 30 mg/$m^2$, 40 mg/$m^2$, and 50 mg/$m^2$. Other combinations of doses including two or more of these alternative doses are also possible. The hexitol derivative can be in the form of a pharmaceutical composition. The doses can be assembled into a blister pack as is conventionally used for packaging of pharmaceutical doses. The kit can further comprise instructions for use.

Accordingly, one aspect of the present invention is a method of treating malignancies of the central nervous system such as glioblastoma multiforme or medulloblastoma in pediatric patients by administration of a therapeutically effective quantity of a substituted hexitol derivative according to the present invention as described above.

The method of treating malignancies of the central nervous system such as glioblastoma multiforme or medulloblastoma in pediatric patients can employ one of the methods to improve the efficacy and/or reduce the side effects of the administration of the substituted hexitol described above.

The method of treating malignancies of the central nervous system such as glioblastoma multiforme or medulloblastoma in pediatric patients can employ a composition according to the present invention as described above.

The method of treating malignancies of the central nervous system such as glioblastoma multiforme or medulloblastoma in pediatric patients can further comprise administration of a therapeutically effective quantity of an inhibitor of PARP.

The method of treating malignancies of the central nervous system such as glioblastoma multiforme or medulloblastoma in pediatric patients can further comprise administration of a therapeutically effective quantity of an agent that counters loss of PTEN function as described above.

The invention is illustrated by the following Examples. These Examples are included for illustrative purposes only, and are not intended to limit the invention. In some cases, as stated below, these Examples provide results for cell lines other than cell lines from central nervous system malignancies; in such cases, as detailed in the specific examples, the results are relevant to treatment of central nervous system malignancies because they illustrate a mechanism that is also associated with resistance in cells of central nervous system malignancies.

Example 1

Activity of Dianhydrogalactitol to Against Medulloblastoma and Pediatric High Grade Glioma Cell Lines Medulloblastoma (MB) is the most common malignant pediatric brain tumor, accounting for 15-30% of all childhood intracranial neoplasms. High grade gliomas (HGG) are much rarer in children than in adults, comprising only 5%-10% of childhood brain tumors. Although multidisciplinary treatment has improved the 5-year survival rates in children significantly, the prognosis for recurrent MB and HGG remains poor with median overall survival<1 year. Temozolomide (TMZ) is frequently employed in the treatment of MB and pediatric HGG; however, clinical evidence is lacking and poor outcomes due to high-expression of the repair protein $O^6$-methylguanine-DNA methyltransferase (MGMT), which is correlated with TMZ resistance, have been reported. Dianhydrogalactitol (VAL-083) is a structurally unique bi-functional alkylating agent causing DNA crosslinks at $N^7$ position of guanine. VAL-083 readily crosses the blood brain barrier and has been shown to accumulate in brain tumor tissue. Furthermore, VAL-083 demonstrated clinical activity against MB and HGG in historical NCI-sponsored clinical studies. We have recently shown that VAL-083 demonstrates cytotoxic activity in GBM independent of MGMT expression in vitro and in vivo. We have further shown that VAL-083 is highly effective against GBM cancer stem cells (CSC) and non-CSC and that it acts as a radiosensitizer in GBM cell lines, in vitro. VAL-083 is currently in phase II clinical trials for recurrent GBM in adults. In the current adult GBM clinical trial VAL-083 displayed a favorable safety-profile and preliminary analysis supports a survival benefit at doses chosen for further investigation. Based on these recent results and data supporting VAL-083's clinical activity in historical MB and HGG studies, we sought to investigate the cytotoxic activity of VAL-083 as a potential therapeutic alternative for pediatric brain tumors by studying the drug against MB and pediatric HGG cell lines in vitro.

Materials and Methods

Cell Lines and Culture Conditions:

All cells except for BT74 were cultured in DMEM (Dulbecco's Modified Eagle's Medium medium; Invitrogen/Gibco) with 10% FBS (fetal bovine serum; Invitrogen/Gibco) at 37° C. with 5% $CO_2$, and subcultured twice weekly during the experimental period. BT74 cells were were grown non-adherently using NeuralBasal medium with Neurocult supplement and growth factors, EGF (20 ng/ml), FGF (20 ng/mL) and heparin (2 mg/mL). SF188 (pediatric) and U251 (adult) GBM cell lines were obtained from the ATCC.

Drugs:

TMZ was purchased from Sigma-Aldrich and dissolved in DMSO (dimethyl sulfoxide; Sigma-Aldrich). Stock solution of 100 mM was kept at −20° C. before use. Dianhydrogalactitol (also referred to herein as "VAL-083") was prepared as a stock solution of 100 mM by dissolving the lyophilized powder in the injection vial in sterile PBS (phosphate buffered saline) and kept at −20° C. before use.

Growth Assays:

Each cell line was seeded at 3,000 cells/well in 100 μL medium in 96-well plate (BD Falcon) and incubated overnight. Cells were then treated with TMZ or VAL083 at concentrations of 0.1-100 μM in the fresh medium for 72 h. The cells were fixed in 2% paraformaldehyde (Sigma-Aldrich) with nuclear dye Hoechst 33342 (1 μg/ml) (Sigma-Aldrich). After gentle wash by PBS, the cells were kept in fresh PBS and the plates were kept at 4° C. in the dark before the HCS (high content screening; ThermoFisher Scientific) analysis. Twenty view fields per well were scanned and analyzed. Growth inhibition was calculated as a percentage of the control without the solvent and the drug, and the samples treated with solvent alone served as a reference. There are three replicates for each treatment and the experiments were repeated once.

Neurosphere Assays:

Neurosphere assays were performed by plating approximately $10^4$ cells/well into a low adherent 6 well dish using neurobasal medium supplemented with human recombinant EGF (20 ng/ml), human recombinant FGF (20 ng/ml) and heparin (2 μg/ml). Neurospheres were grown for 5-6 days following plating. Spheres>30 μm were counted and photographed using an Aniovert 40CFL microscope and AxioCam MRc camera. NeuroCult Chemical Dissociation kit (Stem Cell Technologies, cat. #05707) was used to passage cells, which are counted and replated as single cells. All drug treatments were done at the time of plating, and repeated during serial passaging.

Human MB cell lines DAOY, UW228, ONS-76 and UW426 and pediatric HGG cell line SF188 were treated with VAL-083 at concentrations of 0.1-100 μM for 72 h. Growth inhibition was measured by high content screening analysis. Neurosphere formation of DAOY and SF188 cells was determined by neurosphere colony assay.

Results

VAL-083 inhibited growth of all cell lines (DAOY, UW228, ONS-76 UW426 and SF188) with $IC_{50}$ at low micromolar concentrations. DAOY, UW228 and SF188 cells were most sensitive to VAL-083. Primary neurosphere formation of DAOY cells was completely inhibited at 5 μM VAL-083 and VAL-083 was superior to TMZ against primary neurospheres formation of SF-188 cells; complete inhibition of SF-188 neurospheres was observed with the combination of VAL-083 and TMZ.

Example 2

Additional Applications for Use of Dianhydrogalactitol to Treat Central Nervous System Malignancies Additional results for the use of dianhydrogalactitol to treat central nervous system malignancies, including glioblastoma multiforme, are provided below.

FIG. 1 is a table showing a summary of glioblastoma multiforme (GBM) models and their response to dianhydrogalactitol (VAL-083).

FIG. 2 shows the temozolomide (TMZ) resistance and MGMT status for three cell lines, SF188, U251, and T98G. SF188 is a pediatric high grade glioma cell line. In FIG. 2, the protein actin is used as a control. Western blots are shown.

Figure 3:
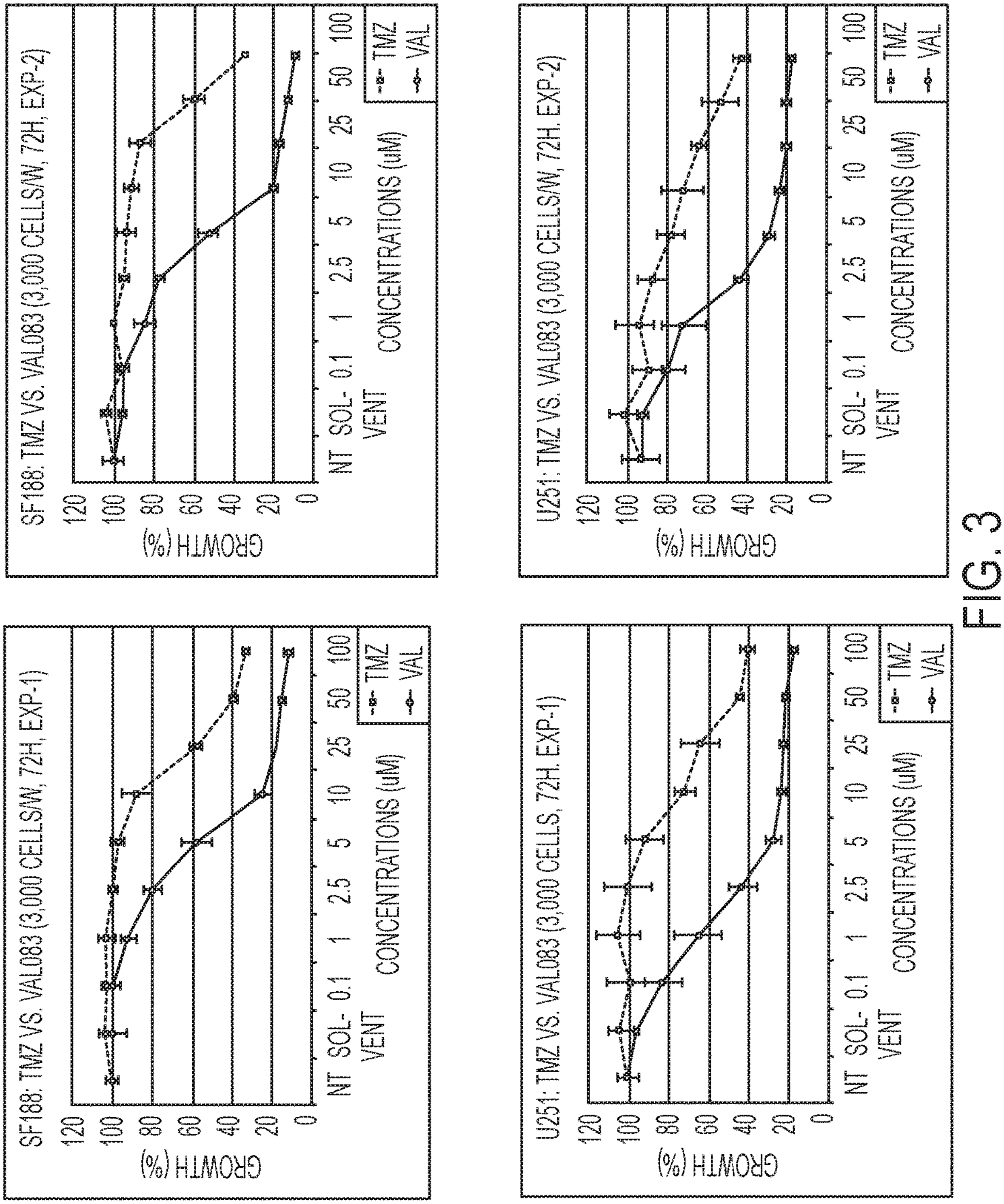
FIG. 3 shows the results for survival for SF188 (top panels), U251 (middle panels), and T98G (bottom panels) for 0.1, 1, 2.5, 5, 10, 25, 50, and 100 μM of temozolomide (TMZ) and dianhydrogalactitol (VAL). Two experiments are shown for each cell line.
Figure 3:
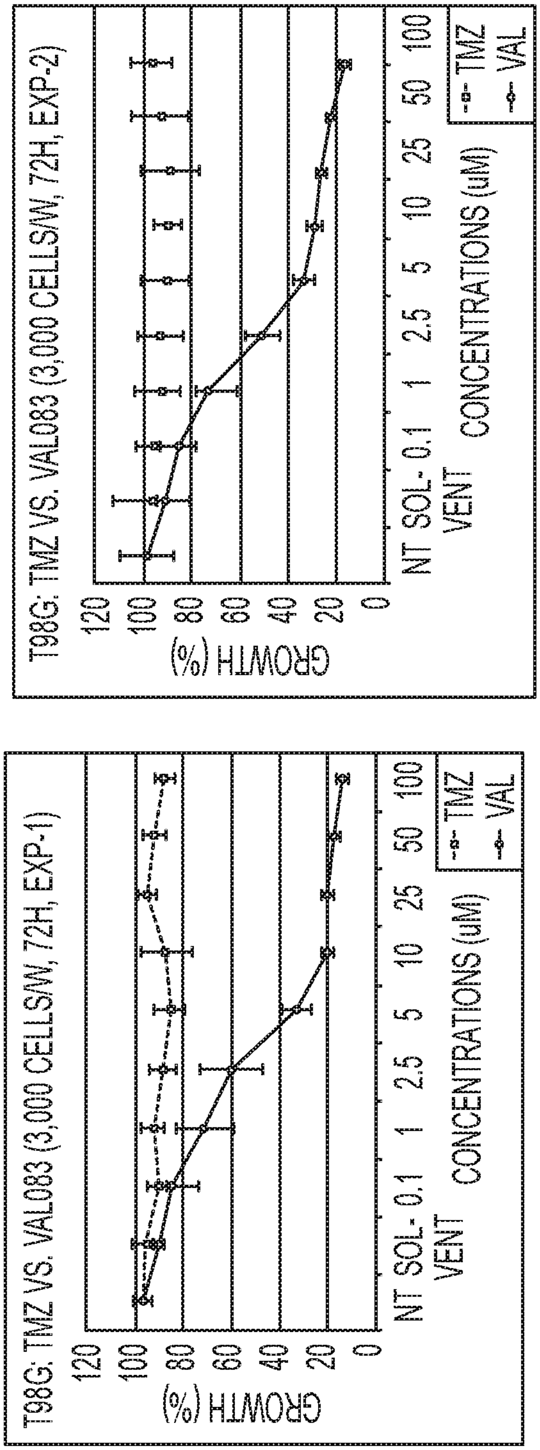

FIG. 3 shows the results for survival for SF188 (top panels), U251 (middle panels), and T98G (bottom panels) for 0.1, 1, 2.5, 5, 10, 25, 50, and 100 μM of temozolomide (TMZ) and dianhydrogalactitol (VAL). Two experiments are shown for each cell line.

Figure 4:
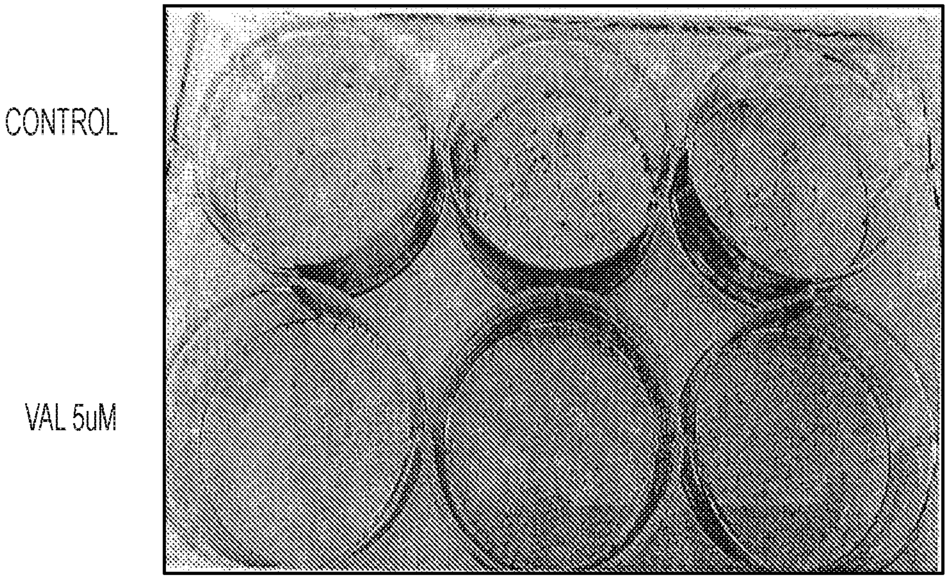
FIG. 4 shows that dianhydrogalactitol at 5 μM provided more than 95% suppression of colony formation in a colony formation assay for SF188.

FIG. 4 shows that dianhydrogalactitol at 5 μM provided more than 95% suppression of colony formation in a colony formation assay for SF188.

Figure 5:
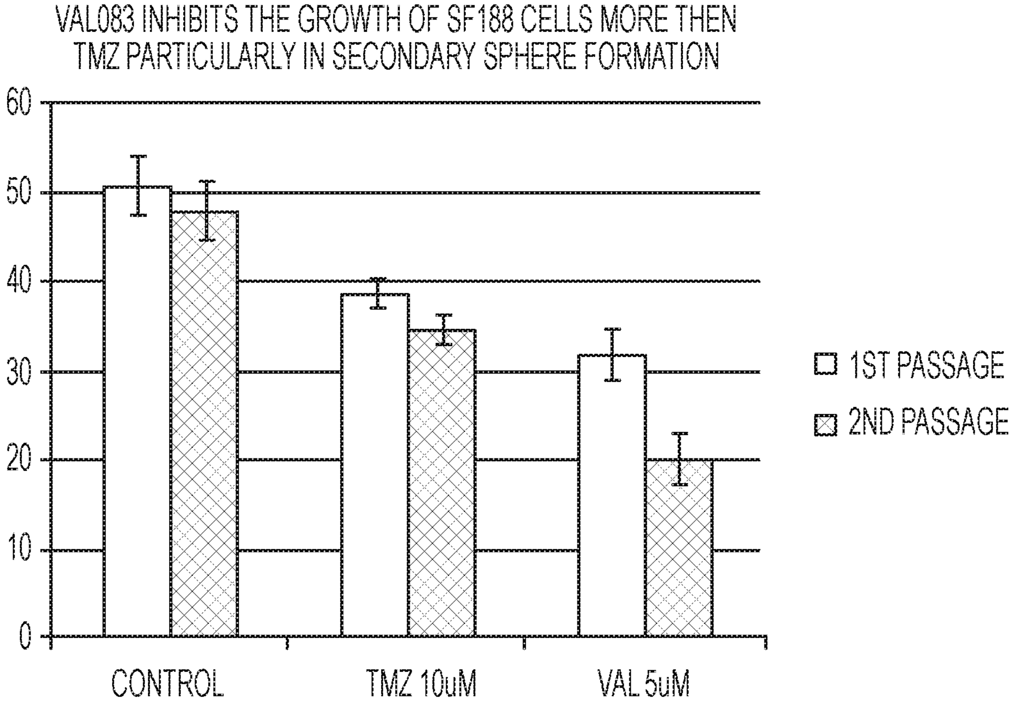
FIG. 5 shows that dianhydrogalactitol (VAL) inhibits the growth of SF188 more than does temozolomide (TMZ) particularly in secondary sphere formation. Dianhydrogalactitol was used at 5 μM and temozolomide was used at 10 μM.

FIG. 5 shows that dianhydrogalactitol (VAL) inhibits the growth of SF188 more than does temozolomide (TMZ) particularly in secondary sphere formation. Dianhydrogalactitol was used at 5 μM and temozolomide was used at 10 μM.

Figure 6:
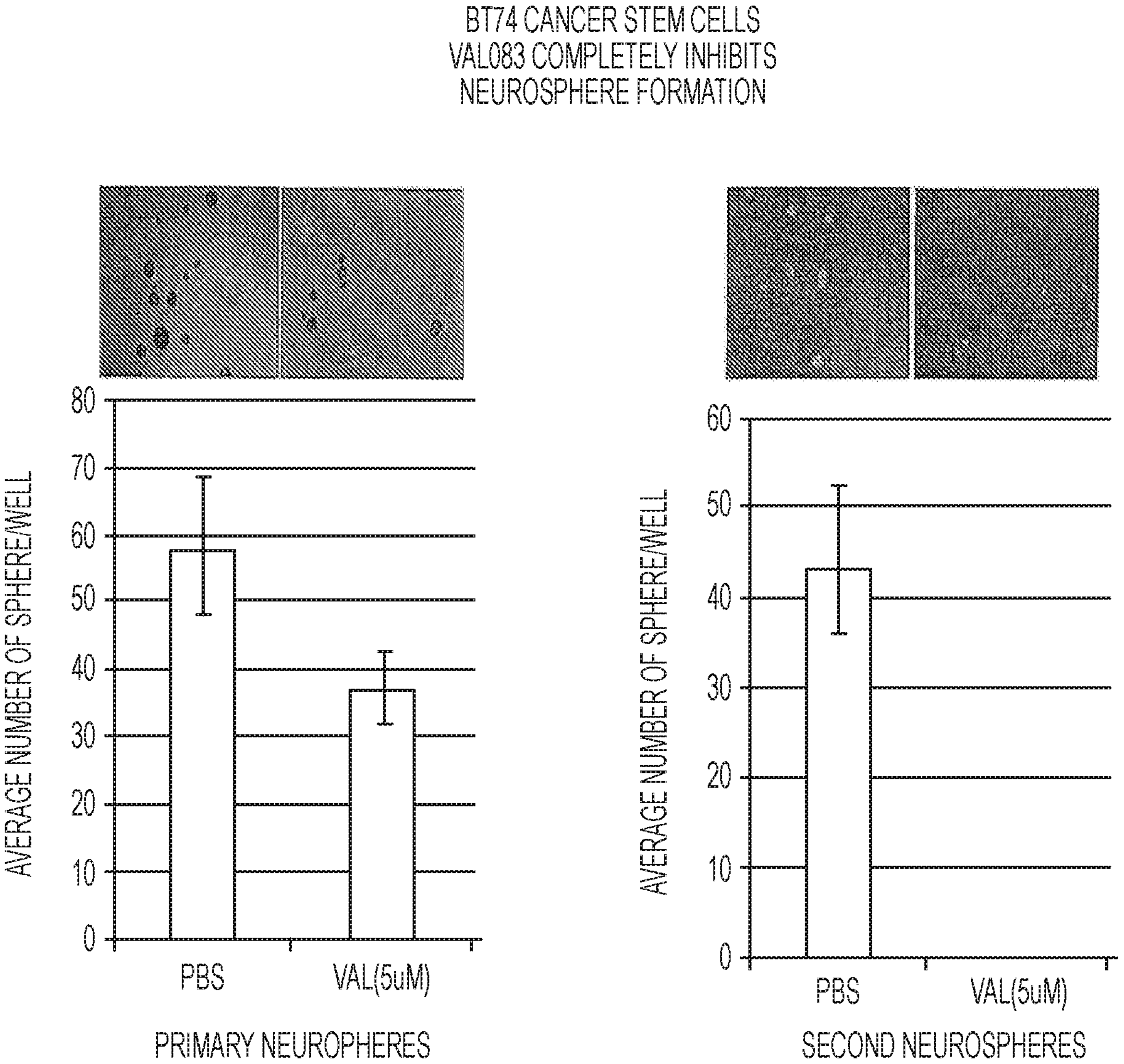
FIG. 6 shows that dianhydrogalactitol (VAL083) completely inhibits neurosphere formation for BT74 cancer stem cells for both primary neurospheres and secondary neurospheres. Dianhydrogalactitol was used at 5 μM.

FIG. 6 shows that dianhydrogalactitol (VAL083) completely inhibits neurosphere formation for BT74 cancer stem cells for both primary neurospheres and secondary neurospheres. Dianhydrogalactitol was used at 5 μM.

Figure 7:
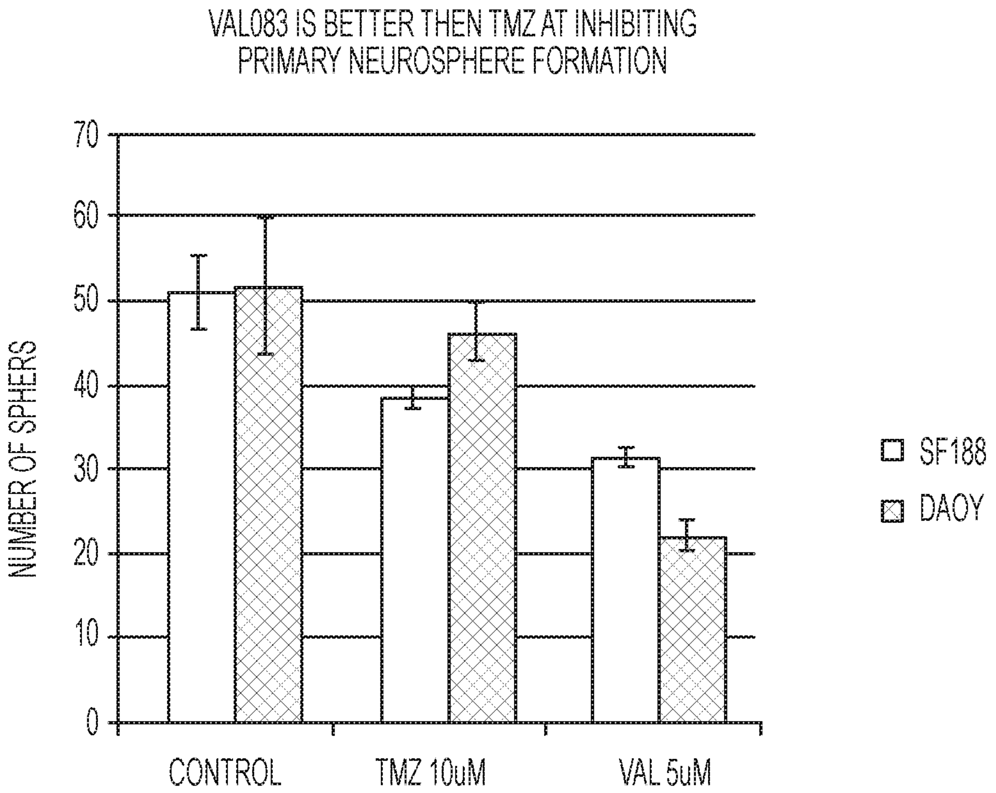
FIG. 7 shows that dianhydrogalactitol (VAL083) is more effective than temozolomide (TMZ) at inhibiting primary neurosphere formation for SF188 and DAOY cell lines (DAOY is a medulloblastoma cell line). Dianhydrogalactitol was used at 5 μM and temozolomide was used at 10 μM.

FIG. 7 shows that dianhydrogalactitol (VAL083) is more effective than temozolomide (TMZ) at inhibiting primary neurosphere formation for SF188 and DAOY cell lines (DAOY is a medulloblastoma cell line). Dianhydrogalactitol was used at 5 μM and temozolomide was used at 10 μM.

FIG. 8 shows that dianhydrogalactitol at 5 μM provided 100 percent suppression of colony formation for DAOY medulloblastoma cells and >80% suppression of colony formation for SF188 glioblastoma cells.

For the results shown in FIGS. 1-8, the methods and materials were as follows. For cell lines and culture conditions, all cells were cultured in DMEM (Dulbecco's Modified Eagle's Medium; Invitrogen/Gibco) with 10% FBS (fetal bovine serum; Invitrogen/Gibco) at 37° C. with 5% $CO_2$, and subcultured twice weekly during the experimental period. Temozolomide was purchased from Sigma-Aldrich and dissolved in DMSO (Sigma-Aldrich). A stock solution of 100 mM was kept at −20° C. before use. For dianhydrogalactitol, a stock solution of 100 mM was prepared by dissolving the lyophilized powder in the injection vial in sterile phosphate buffered saline (PBS) and kept at −20° C. before use. Each cell line was seeded at 3,000 cells/well in 100 μL medium in a 96-well plate (BD Falcon) and incubated overnight. Cells were then treated with temozolomide or dianhydrogalactitol at the indicated concentrations of 0.1-100 μM in the fresh medium for 72 h. The cells were fixed in paraformaldehyde (Sigma-Aldrich) with nuclear dye Hoechst 33342 (1 μg/mL) (Sigma-Aldrich). After a gentle wash with PBS, the cells were kept in fresh PBS and the plates were kept at 4° C. in the dark before the HCS (high content screening; ThermoFisher Scientific) analysis. Twenty view fields per well were scanned and analyzed. Growth inhibition was calculated as a percentage of the control without the solvent and the drug, and the samples treated with solvent alone served as a reference. There are three replicates for each treatment and the experiments were repeated once.

Figure 9:
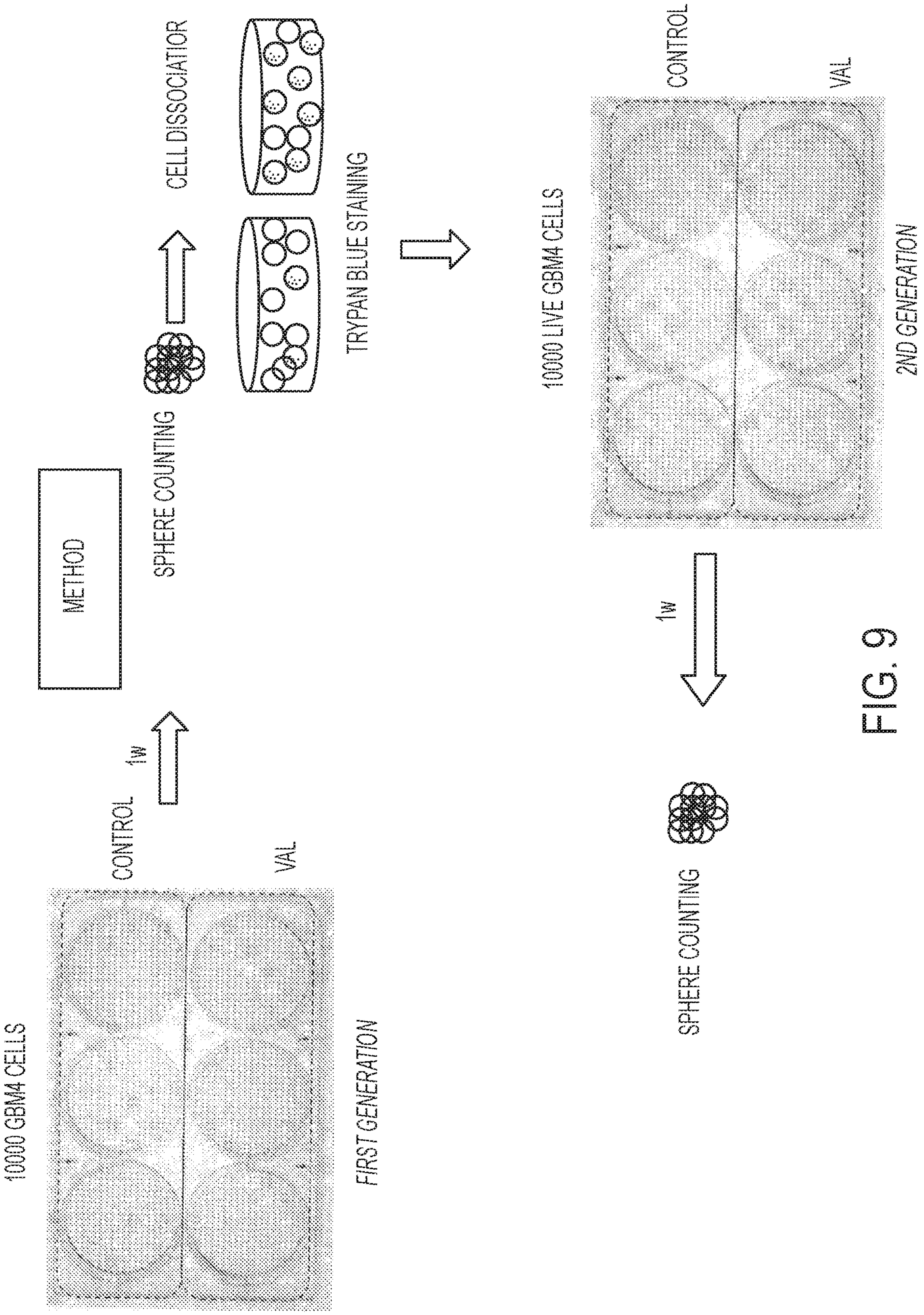
FIG. 9 shows the method of sphere counting for glioblastoma multiforme cells (GBM4) (both control and treated with dianhydrogalactitol (VAL)).

FIG. 9 shows the method of sphere counting for glioblastoma multiforme cells (GBM4) (both control and treated with dianhydrogalactitol (VAL)).

Figure 10:
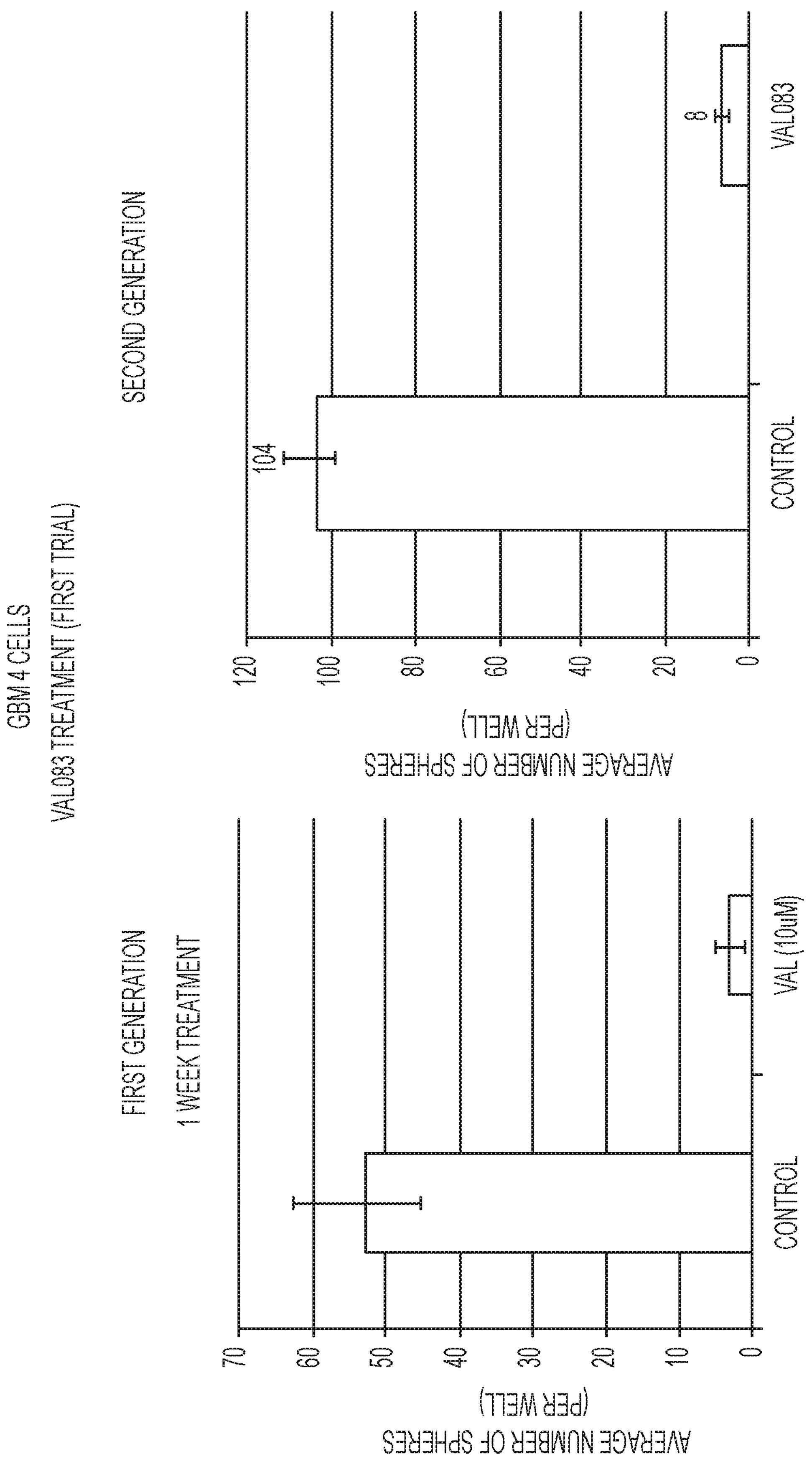
FIG. 10 shows inhibition of both first and second generation GBM4 (patient-derived adult GBM cancer stem cell) cells by 10 μM dianhydrogalactitol (VAL).

FIG. 10 shows inhibition of both first and second generation GBM4 cells by 10 μM dianhydrogalactitol (VAL).

Figure 11:
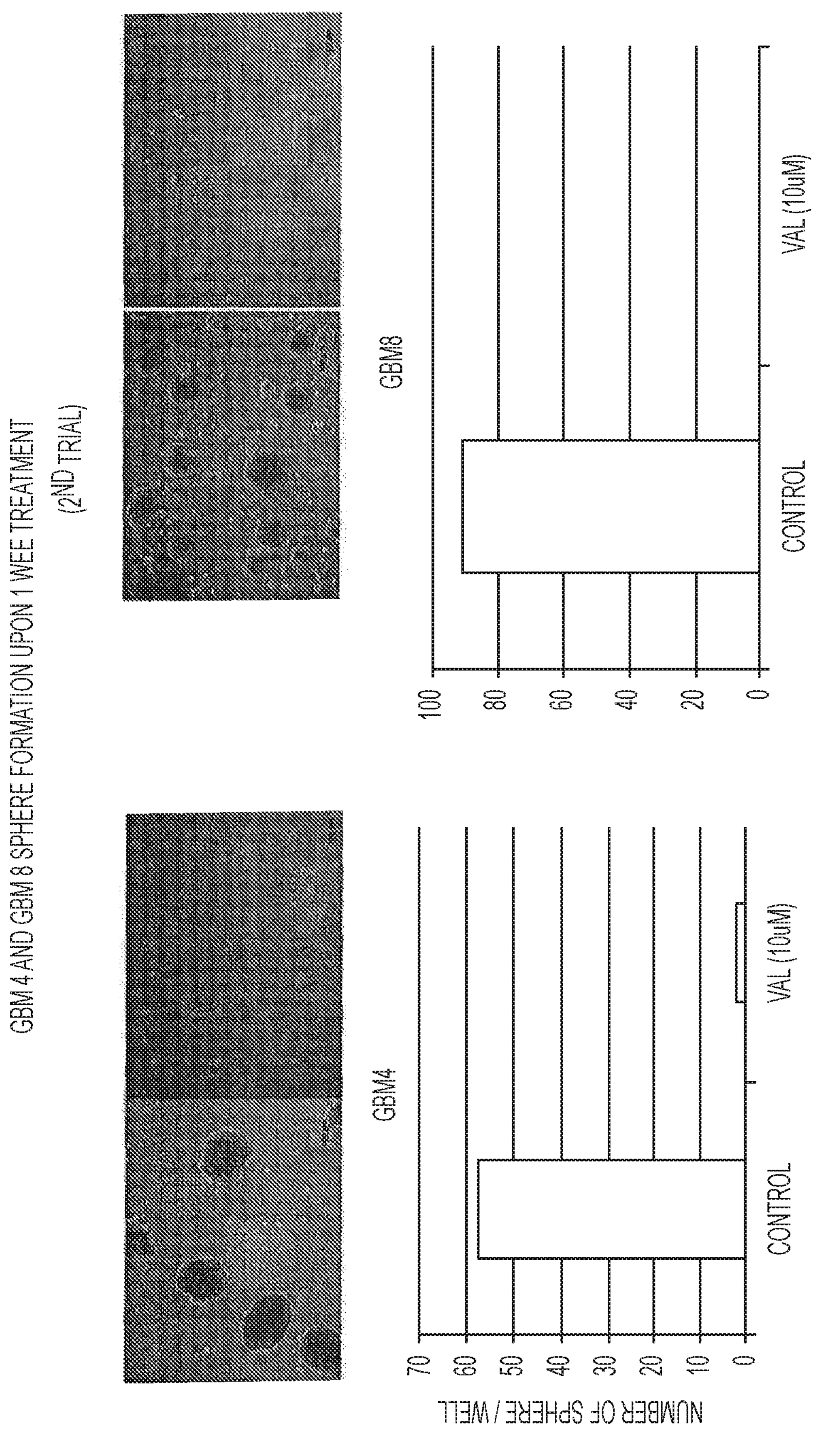
FIG. 11 shows inhibition of sphere treatment for both GBM4 and GBM8 (patient-derived adult GBM cancer stem cell) cells upon a 1-week treatment by 10 μM dianhydrogalactitol (VAL).

FIG. 11 shows inhibition of sphere treatment for both GBM4 and GBM8 cells upon a 1-week treatment by μM dianhydrogalactitol (VAL).

Figure 12:
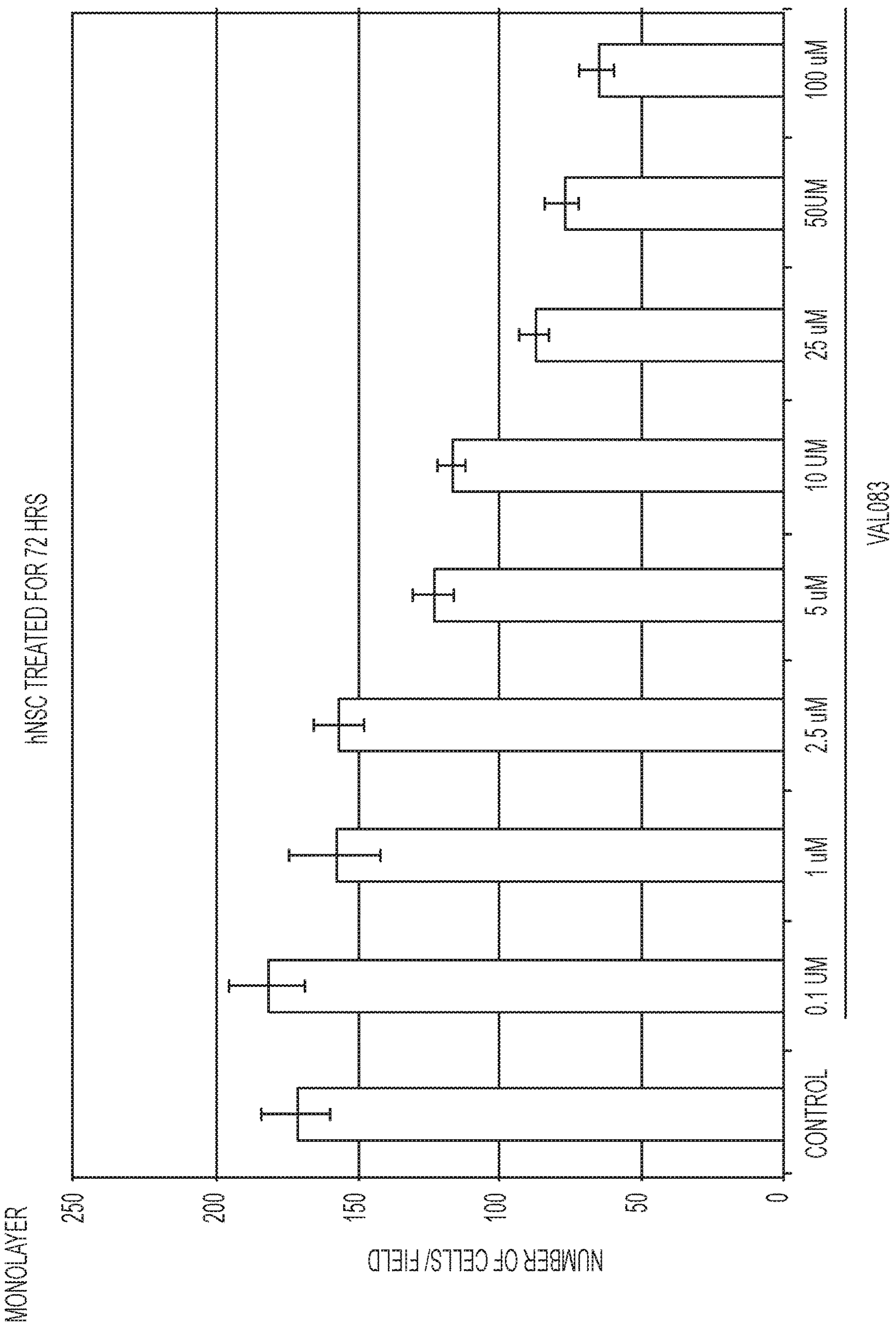
FIG. 12 shows the control for the effect of dianhydrogalactitol on human neural stem cells (hNSC). The graph shows the effects of various concentrations of dianhydrogalactitol (VAL083) (0.1 μM, 1 μM, 2.5 μM, 5 μM, 10 μM, 25 μM, 50 μM, and 100 μM) on hNSC treated for 72 hours in a monolayer.

FIG. 12 is a graph showing the effects of various concentrations of dianhydrogalactitol (VAL083) (0.1 μM, 1 μM, 2.5 μM, 5 μM, 10 μM, 25 μM, 50 μM, and 100 μM) on hNSC treated for 72 hours in a monolayer.

Figure 13:
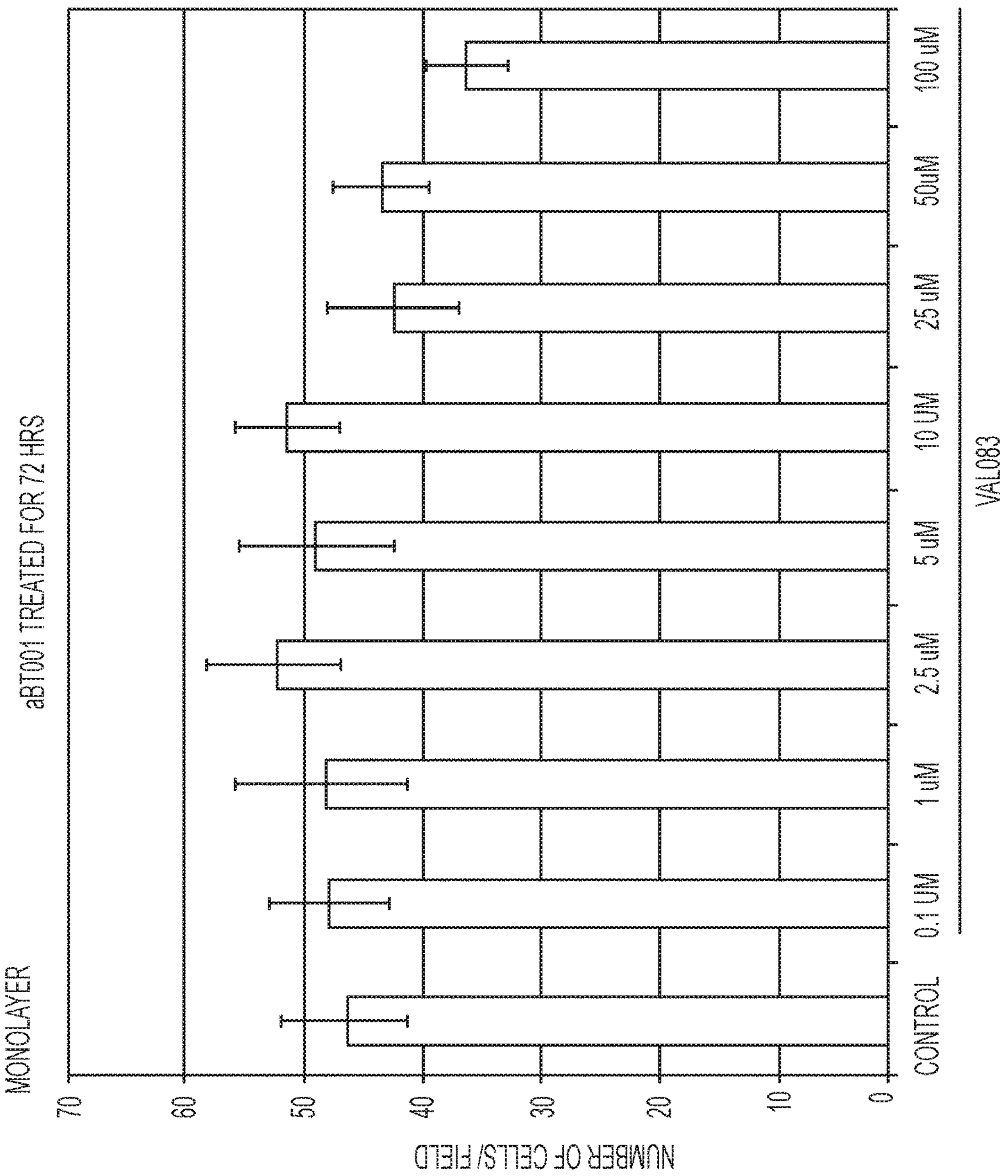
FIG. 13 is a graph showing the effects of various concentrations of dianhydrogalactitol (VAL083) (0.1 μM, 1 μM, 2.5 μM, 5 μM, 10 μM, 25 μM, 50 μM, and 100 μM) on aBT001 (patient-derived adult GBM cells) treated for 72 hours in a monolayer.

FIG. 13 is a graph showing the effects of various concentrations of dianhydrogalactitol (VAL083) (0.1 μM, 1 μM, 2.5 μM, 5 μM, 10 μM, 25 μM, 50 μM, and 100 μM) on aBT001 treated for 72 hours in a monolayer.

Figure 14:
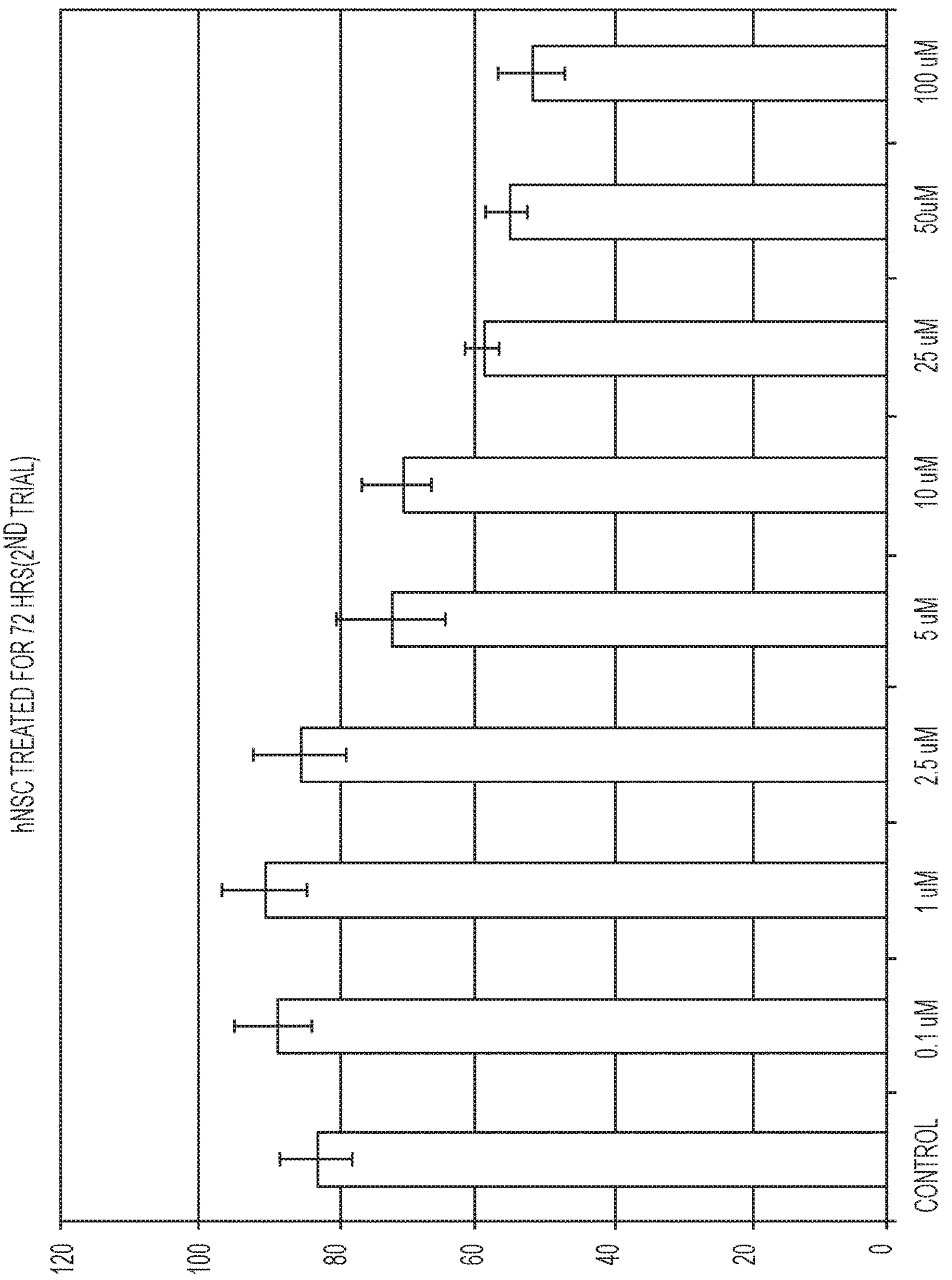
FIG. 14 is a graph showing the effects of various concentrations of dianhydrogalactitol (VAL083) (0.1 μM, 1 μM, 2.5 μM, 5 μM, 10 μM, 25 μM, 50 μM, and 100 μM) on hNSC treated for 72 hours in a monolayer in another experiment.

FIG. 14 is a graph showing the effects of various concentrations of dianhydrogalactitol (VAL083) (0.1 μM, 1 μM, 2.5 μM, 5 μM, 10 μM, 25 μM, 50 μM, and 100 μM) on hNSC treated for 72 hours in a monolayer in another experiment.

Figure 15:
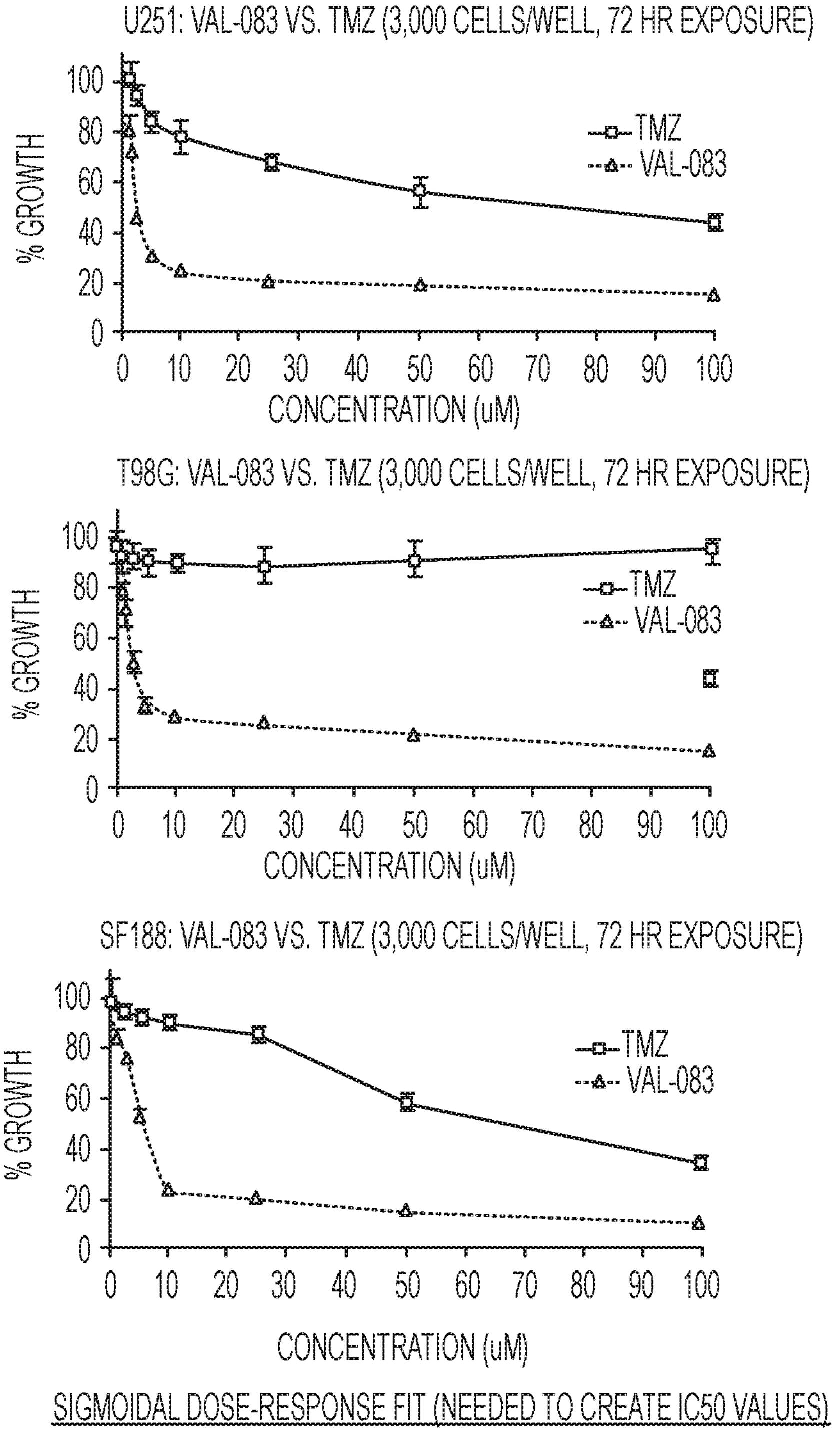
FIG. 15 is a series of graphs showing regular dose response curves and sigmoidal dose response curves for U251, T98G, and SF188 cell lines treated with dianhydrogalactitol and temozolomide at various concentrations.
Figure 15:
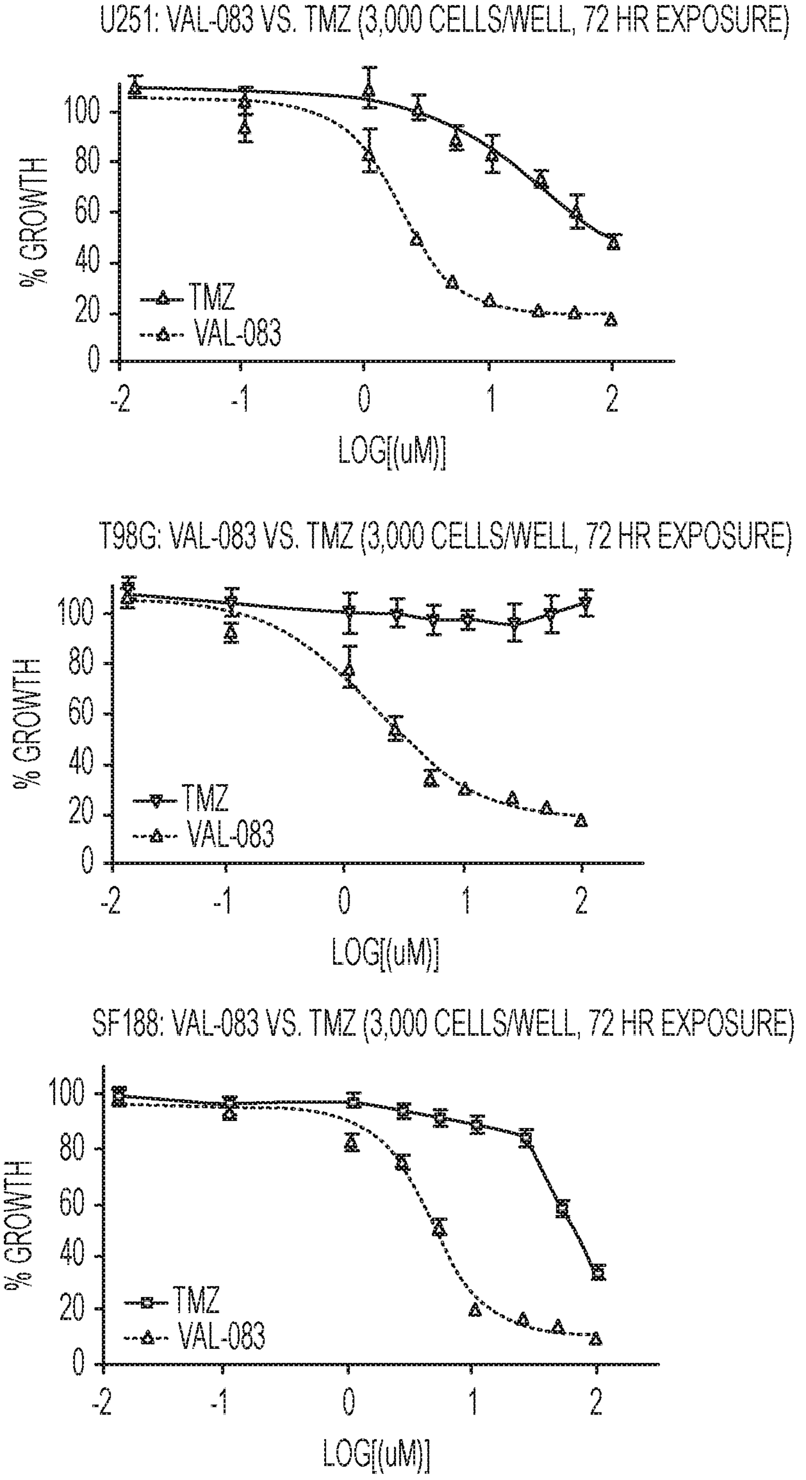

FIG. 15 is a series of graphs showing regular dose response curves and sigmoidal dose response curves for U251, T98G, and SF188 cell lines treated with dianhydrogalactitol and temozolomide at various concentrations.

FIG. 16 is a table showing IC50 values calculated from the sigmoidal dose response curves of FIG. 15.

Figure 17:
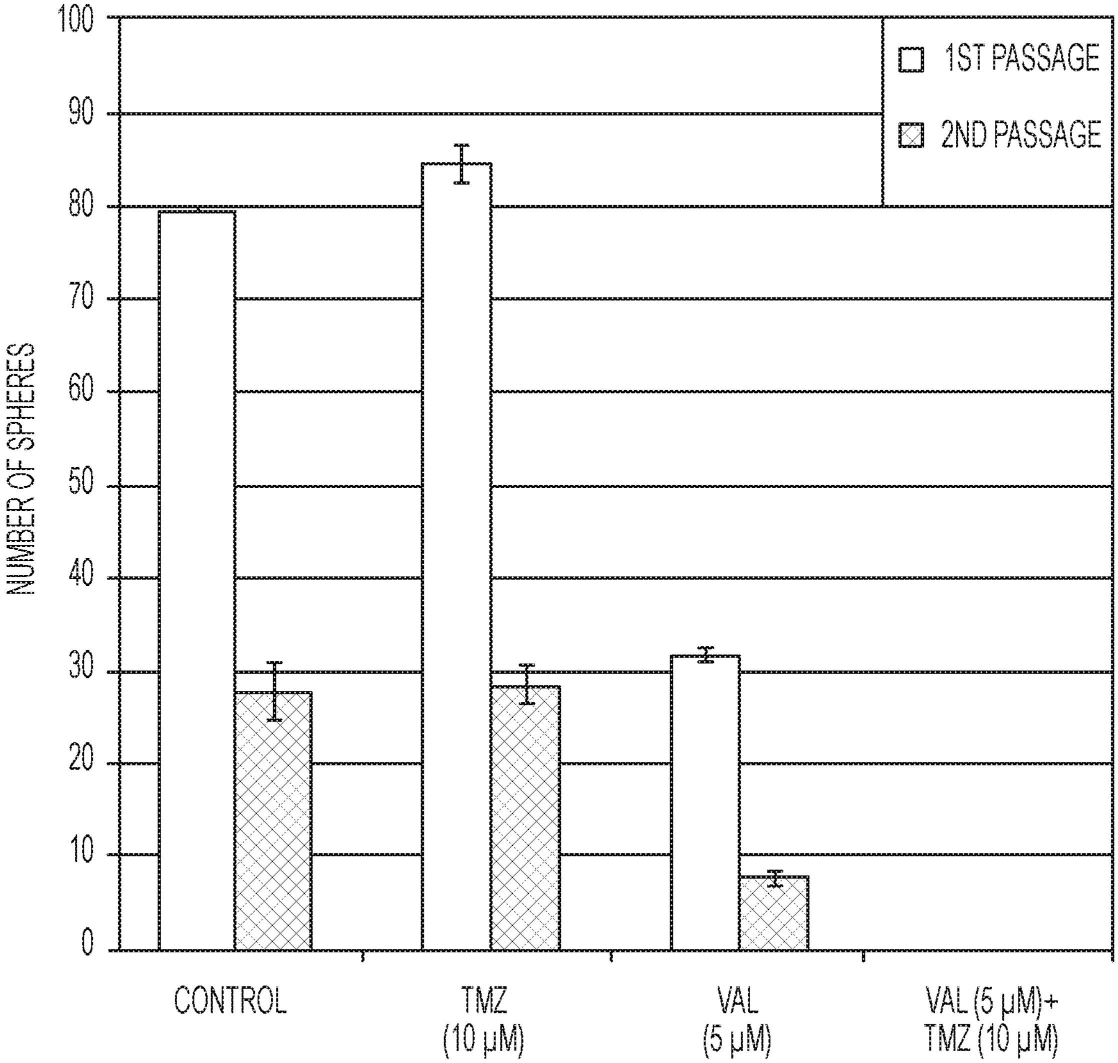
FIG. 17 is a graph showing the effects of sequential combination treatment with dianhydrogalactitol (VAL-083) and temozolomide (TMZ) on the pediatric high grade glioma cell line SF188; treatment was with TMZ for 3 days, then a wash, then treatment with dianhydrogalactitol for 3 days. The combination completely inhibited neurosphere formation.

FIG. 17 is a graph showing the effects of sequential combination treatment with dianhydrogalactitol (VAL-083) and temozolomide (TMZ) on the pediatric high grade glioma cell line SF188; treatment was with TMZ for 3 days, then a wash, then treatment with dianhydrogalactitol for 3 days. The combination completely inhibited neurosphere formation.

Figure 18:
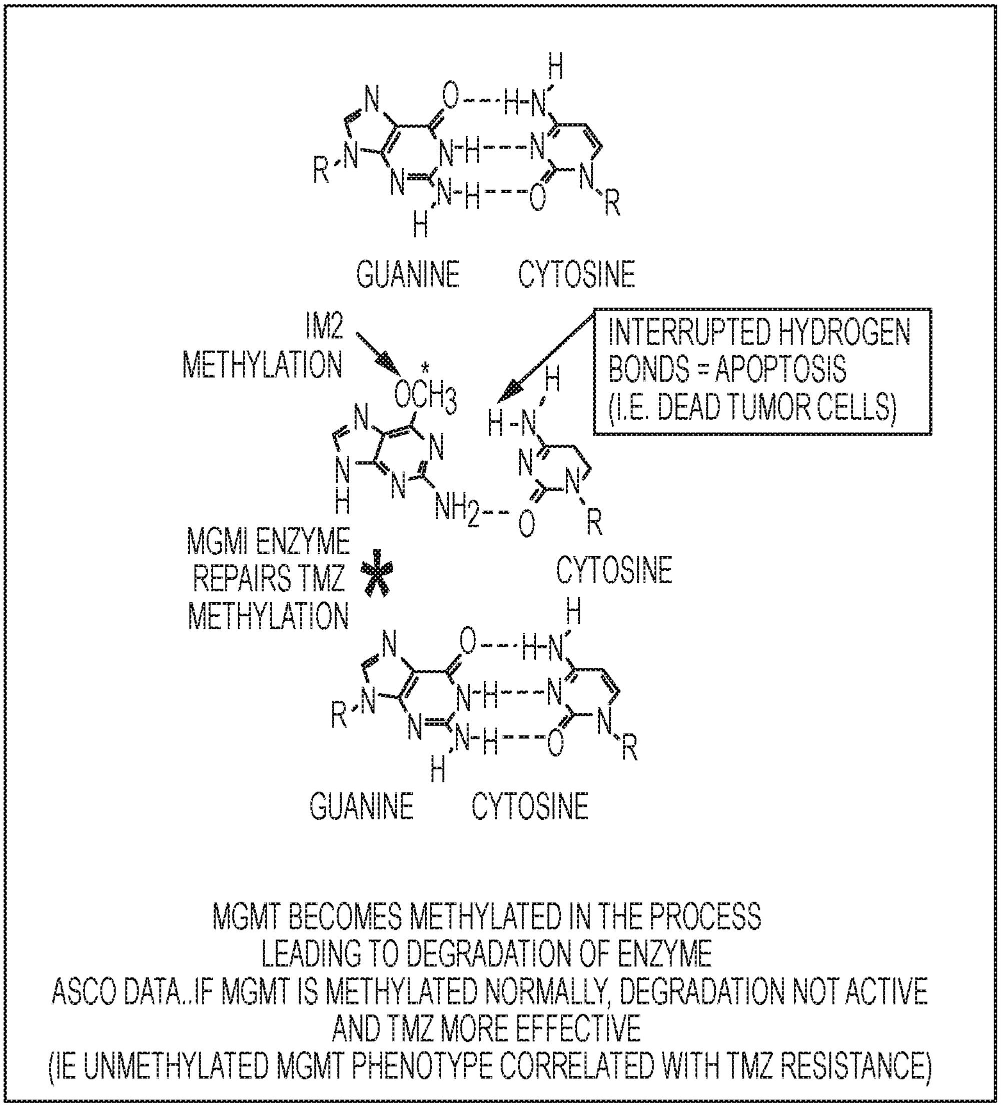
FIG. 18 is a diagram showing the anticipated mechanism of action of dianhydrogalactitol as targeting the N7 of guanine leading to an interstrand crosslink between two guanines on opposite DNA strands.

FIG. 18 is a diagram showing the activity of dianhydrogalactitol as inducing alkylation at $N^7$ of DNA.

Figure 19:
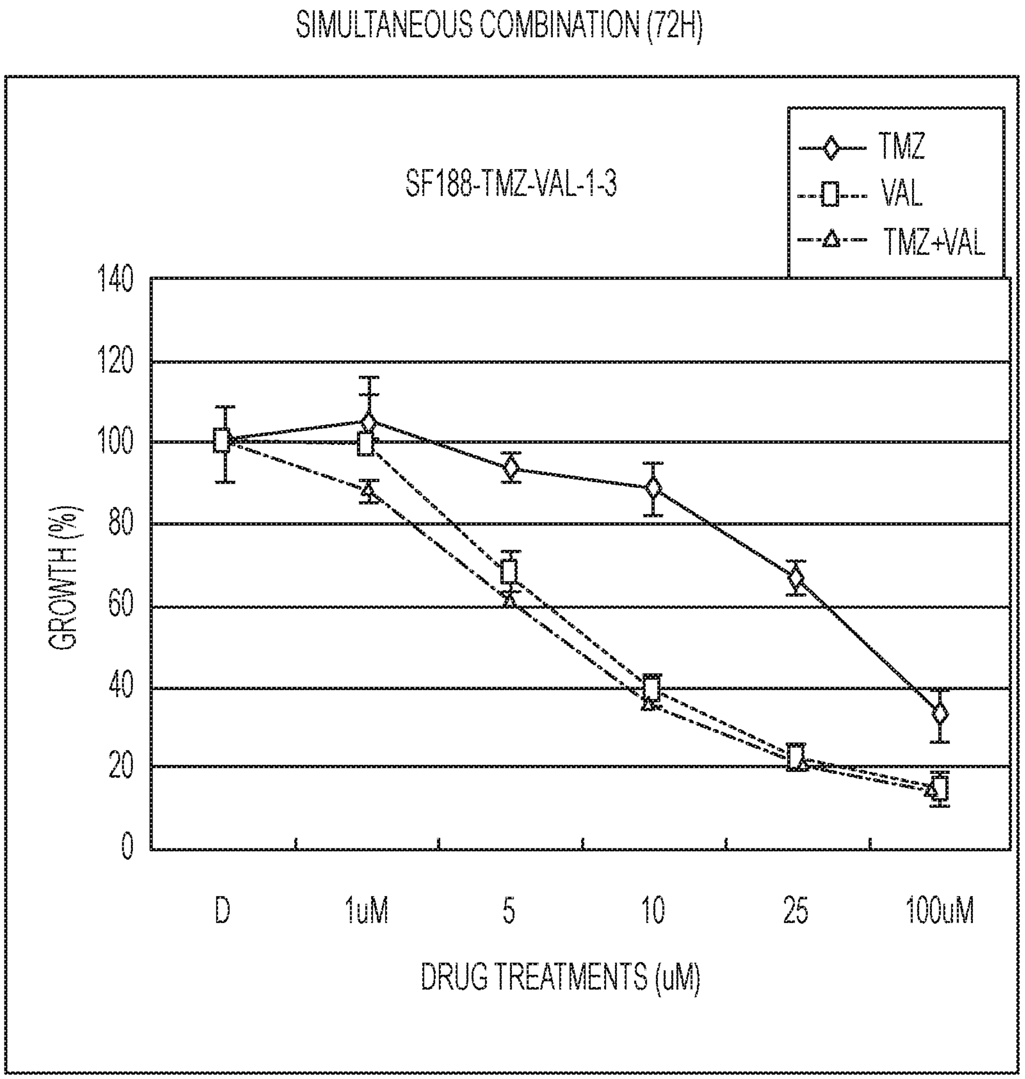
FIG. 19 is a graph showing the effect of simultaneous combination treatment of SF188 cells with temozolomide and dianhydrogalactitol (VAL). The simultaneous combination does not increase the effect compared to dianhydrogalactitol (VAL) alone.

FIG. 19 is a graph showing the effect of simultaneous combination treatment of SF188 cells with temozolomide and dianhydrogalactitol.

Figure 20:
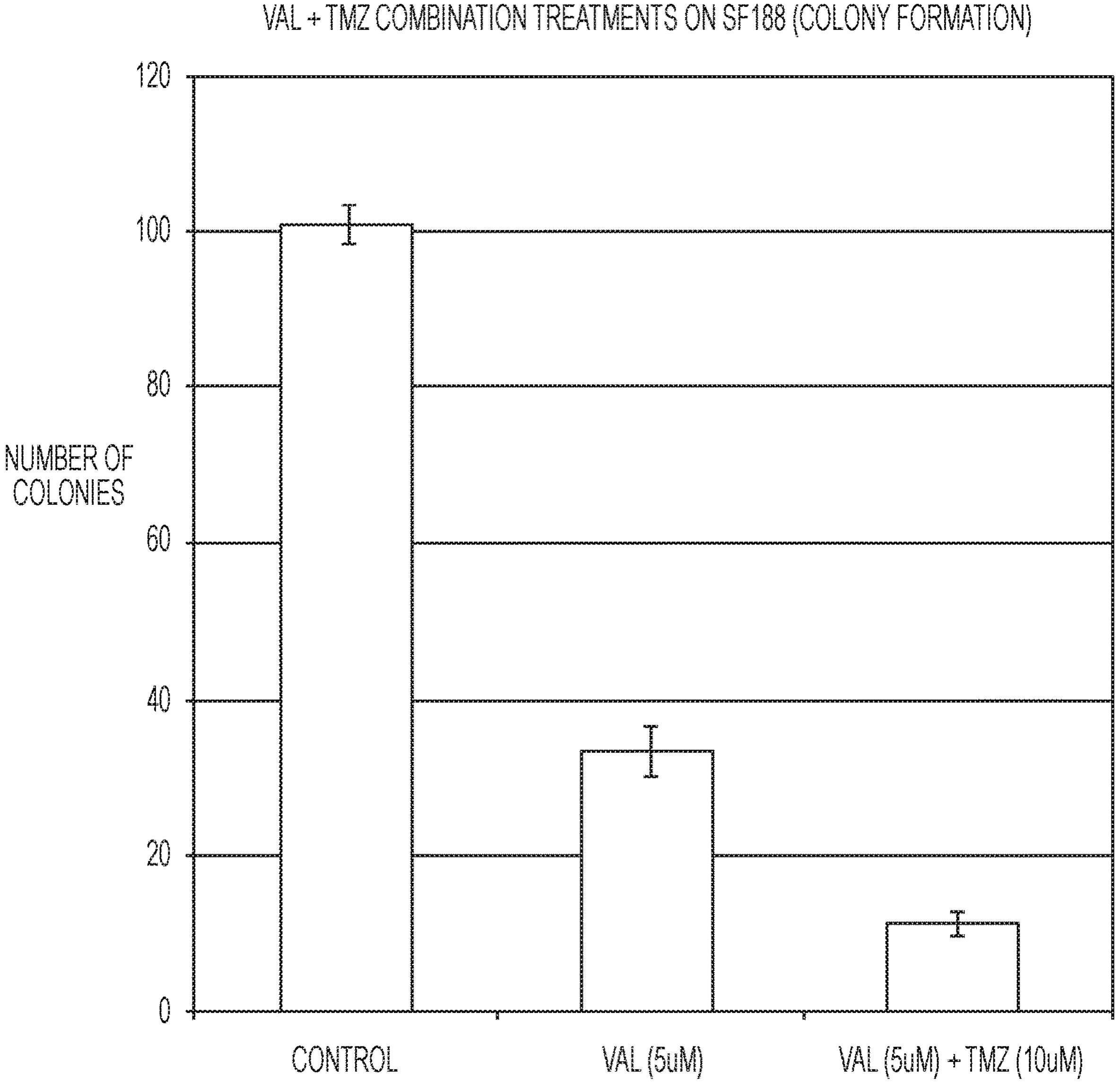
FIG. 20 is a graph showing the effect of simultaneous combination treatment of SF188 cells with temozolomide and dianhydrogalactitol (VAL) in reducing colony formation.

FIG. 20 is a graph showing the effect of simultaneous combination treatment of SF188 cells with temozolomide and dianhydrogalactitol in reducing colony formation.

Figure 21:
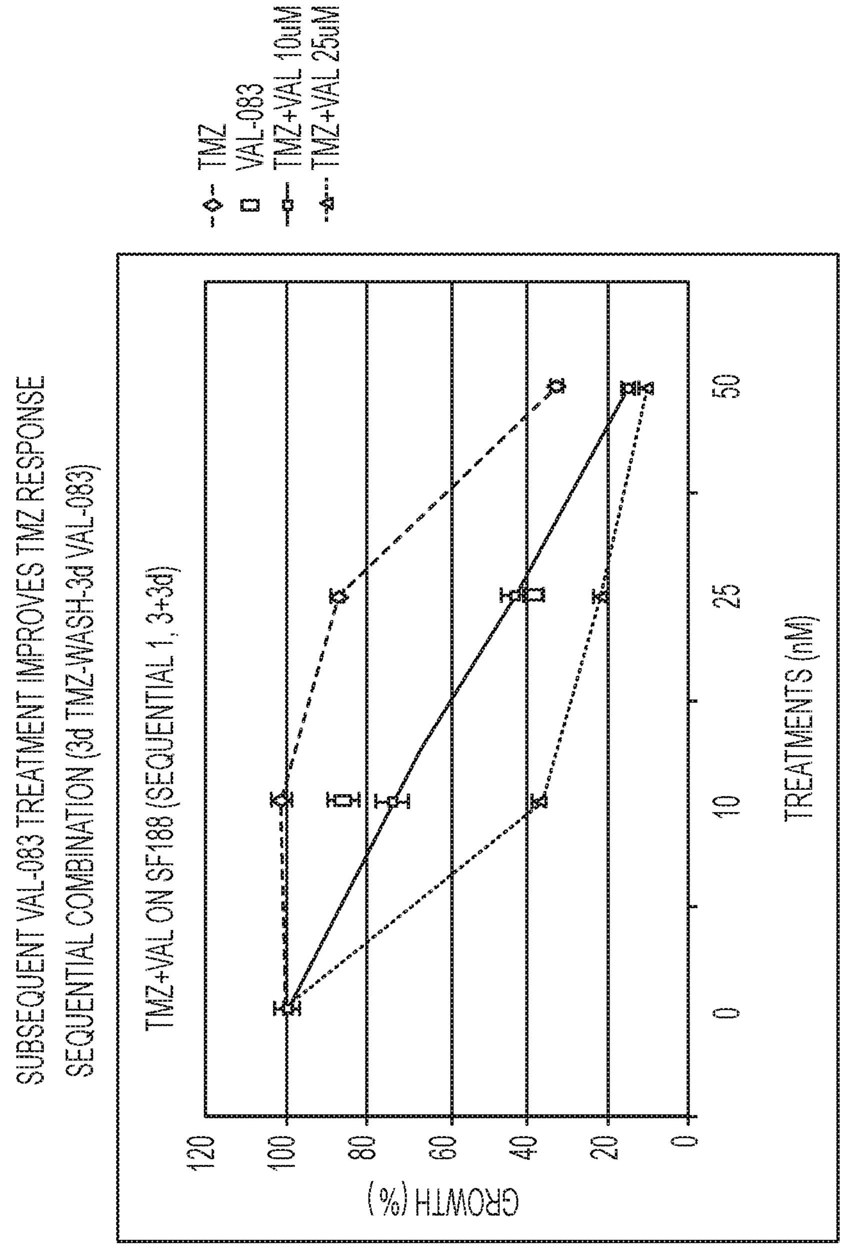
FIG. 21 is a graph showing the effects of sequential combination treatment with dianhydrogalactitol (VAL-083) and temozolomide (TMZ) on the pediatric high grade glioma cell line SF188; treatment was with TMZ for 3 days, then a wash, then treatment with dianhydrogalactitol for 3 days; two concentrations of dianhydrogalactitol, 10 μM and 25 μM were used.

FIG. 21 is a graph showing the effects of sequential combination treatment with dianhydrogalactitol (VAL-083) and temozolomide (TMZ) on the pediatric high grade glioma cell line SF188; treatment was with TMZ for 3 days, then a wash, then treatment with dianhydrogalactitol for 3 days; two concentrations of dianhydrogalactitol, 10 μM and 25 μM were used.

Figure 22:
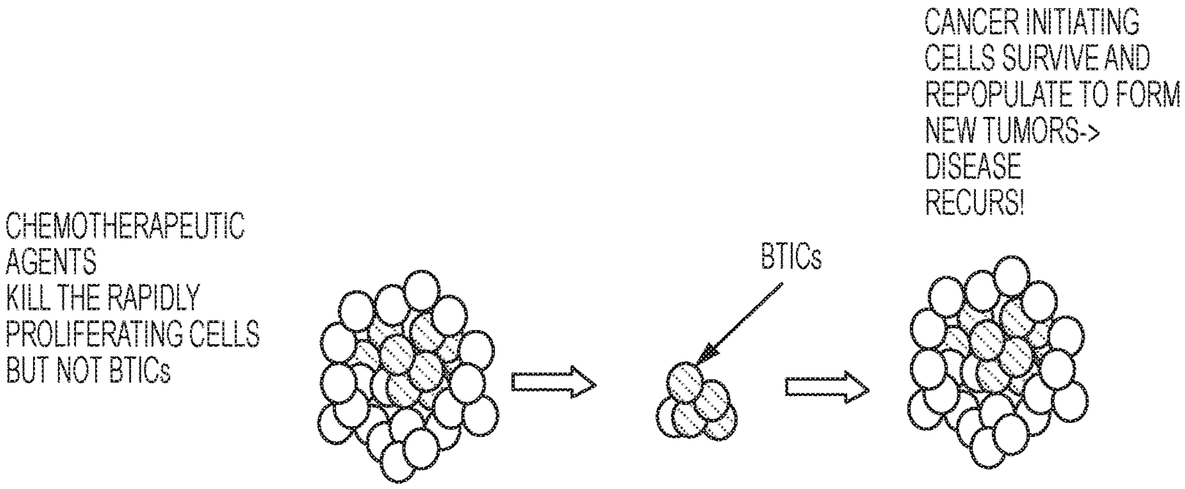
FIG. 22 is a schematic diagram showing the mechanism by which the survival of cancer stem cells results in recurrence of the malignancy.

FIG. 22 is a schematic diagram showing the mechanism by which the survival of cancer stem cells results in recurrence of the malignancy.

Figure 23:
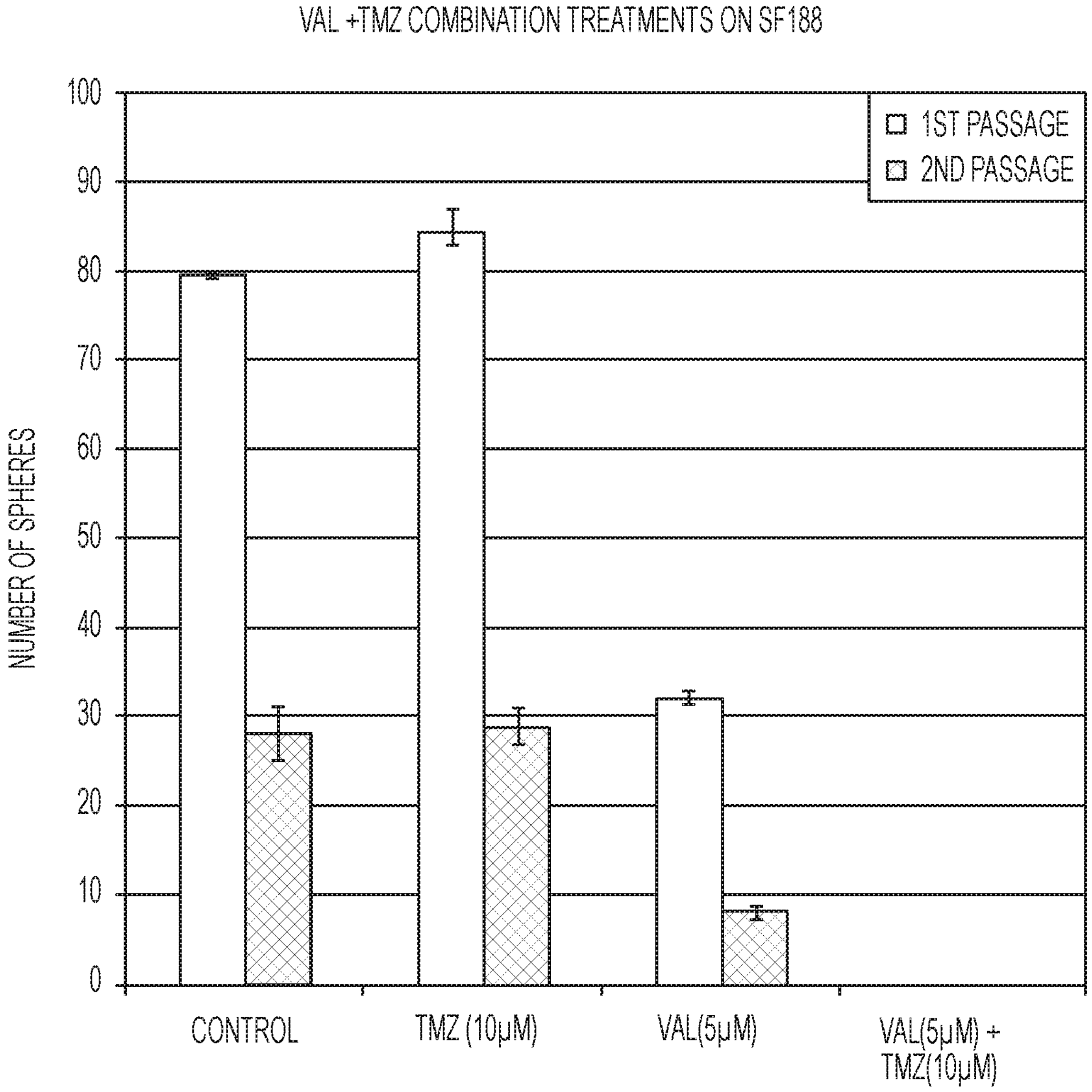
FIG. 23 is a graph showing the effect of combination dianhydrogalactitol (VAL) and temozolomide (TMZ) treatment on first-passage and second-passage SF188 cells.

FIG. 23 is a graph showing the effect of combination dianhydrogalactitol and temozolomide treatment on first-passage and second-passage SF188 cells.

Figure 24:
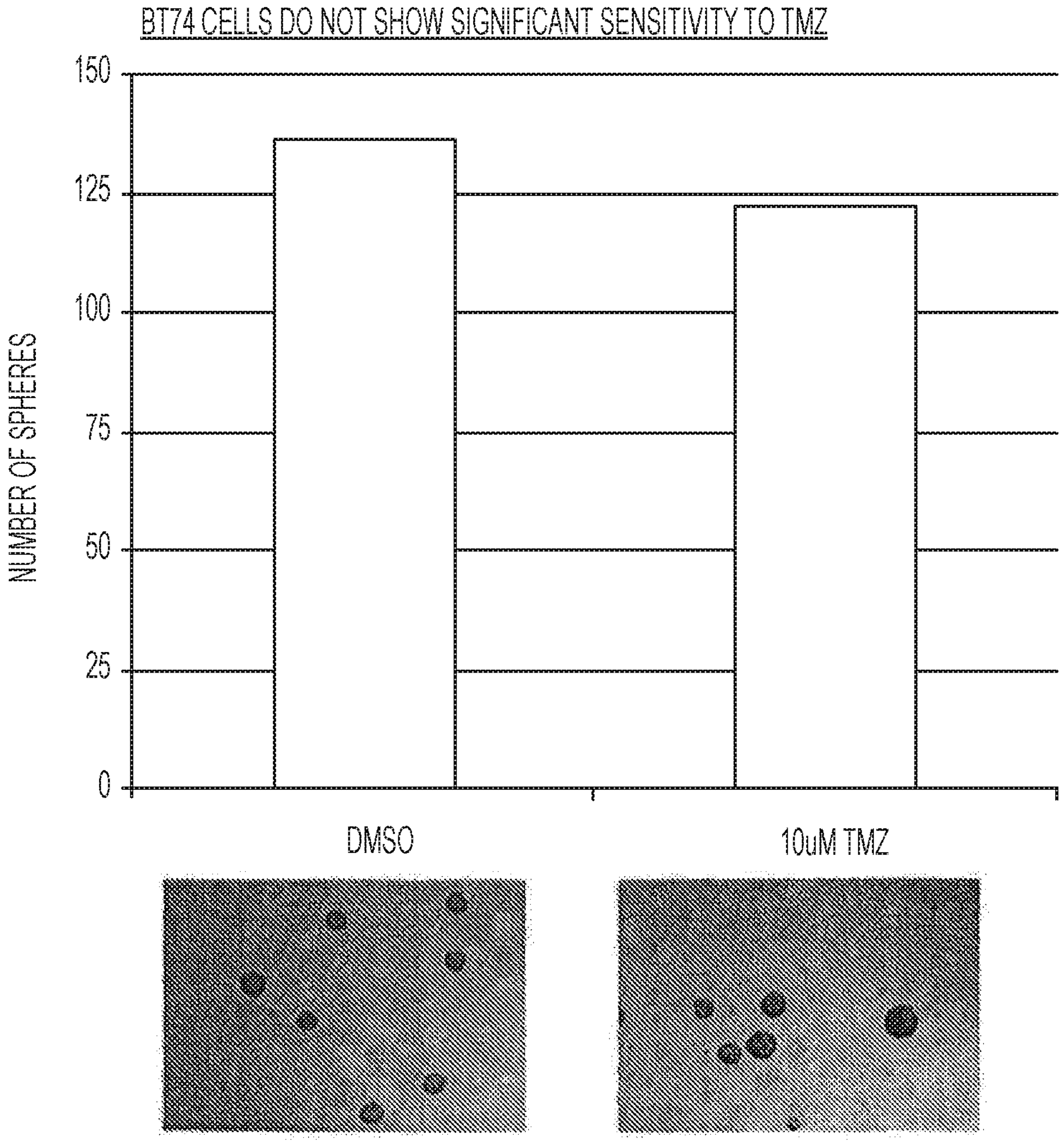
FIG. 24 is a graph showing that BT74 cancer stem cells do not show significant sensitivity to temozolomide.

FIG. 24 is a graph showing that BT74 cancer stem cells do not show significant sensitivity to temozolomide.

Figure 25:
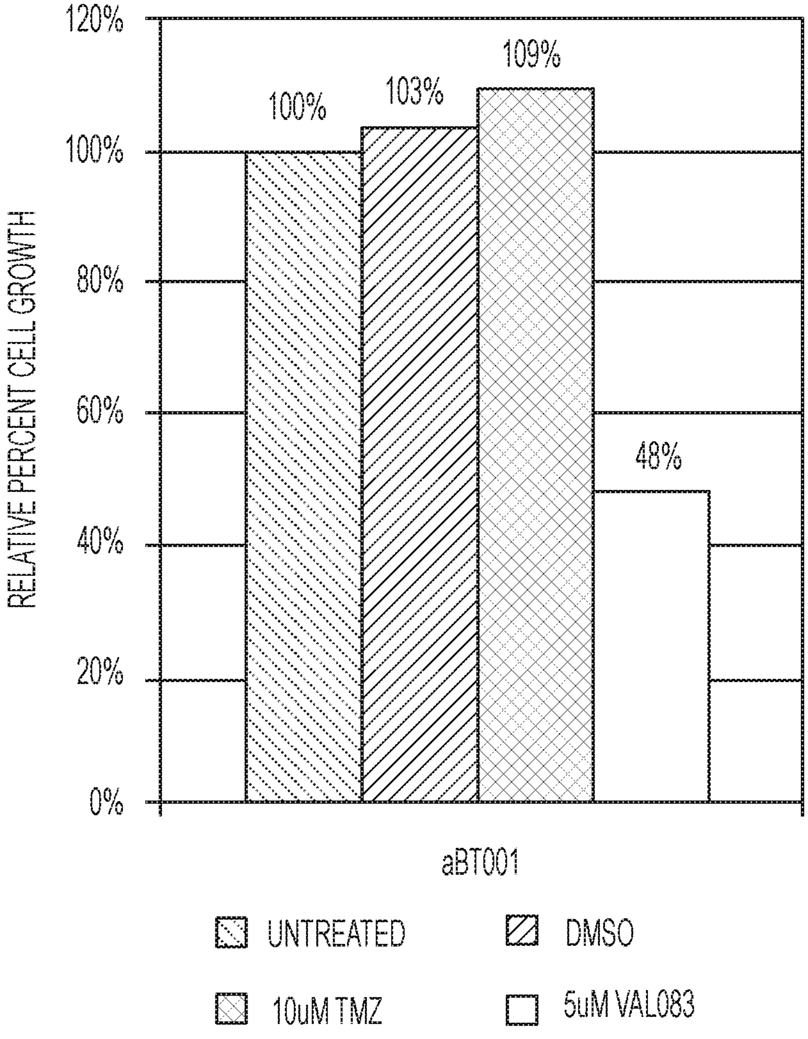
FIG. 25 is a graph showing the effect of dianhydrogalactitol (VAL083) on primary freshly isolated aBT001 GBM cultures.

FIG. 25 is a graph showing the effect of dianhydrogalactitol on primary freshly isolated GBM cultures.

Figure 26:
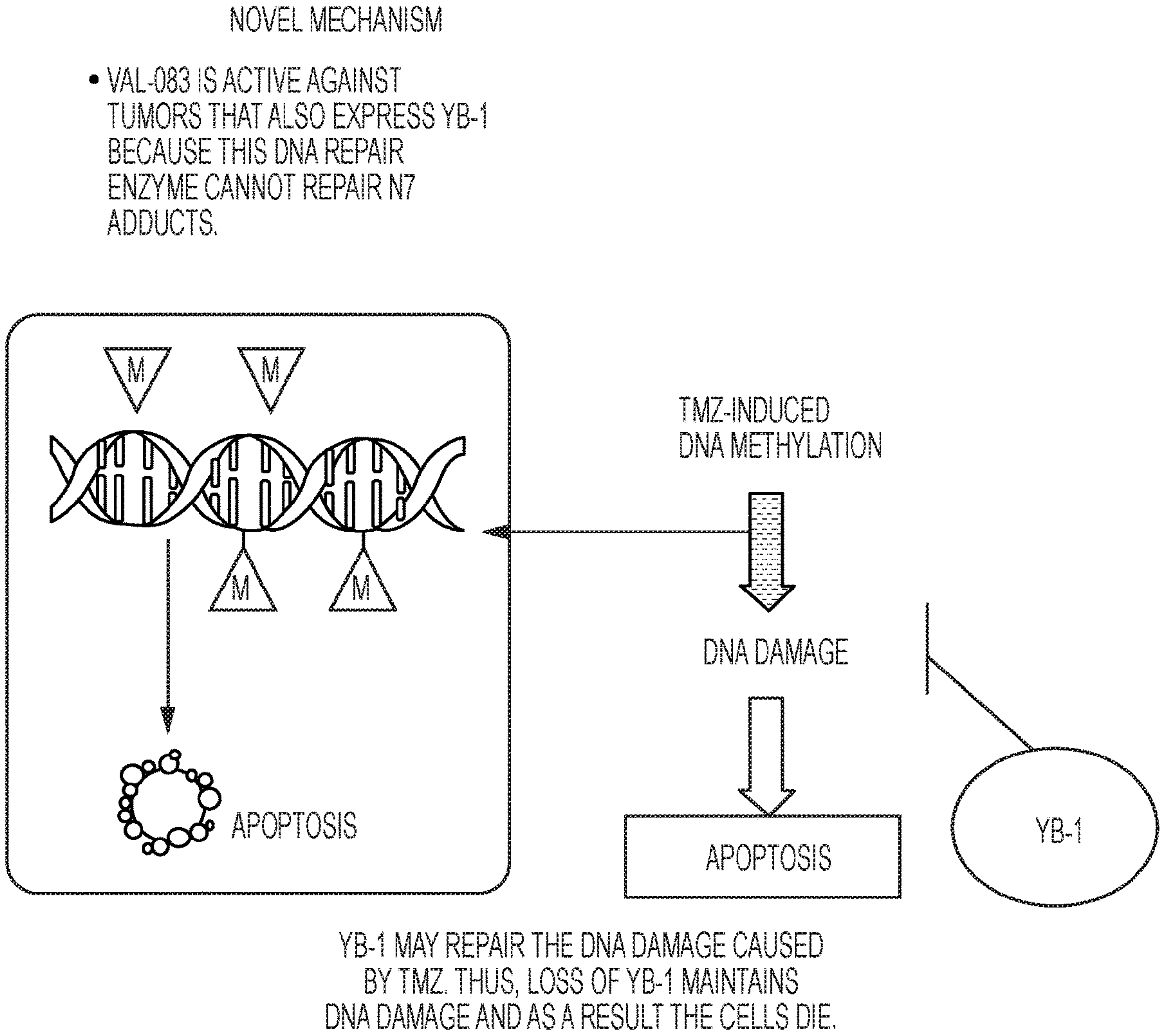
FIG. 26 is a diagram showing that dianhydrogalactitol is active against tumors that express YB-1 because this DNA repair enzyme cannot repair $N^7$-adducts generated by dianhydrogalactitol treatment.

FIG. 26 is a diagram showing that dianhydrogalactitol is active against tumors that express YB-1 because this DNA repair enzyme cannot repair $N^7$-adducts generated by dianhydrogalactitol treatment.

Figure 27:
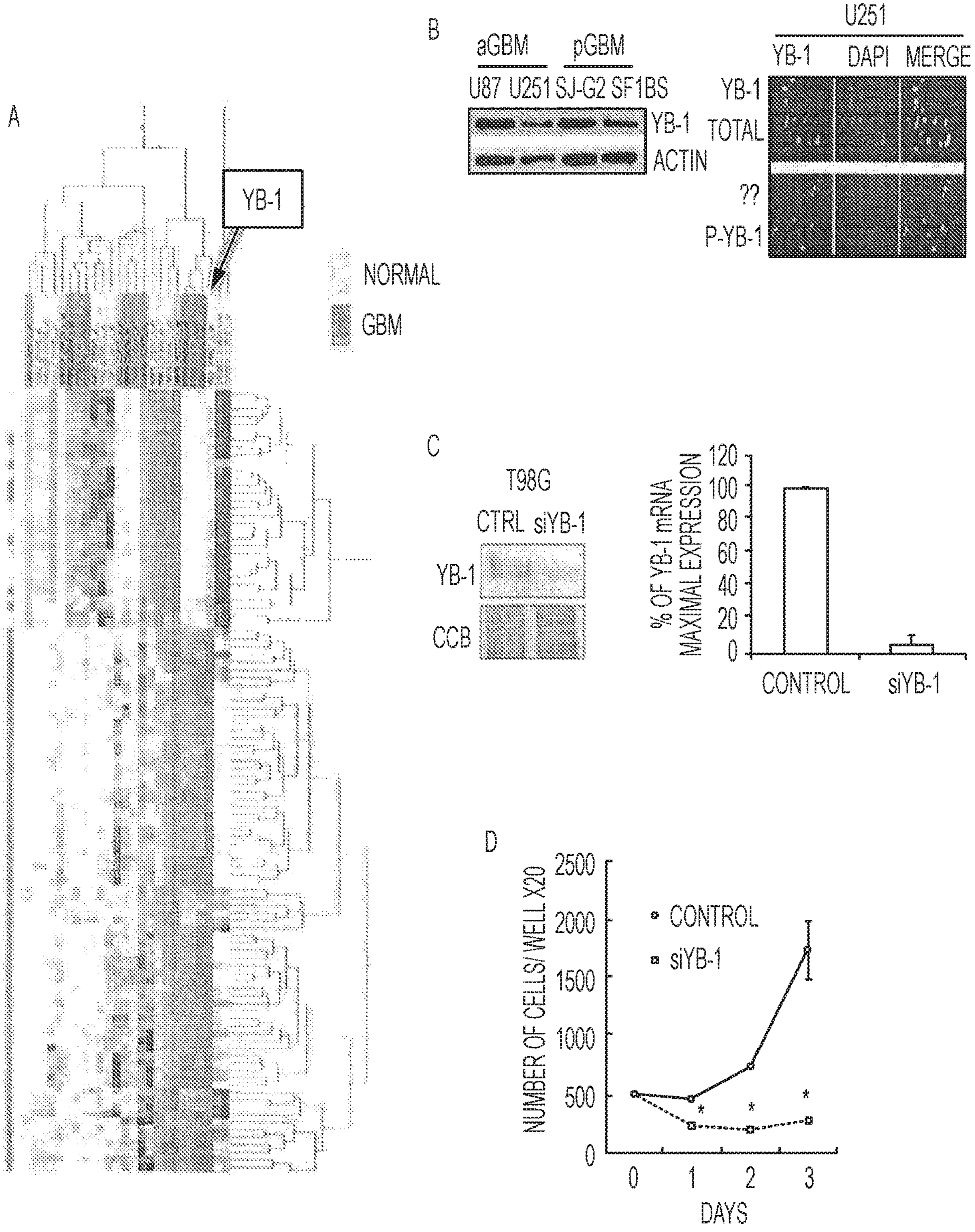
FIG. 27 is a diagram and graph showing that inhibition of YB-1 in adult glioblastoma increases sensitivity to temozolomide.

FIG. 27 is a diagram and graph showing that inhibition of YB-1 in adult glioblastoma increases sensitivity to temozolomide.

Figure 28:
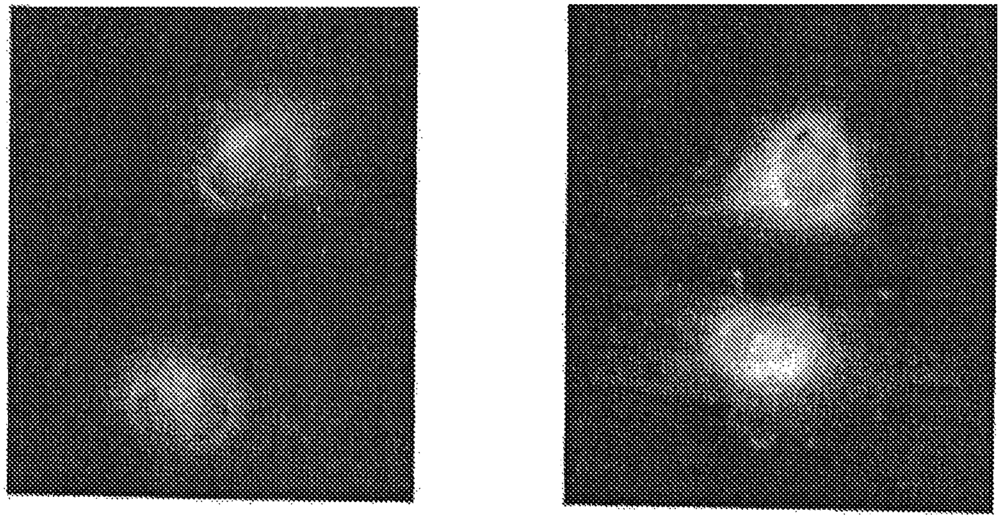
FIG. 28 shows that YB-1 remains nuclear in the presence of temozolomide; temozolomide was used at 10 μM; the left panel was a control; the right panel was treated with temozolomide; magnification was 200×.

FIG. 28 shows that YB-1 remains nuclear in the presence of temozolomide; temozolomide was used at 10 μM; the left panel was a control; the right panel was treated with temozolomide; magnification was 200 x.

Figure 29:
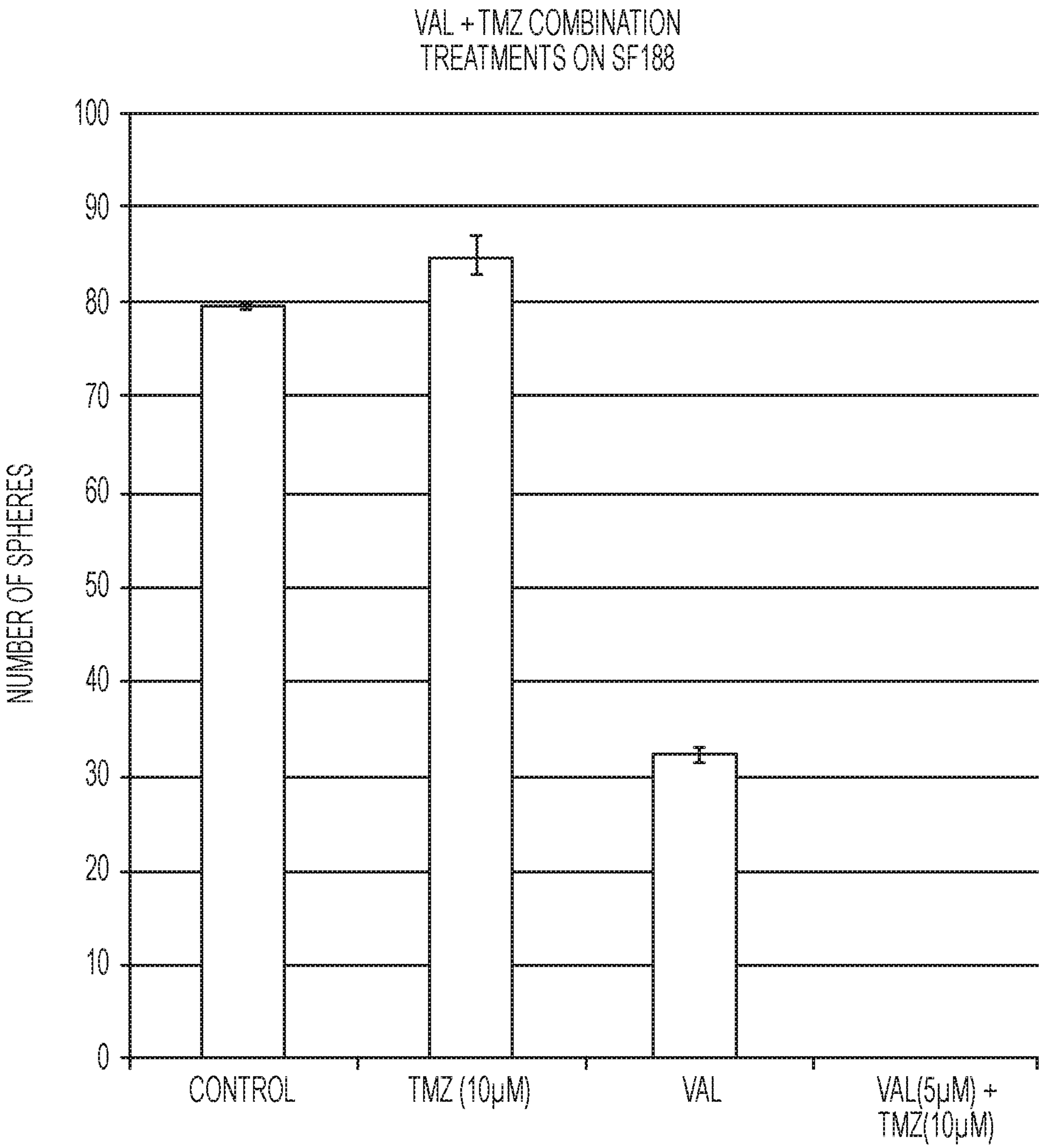
FIG. 29 is a graph showing the effect of simultaneous treatment with temozolomide and dianhydrogalactitol in reducing neurosphere formation by SF188 cells; temozolomide was used at 10 μM; dianhydrogalactitol was used at 5 μM.

FIG. 29 is a graph showing the effect of simultaneous treatment with temozolomide and dianhydrogalactitol in reducing neurosphere formation by SF188 cells; temozolomide was used at 10 μM; dianhydrogalactitol was used at 5 μM.

Figure 30:
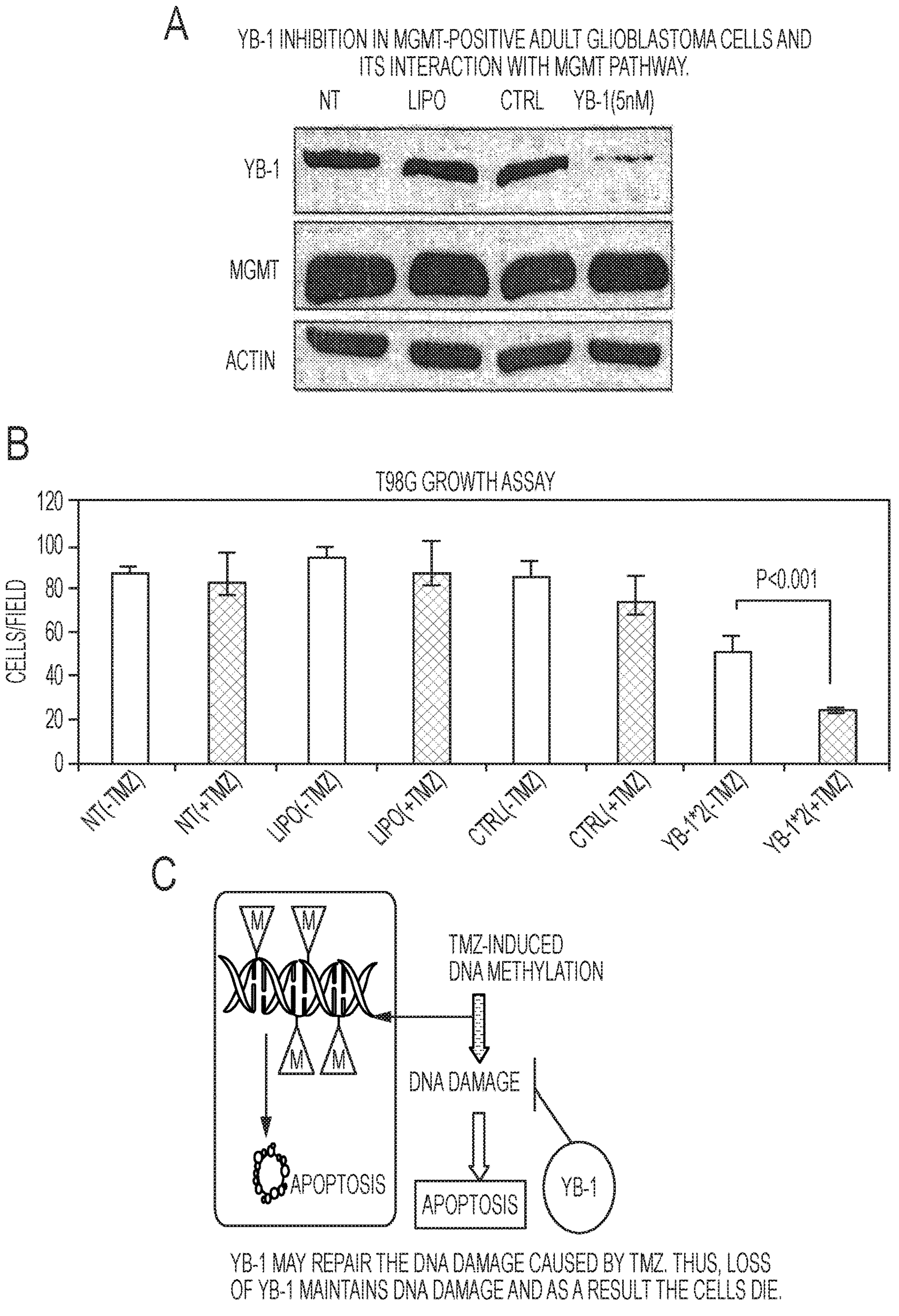
FIG. 30 is a diagram showing the inhibition of YB-1 in MGMT-positive adult glioblastoma cells and its interaction with the MGMT pathway.

FIG. 30 is a diagram showing the inhibition of YB-1 in MGMT-positive adult glioblastoma cells and its interaction with the MGMT pathway.

Figure 31:
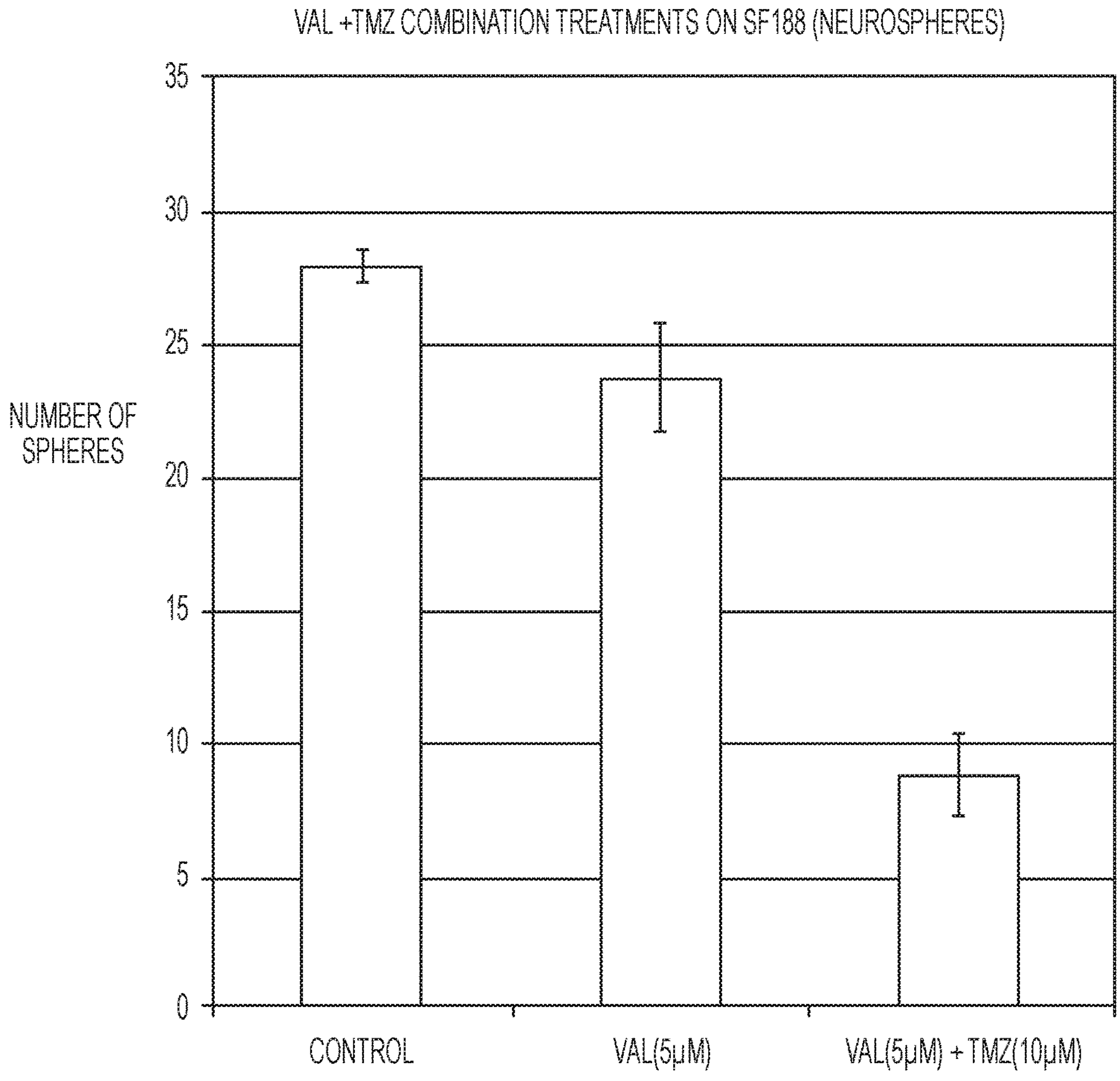
FIG. 31 is a graph showing that the combination of dianhydrogalactitol and temozolomide reduced neurosphere formation for the SF188 cell line more than did treatment with dianhydrogalactitol alone; dianhydrogalactitol was used at 5 μM and temozolomide was used at 10 μM.

FIG. 31 is a graph showing that the combination of dianhydrogalactitol and temozolomide reduced neurosphere formation for the SF188 cell line more than did treatment with dianhydrogalactitol alone; dianhydrogalactitol was used at 5 μM and temozolomide was used at 10 μM.

Figure 32:
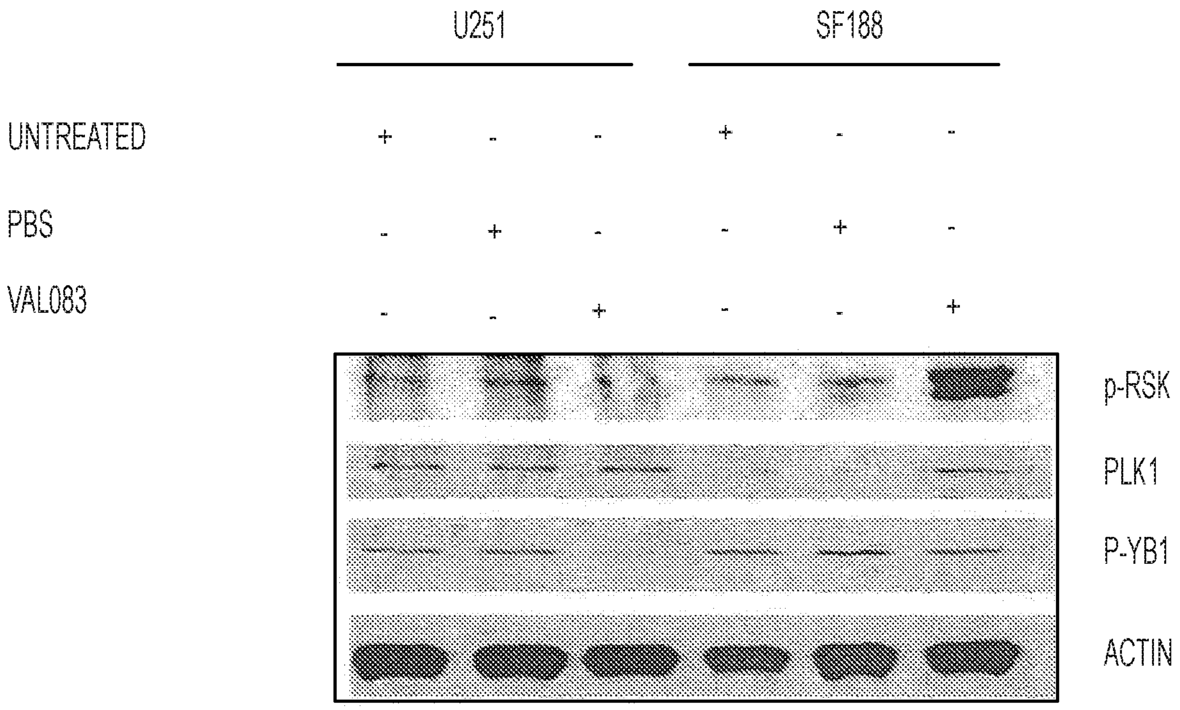
FIG. 32 shows Western blots of U251 and SF188 cells for p-RSK, PLK1, P-YB-1, and actin as a control. Glioblastoma cells were treated with 5 μM dianhydrogalactitol, PBS, or untreated for 72 h, harvested, and Western blots were performed.

FIG. 32 shows Western blots of U251 and SF188 cells for p-RSK, PLK1, P-YB-1, and actin as a control. Glioblastoma cells were treated with 5 μM dianhydrogalactitol, PBS, or untreated for 72 h, harvested, and Western blots were performed.

Figure 33:
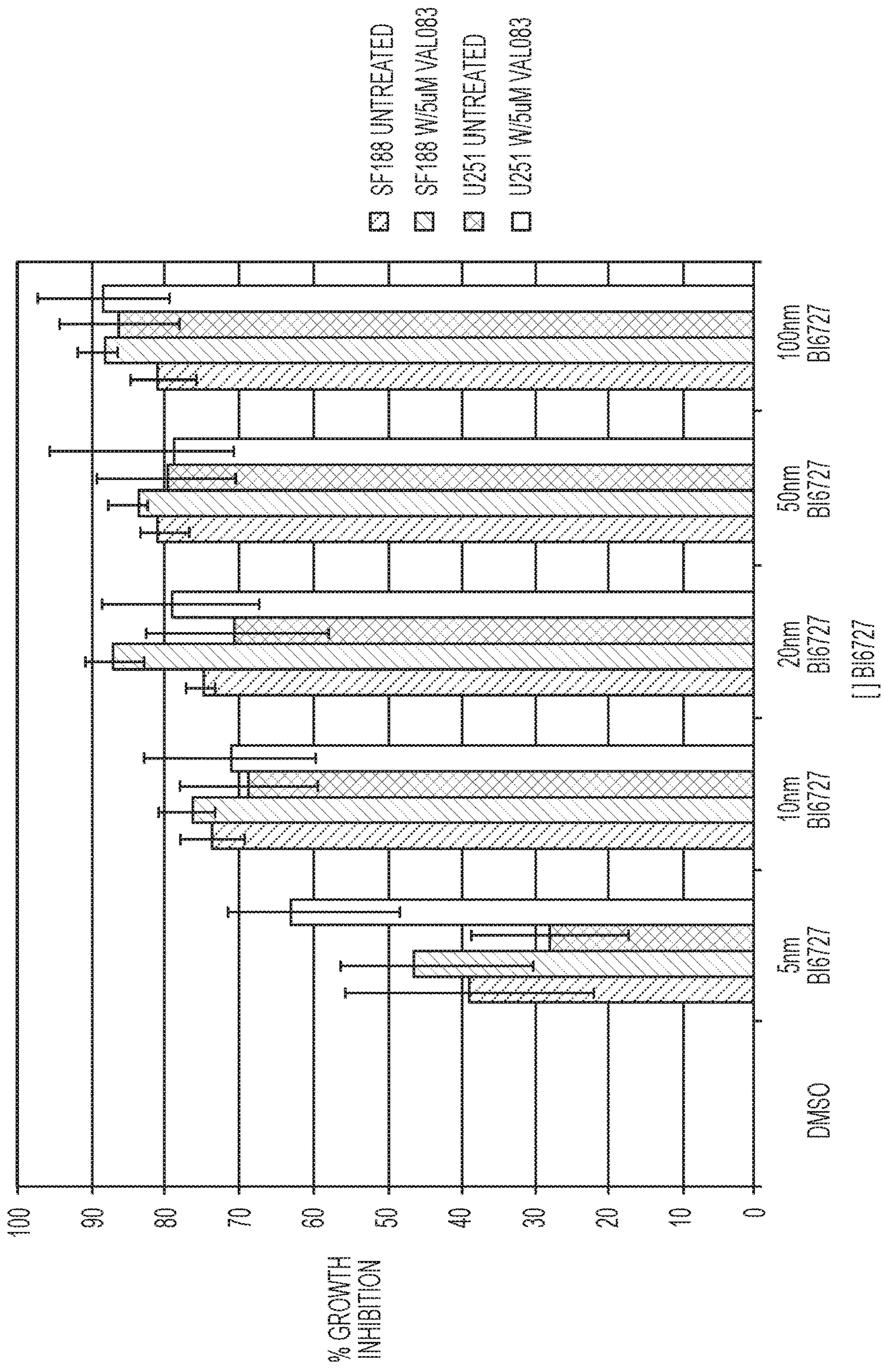
FIG. 33 is a graph showing the effect of pretreatment of dianhydrogalactitol prior to the administration of the Polo kinase inhibitor BI6727 for SF188 and U251 cell lines. After treatment with 5 μM dianhydrogalactitol for 72 hours, the cells were seeded into 96-well plates and treated with ranges of BI6727 for 72 hours with untreated controls.

FIG. 33 is a graph showing the effect of pretreatment of dianhydrogalactitol prior to the administration of the Polo kinase inhibitor BI6727 for SF188 and U251 cell lines. After treatment with 5 μM dianhydrogalactitol for 72 hours, the cells were seeded into 96-well plates and treated with ranges of BI6727 for 72 hours with untreated controls.

Figure 34:
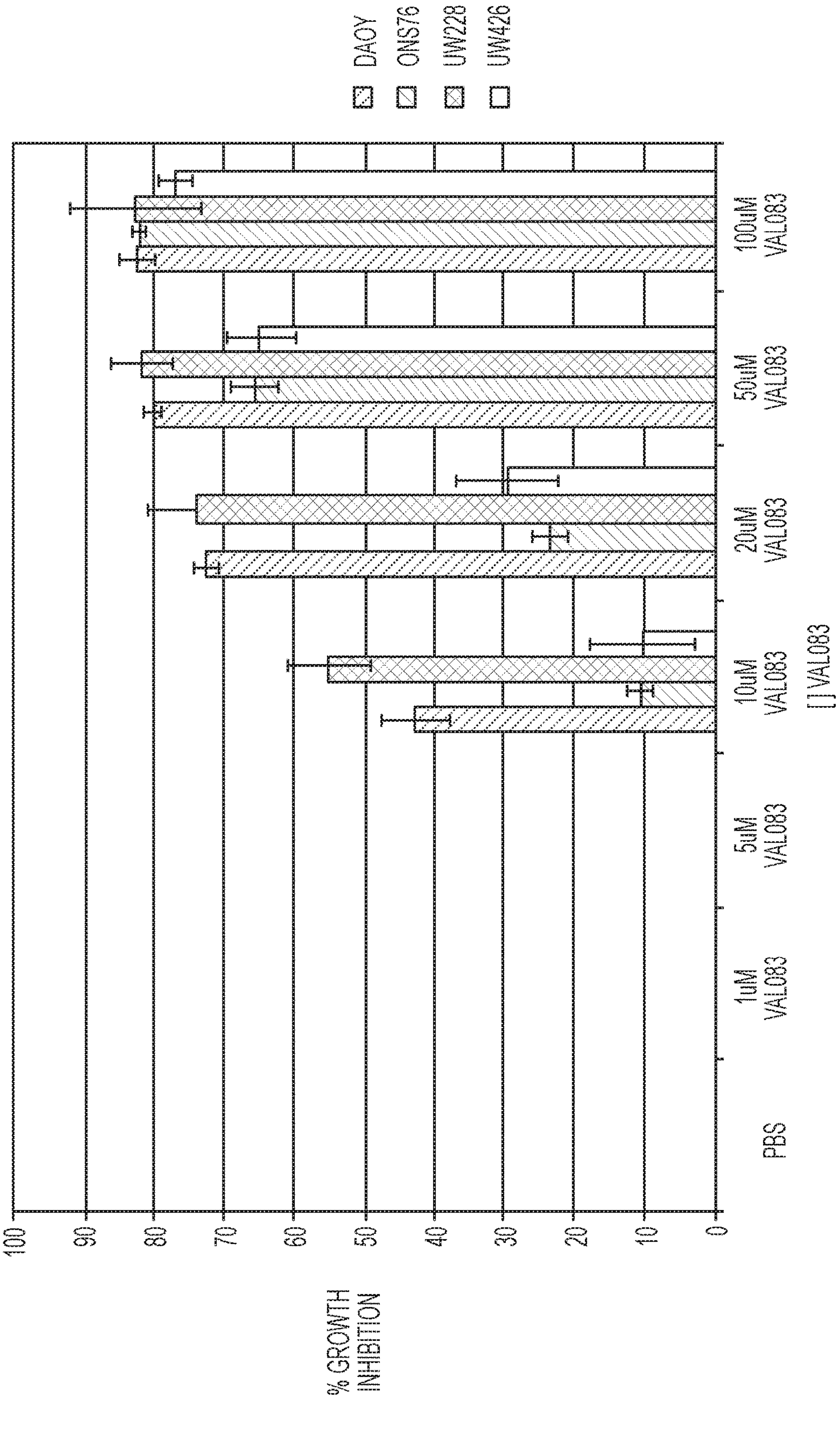
FIG. 34 is a graph showing the inhibition of growth of the medulloblastoma cell lines DAOY, ONS76, UW228, and UW426 by dianhydrogalactitol. The medulloblastoma cell lines were seeded into 96-well plates and treated with increasing concentrations of dianhydrogalactitol for 72 hours.

FIG. 34 is a graph showing the inhibition of growth of the medulloblastoma cell lines DAOY, ONS76, UW228, and UW426 by dianhydrogalactitol. The medulloblastoma cell lines were seeded into 96-well plates and treated with increasing concentrations of dianhydrogalactitol for 72 hours.

Figure 35:
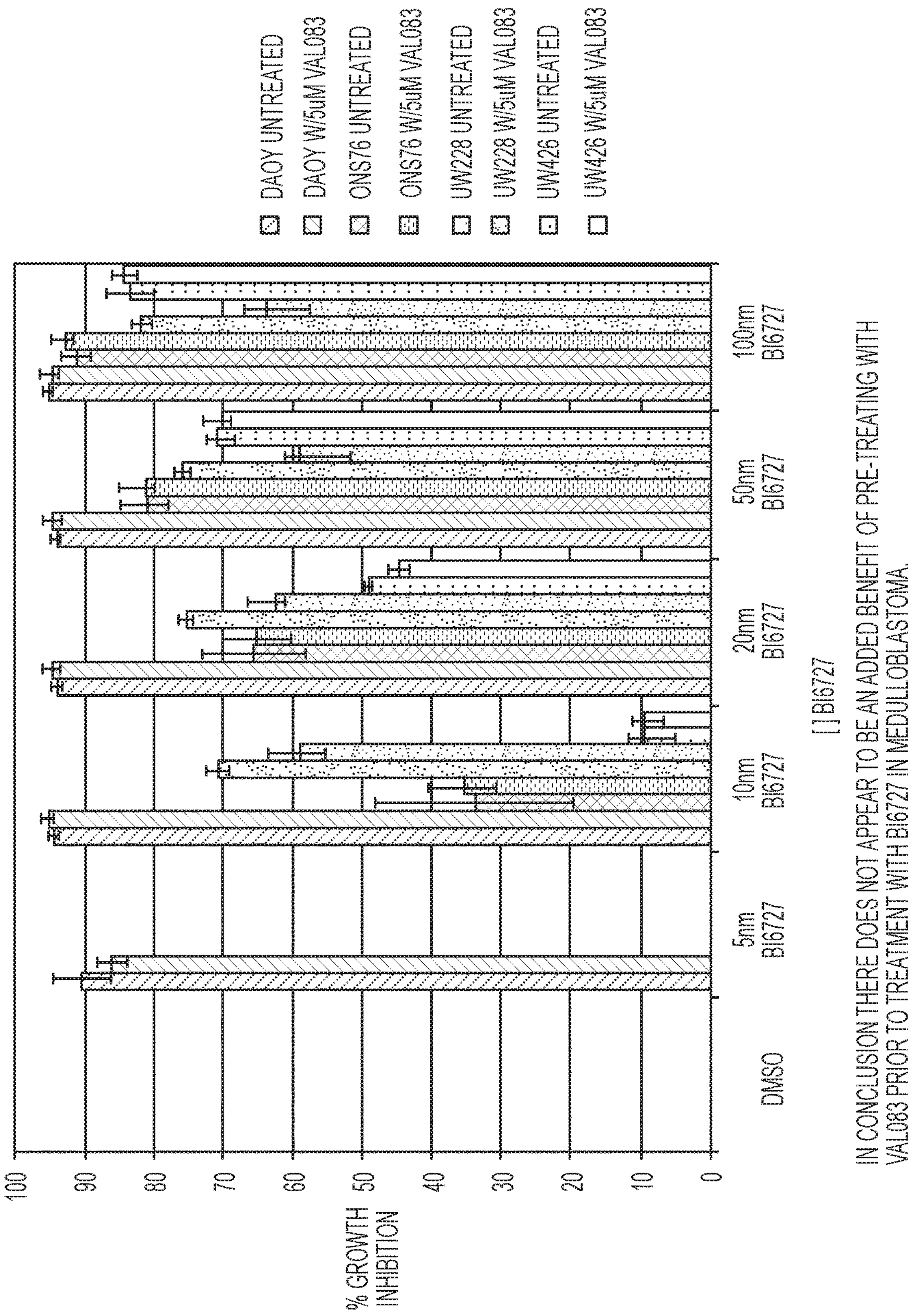
FIG. 35 is a graph showing the effect of pretreatment of dianhydrogalactitol prior to the administration of the Polo kinase inhibitor BI6727 for the medulloblastoma cell lines DAOY, ONS76, UW228, and UW426. After treatment with 5 μM dianhydrogalactitol for 72 hours, the cells were seeded into 96-well plates and treated with ranges of BI6727 for 72 hours with untreated controls.

FIG. 35 is a graph showing the effect of pretreatment of dianhydrogalactitol prior to the administration of the Polo kinase inhibitor BI6727 for the medulloblastoma cell lines DAOY, ONS76, UW228, and UW426. After treatment with 5 μM dianhydrogalactitol for 72 hours, the cells were seeded into 96-well plates and treated with ranges of BI6727 for 72 hours with untreated controls.

In conclusion, dianhydrogalactitol will inhibit the growth of brain tumor cells independent of MGMT status and can be used to overcome TMZ resistance. Dianhydrogalactitol is active against TMZ-resistant glioblastoma multiforme cell lines and also against BTICs (brain tumor initiating cells with stem-cell-like properties. Dianhydrogalactitol is synergistic with temozolomide when combined sequentially. Dianhydrogalactitol is also active against tumors that also express YB-1 because this DNA repair enzyme cannot repair $N^7$ adducts. Temozolomide (TMZ) and dianhydrogalactitol are both alkylating agents. TMZ (Temozolomide) undergoes rapid chemical conversion at physiological pH to the active compound, monomethyl triazeno imidazole carboxamide (MTIC). The cytotoxicity of MTIC is thought to be due primarily to methylation of DNA at the $O^6$ position of guanine. The level or activity of DNA repair protein $O^6$-methyguanine-DNA methyltransferase (MGMT) is primarily responsible for the development of TMZ resistance. However, dianhydrogalactitol is thought to act at $N^7$ of guanine by forming inter-strand cross-linking at $N^7$ of guanine. Formation of cross-links induced by the nitrogen mustards is not broken/repaired by MGMT. Thus, dianhydrogalactitol activity should be independent of MGMT.

Example 3

Activity of Dianhydrogalactitol is Independent of MMR

The activity of dianhydrogalactitol is independent of MMR and independent of p53 status. The results of this Example are from studies with ovarian cancer cell lines; however, as MMR is a mechanism of DNA repair that is associated with the development of resistance to chemotherapy in central nervous system malignancies, including juvenile glioblastoma and medulloblastoma, the development of therapies that are independent of MMR is important for the use of such therapies in a manner that does not provoke drug resistance.

Methods:

The cell lines used were verified for tissue type by molecular analysis and were free of mycoplasma infection. The p53 status was established from sequencing the DNA. The drugs used were obtained from Sigma (cisplatin and oxaliplatin) or supplied by Del Mar Pharmaceuticals (dianhydrogalactitol).

The analysis of cytotoxicity, depicted as IC50 (concentration inhibiting growth of cells by 50%) or as fraction of cells affected (Fa) at a specified concentration of drug, is based on the data generated from the MTT growth inhibition assay following a 5-day drug exposure period. The IC50 values were generated by fitting Fa values from a range of drug concentrations to a four-parameter logistic dose-response sigmoidal equation using the Graphpad Prism v.6 software. Resistance factors (for the ovarian panel) were calculated as the ratio of IC50 in the specific tumor model to the IC50 in A2780.

Figure 36:
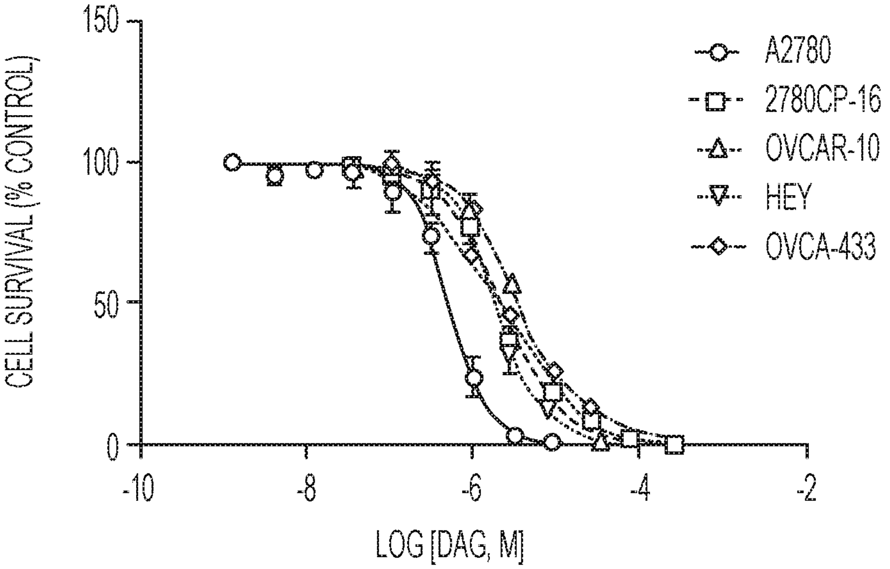
FIG. 36 is a graph showing the dose-response curves of dianhydrogalactitol in an ovarian tumor cell panel in connection with the demonstration of MMR independence and p53 independence of dianhydrogalactitol anti-neoplastic activity in Example 3.
Figure 38:
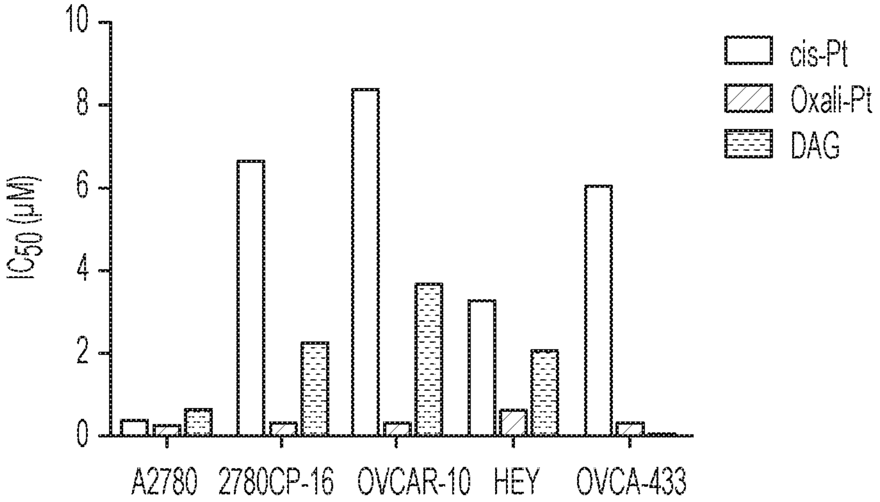
FIG. 38 is a graph showing the activity (as IC50) of dianhydrogalactitol relative to cisplatin and oxaliplatin shown as bar plots in connection with the demonstration of MMR independence and p53 independence of dianhydrogalactitol anti-neoplastic activity in Example 3.
Figure 39:
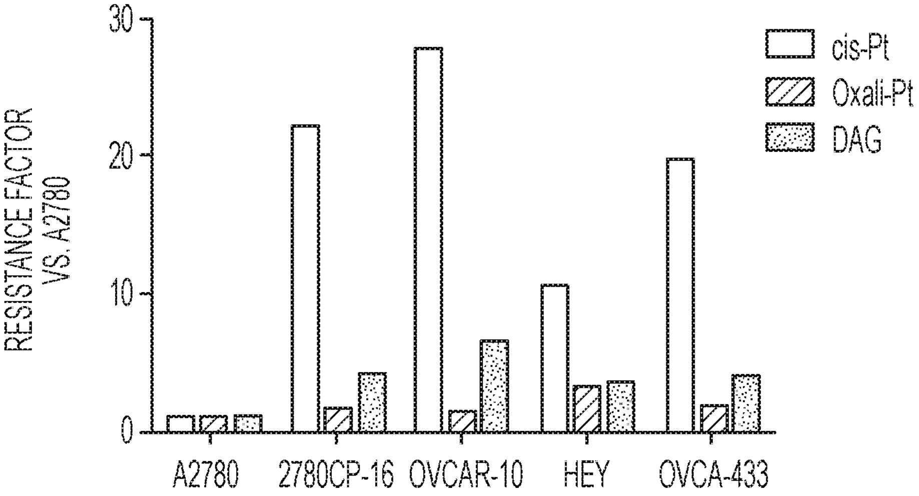
FIG. 39 is a graph showing the resistance factors relative to A2780 and indicating that dianhydrogalactitol can circumvent cisplatin resistance effectively in the HEY model, and to a slightly lesser extent in the 2780CP-16, OVCAR-10 and OVCA-433 cell lines.

Results:

Cytotoxicity was determined against cisplatin-sensitive A2780 and cisplatin-resistant 2780CP-16, OVCAR-10, Hey and OVCA-433 tumor models with different status for p53 and mismatch repair (MMR) DNA repair system (A2780: p53 wild-type, MMR proficient; 2780CP-16: heterogenic p53 wt/V172Fmut, MMR deficient; OVCAR-10: p53 V172F mutant, MMR proficient; HEY: p53 P72R mutant, MMR proficient; OVCA-433: p53 P72R mutant, MMR proficient). Dose-response curves for dianhydrogalactitol in the ovarian tumor cell panel are shown in FIG. 36. The corresponding IC50 values for dianhydrogalactitol are shown in FIG. 37. IC50 for dianhydrogalactitol was about 0.5 μM in A2780 cells and in the 2-4 μM range for the cisplatin-resistant models. The activity (as IC50) of dianhydrogalactitol relative to cisplatin and oxaliplatin is shown as bar plots in FIG. 38. In the A2780 model, all three drugs demonstrated comparable potencies (IC50, 0.2-0.5 μM), but resistance of other models to cisplatin was apparent from the relatively higher IC50 values of about 3-8 μM. Oxaliplatin, in contrast, had good potencies against both cisplatin-sensitive (0.2 μM) and cisplatin-resistant cells (0.2-0.6 μM). The activity of dianhydrogalactitol against resistant models was in between those of cisplatin and oxaliplatin, but examination of activities as resistance factors (RF) relative to A2780, normalized to an RF of 1 (for A2780), indicates that dianhydrogalactitol can circumvent cisplatin resistance effectively in the HEY model, and to a slightly lesser extent in the 2780CP-16, OVCAR-10 and OVCA-433 cell lines (FIG. 39). This indicates that VAL-083 can circumvent cisplatin resistance in ovarian cancer lines, independent of their p53 status and MMR status.

Mismatch repair system (MMR) is a DNA repair system that is involved in the repair of mismatched Watson Crick base pairs. Deficient MMR results in accumulation of mutations in the surviving cells and is frequent in many cancer types, including GBM and medulloblastoma. As shown above, the MMR system is involved in the repair of DNA lesions resulting from several alkylating chemotherapeutics, including TMZ and cisplatin. Cells that are deficient in MMR are less sensitive or completely resistant to these drugs. Due to the distinct mechanism of action of dianhydrogalactitol, its cytotoxic activity appears independent of MMR with an IC50 value of 2.2 μM in MMR-deficient cell line 2780CP-16 (lacking MMR component MLH1). Therefore, these results are relevant to the treatment of glioblastoma and medulloblastoma in juvenile patients because of the fact that the development of resistance to chemotherapy in these malignancies is frequently associated with MMR DNA repair activity.

A summary of the activity of dianhydrogalactitol, temozolomide, cisplatin, and nitrosoureas in cells that are either MGMT-positive or MGMT-negative or MMR-proficient or MMR-deficient in all possible combinations (MGMT-positive/MMR-proficient; MGMT-positive/MMR-deficient; MGMT-negative/MMR-proficient; or MGMT-negative/MMR-deficient) is shown in Table 1.

TABLE 1

| | | |
|---|---|---|
| Dianhydrogalactitol | MGM Positive | MGMT Negative |
| MMR-Proficient | Sensitive | Sensitive |
| MMR-Deficient | Sensitive | Sensitive |
| Temozolomide[1] | MGMT Positive | MGMT Negative |
| MMR-Proficient | Resistant | Sensitive |
| MMR-Deficient | Resistant | Resistant |
| Cisplatin[2,3] | MGMT Positive | MGMT Negative |
| MMR-Proficient | Sensitive | Sensitive |
| MMR-Deficient | Resistant | Resistant |
| Nitrosoureas[1,4] | MGMT Negative | MGMT Negative |
| MMR-Proficient | Resistant | Sensitive |
| MMR-Deficient | Resistant | Sensitive |

The references for Table 1 are as follows: [1]M. Sanada et al., *Carcinogenesis* 12: 2657-2663 (2007); [2]M. Kartalou et al., *Mutat. Res.* 478: 23-43 (2001); [3]Y. Sedletska et al., *J. Mol. Biol.* 369: 27-40 (2007); [4]B. Cui et al., *Mol. Pharmacol.* 75: 1356-1363 (2009).

Table 1 shows that dianhydrogalactitol is capable of exerting its anti-neoplastic in any combination of MGMT-positive or -negative and MMR-proficient or -deficient environments, in contrast to temozolomide, cisplatin, and nitrosoureas.

Example 4

Synergism of Dianhydrogalactitol with Olaparib

Dianhydrogalactitol has super-additive activity when administered with olaparib in the A2780 ovarian cancer cell line. Although these results are in an ovarian cancer cell line, they are relevant for treatment of juvenile glioblastoma and medulloblastoma because the same synergism or super-additivity is expected to occur in cells of those malignancies. A2780 ovarian cancer cells exposed to dianhydrogalactitol or olaparib individually or simultaneously were assessed for cytotoxicity 5 days later.

Figure 40:
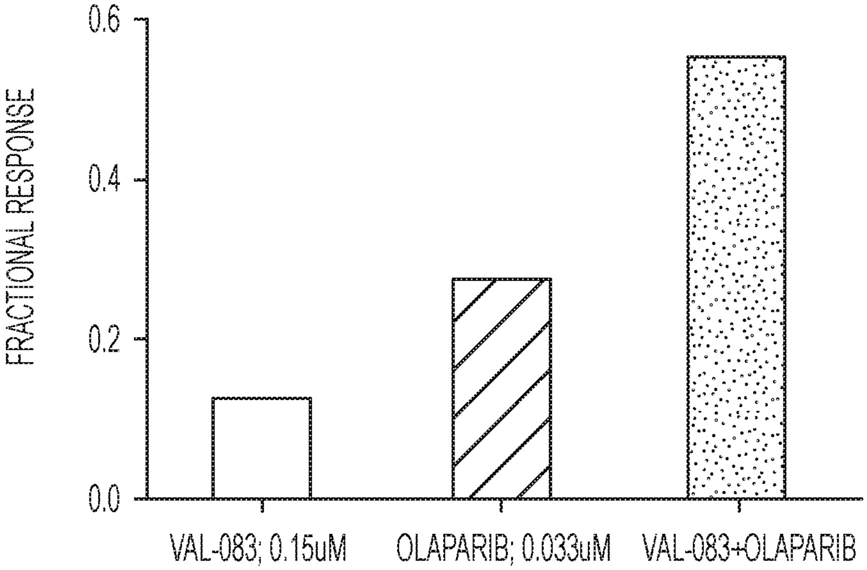
FIG. 40 is a graph showing that dianhydrogalactitol has synergistic activity when administered with olaparib in the A2780 ovarian cancer cell line in Example 4.

The fraction of cells affected (Fa) was determined and are presented in FIG. 40. At the concentrations shown, the Fa was about 15-25% for the individual drug, but the combination resulted in Fa of 56%, which by the Bliss model indicates that the cytotoxicity of the combination is super-additive. Thus, PARP inhibitors including olaparib provide potential for synergistic interaction with dianhydrogalactitol.

Example 5

Synergism of Dianhydrogalactitol with Cisplatin and Oxaliplatin

Dianhydrogalactitol has demonstrated synergism or super-additivity in combination with the platinum-containing anti-neoplastic agents cisplatin and oxaliplatin. Although the results are in NSCLC cell lines, they are relevant for treatment of juvenile glioblastoma and medulloblastoma because cisplatin is frequently used to treat these malignancies and a more effective drug combination would be extremely desirable. The analysis of cytotoxicity, depicted as $IC_{50}$ or as fraction of cells affected (Fa) at a specified concentration of drug A alone, drug B alone, or a combination of drug A+drug B, is based on the MTT growth inhibition data using a 5-day drug exposure protocol. The $IC_{50}$ values were generated by fitting Fa values from a range of drug concentrations to a four-parameter logistic dose-response sigmoidal equation. The determination of predictive additive effect of [drug A+drug B] combination is defined by the equation described by Tallarida (R. J. Tallarida, "Drug Synergism: Its Detection and Application," *J. Pharm. Exp. Ther.* 298: 265-272 (2001)) as follows:

$$\text{Additive effect of [drug } A\text{+drug } B]=FaA+(1-FaA)FaB.$$

Figure 42:
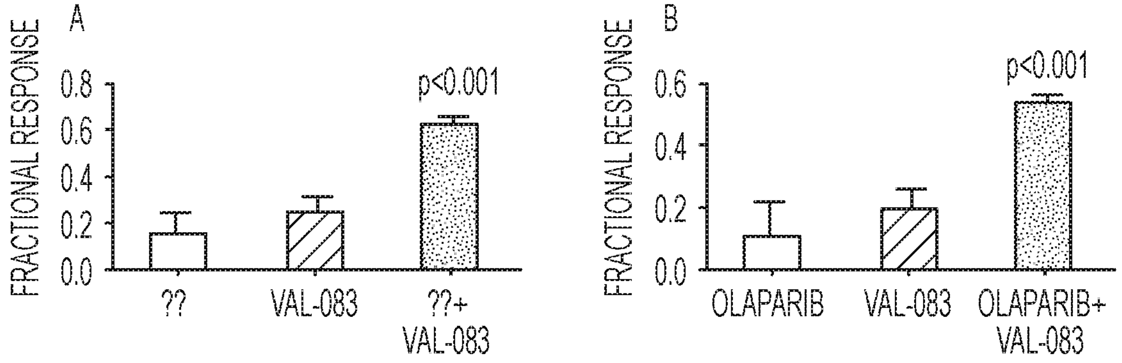
FIG. 42 is a graph showing the synergism of dianhydrogalactitol with cisplatin and oxaliplatin in the NSCLC cell line A549 (wild-type p53 and wild-type EGFR) in Example 5.
Figure 43:
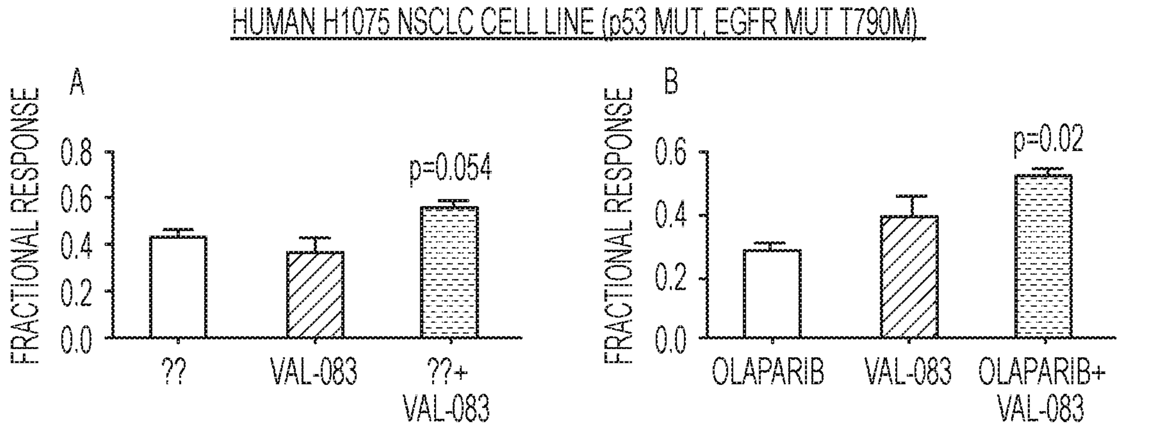
FIG. 43 is a graph showing the synergism of dianhydrogalactitol with cisplatin and oxaliplatin in the NSCLC H1975 (mutated p53 and mutated EGFR with the T790M mutation) in Example 5.

The results are shown in FIGS. 41, 42, and 43 for the NSCLC cell lines H460 (wild-type p53 and wild-type EGFR), A549 (wild-type p53 and wild-type EGFR), and H1975 (mutated p53 and mutated EGFR with the T790M mutation). Data, where applicable, are shown as Mean+/−SE, N=4 for FIGS. 41, 42, and 43. Fa: Fraction of cells affected. The tables provide CI values for the Fa shown and achieved at indicated drug concentrations, i.e. ED75: effective dose that kills 75% of cells.

Advantages of the Invention

The present invention provides effective methods and compositions for treating a number of central nervous system malignancies affecting pediatric patients, including, but not limited to, glioblastoma multiforme, including high grade glioma, and medulloblastoma. These methods and compositions are well tolerated and do not cause significant side effects. They can be used together with radiation, surgery, or other chemotherapeutic agents.

Methods according to the present invention possess industrial applicability for the preparation of a medicament for the treatment of a number of diseases and conditions in subjects, including the malignancies of the central nervous system in pediatric patients as described above. Compositions according to the present invention possess industrial applicability as pharmaceutical compositions.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patents and patent publications, are incorporated herein by reference.

What is claimed is:

1. A method for the treatment of an ovarian cancer comprising administering a therapeutically effective quantity of dianhydrogalactitol and a therapeutically effective quantity of olaparib to treat the ovarian cancer.

2. The method of claim 1, wherein dianhydrogalactitol and olaparib are administered simultaneously or substantially simultaneously.

3. The method of claim 1, wherein dianhydrogalactitol and olaparib are administered sequentially.

4. The method of claim 1, wherein dianhydrogalactitol and olaparib are administered simultaneously and wherein dianhydrogalactitol and olaparib are administered as a single pharmaceutical composition.

* * * * *